US010202612B2

(12) United States Patent
Damaj et al.

(10) Patent No.: US 10,202,612 B2
(45) **Date of Patent: *Feb. 12, 2019**

(54) COMPOSITIONS, ORGANISMS, SYSTEMS, AND METHODS FOR EXPRESSING A GENE PRODUCT IN PLANTS

(71) Applicant: THE TEXAS A&M UNIVERSITY SYSTEM, College Station, TX (US)

(72) Inventors: Mona Damaj, Weslaco, TX (US); T. Erik Mirkov, Harlingen, TX (US)

(73) Assignee: The Texas A&M University System, College Station, TX (US)

( * ) Notice: Subject to any disclaimer, the term of this patent is extended or adjusted under 35 U.S.C. 154(b) by 495 days.

This patent is subject to a terminal disclaimer.

(21) Appl. No.: 14/185,684

(22) Filed: Feb. 20, 2014

(65) Prior Publication Data

US 2014/0208462 A1 Jul. 24, 2014

Related U.S. Application Data

(63) Continuation of application No. 13/104,158, filed on May 10, 2011, now Pat. No. 8,710,207.

(60) Provisional application No. 61/400,976, filed on Aug. 5, 2010, provisional application No. 61/395,197, filed on May 10, 2010.

(51) Int. Cl.

| | |
|---|---|
| ***C12N 15/82*** | (2006.01) |
| ***C12N 15/52*** | (2006.01) |
| ***C12N 9/36*** | (2006.01) |

(52) U.S. Cl.

CPC ....... *C12N 15/8216* (2013.01); *C12N 9/2462* (2013.01); *C12N 15/52* (2013.01); *C12N 15/8222* (2013.01); *C12N 15/8237* (2013.01); *C12N 15/8241* (2013.01)

(58) Field of Classification Search

None

See application file for complete search history.

(56) References Cited

U.S. PATENT DOCUMENTS

| | | | | |
|---|---|---|---|---|
| 5,994,123 | A | 11/1999 | Olszewski et al. | |
| 6,093,569 | A | 7/2000 | Olszewski et al. | |
| 7,253,276 | B2 * | 8/2007 | Damaj | C07K 14/415 435/320.1 |
| 2002/0042928 | A1 * | 4/2002 | McCaslin | A01H 1/02 800/260 |
| 2003/0074684 | A1 * | 4/2003 | Graham | C12N 9/1051 800/278 |
| 2004/0040061 | A1 * | 2/2004 | Horn | C07K 14/005 800/288 |
| 2004/0073965 | A1 * | 4/2004 | Mirkov | C07K 14/415 800/278 |
| 2007/0130655 | A1 | 6/2007 | Mirkov et al. | |

FOREIGN PATENT DOCUMENTS

| | | | | |
|---|---|---|---|---|
| CN | 1276014 | A | 12/2000 | |
| WO | 99/09190 | A1 | 2/1999 | |
| WO | 02/42450 | A1 | 5/2002 | |
| WO | WO02/42450 | * | 5/2005 | C12N 15/11 |

OTHER PUBLICATIONS

Hobbs et al. Transgene copy number can be positively or negatively associated with transgene expression. Plant Molecular Biology. 1993. 21:17-26.*

Chan et al. Gene stacking in *Phalaenopsis* orchid enhances dual tolerance to pathogen attack. Transgenic Research. 2005. 14:279-288.*

Anonymous. Issue Abstract. In Vitro Cellular & Developmental Biology. 2009. excerpt pp. S-xxxiv, and S81-S82.*

Barros. Downstream processing of recombinant proteins from transgenic plant systems: phenolic compound removal from monoclonal antibody expression lemna minor and purification of bovine lysozyme from sugarcane. Dissertation. Texas A&M University. 2012. excerpt pp. iii, iv, 55-65, 108, and 122-126.*

Barros et al. Recovery of bovine lysozyme from transgenic sugarcane stalks: extraction, membrane filtration, and purification. Bioprocess Biosyst Eng. 2013. 36:1407-1416.*

Christensen et al. Maize polyubiquitin genes: structure, thermal perturbation of expression and transcript splicing, and promoter activity following transfer to protoplasts by electroporation. Plant Molecular Biology. 1992. 18: 675-689.*

Giddings et al. Transgenic plants as factories for biopharmaceuticals. Nature Biotechnology. 2000. 18: 1151-1155.*

Halpin et al. Enabling technologies for manipulating multiple genes on complex pathways. Plant Molecular Biology. 2001. 47: 295-310.*

(Continued)

*Primary Examiner* — Ashley K Buran

(74) *Attorney, Agent, or Firm* — Baker & McKenzie LLP

(57) ABSTRACT

The present disclosure relates, in some embodiments, to compositions, organisms, systems, and methods for expressing a gene product in a plant using a expression control sequence (ECS) operable in monocots and/or dicots. For example, (i) an isolated nucleic acid may comprise an ECS (e.g., a sugarcane bacilliform virus promoter) and, optionally, an exogenous nucleic acid (ExNA) operably linked to the ECS; (ii) an expression vector may comprise an ECS; an ExNA; and, optionally, a 3' termination sequence, wherein the ECS has promoter activity sufficient to express the ExNA in at least one monocot and at least one dicot; (iii) a microorganism, plant cell, or plant may comprise an isolated nucleic acid; (iv) a method for constitutively expressing an ExNA in a plant (e.g., a monocot and/or a dicot) may comprise, contacting an expression vector with the cytosol of a cell of the plant, wherein the expression vector comprises the ExNA and an ECS operable to drive expression of the ExNA; and/or (v) a method of directing constitutive expression of a nucleic acid in a plant (e.g., a monocot and/or a dicot) may comprise transforming the plant with an expression nucleic acid comprising an ECS, an ExNA, and a 3' termination sequence.

27 Claims, 17 Drawing Sheets
(6 of 17 Drawing Sheet(s) Filed in Color)

Specification includes a Sequence Listing.

(56) References Cited

OTHER PUBLICATIONS

Chen, W.H., et al., "Transformation of sugarcane protoplasts by direct uptake of a selectable chimaeric gene," Plant Reports (1987), vol. 6, pp. 297-301.
Chiera, J.M., et al., "Genetic Transformation and Hybridization: Isolation of two highly active soybean (*Glycine max* (L.) Merr.) promoters and their characterization using a new automated image collection and analysis system," Plant Cell Report, (2007), 21 pages.
Chiera, J.M., et al., "Quantification and extension of transient GFP expression by the co-introduction of a suppressor of silencing," Transgenic Res, (2008), vol. 17, pp. 1143-1154.
Jefferson, R.A., et al., "GUS fusionsβ-glucuronidase as a sensitive and versatile gene fusion marker in higher plants,", The EMBO Journal, vol. 6, No. 13, pp. 3901-3907, (1987).
Yoo, S-D., et al., "*Arabidopsis mesophyll* protoplasts: a versatile cell system for transient gene expression analysis," Nature Protocols, vol. 2, No. 7, (2007), pp. 1565-1572.
Larkin, M.A., et al., "Clustal W and Clustal X version 2.0," Bioinformatics, vol. 23, No. 21, (2007), pp. 2947-2948.
Pearson, W.R., "Rapid Sequence Comparison: Rapid and Sensitive Sequence Comparison with FASTP and FASTA," Methods in Enzymology, vol. 183, (1990), pp. 63-98.
Pearson, W.R., et al., "Improved tools for biological sequence comparison," Proc. Natl. Acad. Sci., vol. 85, (Apr. 1988), pp. 2444-2448.
Lodish, H., et al., "Molecular Cell Biology, 4th ed.," Chapter 10: Regulation of Transcription Initiation, 10.2: Bacterial Transcription Initiation, pp. 346-358, (2002).
Griffiths, A.J.F., et al., "An Introduction to Genetic Analysis, 6th ed.," Chapter 15: Applications of Recombinant DNA Technology, pp. 459-492, (1996).
Mangwende, T., et al., "The P0 gene of Sugarcane yellow leaf virus encodes an RNA silencing suppressor with unique activities," Virology, vol. 284, (2009), pp. 38-50.
Ohara, S., et al., "Rabies Virus Vector Transgene Expression Level and Cytotoxicity Improvement Induced by Deletion of Glycoprotein Gene," PLOS ONE, vol. 8, Issue 11, (Nov. 2013), pp. 1-10.
Mohan, B.R., et al., "Genes and cis-Acting Sequences Involved in Replication of Barley Yellow Dwarf Virus—PAV RNA," Virology, vol. 212, (1995), pp. 186-195.
Park, J-W., et al., "Tomato Bushy Stunt Virus Genomic RNA Accumulation is Regulated by Interdependent cis-Acting Elements within the Movement Protein Open Reading Frames," Journal of Virology, (Dec. 2002), vol. 76, No. 24, pp. 12747-12757.
Samac, D.A., et al., "A comparison of constitutive promoters for expression of transgenes in alfalfa (*Medicago sativa*)," Transgenic Research, (2004), vol. 13, pp. 349-361.
Schenk, P.M., et al., "A promoter from sugarcane *Bacilliform badnavirus* drives transgene expression in banana and other monocot and dicot plants," Plant Molecular Biology, (1999), vol. 39, pp. 1221-1230.
Geijskes, R.J., et al., "Sequence analysis of an Australian isolate of sugarcane *Bacilliform badnavirus,*" Archives of Virology, (2002), vol. 147, pp. 2393-2404.
Chinese Office Action, Application No. 201180034249.9, dated Feb. 14, 2014, listing of documents of interest on pp. 1, 7 and 8.
Benfey, P.N., et al., "The CaMV 35S enhancer contains at least two domains which can confer different developmental and tissue-specific expression patterns," The EMBO Journal, (1989), vol. 8, No. 8, pp. 2195-2202.
Collins English Dictionary, Transgene, (2009), Unabridged 10th Edition.
Braithwaite, K.S., et al., "A variable region of the Sugarcane *Bacilliform* Virus (SCBV) genome can be used to generate promoters for transgene expression in sugarcane," Plant Cell Rep, (2004), vol. 23, pp. 319-326.
Australian Examination Report, dated Dec. 30, 2014, AU Application No. 2011252008, 3 pages.
Hyvönen, M., "Guide to Expression Construct Cloning" (2004), 16 pages, http://camelot.bioc.cam.ac.uk/~-marko/methods/cloning.pdf.
Stanke, M. and Morgenstern, B., "Augustus: a web server for gene prediction in eukaryotes that allows user-defined constraints", Nucleic Acids Research 2005, vol. 33, Web Server issue, W464-467.
Solovyev, V., et al., "Automatic annotation of eukaryotic genes, pseudogenes and promoters", Genome Biology 2006, 7(Suppl 1):S10, 12 pages.
Hyatt, D., et al., "Prodigal: prokaryotic gene recognition and translation initiation site identification", BMC Bioinformatics 2010, 11:119, http:www.biomedcentral.com/1471-2105/11/119, 11 pages.
Korf, I., "Gene finding in novel genomes", BMC Bioinformatics 2004, 5:59, http://www.biomedcentral.com/1471-2105/5/59, 9 pages.
Rushton, P.J., et al., "Synthetic Plant Promoters Containing Defined Regulatory Elements Provide Novel Insights into Pathogen-and Wound-Induced Signaling", The Plant Cell, vol. 14, 749-762, Apr. 2002, www.plantcell.org © 2002 American Society of Plant Biologists.
Shahmuradov, I., et al., PlantProm: a database of plant promoter sequences, Nucleic Acids Research, 2003, vol. 31, No. 1, pp. 114-117, © 2003 Oxford University Press, http://nar.oxfordjournals.org/.
Rombauts, S., et al., "Computational Approaches to Identify Promoters and cis-Regulatory Elements in Plant Genomes", Plant Physiol, 2003, vol. 132, pp. 1162-1176, Copyright © 2003 American Society of Plant Biologists.
Molina, C., et al., "Genome wide analysis of Arabidopsis core promoters", BMC Genomics 2005, 6:25, http://www.biomedcentral.com/1471-2164/6/25, 12 pages.
Dieterich, C., et al., "Comparative promoter region analysis powered by CORG", BMC Genomics 2005, 6:24, http://www.biomedcentral.com/1471-2164/6/24, 10 pages.
Komarnytsky, S., et al., "Functional Analysis of Promoter Elements in Plants", Genetic Engineering, vol. 25, Kluwer Academic/Plenum Publishers, 2003, pp. 113-141.
Examination Report dated Nov. 21, 2017 in connection with Australian Application No. 2016203951, 3 pages.

* cited by examiner (A) (B) (C) (D) (E) (F)

Mutant D. SCBV21Δnt1-nt1105-EYFP-Nos

Mutant E. SCBV21Δnt1-nt1010_Δnt1732-nt1837-EYFP-Nos

Mutant F. SCBV21Δnt1-nt1105_Δnt1732-nt1837-EYFP-Nos

SCBV21-EYFP-Nos

SCBV21 Δnt1014-nt1837-EYFP-Nos

SCBV21 Δnt1-nt1010-EYFP-Nos

SCBV21 Δnt1-nt1104-EYFP-Nos

SCBV21 Δnt1-nt1010_Δnt1732-nt1837-EYFP-Nos

SCBV21 Δnt1-nt1104_Δnt1732-nt1837-EYFP-Nos

SEQUENCE LISTING

<160> NUMBER OF SEQ ID NOS: 50

<210> SEQ ID NO 1
<211> LENGTH: 1816
<212> TYPE: DNA
<213> ORGANISM: Sugarcane bacilliform virus
<220> FEATURE:
<221> NAME/KEY: promoter
<222> LOCATION: (1)..(1786)
<223> OTHER INFORMATION: SCBV21 Promoter
<220> FEATURE:
<221> NAME/KEY: misc_signal
<222> LOCATION: (520)..(524)
<223> OTHER INFORMATION: Possible W-box WBOXATNPR1
<220> FEATURE:
<221> NAME/KEY: misc_signal
<222> LOCATION: (1055)..(1104)
<223> OTHER INFORMATION: Transcription start site TSSI
<220> FEATURE:
<221> NAME/KEY: misc_signal
<222> LOCATION: (1162)..(1166)
<223> OTHER INFORMATION: Possible W-box WBOXATNPR1
<220> FEATURE:
<221> NAME/KEY: misc_signal
<222> LOCATION: (1309)..(1313)
<223> OTHER INFORMATION: Possible W-box WBOXATNPR1
<220> FEATURE:
<221> NAME/KEY: CAAT_signal
<222> LOCATION: (1475)..(1478)
<223> OTHER INFORMATION: Possible CAAT signal
<220> FEATURE:
<221> NAME/KEY: misc_signal
<222> LOCATION: (1502)..(1509)
<223> OTHER INFORMATION: Possible auxin responsive element
AUXRETGA1GMGH3
<220> FEATURE:
<221> NAME/KEY: CAAT_signal
<222> LOCATION: (1511)..(1514)
<223> OTHER INFORMATION: Possible CAAT signal
<220> FEATURE:
<221> NAME/KEY: CAAT_signal
<222> LOCATION: (1540)..(1543)
<223> OTHER INFORMATION: Possible CAAT signal
<220> FEATURE:
<221> NAME/KEY: CAAT_signal
<222> LOCATION: (1558)..(1561)
<223> OTHER INFORMATION: Possible CAAT signal
<220> FEATURE:
<221> NAME/KEY: misc_signal
<222> LOCATION: (1737)..(1786)
<223> OTHER INFORMATION: Transcription start site TSS2
<220> FEATURE:
<221> NAME/KEY: TATA_signal
<222> LOCATION: (1747)..(1753)
<223> OTHER INFORMATION: Possible TATA signal
<220> FEATURE:
<221> NAME/KEY: misc_signal
<222> LOCATION: (1787)..(1787)
<223> OTHER INFORMATION: Transcription start site

<400> SEQUENCE: 1
gaagaacagc atgctgaaca tctgtggaag atgctacaga tatgcaagaa gaatgggtta 60
atcttaagcc cttccaagta taaattggag taaaaagagt tgactttctt ggttcaacaa 120
ttggagataa tcagttagct gttcaagaac atatagtctc caagatagct gattttgatg 180
aagaacgtct caagaccaag gaaggactga aaagctggct ggcaacactc aattatgcca 240
gaaatcacat caaggatatg ggaaaactcc ttggaccctt atatcctaaa acttcagaaa 300
agggagcaaa aggattaaat tctgaagatt ggaaattaat cagcagaatc aagacaatgg 360
tcagaaatct gccaaatctg actattccac cagaggatgc atatattatc attgaaacag 420
atgcttgtgc aactggttgg ggtgcagttt gcaaatggaa gaaatccaag gcagacccaa 480
gaagctccga gctcatatgt cgatatgcaa gtgggaaatt tgacaaacca aaagggacat 540
gtgatgcaga aatctatgga gtaatgaatg ggctggagaa aatgagactc ttttatcttg 600
ataaaaggga aatcactgtg aggacagata gtgccgcaat agagaggttc tacaacaaga 660
gtgttgaaca taaaccctca gaaatccgtt ggataaggtt tatggactat atcactggag 720
caggaccaaa gattgtgatt gagcatatca aaggaaaaca caatggtctg gcagatatcc 780
tctcaagatt gaaagcaaaa ctggcagaat caccttcaga agaagtggtt ttacttgcga 840
aagctttaaa ggaagttgca tactatcctg aacacccgca agtgccaaaa ctaattgaat 900
ggggaaagca aattcttgat ccatttccca agttcaagaa ggacatgttt gaaaaaactg 960
aacacatcat gatggctagt caagagccta cactgctttg tggatgtaga aggcctgcat 1020
atcagttcac atctggcaca aaactcaacc caagcaggaa gttctataaa tgtgcaatga 1080
acatgtgcca ctgctggtat tgggcagatc ttttagaaga atatgtccaa gaacgaattg 1140
aagtgttcat gattgagaac tttgacaaga aaatgggaat tcaagatgta ccaagtacat 1200
caaatgctaa cattccagga aattttaaat ctcttgcaga tttgaagaag gataaagaag 1260
ctaaagctga atatcaagac atgcttgata atcatcgttc aagcattatt gacagaccaa 1320
ggccaacaga tgaacacttc aagcctggat acatgtacac cgattccctg cagaagatca 1380
aggaggacta cgcaagccca agacaggagg aaccaccatg agaagacatt gagttctggt 1440
tatgcaagga agaagactac cacacagaag acctcaatac agaagatgca gttgatctta 1500
ctgacgtaag caatgacgat cagtggaggc gatcgtaagc aatgatgcac ggaaggacaa 1560
ttatggagcg tggaggaccc atcaagcact cagaacgcga acctcaactt tcggcgccag 1620
caccttgtat ctttagttgg tgtgtgtctt tttcggcatc tgtgccacct tacctttgtc 1680
ggccacgttg cctatgctta gcacctacgc aagcatagcg ctcggctggt gtgtgttccc 1740
tctgcctata taaggcatgg ttgtaagact cttacactca tcggtagttc accacatgat 1800
catttgagca agtttg 1816

<210> SEQ ID NO 2
<211> LENGTH: 4035
<212> TYPE: DNA
<213> ORGANISM: Artificial Sequence
<220> FEATURE:
<223> OTHER INFORMATION: Expression cassette SCBV21-GUS-NOS
<220> FEATURE:
<221> NAME/KEY: promoter
<222> LOCATION: (30)..(1845)
<223> OTHER INFORMATION: SCBV21 Promoter
<220> FEATURE:
<221> NAME/KEY: misc_feature
<222> LOCATION: (1893)..(3704)
<223> OTHER INFORMATION: GUS coding sequence
<220> FEATURE:
<221> NAME/KEY: terminator
<222> LOCATION: (3777)..(4030)
<223> OTHER INFORMATION: NOS

<400> SEQUENCE: 2
aagcttgggc cgcgaattca ctagtgattg aagaacagca tgctgaacat ctgtggaaga 60
tgctacagat atgcaagaag aatgggttaa tcttaagccc ttccaagtat aaattggagt 120
aaaaagagtt gactttcttg gttcaacaat tggagataat cagttagctg ttcaagaaca 180
tatagtctcc aagatagctg attttgatga agaacgtctc aagaccaagg aaggactgaa 240
aagctggctg gcaacactca attatgccag aaatcacatc aaggatatgg gaaaactcct 300
tggaccctta tatcctaaaa cttcagaaaa gggagcaaaa ggattaaatt ctgaagattg 360
gaaattaatc agcagaatca agacaatggt cagaaatctg ccaaatctga ctattccacc 420
agaggatgca tatattatca ttgaaacaga tgcttgtgca actggttggg gtgcagtttg 480
caaatggaag aaatccaagg cagacccaag aagctccgag ctcatatgtc gatatgcaag 540
tgggaaattt gacaaaccaa aagggacatg tgatgcagaa atctatggag taatgaatgg 600
gctggagaaa atgagactct tttatcttga taaaagggaa atcactgtga ggacagatag 660
tgccgcaata gagaggttct acaacaagag tgttgaacat aaaccctcag aaatccgttg 720
gataaggttt atggactata tcactggagc aggaccaaag attgtgattg agcatatcaa 780
aggaaaacac aatggtctgg cagatatcct ctcaagattg aaagcaaaac tggcagaatc 840
accttcagaa gaagtggttt tacttgcgaa agctttaaag gaagttgcat actatcctga 900
acacccgcaa gtgccaaaac taattgaatg gggaaagcaa attcttgatc catttcccaa 960
gttcaagaag gacatgtttg aaaaaactga acacatcatg atggctagtc aagagcctac 1020
actgctttgt ggatgtagaa ggcctgcata tcagttcaca tctggcacaa aactcaaccc 1080
aagcaggaag ttctataaat gtgcaatgaa catgtgccac tgctggtatt gggcagatct 1140
tttagaagaa tatgtccaag aacgaattga agtgttcatg attgagaact ttgacaagaa 1200

-continued

```
aatgggaatt caagatgtac caagtacatc aaatgctaac attccaggaa attttaaatc   1260
tcttgcagat ttgaagaagg ataaagaagc taaagctgaa tatcaagaca tgcttgataa   1320
tcatcgttca agcattattg acagaccaag gccaacagat gaacacttca agcctggata   1380
catgtacacc gattccctgc agaagatcaa ggaggactac gcaagcccaa gacaggagga   1440
accaccatga gaagacattg agttctggtt atgcaaggaa gaagactacc acacagaaga   1500
cctcaataca gaagatgcag ttgatcttac tgacgtaagc aatgacgatc agtggaggcg   1560
atcgtaagca atgatgcacg gaaggacaat tatggagcgt ggaggaccca tcaagcactc   1620
agaacgcgaa cctcaacttt cggcgccagc accttgtatc tttagttggt gtgtgtcttt   1680
ttcggcatct gtgccacctt acctttgtcg gccacgttgc ctatgcttag cacctacgca   1740
agcatagcgc tcggctggtg tgtgttccct ctgcctatat aaggcatggt tgtaagactc   1800
ttacactcat cggtagttca ccacatgatc atttgagcaa gtttgaatcg aattcccgcg   1860
gccctagagg atccccgggt ggtcagtccc ttatgttacg tcctgtagaa accccaaccc   1920
gtgaaatcaa aaaactcgac ggcctgtggg cattcagtct ggatcgcgaa aactgtggaa   1980
ttgatcagcg ttggtgggaa agcgcgttac aagaaagccg ggcaattgct gtgccaggca   2040
gttttaacga tcagttcgcc gatgcagata ttcgtaatta tgcgggcaac gtctggtatc   2100
agcgcgaagt ctttataccg aaaggttggg caggccagcg tatcgtgctg cgtttcgatg   2160
cggtcactca ttacggcaaa gtgtgggtca ataatcagga agtgatggag catcagggcg   2220
gctatacgcc atttgaagcc gatgtcacgc cgtatgttat tgccgggaaa agtgtacgta   2280
tcaccgtttg tgtgaacaac gaactgaact ggcagactat cccgccggga atggtgatta   2340
ccgacgaaaa cggcaagaaa aagcagtctt acttccatga tttctttaac tatgccggaa   2400
tccatcgcag cgtaatgctc tacaccacgc cgaacacctg ggtggacgat atcaccgtgg   2460
tgacgcatgt cgcgcaagac tgtaaccacg cgtctgttga ctggcaggtg gtggccaatg   2520
gtgatgtcag cgttgaactg cgtgatgcgg atcaacaggt ggttgcaact ggacaaggca   2580
ctagcgggac tttgcaagtg gtgaatccgc acctctggca accgggtgaa ggttatctct   2640
atgaactgtg cgtcacagcc aaaagccaga cagagtgtga tatctacccg cttcgcgtcg   2700
gcatccggtc agtggcagtg aagggcgaac agttcctgat taaccacaaa ccgttctact   2760
ttactggctt tggtcgtcat gaagatgcgg acttgcgtgg caaaggattc gataacgtgc   2820
tgatggtgca cgaccacgca ttaatggact ggattggggc caactcctac cgtacctcgc   2880
attaccctta cgctgaagag atgctcgact gggcagatga acatggcatc gtggtgattg   2940
atgaaactgc tgctgtcggc tttaacctct ctttaggcat tggtttcgaa gcgggcaaca   3000
agccgaaaga actgtacagc gaagaggcag tcaacgggga aactcagcaa gcgcacttac   3060
aggcgattaa agagctgata gcgcgtgaca aaaaccaccc aagcgtggtg atgtggagta   3120
ttgccaacga accggatacc cgtccgcaag gtgcacggga atatttcgcg ccactggcgg   3180
aagcaacgcg taaactcgac ccgacgcgtc cgatcacctg cgtcaatgta atgttctgcg   3240
acgctcacac cgataccatc agcgatctct ttgatgtgct gtgcctgaac cgttattacg   3300
gatggtatgt ccaaagcggc gatttggaaa cggcagagaa ggtactggaa aaagaacttc   3360
tggcctggca ggagaaactg catcagccga ttatcatcac cgaatacggc gtggatacgt   3420
tagccgggct gcactcaatg tacaccgaca tgtggagtga agagtatcag tgtgcatggc   3480
tggatatgta tcaccgcgtc tttgatcgcg tcagcgccgt cgtcggtgaa caggtatgga   3540
atttcgccga ttttgcgacc tcgcaaggca tattgcgcgt tggcggtaac aagaaaggga   3600
```

```
tcttcactcg cgaccgcaaa ccgaagtcgg cggcttttct gctgcaaaaa cgctggactg   3660

gcatgaactt cggtgaaaaa ccgcagcagg gaggcaaaca atgaatcaac aactctcctg   3720

gcgcaccatc gtcggctaca gcctcgggaa ttgctaccga gctcgaattt ccccgatcgt   3780

tcaaacattt ggcaataaag tttcttaaga ttgaatcctg ttgccggtct tgcgatgatt   3840

atcatataat ttctgttgaa ttacgttaag catgtaataa ttaacatgta atgcatgacg   3900

ttatttatga gatgggtttt tatgattaga gtcccgcaat tatacattta atacgcgata   3960

gaaaacaaaa tatagcgcgc aaactaggat aaattatcgc gcgcggtgtc atctatgtta   4020

ctagatcggg aattc                                                    4035


<210> SEQ ID NO 3
<211> LENGTH: 2877
<212> TYPE: DNA
<213> ORGANISM: Artificial Sequence
<220> FEATURE:
<223> OTHER INFORMATION: Expression cassette SCBV21-EYFP-NOS
<220> FEATURE:
<221> NAME/KEY: promoter
<222> LOCATION: (37)..(1852)
<223> OTHER INFORMATION: SCBV21 Promoter
<220> FEATURE:
<221> NAME/KEY: misc_feature
<222> LOCATION: (1874)..(2602)
<223> OTHER INFORMATION: EYFP coding sequence
<220> FEATURE:
<221> NAME/KEY: terminator
<222> LOCATION: (2612)..(2865)
<223> OTHER INFORMATION: NOS

<400> SEQUENCE: 3

gtcgacctgc aggcggccgc gaattcacta gtgattgaag aacagcatgc tgaacatctg     60

tggaagatgc tacagatatg caagaagaat gggttaatct taagcccttc caagtataaa    120

ttggagtaaa aagagttgac tttcttggtt caacaattgg agataatcag ttagctgttc    180

aagaacatat agtctccaag atagctgatt ttgatgaaga acgtctcaag accaaggaag    240

gactgaaaag ctggctggca acactcaatt atgccagaaa tcacatcaag gatatgggaa    300

aactccttgg acccttatat cctaaaactt cagaaaaggg agcaaaagga ttaaattctg    360

aagattggaa attaatcagc agaatcaaga caatggtcag aaatctgcca aatctgacta    420

ttccaccaga ggatgcatat attatcattg aaacagatgc ttgtgcaact ggttggggtg    480

cagtttgcaa atggaagaaa tccaaggcag acccaagaag ctccgagctc atatgtcgat    540

atgcaagtgg gaaatttgac aaaccaaaag ggacatgtga tgcagaaatc tatggagtaa    600

tgaatgggct ggagaaaatg agactctttt atcttgataa aagggaaatc actgtgagga    660

cagatagtgc cgcaatagag aggttctaca acaagagtgt tgaacataaa ccctcagaaa    720

tccgttggat aaggtttatg gactatatca ctggagcagg accaaagatt gtgattgagc    780

atatcaaagg aaaacacaat ggtctggcag atatcctctc aagattgaaa gcaaaactgg    840

cagaatcacc ttcagaagaa gtggttttac ttgcgaaagc tttaaaggaa gttgcatact    900

atcctgaaca cccgcaagtg ccaaaactaa ttgaatgggg aaagcaaatt cttgatccat    960

ttcccaagtt caagaaggac atgtttgaaa aaactgaaca catcatgatg gctagtcaag   1020

agcctacact gctttgtgga tgtagaaggc ctgcatatca gttcacatct ggcacaaaac   1080

tcaacccaag caggaagttc tataaatgtg caatgaacat gtgccactgc tggtattggg   1140

cagatctttt agaagaatat gtccaagaac gaattgaagt gttcatgatt gagaactttg   1200
```

-continued

```
acaagaaaat gggaattcaa gatgtaccaa gtacatcaaa tgctaacatt ccaggaaatt   1260

ttaaatctct tgcagatttg aagaaggata aagaagctaa agctgaatat caagacatgc   1320

ttgataatca tcgttcaagc attattgaca gaccaaggcc aacagatgaa cacttcaagc   1380

ctggatacat gtacaccgat tccctgcaga agatcaagga ggactacgca agcccaagac   1440

aggaggaacc accatgagaa gacattgagt tctggttatg caaggaagaa gactaccaca   1500

cagaagacct caatacagaa gatgcagttg atcttactga cgtaagcaat gacgatcagt   1560

ggaggcgatc gtaagcaatg atgcacggaa ggacaattat ggagcgtgga ggacccatca   1620

agcactcaga acgcgaacct caactttcgg cgccagcacc ttgtatcttt agttggtgtg   1680

tgtctttttc ggcatctgtg ccaccttacc tttgtcggcc acgttgccta tgcttagcac   1740

ctacgcaagc atagcgctcg gctggtgtgt gttccctctg cctatataag gcatggttgt   1800

aagactctta cactcatcgg tagttcacca catgatcatt tgagcaagtt tgaatcgaat   1860

tcccgcggcc gccatggtga gcaagggcga ggagctgttc accggggtgg tgcccatcct   1920

ggtcgagctg gacggcgacg taaacggcca caagttcagc gtgtccggcg agggcgaggg   1980

cgatgccacc tacggcaagc tgaccctgaa gttcatctgc accaccggca agctgcccgt   2040

gccctggccc accctcgtga ccaccttcgg ctacggcctg cagtgcttcg cccgctaccc   2100

cgaccacatg aagcagcacg acttcttcaa gtccgccatg cccgaaggct acgtccagga   2160

gcgcaccatc ttcttcaagg acgacggcaa ctacaagacc cgcgccgagg tgaagttcga   2220

gggcgacacc ctggtgaacc gcatcgagct gaagggcatc gacttcaagg aggacggcaa   2280

catcctgggg cacaagctgg agtacaacta caacagccac aacgtctata tcatggccga   2340

caagcagaag aacggcatca aggtgaactt caagatccgc cacaacatcg aggacggcag   2400

cgtgcagctc gccgaccact accagcagaa cacccccatc ggcgacggcc ccgtgctgct   2460

gcccgacaac cactacctga gctaccagtc cgccctgagc aaagacccca acgagaagcg   2520

cgatcacatg gtcctgctgg agttcgtgac cgccgccggg atcactctcg gcatggacga   2580

gctgtacaag agatctatct agcgagctcg atcgttcaaa catttggcaa taaagtttct   2640

taagattgaa tcctgttgcc ggtcttgcga tgattatcat ataatttctg ttgaattacg   2700

ttaagcatgt aataattaac atgtaatgca tgacgttatt tatgagatgg gtttttatga   2760

ttagagtccc gcaattatac atttaatacg cgatagaaaa caaaatatag cgcgcaaact   2820

aggataaatt atcgcgcgcg gtgtcatcta tgttactaga tcggggatgg gggatcc      2877
```

```
<210> SEQ ID NO 4
<211> LENGTH: 3038
<212> TYPE: DNA
<213> ORGANISM: Artificial Sequence
<220> FEATURE:
<223> OTHER INFORMATION: Expression cassette 35S-GUS-NOS
<220> FEATURE:
<221> NAME/KEY: promoter
<222> LOCATION: (25)..(859)
<223> OTHER INFORMATION: 35S Promoter
<220> FEATURE:
<221> NAME/KEY: misc_feature
<222> LOCATION: (896)..(2707)
<223> OTHER INFORMATION: GUS coding sequence
<220> FEATURE:
<221> NAME/KEY: terminator
<222> LOCATION: (2780)..(3033)
<223> OTHER INFORMATION: NOS
<300> PUBLICATION INFORMATION:
<308> DATABASE ACCESSION NUMBER: AF502128
<309> DATABASE ENTRY DATE: 2002-06-05
<313> RELEVANT RESIDUES IN SEQ ID NO: (1)..(3038)
```

-continued

<400> SEQUENCE: 4

```
aagcttgcat gcctgcaggt ccccagatta gccttttcaa tttcagaaag aatgctaacc     60
cacagatggt tagagaggct tacgcagcag gtctcatcaa gacgatctac ccgagcaata    120
atctccagga aatcaaatac cttcccaaga aggttaaaga tgcagtcaaa agattcagga    180
ctaactgcat caagaacaca gagaaagata tatttctcaa gatcagaagt actattccag    240
tatggacgat tcaaggcttg cttcacaaac caaggcaagt aatagagatt ggagtctcta    300
aaaaggtagt tcccactgaa tcaaaggcca tggagtcaaa gattcaaata gaggacctaa    360
cagaactcgc cgtaaagact ggcgaacagt tcatacagag tctcttacga ctcaatgaca    420
agaagaaaat cttcgtcaac atggtggagc acgacacact tgtctactcc aaaaatatca    480
aagatacagt ctcagaagac caaagggcaa ttgagacttt tcaacaaagg gtaatatccg    540
gaaacctcct cggattccat tgcccagcta tctgtcactt tattgtgaag atagtggaaa    600
aggaaggtgg ctcctacaaa tgccatcatt gcgataaagg aaaggccatc gttgaagatg    660
cctctgccga cagtggtccc aaagatggac ccccacccac gaggagcatc gtggaaaaag    720
aagacgttcc aaccacgtct tcaaagcaag tggattgatg tgatatctcc actgacgtaa    780
gggatgacgc acaatcccac tatccttcgc aagacccttc ctctatataa ggaagttcat    840
ttcatttgga gagaacacgg gggactctag aggatccccg ggtggtcagt cccttatgtt    900
acgtcctgta gaaaccccaa cccgtgaaat caaaaaactc gacggcctgt gggcattcag    960
tctggatcgc gaaaactgtg gaattgatca gcgttggtgg gaaagcgcgt tacaagaaag   1020
ccgggcaatt gctgtgccag gcagttttaa cgatcagttc gccgatgcag atattcgtaa   1080
ttatgcgggc aacgtctggt atcagcgcga agtctttata ccgaaaggtt gggcaggcca   1140
gcgtatcgtg ctgcgtttcg atgcggtcac tcattacggc aaagtgtggg tcaataatca   1200
ggaagtgatg gagcatcagg gcggctatac gccatttgaa gccgatgtca cgccgtatgt   1260
tattgccggg aaaagtgtac gtatcaccgt ttgtgtgaac aacgaactga actggcagac   1320
tatcccgccg ggaatggtga ttaccgacga aaacggcaag aaaaagcagt cttacttcca   1380
tgatttcttt aactatgccg gaatccatcg cagcgtaatg ctctacacca cgccgaacac   1440
ctgggtggac gatatcaccg tggtgacgca tgtcgcgcaa gactgtaacc acgcgtctgt   1500
tgactggcag gtggtggcca atggtgatgt cagcgttgaa ctgcgtgatg cggatcaaca   1560
ggtggttgca actggacaag gcactagcgg gactttgcaa gtggtgaatc cgcacctctg   1620
gcaaccgggt gaaggttatc tctatgaact gtgcgtcaca gccaaaagcc agacagagtg   1680
tgatatctac ccgcttcgcg tcggcatccg gtcagtggca gtgaagggcg aacagttcct   1740
gattaaccac aaaccgttct actttactgg ctttggtcgt catgaagatg cggacttgcg   1800
tggcaaagga ttcgataacg tgctgatggt gcacgaccac gcattaatgg actggattgg   1860
ggccaactcc taccgtacct cgcattaccc ttacgctgaa gagatgctcg actgggcaga   1920
tgaacatggc atcgtggtga ttgatgaaac tgctgctgtc ggctttaacc tctctttagg   1980
cattggtttc gaagcgggca acaagccgaa agaactgtac agcgaagagg cagtcaacgg   2040
ggaaactcag caagcgcact tacaggcgat taaagagctg atagcgcgtg acaaaaacca   2100
cccaagcgtg gtgatgtgga gtattgccaa cgaaccggat acccgtccgc aaggtgcacg   2160
ggaatatttc gcgccactgg cggaagcaac gcgtaaactc gacccgacgc gtccgatcac   2220
ctgcgtcaat gtaatgttct gcgacgctca caccgatacc atcagcgatc tctttgatgt   2280
```

-continued

```
gctgtgcctg aaccgttatt acggatggta tgtccaaagc ggcgatttgg aaacggcaga   2340

gaaggtactg gaaaaagaac ttctggcctg gcaggagaaa ctgcatcagc cgattatcat   2400

caccgaatac ggcgtggata cgttagccgg gctgcactca atgtacaccg acatgtggag   2460

tgaagagtat cagtgtgcat ggctggatat gtatcaccgc gtctttgatc gcgtcagcgc   2520

cgtcgtcggt gaacaggtat ggaatttcgc cgattttgcg acctcgcaag gcatattgcg   2580

cgttggcggt aacaagaaag ggatcttcac tcgcgaccgc aaaccgaagt cggcggcttt   2640

tctgctgcaa aaacgctgga ctggcatgaa cttcggtgaa aaaccgcagc agggaggcaa   2700

acaatgaatc aacaactctc ctggcgcacc atcgtcggct acagcctcgg gaattgctac   2760

cgagctcgaa tttccccgat cgttcaaaca tttggcaata aagtttctta agattgaatc   2820

ctgttgccgg tcttgcgatg attatcatat aatttctgtt gaattacgtt aagcatgtaa   2880

taattaacat gtaatgcatg acgttattta tgagatgggt ttttatgatt agagtcccgc   2940

aattatacat ttaatacgcg atagaaaaca aaatatagcg cgcaaactag gataaattat   3000

cgcgcgcggt gtcatctatg ttactagatc gggaattc                           3038
```

<210> SEQ ID NO 5
<211> LENGTH: 1893
<212> TYPE: DNA
<213> ORGANISM: Artificial Sequence
<220> FEATURE:
<223> OTHER INFORMATION: Expression cassette 35S-EYFP-NOS
<220> FEATURE:
<221> NAME/KEY: promoter
<222> LOCATION: (25)..(859)
<223> OTHER INFORMATION: 35S Promoter
<220> FEATURE:
<221> NAME/KEY: misc_feature
<222> LOCATION: (879)..(1607)
<223> OTHER INFORMATION: EYFP coding sequence
<220> FEATURE:
<221> NAME/KEY: terminator
<222> LOCATION: (1617)..(1870)
<223> OTHER INFORMATION: NOS

<400> SEQUENCE: 5

```
aagcttgcat gcctgcaggt ccccagatta gccttttcaa tttcagaaag aatgctaacc     60

cacagatggt tagagaggct tacgcagcag gtctcatcaa gacgatctac ccgagcaata    120

atctccagga aatcaaatac cttcccaaga aggttaaaga tgcagtcaaa agattcagga    180

ctaactgcat caagaacaca gagaaagata tatttctcaa gatcagaagt actattccag    240

tatggacgat tcaaggcttg cttcacaaac caaggcaagt aatagagatt ggagtctcta    300

aaaaggtagt tcccactgaa tcaaaggcca tggagtcaaa gattcaaata gaggacctaa    360

cagaactcgc cgtaaagact ggcgaacagt tcatacagag tctcttacga ctcaatgaca    420

agaagaaaat cttcgtcaac atggtggagc acgacacact tgtctactcc aaaaatatca    480

aagatacagt ctcagaagac caaagggcaa ttgagacttt tcaacaaagg gtaatatccg    540

gaaacctcct cggattccat tgcccagcta tctgtcactt tattgtgaag atagtggaaa    600

aggaaggtgg ctcctacaaa tgccatcatt gcgataaagg aaaggccatc gttgaagatg    660

cctctgccga cagtggtccc aaagatggac ccccacccac gaggagcatc gtggaaaaag    720

aagacgttcc aaccacgtct tcaaagcaag tggattgatg tgatatctcc actgacgtaa    780

gggatgacgc acaatcccac tatccttcgc aagacccttc ctctatataa ggaagttcat    840

ttcatttgga gagaacacgg gggactctag aggatcccat ggtgagcaag ggcgaggagc    900

tgttcaccgg ggtggtgccc atcctggtcg agctggacgg cgacgtaaac ggccacaagt    960
```

-continued tcagcgtgtc cggcgagggc gagggcgatg ccacctacgg caagctgacc ctgaagttca 1020
tctgcaccac cggcaagctg cccgtgccct ggcccaccct cgtgaccacc ttcggctacg 1080
gcctgcagtg cttcgcccgc taccccgacc acatgaagca gcacgacttc ttcaagtccg 1140
ccatgcccga aggctacgtc caggagcgca ccatcttctt caaggacgac ggcaactaca 1200
agacccgcgc cgaggtgaag ttcgagggcg acaccctggt gaaccgcatc gagctgaagg 1260
gcatcgactt caaggaggac ggcaacatcc tggggcacaa gctggagtac aactacaaca 1320
gccacaacgt ctatatcatg gccgacaagc agaagaacgg catcaaggtg aacttcaaga 1380
tccgccacaa catcgaggac ggcagcgtgc agctcgccga ccactaccag cagaacaccc 1440
ccatcggcga cggccccgtg ctgctgcccg acaaccacta cctgagctac cagtccgccc 1500
tgagcaaaga ccccaacgag aagcgcgatc acatggtcct gctggagttc gtgaccgccg 1560
ccgggatcac tctcggcatg gacgagctgt acaagagatc tatctagcga gctcgatcgt 1620
tcaaacattt ggcaataaag tttcttaaga ttgaatcctg ttgccggtct tgcgatgatt 1680
atcatataat ttctgttgaa ttacgttaag catgtaataa ttaacatgta atgcatgacg 1740
ttatttatga gatgggtttt tatgattaga gtcccgcaat tatacattta atacgcgata 1800
gaaaacaaaa tatagcgcgc aaactaggat aaattatcgc gcgcggtgtc atctatgtta 1860
ctagatcggg gaattcctgc agcccgggga tcc 1893

<210> SEQ ID NO 6
<211> LENGTH: 1890
<212> TYPE: DNA
<213> ORGANISM: Artificial Sequence
<220> FEATURE:
<223> OTHER INFORMATION: Expression cassette E35S-EYFP-NOS
<220> FEATURE:
<221> NAME/KEY: promoter
<222> LOCATION: (73)..(829)
<223> OTHER INFORMATION: E35S Promoter
<220> FEATURE:
<221> NAME/KEY: misc_feature
<222> LOCATION: (887)..(1615)
<223> OTHER INFORMATION: EYFP coding sequence
<220> FEATURE:
<221> NAME/KEY: terminator
<222> LOCATION: (1625)..(1878)
<223> OTHER INFORMATION: NOS

<400> SEQUENCE: 6
aagcttgatc tgcattaatg aatcggccaa cgcgcgggga gaggcggttt gcgtattggc 60
tagagcagct tgccaacatg gtggagcacg acactctcgt ctactccaag aatatcaaag 120
atacagtctc agaagaccaa agggctattg agacttttca acaaagggta atatcgggaa 180
acctcctcgg attccattgc ccagctatct gtcacttcat caaaaggaca gtagaaaagg 240
aaggtggcac ctacaaatgc catcattgcg ataaaggaaa ggctatcgtt caagatgcct 300
ctgccgacag tggtcccaaa gatggacccc cacccacgag gagcatcgtg gaaaaagaag 360
acgttccaac cacgtcttca aagcaagtgg attgatgtga taacatggtg gagcacgaca 420
ctctcgtcta ctccaagaat atcaaagata cagtctcaga agaccaaagg gctattgaga 480
cttttcaaca aagggtaata tcgggaaacc tcctcggatt ccattgccca gctatctgtc 540
acttcatcaa aaggacagta gaaaaggaag gtggcaccta caaatgccat cattgcgata 600
aaggaaaggc tatcgttcaa gatgcctctg ccgacagtgg tcccaaagat ggacccccac 660
ccacgaggag catcgtggaa aaagaagacg ttccaaccac gtcttcaaag caagtggatt 720
gatgtgatat ctccactgac gtaagggatg acgcacaatc ccactatcct tcgcaagacc 780
cttcctctat ataaggaagt tcatttcatt tggagaggac acgctgaaat caccagtctc 840
tctctacaaa tctatctctc tcgattcgca gatctgtcga tcgaccatgg tgagcaaggg 900
cgaggagctg ttcaccgggg tggtgcccat cctggtcgag ctggacggcg acgtaaacgg 960
ccacaagttc agcgtgtccg gcgagggcga gggcgatgcc acctacggca agctgaccct 1020
gaagttcatc tgcaccaccg gcaagctgcc cgtgccctgg cccaccctcg tgaccacctt 1080
cggctacggc ctgcagtgct tcgcccgcta ccccgaccac atgaagcagc acgacttctt 1140
caagtccgcc atgcccgaag gctacgtcca ggagcgcacc atcttcttca aggacgacgg 1200
caactacaag acccgcgccg aggtgaagtt cgagggcgac accctggtga accgcatcga 1260
gctgaagggc atcgacttca aggaggacgg caacatcctg gggcacaagc tggagtacaa 1320
ctacaacagc cacaacgtct atatcatggc cgacaagcag aagaacggca tcaaggtgaa 1380
cttcaagatc cgccacaaca tcgaggacgg cagcgtgcag ctcgccgacc actaccagca 1440
gaacaccccc atcggcgacg gccccgtgct gctgcccgac aaccactacc tgagctacca 1500
gtccgccctg agcaaagacc ccaacgagaa gcgcgatcac atggtcctgc tggagttcgt 1560
gaccgccgcc gggatcactc tcggcatgga cgagctgtac aagagatcta tctagcgagc 1620
tcgatcgttc aaacatttgg caataaagtt tcttaagatt gaatcctgtt gccggtcttg 1680
cgatgattat catataattt ctgttgaatt acgttaagca tgtaataatt aacatgtaat 1740
gcatgacgtt atttatgaga tgggttttta tgattagagt cccgcaatta tacatttaat 1800
acgcgataga aaacaaaata tagcgcgcaa actaggataa attatcgcgc gcggtgtcat 1860
ctatgttact agatcgggga tgggggatcc 1890

<210> SEQ ID NO 7
<211> LENGTH: 4178
<212> TYPE: DNA
<213> ORGANISM: Artificial Sequence
<220> FEATURE:
<223> OTHER INFORMATION: Expression cassette Pr4-GUS-NOS
<220> FEATURE:
<221> NAME/KEY: promoter
<222> LOCATION: (1)..(966)
<223> OTHER INFORMATION: Pr4 Promoter
<220> FEATURE:
<221> NAME/KEY: misc_feature
<222> LOCATION: (668)..(668)
<223> OTHER INFORMATION: n is a, c, g, or t
<220> FEATURE:
<221> NAME/KEY: misc_feature
<222> LOCATION: (671)..(671)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (967)..(1977)
<223> OTHER INFORMATION: First exon (5'UTR) and first intron
<220> FEATURE:
<221> NAME/KEY: misc_feature
<222> LOCATION: (2036)..(3847)
<223> OTHER INFORMATION: GUS coding sequence
<220> FEATURE:
<221> NAME/KEY: terminator
<222> LOCATION: (3920)..(4173)
<223> OTHER INFORMATION: NOS

<400> SEQUENCE: 7
aagcttgcat gcctgcagtg cagcgtgacc cggtcgtgcc cctctctaga gataatgagc 60

```
attgcatgtc taagttataa aaaattacca catatttttt ttgtcacact tgtttgaagt    120
gcagtttatc tatctttata catatattta aactttactc tacgaataat ataatctata    180
gtactacaat aatatcagtg ttttagagaa tcatataaat gaacagttag acatggtcta    240
aaggacaatt gagtattttg acaacaggac tctacagttt tatcttttta gtgtgcatgt    300
gttctccttt ttttttgcaa atagcttcac ctatataata cttcatccat tttattagta    360
catccattta gggtttaggg ttaatggttt ttatagacta attttttttag tacatctatt    420
ttattctatt ttagcctcta aattaagaaa actaaaactc tattttagtt tttttattta    480
ataatttaga tataaaatag aataaaataa agtgactaaa aattaaacaa ataccccttta    540
agaaattaaa aaaactaagg aaacattttt cttgtttcga gtagataatg ccagcctgtt    600
aaacgccgtc gacgagtcta acggacacca accagcgaac cagcagcgtc gcgtcgggcc    660
aagcgaanca nacggcacgg natctctgtc gctgcctcca ccgttggact tgctccgctg    720
tcggcatcca gaaattgcgt ggcggcaggc agacgtgagc cggcacgagg cggcctcctc    780
ctcctctcac ggcacggcag ctacgggggga ttcctttccc accgctcctt cgctttccct    840
tcctcgcccg ccgtaataaa tagacacccc ctccacaccc tctttcccca acctcgtgtt    900
gttcggagcg cacacacaca caaccagatc tcccccaaat ccacccgtcg gcacctccgc    960
ttcaaggtac gccgctcgtc ctcccccccc cccctctct accttctcta gatcggcgtt   1020
ccggtccatg gttagggccc ggtagttcta cttctgttca tgtttgtgtt agatccgtgt   1080
ttgtgttaga tccgtgctgc tagcgttcgt acacggatgc gacctgtacg tcagacacgt   1140
tctgattgct aacttgccag tgtttctctt tggggaatcc tgggatggct ctagccgttc   1200
cgcagacggg atcgatttca tgattttttt tgtttcgttg catagggntt ggtttgccct   1260
tttcctttat ttcaatatat gccgtgccac ttgtttgtcg ggtcatcttt tcatngcttt   1320
tttttgtctt ggttgtgatg atgtggtctg gttgggcggt cgttctagat cggagtagaa   1380
ttctgtttca aactacctgg tggatttatt aattttggat ctgtatgtgt gtgccataca   1440
tattcatagt tacgaattga agatgatgga tggaaatatc gatctaggat aggtatacat   1500
gttgatgcgg gttttactga tgcatataca gagatgcttt tnttcgcttg gttgtgatga   1560
tgtggtgtgg ttgggcggtc gttcattcgt tctagatcgg agtagaatac tgtttcaaac   1620
tacctggtgt atttattaat tttggaactg tatgtgtgtg tcatacatct tcatagttac   1680
gagtttaaga tggatggaaa tatcgatcta ggataggtat acatgttgat gtgggtttta   1740
ctgatgcata tacatgatgg catatgcagc atctattcat atgctctaac cttgagtacc   1800
tatctattat aataaacaag tatgttttat aattattttg atcttgatat acttggatga   1860
tggcatatgc agcagctata tgtggatttt tttagccctg ccttcatacg ctatttattt   1920
gcttggtact gtttcttttg tcgatgctca ccctgttgtt tggtgttact tctgcaggtc   1980
gactctagag gatctgatat ctgatcagaa gacaccatgg ggtggtcagt cccttatgtt   2040
acgtcctgta gaaaccccaa cccgtgaaat caaaaaactc gacggcctgt gggcattcag   2100
tctggatcgc gaaaactgtg gaattgatca gcgttggtgg gaaagcgcgt tacaagaaag   2160
ccgggcaatt gctgtgccag gcagttttaa cgatcagttc gccgatgcag atattcgtaa   2220
ttatgcgggc aacgtctggt atcagcgcga agtctttata ccgaaaggtt gggcaggcca   2280
gcgtatcgtg ctgcgtttcg atgcggtcac tcattacggc aaagtgtggg tcaataatca   2340
ggaagtgatg gagcatcagg gcggctatac gccatttgaa gccgatgtca cgccgtatgt   2400
```

```
tattgccggg aaaagtgtac gtatcaccgt ttgtgtgaac aacgaactga actggcagac   2460

tatcccgccg ggaatggtga ttaccgacga aaacggcaag aaaaagcagt cttacttcca   2520

tgatttcttt aactatgccg gaatccatcg cagcgtaatg ctctacacca cgccgaacac   2580

ctgggtggac gatatcaccg tggtgacgca tgtcgcgcaa gactgtaacc acgcgtctgt   2640

tgactggcag gtggtggcca atggtgatgt cagcgttgaa ctgcgtgatg cggatcaaca   2700

ggtggttgca actggacaag gcactagcgg gactttgcaa gtggtgaatc cgcacctctg   2760

gcaaccgggt gaaggttatc tctatgaact gtgcgtcaca gccaaaagcc agacagagtg   2820

tgatatctac ccgcttcgcg tcggcatccg gtcagtggca gtgaagggcg aacagttcct   2880

gattaaccac aaaccgttct actttactgg ctttggtcgt catgaagatg cggacttgcg   2940

tggcaaagga ttcgataacg tgctgatggt gcacgaccac gcattaatgg actggattgg   3000

ggccaactcc taccgtacct cgcattaccc ttacgctgaa gagatgctcg actgggcaga   3060

tgaacatggc atcgtggtga ttgatgaaac tgctgctgtc ggctttaacc tctctttagg   3120

cattggtttc gaagcgggca acaagccgaa agaactgtac agcgaagagg cagtcaacgg   3180

ggaaactcag caagcgcact tacaggcgat taaagagctg atagcgcgtg acaaaaacca   3240

cccaagcgtg gtgatgtgga gtattgccaa cgaaccggat acccgtccgc aaggtgcacg   3300

ggaatatttc gcgccactgg cggaagcaac gcgtaaactc gacccgacgc gtccgatcac   3360

ctgcgtcaat gtaatgttct gcgacgctca caccgatacc atcagcgatc tctttgatgt   3420

gctgtgcctg aaccgttatt acggatggta tgtccaaagc ggcgatttgg aaacggcaga   3480

gaaggtactg gaaaaagaac ttctggcctg gcaggagaaa ctgcatcagc cgattatcat   3540

caccgaatac ggcgtggata cgttagccgg gctgcactca atgtacaccg acatgtggag   3600

tgaagagtat cagtgtgcat ggctggatat gtatcaccgc gtctttgatc gcgtcagcgc   3660

cgtcgtcggt gaacaggtat ggaatttcgc cgattttgcg acctcgcaag gcatattgcg   3720

cgttggcggt aacaagaaag ggatcttcac tcgcgaccgc aaaccgaagt cggcggcttt   3780

tctgctgcaa aaacgctgga ctggcatgaa cttcggtgaa aaaccgcagc agggaggcaa   3840

acaatgaatc aacaactctc ctggcgcacc atcgtcggct acagcctcgg gaattgctac   3900

cgagctcgaa tttccccgat cgttcaaaca tttggcaata aagtttctta agattgaatc   3960

ctgttgccgg tcttgcgatg attatcatat aatttctgtt gaattacgtt aagcatgtaa   4020

taattaacat gtaatgcatg acgttattta tgagatgggt ttttatgatt agagtcccgc   4080

aattatacat ttaatacgcg atagaaaaca aaatatagcg cgcaaactag gataaattat   4140

cgcgcgcggt gtcatctatg ttactagatc gggaattc                           4178
```

<210> SEQ ID NO 8
<211> LENGTH: 3020
<212> TYPE: DNA
<213> ORGANISM: Artificial Sequence
<220> FEATURE:
<223> OTHER INFORMATION: Expression cassette Pr4-EYFP-NOS
<220> FEATURE:
<221> NAME/KEY: promoter
<222> LOCATION: (1)..(966)
<223> OTHER INFORMATION: Pr4 Promoter
<220> FEATURE:
<221> NAME/KEY: misc_feature
<222> LOCATION: (668)..(668)
<223> OTHER INFORMATION: n is a, c, g, or t
<220> FEATURE:
<221> NAME/KEY: misc_feature
<222> LOCATION: (671)..(671)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (967)..(1977)
<223> OTHER INFORMATION: First exon (5'UTR) and first intron
<220> FEATURE:
<221> NAME/KEY: misc_feature
<222> LOCATION: (2017)..(2745)
<223> OTHER INFORMATION: EYFP coding sequence
<220> FEATURE:
<221> NAME/KEY: terminator
<222> LOCATION: (2755)..(3008)
<223> OTHER INFORMATION: NOS

<400> SEQUENCE: 8
aagcttgcat gcctgcagtg cagcgtgacc cggtcgtgcc cctctctaga gataatgagc 60
attgcatgtc taagttataa aaaattacca catatttttt ttgtcacact tgtttgaagt 120
gcagtttatc tatctttata catatattta aactttactc tacgaataat ataatctata 180
gtactacaat aatatcagtg ttttagagaa tcatataaat gaacagttag acatggtcta 240
aaggacaatt gagtattttg acaacaggac tctacagttt tatcttttta gtgtgcatgt 300
gttctccttt ttttttgcaa atagcttcac ctatataata cttcatccat tttattagta 360
catccattta gggtttaggg ttaatggttt ttatagacta atttttttag tacatctatt 420
ttattctatt ttagcctcta aattaagaaa actaaaactc tattttagtt tttttattta 480
ataatttaga tataaaatag aataaaataa agtgactaaa aattaaacaa ataccettta 540 agaaattaaa aaaactaagg aaacattttt cttgtttcga gtagataatg ccagcctgtt 600
aaacgccgtc gacgagtcta acggacacca accagcgaac cagcagcgtc gcgtcgggcc 660
aagcgaanca nacggcacgg natctctgtc gctgcctcca ccgttggact tgctccgctg 720
tcggcatcca gaaattgcgt ggcggcaggc agacgtgagc cggcacgagg cggcctcctc 780
ctcctctcac ggcacggcag ctacggggga ttcctttccc accgctcctt cgctttccct 840
tcctcgcccg ccgtaataaa tagacacccc ctccacaccc tctttcccca acctcgtgtt 900
gttcggagcg cacacacaca caaccagatc tcccccaaat ccacccgtcg gcacctccgc 960
ttcaaggtac gccgctcgtc ctcccccccc cccccctctct accttctcta gatcggcgtt 1020
ccggtccatg gttagggccc ggtagttcta cttctgttca tgtttgtgtt agatccgtgt 1080
ttgtgttaga tccgtgctgc tagcgttcgt acacggatgc gacctgtacg tcagacacgt 1140
tctgattgct aacttgccag tgtttctctt tggggaatcc tgggatggct ctagccgttc 1200
cgcagacggg atcgatttca tgattttttt tgtttcgttg catagggntt ggtttgccct 1260
tttcctttat ttcaatatat gccgtgccac ttgtttgtcg ggtcatcttt tcatngcttt 1320
tttttgtctt ggttgtgatg atgtggtctg gttgggcggt cgttctagat cggagtagaa 1380
ttctgtttca aactacctgg tggatttatt aattttggat ctgtatgtgt gtgccataca 1440
tattcatagt tacgaattga agatgatgga tggaaatatc gatctaggat aggtatacat 1500
gttgatgcgg gttttactga tgcatataca gagatgcttt tnttcgcttg gttgtgatga 1560
tgtggtgtgg ttgggcggtc gttcattcgt tctagatcgg agtagaatac tgtttcaaac 1620
tacctggtgt atttattaat tttggaactg tatgtgtgtg tcatacatct tcatagttac 1680
gagtttaaga tggatggaaa tatcgatcta ggataggtat acatgttgat gtgggtttta 1740
ctgatgcata tacatgatgg catatgcagc atctattcat atgctctaac cttgagtacc 1800
tatctattat aataaacaag tatgttttat aattattttg atcttgatat acttggatga 1860
tggcatatgc agcagctata tgtggatttt tttagccctg ccttcatacg ctatttattt 1920
gcttggtact gtttcttttg tcgatgctca ccctgttgtt tggtgttact tctgcaggtc 1980
gactctagag gatctgatat ctgatcagaa gacaccatgg tgagcaaggg cgaggagctg 2040
ttcaccgggg tggtgcccat cctggtcgag ctggacggcg acgtaaacgg ccacaagttc 2100
agcgtgtccg gcgagggcga gggcgatgcc acctacggca agctgaccct gaagttcatc 2160
tgcaccaccg gcaagctgcc cgtgccctgg cccaccctcg tgaccacctt cggctacggc 2220
ctgcagtgct tcgcccgcta ccccgaccac atgaagcagc acgacttctt caagtccgcc 2280
atgcccgaag gctacgtcca ggagcgcacc atcttcttca aggacgacgg caactacaag 2340
acccgcgccg aggtgaagtt cgagggcgac accctggtga accgcatcga gctgaagggc 2400
atcgacttca aggaggacgg caacatcctg gggcacaagc tggagtacaa ctacaacagc 2460
cacaacgtct atatcatggc cgacaagcag aagaacggca tcaaggtgaa cttcaagatc 2520
cgccacaaca tcgaggacgg cagcgtgcag ctcgccgacc actaccagca gaacaccccc 2580
atcggcgacg gccccgtgct gctgcccgac aaccactacc tgagctacca gtccgccctg 2640
agcaaagacc ccaacgagaa gcgcgatcac atggtcctgc tggagttcgt gaccgccgcc 2700
gggatcactc tcggcatgga cgagctgtac aagagatcta tctagcgagc tcgatcgttc 2760
aaacatttgg caataaagtt tcttaagatt gaatcctgtt gccggtcttg cgatgattat 2820
catataattt ctgttgaatt acgttaagca tgtaataatt aacatgtaat gcatgacgtt 2880
atttatgaga tgggttttta tgattagagt cccgcaatta tacatttaat acgcgataga 2940
aaacaaaata tagcgcgcaa actaggataa attatcgcgc gcggtgtcat ctatgttact 3000
agatcgggga tgggggatcc 3020

<210> SEQ ID NO 9
<211> LENGTH: 4102
<212> TYPE: DNA
<213> ORGANISM: Artificial Sequence
<220> FEATURE:
<223> OTHER INFORMATION: Expression cassette Ubi-GUS-NOS
<220> FEATURE:
<221> NAME/KEY: promoter
<222> LOCATION: (1)..(995)
<223> OTHER INFORMATION: Ubi Promoter
<220> FEATURE:
<221> NAME/KEY: misc_feature
<222> LOCATION: (996)..(2005)
<223> OTHER INFORMATION: First exon (5'UTR) and first intron
<220> FEATURE:
<221> NAME/KEY: misc_feature
<222> LOCATION: (2022)..(3833)
<223> OTHER INFORMATION: GUS coding sequence
<220> FEATURE:
<221> NAME/KEY: terminator
<222> LOCATION: (3843)..(4096)
<223> OTHER INFORMATION: NOS

<400> SEQUENCE: 9
aagcttgcat gccctgcagt gcagcgtgac ccggtcgtgc ccctctctag agataatgag 60
cattgcatgt ctaagttata aaaaattacc acatattttt tttgtcacac ttgtttgaag 120
tgcagtttat ctatctttat acatatattt aaactttact ctacgaataa tataatctat 180
agtactacaa taatatcagt gttttagaga atcatataaa tgaacagtta gacatggtct 240
aaaggacaat tgagtatttt gacaacagga ctctacagtt ttatcttttt agtgtgcatg 300
tgttctcctt ttttttgca aatagcttca cctatataat acttcatcca ttttattagt 360

-continued

```
acatccattt agggtttagg gttaatggtt tttatagact aatttttttta gtacatctat    420
tttattctat tttagcctct aaattaagaa aactaaaact ctattttagt tttttttattt    480
aataatttag atataaaata gaataaaata aagtgactaa aaattaaaca aatacccttt    540
aagaaattaa aaaaactaag gaaacatttt tcttgtttcg agtagataat gccagcctgt    600
taaacgccgt cgacgagtct aacggacacc aaccagcgaa ccagcagcgt cgcgtcgggc    660
caagcgaagc agacggcacg gcatctctgt cgctgcctct ggacccctct cgagagttcc    720
gctccaccgt tggacttgct ccgctgtcgg catccagaaa ttgcgtggcg gagcggcaga    780
cgtgagccgg cacggcaggc ggcctcctcc tcctctcacg gcacggcagc tacgggggat    840
tcctttccca ccgctccttc gctttccctt cctcgcccgc cgtaataaat agacaccccc    900
tccacaccct ctttccccaa cctcgtgttg ttcggagcgc acacacacac aaccagatct    960
cccccaaatc cacccgtcgg cacctccgct tcaaggtacg ccgctcgtcc tccccccccc   1020
cccctctcta ccttctctag atcggcgttc cggtccatgg ttagggcccg gtagttctac   1080
ttctgttcat gtttgtgtta gatccgtgtt tgtgttagat ccgtgctgct agcgttcgta   1140
cacggatgcg acctgtacgt cagacacgtt ctgattgcta acttgccagt gtttctcttt   1200
ggggaatcct gggatggctc tagccgttcc gcagacggga tcgatttcat gatttttttt   1260
gtttcgttgc atagggtttg gtttgccctt ttcctttatt tcaatatatg ccgtgcactt   1320
gtttgtcggg tcatcttttc atgctttttt ttgtcttggt tgtgatgatg tggtctggtt   1380
gggcggtcgt tctagatcgg agtagaattc tgtttcaaac tacctggtgg atttattaat   1440
tttggatctg tatgtgtgtg ccatacatat tcatagttac gaattgaaga tgatggatgg   1500
aaatatcgat ctaggatagg tatacatgtt gatgcgggtt ttactgatgc atatacagag   1560
atgctttttg ttcgcttggt tgtgatgatg tggtgtggtt gggcggtcgt tcattcgttc   1620
tagatcggag tagaatactg tttcaaacta cctggtgtat ttattaattt tggaactgta   1680
tgtgtgtgtc atacatcttc atagttacga gtttaagatg gatggaaata tcgatctagg   1740
ataggtatac atgttgatgt gggttttact gatgcatata catgatggca tatgcagcat   1800
ctattcatat gctctaacct tgagtaccta tctattataa taaacaagta tgttttataa   1860
ttattttgat cttgatatac ttggatgatg gcatatgcag cagctatatg tggatttttt   1920
tagccctgcc ttcatacgct atttatttgc ttggtactgt ttcttttgtc gatgctcacc   1980
ctgttgtttg gtgttacttc tgcaggtcga ctctagagga tatgttacgt cctgtagaaa   2040
ccccaacccg tgaaatcaaa aaactcgacg gcctgtgggc attcagtctg gatcgcgaaa   2100
actgtggaat tgatcagcgt tggtgggaaa gcgcgttaca agaaagccgg gcaattgctg   2160
tgccaggcag ttttaacgat cagttcgccg atgcagatat tcgtaattat gcgggcaacg   2220
tctggtatca gcgcgaagtc tttataccga aaggttgggc aggccagcgt atcgtgctgc   2280
gtttcgatgc ggtcactcat tacggcaaag tgtgggtcaa taatcaggaa gtgatggagc   2340
atcagggcgg ctatacgcca tttgaagccg atgtcacgcc gtatgttatt gccgggaaaa   2400
gtgtacgtat caccgtttgt gtgaacaacg aactgaactg gcagactatc ccgccgggaa   2460
tggtgattac cgacgaaaac ggcaagaaaa agcagtctta cttccatgat ttctttaact   2520
atgccggaat ccatcgcagc gtaatgctct acaccacgcc gaacacctgg gtggacgata   2580
tcaccgtggt gacgcatgtc gcgcaagact gtaaccacgc gtctgttgac tggcaggtgg   2640
tggccaatgg tgatgtcagc gttgaactgc gtgatgcgga tcaacaggtg gttgcaactg   2700
```

```
gacaaggcac tagcgggact ttgcaagtgg tgaatccgca cctctggcaa ccgggtgaag   2760

gttatctcta tgaactgtgc gtcacagcca aaagccagac agagtgtgat atctacccgc   2820

ttcgcgtcgg catccggtca gtggcagtga agggcgaaca gttcctgatt aaccacaaac   2880

cgttctactt tactggcttt ggtcgtcatg aagatgcgga cttgcgtggc aaaggattcg   2940

ataacgtgct gatggtgcac gaccacgcat taatggactg gattggggcc aactcctacc   3000

gtacctcgca ttacccttac gctgaagaga tgctcgactg ggcagatgaa catggcatcg   3060

tggtgattga tgaaactgct gctgtcggct ttaacctctc tttaggcatt ggtttcgaag   3120

cgggcaacaa gccgaaagaa ctgtacagcg aagaggcagt caacggggaa actcagcaag   3180

cgcacttaca ggcgattaaa gagctgatag cgcgtgacaa aaaccaccca agcgtggtga   3240

tgtggagtat tgccaacgaa ccggataccc gtccgcaagg tgcacgggaa tatttcgcgc   3300

cactggcgga agcaacgcgt aaactcgacc cgacgcgtcc gatcacctgc gtcaatgtaa   3360

tgttctgcga cgctcacacc gataccatca gcgatctctt tgatgtgctg tgcctgaacc   3420

gttattacgg atggtatgtc caaagcggcg atttggaaac ggcagagaag gtactggaaa   3480

aagaacttct ggcctggcag gagaaactgc atcagccgat tatcatcacc gaatacggcg   3540

tggatacgtt agccgggctg cactcaatgt acaccgacat gtggagtgaa gagtatcagt   3600

gtgcatggct ggatatgtat caccgcgtct ttgatcgcgt cagcgccgtc gtcggtgaac   3660

aggtatggaa tttcgccgat tttgcgacct cgcaaggcat attgcgcgtt ggcggtaaca   3720

agaaagggat cttcactcgc gaccgcaaac cgaagtcggc ggcttttctg ctgcaaaaac   3780

gctggactgg catgaacttc ggtgaaaaac cgcagcaggg aggcaaacaa tgacgagctc   3840

gatcgttcaa acatttggca ataaagtttc ttaagattga atcctgttgc cggtcttgcg   3900

atgattatca tataatttct gttgaattac gttaagcatg taataattaa catgtaatgc   3960

atgacgttat ttatgagatg ggtttttatg attagagtcc cgcaattata catttaatac   4020

gcgatagaaa acaaaatata gcgcgcaaac taggataaat tatcgcgcgc ggtgtcatct   4080

atgttactag atcggggaat tc                                            4102
```

<210> SEQ ID NO 10
<211> LENGTH: 3027
<212> TYPE: DNA
<213> ORGANISM: Artificial Sequence
<220> FEATURE:
<223> OTHER INFORMATION: Expression cassette Ubi-EYFP-NOS
<220> FEATURE:
<221> NAME/KEY: promoter
<222> LOCATION: (1)..(995)
<223> OTHER INFORMATION: Ubi Promoter
<220> FEATURE:
<221> NAME/KEY: misc_feature
<222> LOCATION: (996)..(2005)
<223> OTHER INFORMATION: First exon (5'UTR) and first intron
<220> FEATURE:
<221> NAME/KEY: misc_feature
<222> LOCATION: (2030)..(2758)
<223> OTHER INFORMATION: EYFP coding sequence
<220> FEATURE:
<221> NAME/KEY: terminator
<222> LOCATION: (2768)..(3021)
<223> OTHER INFORMATION: NOS

<400> SEQUENCE: 10

```
aagcttgcat gccctgcagt gcagcgtgac ccggtcgtgc ccctctctag agataatgag     60

cattgcatgt ctaagttata aaaaattacc acatattttt tttgtcacac ttgtttgaag    120

tgcagtttat ctatctttat acatatattt aaactttact ctacgaataa tataatctat    180
```

```
agtactacaa taatatcagt gttttagaga atcatataaa tgaacagtta gacatggtct    240
aaaggacaat tgagtatttt gacaacagga ctctacagtt ttatcttttt agtgtgcatg    300
tgttctcctt tttttttgca aatagcttca cctatataat acttcatcca ttttattagt    360
acatccattt agggtttagg gttaatggtt tttatagact aatttttta gtacatctat    420
tttattctat tttagcctct aaattaagaa aactaaaact ctattttagt tttttttattt   480
aataatttag atataaaata gaataaaata aagtgactaa aaattaaaca aataccttt    540
aagaaattaa aaaaactaag gaaacatttt tcttgtttcg agtagataat gccagcctgt    600
taaacgccgt cgacgagtct aacggacacc aaccagcgaa ccagcagcgt cgcgtcgggc    660
caagcgaagc agacggcacg gcatctctgt cgctgcctct ggacccctct cgagagttcc    720
gctccaccgt tggacttgct ccgctgtcgg catccagaaa ttgcgtggcg gagcggcaga    780
cgtgagccgg cacggcaggc ggcctcctcc tcctctcacg gcacggcagc tacgggggat    840
tcctttccca ccgctccttc gctttccctt cctcgcccgc cgtaataaat agacaccccc    900
tccacaccct ctttccccaa cctcgtgttg ttcggagcgc acacacacac aaccagatct    960
cccccaaatc cacccgtcgg cacctccgct tcaaggtacg ccgctcgtcc tccccccccc   1020
cccctctcta ccttctctag atcggcgttc cggtccatgg ttagggcccg gtagttctac   1080
ttctgttcat gtttgtgtta gatccgtgtt tgtgttagat ccgtgctgct agcgttcgta   1140
cacggatgcg acctgtacgt cagacacgtt ctgattgcta acttgccagt gtttctcttt   1200
ggggaatcct gggatggctc tagccgttcc gcagacggga tcgatttcat gatttttttt   1260
gtttcgttgc atagggtttg gtttgccctt ttcctttatt tcaatatatg ccgtgcactt   1320
gtttgtcggg tcatcttttc atgctttttt ttgtcttggt tgtgatgatg tggtctggtt   1380
gggcggtcgt tctagatcgg agtagaattc tgtttcaaac tacctggtgg atttattaat   1440
tttggatctg tatgtgtgtg ccatacatat tcatagttac gaattgaaga tgatggatgg   1500
aaatatcgat ctaggatagg tatacatgtt gatgcgggtt ttactgatgc atatacagag   1560
atgctttttg ttcgcttggt tgtgatgatg tggtgtggtt gggcggtcgt tcattcgttc   1620
tagatcggag tagaatactg tttcaaacta cctggtgtat ttattaattt tggaactgta   1680
tgtgtgtgtc atacatcttc atagttacga gtttaagatg gatggaaata tcgatctagg   1740
ataggtatac atgttgatgt gggttttact gatgcatata catgatggca tatgcagcat   1800
ctattcatat gctctaacct tgagtaccta tctattataa taaacaagta tgttttataa   1860
ttattttgat cttgatatac ttggatgatg gcatatgcag cagctatatg tggatttttt   1920
tagccctgcc ttcatacgct atttatttgc ttggtactgt ttcttttgtc gatgctcacc   1980
ctgttgtttg gtgttacttc tgcagtgcag gtcgactcta gaggatccca tggtgagcaa   2040
gggcgaggag ctgttcaccg gggtggtgcc catcctggtc gagctggacg gcgacgtaaa   2100
cggccacaag ttcagcgtgt ccggcgaggg cgagggcgat gccacctacg gcaagctgac   2160
cctgaagttc atctgcacca ccggcaagct gcccgtgccc tggcccaccc tcgtgaccac   2220
cttcggctac ggcctgcagt gcttcgcccg ctaccccgac cacatgaagc agcacgactt   2280
cttcaagtcc gccatgcccg aaggctacgt ccaggagcgc accatcttct tcaaggacga   2340
cggcaactac aagacccgcg ccgaggtgaa gttcgagggc gacaccctgg tgaaccgcat   2400
cgagctgaag ggcatcgact tcaaggagga cggcaacatc ctggggcaca agctggagta   2460
caactacaac agccacaacg tctatatcat ggccgacaag cagaagaacg gcatcaaggt   2520
```

-continued gaacttcaag atccgccaca acatcgagga cggcagcgtg cagctcgccg accactacca 2580
gcagaacacc cccatcggcg acggccccgt gctgctgccc gacaaccact acctgagcta 2640
ccagtccgcc ctgagcaaag accccaacga gaagcgcgat cacatggtcc tgctggagtt 2700
cgtgaccgcc gccgggatca ctctcggcat ggacgagctg tacaagagat ctatctagcg 2760
agctcgatcg ttcaaacatt tggcaataaa gtttcttaag attgaatcct gttgccggtc 2820
ttgcgatgat tatcatataa tttctgttga attacgttaa gcatgtaata attaacatgt 2880
aatgcatgac gttatttatg agatgggttt ttatgattag agtcccgcaa ttatacattt 2940
aatacgcgat agaaaacaaa atatagcgcg caaactagga taaattatcg cgcgcggtgt 3000
catctatgtt actagatcgg ggaattc 3027

<210> SEQ ID NO 11
<211> LENGTH: 25
<212> TYPE: DNA
<213> ORGANISM: Artificial Sequence
<220> FEATURE:
<223> OTHER INFORMATION: P-2 PCR primer

<400> SEQUENCE: 11
acgcggtaac acgtagtcct aaggt 25

<210> SEQ ID NO 12
<211> LENGTH: 20
<212> TYPE: DNA
<213> ORGANISM: Artificial Sequence
<220> FEATURE:
<223> OTHER INFORMATION: P-W3F PCR primer

<400> SEQUENCE: 12
gacatcaaat ggttgtatcc 20

<210> SEQ ID NO 13
<211> LENGTH: 20
<212> TYPE: DNA
<213> ORGANISM: Artificial Sequence
<220> FEATURE:
<223> OTHER INFORMATION: P-W4F PCR primer

<400> SEQUENCE: 13
acaccgcatt cagagtgaag 20

<210> SEQ ID NO 14
<211> LENGTH: 17
<212> TYPE: DNA
<213> ORGANISM: Artificial Sequence
<220> FEATURE:
<223> OTHER INFORMATION: P-W1R PCR primer

<400> SEQUENCE: 14
ccgcattaac gttctcc 17

<210> SEQ ID NO 15
<211> LENGTH: 34
<212> TYPE: DNA
<213> ORGANISM: Artificial Sequence
<220> FEATURE:
<223> OTHER INFORMATION: SCBV/Prom/F PCR primer

<400> SEQUENCE: 15
gaagaacagc atgctgaaca tctgtggaag atgc 34

<210> SEQ ID NO 16
<211> LENGTH: 38
<212> TYPE: DNA
<213> ORGANISM: Artificial Sequence
<220> FEATURE:
<223> OTHER INFORMATION: SCBV/Prom/R PCR pr

<400> SEQUENCE: 16
caaacttgct caaatgatca tgtggtgaac taccgatg 38

<210> SEQ ID NO 17
<211> LENGTH: 1816
<212> TYPE: DNA
<213> ORGANISM: Sugarcane bacilliform virus
<220> FEATURE:
<221> NAME/KEY: promoter
<222> LOCATION: (1)..(1786)
<223> OTHER INFORMATION: SCBV21 Promoter
<220> FEATURE:
<221> NAME/KEY: misc_signal
<222> LOCATION: (1787)..(1787)
<223> OTHER INFORMATION: Transcription start site
<220> FEATURE:
<221> NAME/KEY: misc_feature
<222> LOCATION: (1813)..(1816)
<223> OTHER INFORMATION: n is a, c, t, or g

<400> SEQUENCE: 17
gaagaacagc atgctgaaca tctgtggaag atgctacaga tatgcaagaa gaatgggtta 60
atcttaagcc cttccaagta taaattggag taaaaagagt tgactttctt ggttcaacaa 120
ttggagataa tcagttagct gttcaagaac atatagtctc caagatagct gattttgatg 180
aagaacgtct caagaccaag gaaggactga aaagctggct ggcaacactc aattatgcca 240
gaaatcacat caaggatatg ggaaaactcc ttggaccctt atatcctaaa acttcagaaa 300
agggagcaaa aggattaaat tctgaagatt ggaaattaat cagcagaatc aagacaatgg 360
tcagaaatct gccaaatctg actattccac cagaggatgc atatattatc attgaaacag 420
atgcttgtgc aactggttgg ggtgcagttt gcaaatggaa gaaatccaag gcagacccaa 480
gaagctccga gctcatatgt cgatatgcaa gtgggaaatt tgacaaacca aaagggacat 540
gtgatgcaga aatctatgga gtaatgaatg ggctggagaa aatgagactc ttttatcttg 600
ataaaaggga aatcactgtg aggacagata gtgccgcaat agagaggttc tacaacaaga 660
gtgttgaaca taaaccctca gaaatccgtt ggataaggtt tatggactat atcactggag 720
caggaccaaa gattgtgatt gagcatatca aaggaaaaca caatggtctg gcagatatcc 780
tctcaagatt gaaagcaaaa ctggcagaat caccttcaga agaagtggtt ttacttgcga 840
aagctttaaa ggaagttgca tactatcctg aacacccgca agtgccaaaa ctaattgaat 900
ggggaaagca aattcttgat ccatttccca agttcaagaa ggacatgttt gaaaaaactg 960
aacacatcat gatggctagt caagagccta cactgctttg tggatgtaga aggcctgcat 1020
atcagttcac atctggcaca aaactcaacc caagcaggaa gttctataaa tgtgcaatga 1080
acatgtgcca ctgctggtat tgggcagatc ttttagaaga atatgtccaa gaacgaattg 1140
aagtgttcat gattgagaac tttgacaaga aaatgggaat tcaagatgta ccaagtacat 1200
caaatgctaa cattccagga aattttaaat ctcttgcaga tttgaagaag gataaagaag 1260
ctaaagctga atatcaagac atgcttgata atcatcgttc aagcattatt gacagaccaa 1320
ggccaacaga tgaacacttc aagcctggat acatgtacac cgattccctg cagaagatca 1380
aggaggacta cgcaagccca agacaggagg aaccaccatg agaagacatt gagttctggt 1440

-continued tatgcaagga agaagactac cacacagaag acctcaatac agaagatgca gttgatctta 1500
ctgacgtaag caatgacgat cagtggaggc gatcgtaagc aatgatgcac ggaaggacaa 1560
ttatggagcg tggaggaccc atcaagcact cagaacgcga acctcaactt tcggcgccag 1620
caccttgtat ctttagttgg tgtgtgtctt tttcggcatc tgtgccacct tacctttgtc 1680
ggccacgttg cctatgctta gcacctacgc aagcatagcg ctcggctggt gtgtgttccc 1740
tctgcctata taaggcatgg ttgtaagact cttacactca tcggtagttc accacatgat 1800
catttgagca agnnnn 1816

<210> SEQ ID NO 18
<211> LENGTH: 1864
<212> TYPE: DNA
<213> ORGANISM: Sugarcane bacilliform virus
<220> FEATURE:
<221> NAME/KEY: promoter
<222> LOCATION: (1)..(1786)
<223> OTHER INFORMATION: SCBV21 Promoter
<220> FEATURE:
<221> NAME/KEY: misc_signal
<222> LOCATION: (1787)..(1787)
<223> OTHER INFORMATION: Transcription start site
<220> FEATURE:
<221> NAME/KEY: misc_feature
<222> LOCATION: (1788)..(1826)
<223> OTHER INFORMATION: n is a, c, g, or t
<220> FEATURE:
<221> NAME/KEY: misc_feature
<222> LOCATION: (1856)..(1860)
<223> OTHER INFORMATION: n is a, c, t, or g
<220> FEATURE:
<221> NAME/KEY: misc_feature
<222> LOCATION: (1861)..(1863)
<223> OTHER INFORMATION: Start codon
<220> FEATURE:
<221> NAME/KEY: misc_feature
<222> LOCATION: (1864)..(1864)
<223> OTHER INFORMATION: n is g or t

<400> SEQUENCE: 18
gaagaacagc atgctgaaca tctgtggaag atgctacaga tatgcaagaa gaatgggtta 60
atcttaagcc cttccaagta taaattggag taaaaagagt tgactttctt ggttcaacaa 120
ttggagataa tcagttagct gttcaagaac atatagtctc caagatagct gattttgatg 180
aagaacgtct caagaccaag gaaggactga aaagctggct ggcaacactc aattatgcca 240
gaaatcacat caaggatatg ggaaaactcc ttggaccctt atatcctaaa acttcagaaa 300
agggagcaaa aggattaaat tctgaagatt ggaaattaat cagcagaatc aagacaatgg 360
tcagaaatct gccaaatctg actattccac cagaggatgc atatattatc attgaaacag 420
atgcttgtgc aactggttgg ggtgcagttt gcaaatggaa gaaatccaag gcagacccaa 480
gaagctccga gctcatatgt cgatatgcaa gtgggaaatt tgacaaacca aaagggacat 540
gtgatgcaga aatctatgga gtaatgaatg ggctggagaa aatgagactc ttttatcttg 600
ataaaaggga aatcactgtg aggacagata gtgccgcaat agagaggttc tacaacaaga 660
gtgttgaaca taaaccctca gaaatccgtt ggataaggtt tatggactat atcactggag 720
caggaccaaa gattgtgatt gagcatatca aaggaaaaca caatggtctg gcagatatcc 780
tctcaagatt gaaagcaaaa ctggcagaat caccttcaga agaagtggtt ttacttgcga 840
aagctttaaa ggaagttgca tactatcctg aacacccgca agtgccaaaa ctaattgaat 900
ggggaaagca aattcttgat ccatttccca agttcaagaa ggacatgttt gaaaaaactg 960
aacacatcat gatggctagt caagagccta cactgctttg tggatgtaga aggcctgcat 1020
atcagttcac atctggcaca aaactcaacc caagcaggaa gttctataaa tgtgcaatga 1080
acatgtgcca ctgctggtat tgggcagatc ttttagaaga atatgtccaa gaacgaattg 1140
aagtgttcat gattgagaac tttgacaaga aaatgggaat tcaagatgta ccaagtacat 1200
caaatgctaa cattccagga aattttaaat ctcttgcaga tttgaagaag gataaagaag 1260
ctaaagctga atatcaagac atgcttgata atcatcgttc aagcattatt gacagaccaa 1320
ggccaacaga tgaacacttc aagcctggat acatgtacac cgattccctg cagaagatca 1380
aggaggacta cgcaagccca agacaggagg aaccaccatg agaagacatt gagttctggt 1440
tatgcaagga agaagactac cacacagaag acctcaatac agaagatgca gttgatctta 1500
ctgacgtaag caatgacgat cagtggaggc gatcgtaagc aatgatgcac ggaaggacaa 1560
ttatggagcg tggaggaccc atcaagcact cagaacgcga acctcaactt tcggcgccag 1620
caccttgtat ctttagttgg tgtgtgtctt tttcggcatc tgtgccacct tacctttgtc 1680
ggccacgttg cctatgctta gcacctacgc aagcatagcg ctcggctggt gtgtgttccc 1740
tctgcctata taaggcatgg ttgtaagact cttacactca tcggtagnnn nnnnnnnnnn 1800
nnnnnnnnnn nnnnnnnnnn nnnnnnttca ccacatgatc atttgagcaa gtttgnnnnn 1860 atgn 1864

<210> SEQ ID NO 19
<211> LENGTH: 5787
<212> TYPE: DNA
<213> ORGANISM: Artificial Sequence
<220> FEATURE:
<223> OTHER INFORMATION: pSK-SCBV21-EYFP-NOS Vector
<220> FEATURE:
<221> NAME/KEY: promoter
<222> LOCATION: (710)..(2525)
<223> OTHER INFORMATION: SCBV21 Promoter
<220> FEATURE:
<221> NAME/KEY: misc_signal
<222> LOCATION: (1764)..(1813)
<223> OTHER INFORMATION: Transcription start site TSS1
<220> FEATURE:
<221> NAME/KEY: misc_signal
<222> LOCATION: (2446)..(2495)
<223> OTHER INFORMATION: Transcription start site TSS2
<220> FEATURE:
<221> NAME/KEY: misc_feature
<222> LOCATION: (2547)..(3275)
<223> OTHER INFORMATION: EYFP coding sequence
<220> FEATURE:
<221> NAME/KEY: terminator
<222> LOCATION: (3285)..(3538)
<223> OTHER INFORMATION: NOS

<400> SEQUENCE: 19
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtgttgttc cagtttggaa caagagtcca ctattaaaga acgtggactc 180
caacgtcaaa gggcgaaaaa ccgtctatca gggcgatggc ccactacgtg aaccatcacc 240
ctaatcaagt tttttggggt cgaggtgccg taaagcacta aatcggaacc ctaaagggag 300
cccccgattt agagcttgac ggggaaagcc ggcgaacgtg gcgagaaagg aagggaagaa 360
agcgaaagga gcgggcgcta gggcgctggc aagtgtagcg gtcacgctgc gcgtaaccac 420
cacacccgcc gcgcttaatg cgccgctaca gggcgcgtcc cattcgccat tcaggctgcg 480
caactgttgg gaagggcgat cggtgcgggc ctcttcgcta ttacgccagc tggcgaaagg 540

```
gggatgtgct gcaaggcgat taagttgggt aacgccaggg ttttcccagt cacgacgttg    600
taaaacgacg gccagtgagc gcgcgtaata cgactcacta tagggcgaat tgggtaccgg    660
gcccccccctc gaggtcgacc tgcaggcggc cgcgaattca ctagtgattg aagaacagca    720
tgctgaacat ctgtggaaga tgctacagat atgcaagaag aatgggttaa tcttaagccc    780
ttccaagtat aaattggagt aaaaagagtt gactttcttg gttcaacaat tggagataat    840
cagttagctg ttcaagaaca tatagtctcc aagatagctg attttgatga agaacgtctc    900
aagaccaagg aaggactgaa aagctggctg gcaacactca attatgccag aaatcacatc    960
aaggatatgg gaaaactcct tggaccctta tatcctaaaa cttcagaaaa gggagcaaaa   1020
ggattaaatt ctgaagattg gaaattaatc agcagaatca agacaatggt cagaaatctg   1080
ccaaatctga ctattccacc agaggatgca tatattatca ttgaaacaga tgcttgtgca   1140
actggttggg gtgcagtttg caaatggaag aaatccaagg cagacccaag aagctccgag   1200
ctcatatgtc gatatgcaag tgggaaattt gacaaaccaa aagggacatg tgatgcagaa   1260
atctatggag taatgaatgg gctggagaaa atgagactct tttatcttga taaaagggaa   1320
atcactgtga ggacagatag tgccgcaata gagaggttct acaacaagag tgttgaacat   1380
aaaccctcag aaatccgttg gataaggttt atggactata tcactggagc aggaccaaag   1440
attgtgattg agcatatcaa aggaaaacac aatggtctgg cagatatcct ctcaagattg   1500
aaagcaaaac tggcagaatc accttcagaa gaagtggttt tacttgcgaa agctttaaag   1560
gaagttgcat actatcctga acacccgcaa gtgccaaaac taattgaatg ggaaagcaa   1620
attcttgatc catttcccaa gttcaagaag gacatgtttg aaaaaactga acacatcatg   1680
atggctagtc aagagcctac actgctttgt ggatgtagaa ggcctgcata tcagttcaca   1740
tctggcacaa aactcaaccc aagcaggaag ttctataaat gtgcaatgaa catgtgccac   1800
tgctggtatt gggcagatct tttagaagaa tatgtccaag aacgaattga agtgttcatg   1860
attgagaact ttgacaagaa aatgggaatt caagatgtac caagtacatc aaatgctaac   1920
attccaggaa attttaaatc tcttgcagat ttgaagaagg ataaagaagc taaagctgaa   1980
tatcaagaca tgcttgataa tcatcgttca agcattattg acagaccaag gccaacagat   2040
gaacacttca agcctggata catgtacacc gattccctgc agaagatcaa ggaggactac   2100
gcaagcccaa gacaggagga accaccatga gaagacattg agttctggtt atgcaaggaa   2160
gaagactacc acacagaaga cctcaataca gaagatgcag ttgatcttac tgacgtaagc   2220
aatgacgatc agtggaggcg atcgtaagca atgatgcacg gaaggacaat tatggagcgt   2280
ggaggaccca tcaagcactc agaacgcgaa cctcaacttt cggcgccagc accttgtatc   2340
tttagttggt gtgtgtcttt ttcggcatct gtgccacctt acctttgtcg gccacgttgc   2400
ctatgcttag cacctacgca agcatagcgc tcggctggtg tgtgttccct ctgcctatat   2460
aaggcatggt tgtaagactc ttacactcat cggtagttca ccacatgatc atttgagcaa   2520
gtttgaatcg aattcccgcg gccgccatgg tgagcaaggg cgaggagctg ttcaccgggg   2580
tggtgcccat cctggtcgag ctggacggcg acgtaaacgg ccacaagttc agcgtgtccg   2640
gcgagggcga gggcgatgcc acctacggca agctgaccct gaagttcatc tgcaccaccg   2700
gcaagctgcc cgtgccctgg cccaccctcg tgaccacctt cggctacggc ctgcagtgct   2760
tcgcccgcta ccccgaccac atgaagcagc acgacttctt caagtccgcc atgcccgaag   2820
gctacgtcca ggagcgcacc atcttcttca aggacgacgg caactacaag acccgcgccg   2880
aggtgaagtt cgagggcgac accctggtga accgcatcga gctgaagggc atcgacttca   2940
```

```
aggaggacgg caacatcctg gggcacaagc tggagtacaa ctacaacagc cacaacgtct   3000
atatcatggc cgacaagcag aagaacggca tcaaggtgaa cttcaagatc cgccacaaca   3060
tcgaggacgg cagcgtgcag ctcgccgacc actaccagca gaacaccccc atcggcgacg   3120
gccccgtgct gctgcccgac aaccactacc tgagctacca gtccgccctg agcaaagacc   3180
ccaacgagaa gcgcgatcac atggtcctgc tggagttcgt gaccgccgcc gggatcactc   3240
tcggcatgga cgagctgtac aagagatcta tctagcgagc tcgatcgttc aaacatttgg   3300
caataaagtt tcttaagatt gaatcctgtt gccggtcttg cgatgattat catataattt   3360
ctgttgaatt acgttaagca tgtaataatt aacatgtaat gcatgacgtt atttatgaga   3420
tgggttttta tgattagagt cccgcaatta tacatttaat acgcgataga aaacaaaata   3480
tagcgcgcaa actaggataa attatcgcgc gcggtgtcat ctatgttact agatcgggga   3540
tgggggatcc actagttcta gagcggccgc caccgcggtg gagctccagc ttttgttccc   3600
tttagtgagg gttaattgcg cgcttggcgt aatcatggtc atagctgttt cctgtgtgaa   3660
attgttatcc gctcacaatt ccacacaaca tacgagccgg aagcataaag tgtaaagcct   3720
ggggtgccta atgagtgagc taactcacat taattgcgtt gcgctcactg cccgctttcc   3780
agtcgggaaa cctgtcgtgc cagctgcatt aatgaatcgg ccaacgcgcg gggagaggcg   3840
gtttgcgtat tgggcgctct tccgcttcct cgctcactga ctcgctgcgc tcggtcgttc   3900
ggctgcggcg agcggtatca gctcactcaa aggcggtaat acggttatcc acagaatcag   3960
gggataacgc aggaaagaac atgtgagcaa aaggccagca aaaggccagg aaccgtaaaa   4020
aggccgcgtt gctggcgttt ttccataggc tccgcccccc tgacgagcat cacaaaaatc   4080
gacgctcaag tcagaggtgg cgaaacccga caggactata aagataccag gcgtttcccc   4140
ctggaagctc cctcgtgcgc tctcctgttc cgaccctgcc gcttaccgga tacctgtccg   4200
cctttctccc ttcgggaagc gtggcgcttt ctcatagctc acgctgtagg tatctcagtt   4260
cggtgtaggt cgttcgctcc aagctgggct gtgtgcacga accccccgtt cagcccgacc   4320
gctgcgcctt atccggtaac tatcgtcttg agtccaaccc ggtaagacac gacttatcgc   4380
cactggcagc agccactggt aacaggatta gcagagcgag gtatgtaggc ggtgctacag   4440
agttcttgaa gtggtggcct aactacggct acactagaag gacagtattt ggtatctgcg   4500
ctctgctgaa gccagttacc ttcggaaaaa gagttggtag ctcttgatcc ggcaaacaaa   4560
ccaccgctgg tagcggtggt ttttttgttt gcaagcagca gattacgcgc agaaaaaaag   4620
gatctcaaga agatcctttg atcttttcta cggggtctga cgctcagtgg aacgaaaact   4680
cacgttaagg gattttggtc atgagattat caaaaaggat cttcacctag atccttttaa   4740
attaaaaatg aagttttaaa tcaatctaaa gtatatatga gtaaacttgg tctgacagtt   4800
accaatgctt aatcagtgag gcacctatct cagcgatctg tctatttcgt tcatccatag   4860
ttgcctgact ccccgtcgtg tagataacta cgatacggga gggcttacca tctggcccca   4920
gtgctgcaat gataccgcga gacccacgct caccggctcc agatttatca gcaataaacc   4980
agccagccgg aagggccgag cgcagaagtg gtcctgcaac tttatccgcc tccatccagt   5040
ctattaattg ttgccgggaa gctagagtaa gtagttcgcc agttaatagt ttgcgcaacg   5100
ttgttgccat tgctacaggc atcgtggtgt cacgctcgtc gtttggtatg gcttcattca   5160
gctccggttc ccaacgatca aggcgagtta catgatcccc catgttgtgc aaaaaagcgg   5220
ttagctcctt cggtcctccg atcgttgtca gaagtaagtt ggccgcagtg ttatcactca   5280
```

```
tggttatggc agcactgcat aattctctta ctgtcatgcc atccgtaaga tgcttttctg   5340

tgactggtga gtactcaacc aagtcattct gagaatagtg tatgcggcga ccgagttgct   5400

cttgcccggc gtcaatacgg gataataccg cgccacatag cagaacttta aaagtgctca   5460

tcattggaaa acgttcttcg gggcgaaaac tctcaaggat cttaccgctg ttgagatcca   5520

gttcgatgta acccactcgt gcacccaact gatcttcagc atcttttact ttcaccagcg   5580

tttctgggtg agcaaaaaca ggaaggcaaa atgccgcaaa aaagggaata agggcgacac   5640

ggaaatgttg aatactcata ctcttccttt ttcaatatta ttgaagcatt tatcagggtt   5700

attgtctcat gagcggatac atatttgaat gtatttagaa aaataaacaa ataggggttc   5760

cgcgcacatt tccccgaaaa gtgccac                                         5787
```

<210> SEQ ID NO 20
<211> LENGTH: 4964
<212> TYPE: DNA
<213> ORGANISM: Artificial Sequence
<220> FEATURE:
<223> OTHER INFORMATION: pSK-SCBV21-EYFP-NOS Vector - deletion B
<220> FEATURE:
<221> NAME/KEY: promoter
<222> LOCATION: (710)..(1722)
<223> OTHER INFORMATION: SCBV21 Promoter deletion B
<220> FEATURE:
<221> NAME/KEY: misc_feature
<222> LOCATION: (1724)..(2452)
<223> OTHER INFORMATION: EYFP coding sequence
<220> FEATURE:
<221> NAME/KEY: terminator
<222> LOCATION: (2462)..(2715)
<223> OTHER INFORMATION: NOS

<400> SEQUENCE: 20

```
ctaaattgta agcgttaata ttttgttaaa attcgcgtta aatttttgtt aaatcagctc     60

atttttaac caataggccg aaatcggcaa aatcccttat aaatcaaaag aatagaccga     120

gatagggttg agtgttgttc cagtttggaa caagagtcca ctattaaaga acgtggactc    180

caacgtcaaa gggcgaaaaa ccgtctatca gggcgatggc ccactacgtg aaccatcacc    240

ctaatcaagt tttttggggt cgaggtgccg taaagcacta aatcggaacc ctaaagggag    300

cccccgattt agagcttgac ggggaaagcc ggcgaacgtg gcgagaaagg aagggaagaa    360

agcgaaagga gcgggcgcta gggcgctggc aagtgtagcg gtcacgctgc gcgtaaccac    420

cacacccgcc gcgcttaatg cgccgctaca gggcgcgtcc cattcgccat tcaggctgcg    480

caactgttgg gaagggcgat cggtgcgggc ctcttcgcta ttacgccagc tggcgaaagg    540

gggatgtgct gcaaggcgat taagttgggt aacgccaggg ttttcccagt cacgacgttg    600

taaaacgacg gccagtgagc gcgcgtaata cgactcacta tagggcgaat tgggtaccgg    660

gccccccctc gaggtcgacc tgcaggcggc cgcgaattca ctagtgattg aagaacagca    720

tgctgaacat ctgtggaaga tgctacagat atgcaagaag aatgggttaa tcttaagccc    780

ttccaagtat aaattggagt aaaaagagtt gactttcttg gttcaacaat tggagataat    840

cagttagctg ttcaagaaca tatagtctcc aagatagctg attttgatga agaacgtctc    900

aagaccaagg aaggactgaa aagctggctg gcaacactca attatgccag aaatcacatc    960

aaggatatgg gaaaactcct tggaccctta tatcctaaaa cttcagaaaa gggagcaaaa   1020

ggattaaatt ctgaagattg gaaattaatc agcagaatca agacaatggt cagaaatctg   1080

ccaaatctga ctattccacc agaggatgca tatattatca ttgaaacaga tgcttgtgca   1140

actggttggg gtgcagtttg caaatggaag aaatccaagg cagacccaag aagctccgag   1200
```

```
ctcatatgtc gatatgcaag tgggaaattt gacaaaccaa aagggacatg tgatgcagaa   1260
atctatggag taatgaatgg gctggagaaa atgagactct tttatcttga taaaagggaa   1320
atcactgtga ggacagatag tgccgcaata gagaggttct acaacaagag tgttgaacat   1380
aaaccctcag aaatccgttg gataaggttt atggactata tcactggagc aggaccaaag   1440
attgtgattg agcatatcaa aggaaaacac aatggtctgg cagatatcct ctcaagattg   1500
aaagcaaaac tggcagaatc accttcagaa gaagtggttt tacttgcgaa agctttaaag   1560
gaagttgcat actatcctga acacccgcaa gtgccaaaac taattgaatg gggaaagcaa   1620
attcttgatc catttcccaa gttcaagaag gacatgtttg aaaaaactga acacatcatg   1680
atggctagtc aagagcctac actgctttgt ggatgtagaa ggcatggtga gcaagggcga   1740
ggagctgttc accggggtgg tgcccatcct ggtcgagctg gacggcgacg taaacggcca   1800
caagttcagc gtgtccggcg agggcgaggg cgatgccacc tacggcaagc tgaccctgaa   1860
gttcatctgc accaccggca agctgcccgt gccctggccc accctcgtga ccaccttcgg   1920
ctacggcctg cagtgcttcg cccgctaccc cgaccacatg aagcagcacg acttcttcaa   1980
gtccgccatg cccgaaggct acgtccagga gcgcaccatc ttcttcaagg acgacggcaa   2040
ctacaagacc cgcgccgagg tgaagttcga gggcgacacc ctggtgaacc gcatcgagct   2100
gaagggcatc gacttcaagg aggacggcaa catcctgggg cacaagctgg agtacaacta   2160
caacagccac aacgtctata tcatggccga caagcagaag aacggcatca aggtgaactt   2220
caagatccgc cacaacatcg aggacggcag cgtgcagctc gccgaccact accagcagaa   2280
cacccccatc ggcgacggcc ccgtgctgct gcccgacaac cactacctga gctaccagtc   2340
cgccctgagc aaagacccca acgagaagcg cgatcacatg gtcctgctgg agttcgtgac   2400
cgccgccggg atcactctcg gcatggacga gctgtacaag agatctatct agcgagctcg   2460
atcgttcaaa catttggcaa taaagtttct taagattgaa tcctgttgcc ggtcttgcga   2520
tgattatcat ataatttctg ttgaattacg ttaagcatgt aataattaac atgtaatgca   2580
tgacgttatt tatgagatgg gtttttatga ttagagtccc gcaattatac atttaatacg   2640
cgatagaaaa caaaatatag cgcgcaaact aggataaatt atcgcgcgcg gtgtcatcta   2700
tgttactaga tcggggatgg gggatccact agttctagag cggccgccac cgcggtggag   2760
ctccagcttt tgttcccttt agtgagggtt aattgcgcgc ttggcgtaat catggtcata   2820
gctgtttcct gtgtgaaatt gttatccgct cacaattcca cacaacatac gagccggaag   2880
cataaagtgt aaagcctggg gtgcctaatg agtgagctaa ctcacattaa ttgcgttgcg   2940
ctcactgccc gctttccagt cgggaaacct gtcgtgccag ctgcattaat gaatcggcca   3000
acgcgcgggg agaggcggtt tgcgtattgg gcgctcttcc gcttcctcgc tcactgactc   3060
gctgcgctcg gtcgttcggc tgcggcgagc ggtatcagct cactcaaagg cggtaatacg   3120
gttatccaca gaatcagggg ataacgcagg aaagaacatg tgagcaaaag gccagcaaaa   3180
ggccaggaac cgtaaaaagg ccgcgttgct ggcgtttttc cataggctcc gcccccctga   3240
cgagcatcac aaaaatcgac gctcaagtca gaggtggcga aacccgacag gactataaag   3300
ataccaggcg tttccccctg gaagctccct cgtgcgctct cctgttccga ccctgccgct   3360
taccggatac ctgtccgcct ttctcccttc gggaagcgtg gcgctttctc atagctcacg   3420
ctgtaggtat ctcagttcgg tgtaggtcgt tcgctccaag ctgggctgtg tgcacgaacc   3480
ccccgttcag cccgaccgct gcgccttatc cggtaactat cgtcttgagt ccaacccggt   3540
```

aagacacgac ttatcgccac tggcagcagc cactggtaac aggattagca gagcgaggta 3600
tgtaggcggt gctacagagt tcttgaagtg gtggcctaac tacggctaca ctagaaggac 3660
agtatttggt atctgcgctc tgctgaagcc agttaccttc ggaaaaagag ttggtagctc 3720
ttgatccggc aaacaaacca ccgctggtag cggtggtttt tttgtttgca agcagcagat 3780
tacgcgcaga aaaaaaggat ctcaagaaga tcctttgatc ttttctacgg ggtctgacgc 3840
tcagtggaac gaaaactcac gttaagggat tttggtcatg agattatcaa aaaggatctt 3900
cacctagatc cttttaaatt aaaaatgaag ttttaaatca atctaaagta tatatgagta 3960
aacttggtct gacagttacc aatgcttaat cagtgaggca cctatctcag cgatctgtct 4020
atttcgttca tccatagttg cctgactccc cgtcgtgtag ataactacga tacgggaggg 4080
cttaccatct ggccccagtg ctgcaatgat accgcgagac ccacgctcac cggctccaga 4140
tttatcagca ataaaccagc cagccggaag ggccgagcgc agaagtggtc ctgcaacttt 4200
atccgcctcc atccagtcta ttaattgttg ccgggaagct agagtaagta gttcgccagt 4260
taatagtttg cgcaacgttg ttgccattgc tacaggcatc gtggtgtcac gctcgtcgtt 4320
tggtatggct tcattcagct ccggttccca acgatcaagg cgagttacat gatcccccat 4380
gttgtgcaaa aaagcggtta gctccttcgg tcctccgatc gttgtcagaa gtaagttggc 4440
cgcagtgtta tcactcatgg ttatggcagc actgcataat tctcttactg tcatgccatc 4500
cgtaagatgc ttttctgtga ctggtgagta ctcaaccaag tcattctgag aatagtgtat 4560
gcggcgaccg agttgctctt gcccggcgtc aatacgggat aataccgcgc cacatagcag 4620
aactttaaaa gtgctcatca ttggaaaacg ttcttcgggg cgaaaactct caaggatctt 4680
accgctgttg agatccagtt cgatgtaacc cactcgtgca cccaactgat cttcagcatc 4740
ttttactttc accagcgttt ctgggtgagc aaaaacagga aggcaaaatg ccgcaaaaaa 4800
gggaataagg gcgacacgga aatgttgaat actcatactc ttcctttttc aatattattg 4860
aagcatttat cagggttatt gtctcatgag cggatacata tttgaatgta tttagaaaaa 4920
taaacaaata ggggttccgc gcacatttcc ccgaaaagtg ccac 4964

<210> SEQ ID NO 21
<211> LENGTH: 4721
<212> TYPE: DNA
<213> ORGANISM: Artificial Sequence
<220> FEATURE:
<223> OTHER INFORMATION: pSK-SCBV21-EYFP-NOS Vector - deletion C
<220> FEATURE:
<221> NAME/KEY: promoter
<222> LOCATION: (674)..(1478)
<223> OTHER INFORMATION: SCBV21 Promoter deletion C
<220> FEATURE:
<221> NAME/KEY: misc_signal
<222> LOCATION: (718)..(767)
<223> OTHER INFORMATION: Transcription start site TSS1
<220> FEATURE:
<221> NAME/KEY: misc_signal
<222> LOCATION: (1400)..(1449)
<223> OTHER INFORMATION: Transcription start site TSS2
<220> FEATURE:
<221> NAME/KEY: misc_feature
<222> LOCATION: (1481)..(2209)
<223> OTHER INFORMATION: EYFP coding sequence
<220> FEATURE:
<221> NAME/KEY: terminator
<222> LOCATION: (2219)..(2472)
<223> OTHER INFORMATION: NOS

<400> SEQUENCE: 21
ctaaattgta agcgttaata ttttgttaaa attcgcgtta aatttttgtt aaatcagctc 60

-continued

```
atttttaac caataggccg aaatcggcaa aatcccttat aaatcaaaag aatagaccga    120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt tttttggggt cgaggtgccg taaagcacta aatcggaacc ctaaagggag    300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tgggtaccgg    660
gcccccccctc gagaggcctg catatcagtt cacatctggc acaaaactca acccaagcag    720
gaagttctat aaatgtgcaa tgaacatgtg ccactgctgg tattgggcag atcttttaga    780
agaatatgtc caagaacgaa ttgaagtgtt catgattgag aactttgaca agaaaatggg    840
aattcaagat gtaccaagta catcaaatgc taacattcca ggaaatttta aatctcttgc    900
agatttgaag aaggataaag aagctaaagc tgaatatcaa gacatgcttg ataatcatcg    960
ttcaagcatt attgacagac caaggccaac agatgaacac ttcaagcctg gatacatgta   1020
caccgattcc ctgcagaaga tcaaggagga ctacgcaagc ccaagacagg aggaaccacc   1080
atgagaagac attgagttct ggttatgcaa ggaagaagac taccacacag aagacctcaa   1140
tacagaagat gcagttgatc ttactgacgt aagcaatgac gatcagtgga ggcgatcgta   1200
agcaatgatg cacggaagga caattatgga gcgtggagga cccatcaagc actcagaacg   1260
cgaacctcaa ctttcggcgc cagcaccttg tatctttagt tggtgtgtgt ctttttcggc   1320
atctgtgcca ccttaccttt gtcggccacg ttgcctatgc ttagcaccta cgcaagcata   1380
gcgctcggct ggtgtgtgtt ccctctgcct atataaggca tggttgtaag actcttacac   1440
tcatcggtag ttcaccacat gatcatttga gcaagtttcc atggtgagca agggcgagga   1500
gctgttcacc ggggtggtgc ccatcctggt cgagctggac ggcgacgtaa acggccacaa   1560
gttcagcgtg tccggcgagg gcgagggcga tgccacctac ggcaagctga ccctgaagtt   1620
catctgcacc accggcaagc tgcccgtgcc ctggcccacc ctcgtgacca ccttcggcta   1680
cggcctgcag tgcttcgccc gctaccccga ccacatgaag cagcacgact tcttcaagtc   1740
cgccatgccc gaaggctacg tccaggagcg caccatcttc ttcaaggacg acggcaacta   1800
caagacccgc gccgaggtga agttcgaggg cgacaccctg gtgaaccgca tcgagctgaa   1860
gggcatcgac ttcaaggagg acggcaacat cctggggcac aagctggagt acaactacaa   1920
cagccacaac gtctatatca tggccgacaa gcagaagaac ggcatcaagg tgaacttcaa   1980
gatccgccac aacatcgagg acggcagcgt gcagctcgcc gaccactacc agcagaacac   2040
ccccatcggc gacggccccg tgctgctgcc cgacaaccac tacctgagct accagtccgc   2100
cctgagcaaa gaccccaacg agaagcgcga tcacatggtc ctgctggagt tcgtgaccgc   2160
cgccgggatc actctcggca tggacgagct gtacaagaga tctatctagc gagctcgatc   2220
gttcaaacat ttggcaataa agtttcttaa gattgaatcc tgttgccggt cttgcgatga   2280
ttatcatata atttctgttg aattacgtta agcatgtaat aattaacatg taatgcatga   2340
cgttatttat gagatgggtt tttatgatta gagtcccgca attatacatt taatacgcga   2400
```

-continued

```
tagaaaacaa aatatagcgc gcaaactagg ataaattatc gcgcgcggtg tcatctatgt   2460
tactagatcg ggatgggggg atccactagt tctagagcgg ccgccaccgc ggtggagctc   2520
cagcttttgt tccctttagt gagggttaat tgcgcgcttg gcgtaatcat ggtcatagct   2580
gtttcctgtg tgaaattgtt atccgctcac aattccacac aacatacgag ccggaagcat   2640
aaagtgtaaa gcctggggtg cctaatgagt gagctaactc acattaattg cgttgcgctc   2700
actgcccgct ttccagtcgg gaaacctgtc gtgccagctg cattaatgaa tcggccaacg   2760
cgcggggaga ggcggtttgc gtattgggcg ctcttccgct tcctcgctca ctgactcgct   2820
gcgctcggtc gttcggctgc ggcgagcggt atcagctcac tcaaaggcgg taatacggtt   2880
atccacagaa tcaggggata acgcaggaaa gaacatgtga gcaaaaggcc agcaaaaggc   2940
caggaaccgt aaaaaggccg cgttgctggc gtttttccat aggctccgcc cccctgacga   3000
gcatcacaaa aatcgacgct caagtcagag gtggcgaaac ccgacaggac tataaagata   3060
ccaggcgttt ccccctggaa gctccctcgt gcgctctcct gttccgaccc tgccgcttac   3120
cggatacctg tccgcctttc tcccttcggg aagcgtggcg ctttctcata gctcacgctg   3180
taggtatctc agttcggtgt aggtcgttcg ctccaagctg ggctgtgtgc acgaaccccc   3240
cgttcagccc gaccgctgcg ccttatccgg taactatcgt cttgagtcca acccggtaag   3300
acacgactta tcgccactgg cagcagccac tggtaacagg attagcagag cgaggtatgt   3360
aggcggtgct acagagttct tgaagtggtg gcctaactac ggctacacta gaaggacagt   3420
atttggtatc tgcgctctgc tgaagccagt taccttcgga aaaagagttg gtagctcttg   3480
atccggcaaa caaaccaccg ctggtagcgg tggttttttt gtttgcaagc agcagattac   3540
gcgcagaaaa aaaggatctc aagaagatcc tttgatcttt tctacggggt ctgacgctca   3600
gtggaacgaa aactcacgtt aagggatttt ggtcatgaga ttatcaaaaa ggatcttcac   3660
ctagatcctt ttaaattaaa aatgaagttt taaatcaatc taaagtatat atgagtaaac   3720
ttggtctgac agttaccaat gcttaatcag tgaggcacct atctcagcga tctgtctatt   3780
tcgttcatcc atagttgcct gactccccgt cgtgtagata actacgatac gggagggctt   3840
accatctggc cccagtgctg caatgatacc gcgagaccca cgctcaccgg ctccagattt   3900
atcagcaata aaccagccag ccggaagggc cgagcgcaga agtggtcctg caactttatc   3960
cgcctccatc cagtctatta attgttgccg ggaagctaga gtaagtagtt cgccagttaa   4020
tagtttgcgc aacgttgttg ccattgctac aggcatcgtg gtgtcacgct cgtcgtttgg   4080
tatggcttca ttcagctccg gttcccaacg atcaaggcga gttacatgat cccccatgtt   4140
gtgcaaaaaa gcggttagct ccttcggtcc tccgatcgtt gtcagaagta agttggccgc   4200
agtgttatca ctcatggtta tggcagcact gcataattct cttactgtca tgccatccgt   4260
aagatgcttt tctgtgactg gtgagtactc aaccaagtca ttctgagaat agtgtatgcg   4320
gcgaccgagt tgctcttgcc cggcgtcaat acgggataat accgcgccac atagcagaac   4380
tttaaaagtg ctcatcattg gaaaacgttc ttcggggcga aaactctcaa ggatcttacc   4440
gctgttgaga tccagttcga tgtaacccac tcgtgcaccc aactgatctt cagcatcttt   4500
tactttcacc agcgtttctg ggtgagcaaa aacaggaagg caaaatgccg caaaaaaggg   4560
aataagggcg acacggaaat gttgaatact catactcttc ctttttcaat attattgaag   4620
catttatcag ggttattgtc tcatgagcgg atacatattt gaatgtattt agaaaaataa   4680
acaaataggg gttccgcgca catttccccg aaaagtgcca c                        4721
```

```
<210> SEQ ID NO 22
<211> LENGTH: 4626
<212> TYPE: DNA
<213> ORGANISM: Artificial Sequence
<220> FEATURE:
<223> OTHER INFORMATION: pSK-SCBV21-EYFP-NOS Vector - deletion D
<220> FEATURE:
<221> NAME/KEY: promoter
<222> LOCATION: (674)..(1383)
<223> OTHER INFORMATION: SCBV21 Promoter deletion D
<220> FEATURE:
<221> NAME/KEY: misc_signal
<222> LOCATION: (1305)..(1354)
<223> OTHER INFORMATION: Transcription start site TSS2
<220> FEATURE:
<221> NAME/KEY: misc_feature
<222> LOCATION: (1386)..(2114)
<223> OTHER INFORMATION: EYFP coding sequence
<220> FEATURE:
<221> NAME/KEY: terminator
<222> LOCATION: (2124)..(2377)
<223> OTHER INFORMATION: NOS

<400> SEQUENCE: 22

ctaaattgta agcgttaata ttttgttaaa attcgcgtta aatttttgtt aaatcagctc     60

atttttaac caataggccg aaatcggcaa aatcccttat aaatcaaaag aatagaccga    120

gatagggttg agtgttgttc cagtttggaa caagagtcca ctattaaaga acgtggactc    180

caacgtcaaa gggcgaaaaa ccgtctatca gggcgatggc ccactacgtg aaccatcacc    240

ctaatcaagt tttttggggt cgaggtgccg taaagcacta aatcggaacc ctaaagggag    300

cccccgattt agagcttgac ggggaaagcc ggcgaacgtg gcgagaaagg aagggaagaa    360

agcgaaagga gcgggcgcta gggcgctggc aagtgtagcg gtcacgctgc gcgtaaccac    420

cacacccgcc gcgcttaatg cgccgctaca gggcgcgtcc cattcgccat tcaggctgcg    480

caactgttgg gaagggcgat cggtgcgggc ctcttcgcta ttacgccagc tggcgaaagg    540

gggatgtgct gcaaggcgat taagttgggt aacgccaggg ttttcccagt cacgacgttg    600

taaaacgacg gccagtgagc gcgcgtaata cgactcacta tagggcgaat tgggtaccgg    660

gcccccccctc gagagatctt ttagaagaat atgtccaaga acgaattgaa gtgttcatga    720

ttgagaactt tgacaagaaa atgggaattc aagatgtacc aagtacatca aatgctaaca    780

ttccaggaaa ttttaaatct cttgcagatt tgaagaagga taaagaagct aaagctgaat    840

atcaagacat gcttgataat catcgttcaa gcattattga cagaccaagg ccaacagatg    900

aacacttcaa gcctggatac atgtacaccg attccctgca gaagatcaag gaggactacg    960

caagcccaag acaggaggaa ccaccatgag aagacattga gttctggtta tgcaaggaag   1020

aagactacca cacagaagac ctcaatacag aagatgcagt tgatcttact gacgtaagca   1080

atgacgatca gtggaggcga tcgtaagcaa tgatgcacgg aaggacaatt atggagcgtg   1140

gaggacccat caagcactca gaacgcgaac ctcaactttc ggcgccagca ccttgtatct   1200

ttagttggtg tgtgtctttt tcggcatctg tgccacctta cctttgtcgg ccacgttgcc   1260

tatgcttagc acctacgcaa gcatagcgct cggctggtgt gtgttccctc tgcctatata   1320

aggcatggtt gtaagactct tacactcatc ggtagttcac cacatgatca tttgagcaag   1380

tttccatggt gagcaagggc gaggagctgt tcaccggggt ggtgcccatc ctggtcgagc   1440

tggacggcga cgtaaacggc cacaagttca gcgtgtccgg cgagggcgag ggcgatgcca   1500

cctacggcaa gctgaccctg aagttcatct gcaccaccgg caagctgccc gtgccctggc   1560

ccaccctcgt gaccaccttc ggctacggcc tgcagtgctt cgcccgctac cccgaccaca   1620
```

-continued

```
tgaagcagca cgacttcttc aagtccgcca tgcccgaagg ctacgtccag gagcgcacca   1680
tcttcttcaa ggacgacggc aactacaaga cccgcgccga ggtgaagttc gagggcgaca   1740
ccctggtgaa ccgcatcgag ctgaagggca tcgacttcaa ggaggacggc aacatcctgg   1800
ggcacaagct ggagtacaac tacaacagcc acaacgtcta tatcatggcc gacaagcaga   1860
agaacggcat caaggtgaac ttcaagatcc gccacaacat cgaggacggc agcgtgcagc   1920
tcgccgacca ctaccagcag aacaccccca tcggcgacgg ccccgtgctg ctgcccgaca   1980
accactacct gagctaccag tccgccctga gcaaagaccc caacgagaag cgcgatcaca   2040
tggtcctgct ggagttcgtg accgccgccg ggatcactct cggcatggac gagctgtaca   2100
agagatctat ctagcgagct cgatcgttca aacatttggc aataaagttt cttaagattg   2160
aatcctgttg ccggtcttgc gatgattatc atataatttc tgttgaatta cgttaagcat   2220
gtaataatta acatgtaatg catgacgtta tttatgagat gggtttttat gattagagtc   2280
ccgcaattat acatttaata cgcgatagaa aacaaaatat agcgcgcaaa ctaggataaa   2340
ttatcgcgcg cggtgtcatc tatgttacta gatcggggat gggggatcca ctagttctag   2400
agcggccgcc accgcggtgg agctccagct tttgttccct ttagtgaggg ttaattgcgc   2460
gcttggcgta atcatggtca tagctgtttc ctgtgtgaaa ttgttatccg ctcacaattc   2520
cacacaacat acgagccgga agcataaagt gtaaagcctg gggtgcctaa tgagtgagct   2580
aactcacatt aattgcgttg cgctcactgc ccgctttcca gtcgggaaac ctgtcgtgcc   2640
agctgcatta atgaatcggc caacgcgcgg ggagaggcgg tttgcgtatt gggcgctctt   2700
ccgcttcctc gctcactgac tcgctgcgct cggtcgttcg gctgcggcga gcggtatcag   2760
ctcactcaaa ggcggtaata cggttatcca cagaatcagg ggataacgca ggaaagaaca   2820
tgtgagcaaa aggccagcaa aaggccagga accgtaaaaa ggccgcgttg ctggcgtttt   2880
tccataggct ccgcccccct gacgagcatc acaaaaatcg acgctcaagt cagaggtggc   2940
gaaacccgac aggactataa agataccagg cgtttccccc tggaagctcc ctcgtgcgct   3000
ctcctgttcc gaccctgccg cttaccggat acctgtccgc ctttctccct tcgggaagcg   3060
tggcgctttc tcatagctca cgctgtaggt atctcagttc ggtgtaggtc gttcgctcca   3120
agctgggctg tgtgcacgaa ccccccgttc agcccgaccg ctgcgcctta tccggtaact   3180
atcgtcttga gtccaacccg gtaagacacg acttatcgcc actggcagca gccactggta   3240
acaggattag cagagcgagg tatgtaggcg gtgctacaga gttcttgaag tggtggccta   3300
actacggcta cactagaagg acagtatttg gtatctgcgc tctgctgaag ccagttacct   3360
tcggaaaaag agttggtagc tcttgatccg gcaaacaaac caccgctggt agcggtggtt   3420
tttttgtttg caagcagcag attacgcgca gaaaaaaagg atctcaagaa gatcctttga   3480
tcttttctac ggggtctgac gctcagtgga acgaaaactc acgttaaggg attttggtca   3540
tgagattatc aaaaaggatc ttcacctaga tccttttaaa ttaaaaatga agttttaaat   3600
caatctaaag tatatatgag taaacttggt ctgacagtta ccaatgctta atcagtgagg   3660
cacctatctc agcgatctgt ctatttcgtt catccatagt tgcctgactc cccgtcgtgt   3720
agataactac gatacgggag ggcttaccat ctggccccag tgctgcaatg ataccgcgag   3780
acccacgctc accggctcca gatttatcag caataaacca gccagccgga agggccgagc   3840
gcagaagtgg tcctgcaact ttatccgcct ccatccagtc tattaattgt tgccgggaag   3900
ctagagtaag tagttcgcca gttaatagtt tgcgcaacgt tgttgccatt gctacaggca   3960
tcgtggtgtc acgctcgtcg tttggtatgg cttcattcag ctccggttcc caacgatcaa   4020
```

```
ggcgagttac atgatccccc atgttgtgca aaaaagcggt tagctccttc ggtcctccga   4080

tcgttgtcag aagtaagttg gccgcagtgt tatcactcat ggttatggca gcactgcata   4140

attctcttac tgtcatgcca tccgtaagat gcttttctgt gactggtgag tactcaacca   4200

agtcattctg agaatagtgt atgcggcgac cgagttgctc ttgcccggcg tcaatacggg   4260

ataataccgc gccacatagc agaactttaa aagtgctcat cattggaaaa cgttcttcgg   4320

ggcgaaaact ctcaaggatc ttaccgctgt tgagatccag ttcgatgtaa cccactcgtg   4380

cacccaactg atcttcagca tcttttactt tcaccagcgt ttctgggtga gcaaaaacag   4440

gaaggcaaaa tgccgcaaaa aagggaataa gggcgacacg gaaatgttga atactcatac   4500

tcttcctttt tcaatattat tgaagcattt atcagggtta ttgtctcatg agcggataca   4560

tatttgaatg tatttagaaa aataaacaaa taggggttcc gcgcacattt ccccgaaaag   4620

tgccac                                                              4626
```

<210> SEQ ID NO 23
<211> LENGTH: 4637
<212> TYPE: DNA
<213> ORGANISM: Artificial Sequence
<220> FEATURE:
<223> OTHER INFORMATION: pSK-SCBV21-EYFP-NOS Vector - deletion E
<220> FEATURE:
<221> NAME/KEY: promoter
<222> LOCATION: (674)..(1394)
<223> OTHER INFORMATION: SCBV21 Promoter deletion E
<220> FEATURE:
<221> NAME/KEY: misc_signal
<222> LOCATION: (718)..(767)
<223> OTHER INFORMATION: Transcription start site TSS1
<220> FEATURE:
<221> NAME/KEY: misc_feature
<222> LOCATION: (1397)..(2125)
<223> OTHER INFORMATION: EYFP coding sequence
<220> FEATURE:
<221> NAME/KEY: terminator
<222> LOCATION: (2135)..(2388)
<223> OTHER INFORMATION: NOS

<400> SEQUENCE: 23

```
ctaaattgta agcgttaata ttttgttaaa attcgcgtta aatttttgtt aaatcagctc     60

atttttaac caataggccg aaatcggcaa aatcccttat aaatcaaaag aatagaccga    120

gatagggttg agtgttgttc cagtttggaa caagagtcca ctattaaaga acgtggactc    180

caacgtcaaa gggcgaaaaa ccgtctatca gggcgatggc ccactacgtg aaccatcacc    240

ctaatcaagt tttttggggt cgaggtgccg taaagcacta aatcggaacc ctaaagggag    300

cccccgattt agagcttgac ggggaaagcc ggcgaacgtg gcgagaaagg aagggaagaa    360

agcgaaagga gcgggcgcta gggcgctggc aagtgtagcg gtcacgctgc gcgtaaccac    420

cacacccgcc gcgcttaatg cgccgctaca gggcgcgtcc cattcgccat tcaggctgcg    480

caactgttgg gaagggcgat cggtgcgggc ctcttcgcta ttacgccagc tggcgaaagg    540

gggatgtgct gcaaggcgat taagttgggt aacgccaggg ttttcccagt cacgacgttg    600

taaaacgacg gccagtgagc gcgcgtaata cgactcacta tagggcgaat tgggtaccgg    660

gccccccctc gagaggcctg catatcagtt cacatctggc acaaaactca acccaagcag    720

gaagttctat aaatgtgcaa tgaacatgtg ccactgctgg tattgggcag atcttttaga    780

agaatatgtc caagaacgaa ttgaagtgtt catgattgag aactttgaca agaaaatggg    840

aattcaagat gtaccaagta catcaaatgc taacattcca ggaaatttta aatctcttgc    900
```

-continued

```
agatttgaag aaggataaag aagctaaagc tgaatatcaa gacatgcttg ataatcatcg    960
ttcaagcatt attgacagac caaggccaac agatgaacac ttcaagcctg gatacatgta   1020
caccgattcc ctgcagaaga tcaaggagga ctacgcaagc ccaagacagg aggaaccacc   1080
atgagaagac attgagttct ggttatgcaa ggaagaagac taccacacag aagacctcaa   1140
tacagaagat gcagttgatc ttactgacgt aagcaatgac gatcagtgga ggcgatcgta   1200
agcaatgatg cacggaagga caattatgga gcgtggagga cccatcaagc actcagaacg   1260
cgaacctcaa ctttcggcgc cagcaccttg tatctttagt tggtgtgtgt ctttttcggc   1320
atctgtgcca ccttaccttt gtcggccacg ttgcctatgc ttagcaccta cgcaagcata   1380
gcgctcggct ggtgccatgg tgagcaaggg cgaggagctg ttcaccgggg tggtgcccat   1440
cctggtcgag ctggacggcg acgtaaacgg ccacaagttc agcgtgtccg gcgagggcga   1500
gggcgatgcc acctacggca agctgaccct gaagttcatc tgcaccaccg gcaagctgcc   1560
cgtgccctgg cccaccctcg tgaccacctt cggctacggc ctgcagtgct tcgcccgcta   1620
ccccgaccac atgaagcagc acgacttctt caagtccgcc atgcccgaag gctacgtcca   1680
ggagcgcacc atcttcttca aggacgacgg caactacaag acccgcgccg aggtgaagtt   1740
cgagggcgac accctggtga accgcatcga gctgaagggc atcgacttca aggaggacgg   1800
caacatcctg gggcacaagc tggagtacaa ctacaacagc cacaacgtct atatcatggc   1860
cgacaagcag aagaacggca tcaaggtgaa cttcaagatc cgccacaaca tcgaggacgg   1920
cagcgtgcag ctcgccgacc actaccagca gaacaccccc atcggcgacg gccccgtgct   1980
gctgcccgac aaccactacc tgagctacca gtccgccctg agcaaagacc ccaacgagaa   2040
gcgcgatcac atggtcctgc tggagttcgt gaccgccgcc gggatcactc tcggcatgga   2100
cgagctgtac aagagatcta tctagcgagc tcgatcgttc aaacatttgg caataaagtt   2160
tcttaagatt gaatcctgtt gccggtcttg cgatgattat catataattt ctgttgaatt   2220
acgttaagca tgtaataatt aacatgtaat gcatgacgtt atttatgaga tgggttttta   2280
tgattagagt cccgcaatta tacatttaat acgcgataga aaacaaaata tagcgcgcaa   2340
actaggataa attatcgcgc gcggtgtcat ctatgttact agatcgggga tgggggatcc   2400
actagttcta gagcggccgc caccgcggtg gagctccagc ttttgttccc tttagtgagg   2460
gttaattgcg cgcttggcgt aatcatggtc atagctgttt cctgtgtgaa attgttatcc   2520
gctcacaatt ccacacaaca tacgagccgg aagcataaag tgtaaagcct ggggtgccta   2580
atgagtgagc taactcacat taattgcgtt gcgctcactg cccgctttcc agtcgggaaa   2640
cctgtcgtgc cagctgcatt aatgaatcgg ccaacgcgcg gggagaggcg gtttgcgtat   2700
tgggcgctct tccgcttcct cgctcactga ctcgctgcgc tcggtcgttc ggctgcggcg   2760
agcggtatca gctcactcaa aggcggtaat acggttatcc acagaatcag gggataacgc   2820
aggaaagaac atgtgagcaa aaggccagca aaaggccagg aaccgtaaaa aggccgcgtt   2880
gctggcgttt ttccataggc tccgcccccc tgacgagcat cacaaaaatc gacgctcaag   2940
tcagaggtgg cgaaacccga caggactata aagataccag gcgtttcccc ctggaagctc   3000
cctcgtgcgc tctcctgttc cgaccctgcc gcttaccgga tacctgtccg cctttctccc   3060
ttcgggaagc gtggcgcttt ctcatagctc acgctgtagg tatctcagtt cggtgtaggt   3120
cgttcgctcc aagctgggct gtgtgcacga accccccgtt cagcccgacc gctgcgcctt   3180
atccggtaac tatcgtcttg agtccaaccc ggtaagacac gacttatcgc cactggcagc   3240
agccactggt aacaggatta gcagagcgag gtatgtaggc ggtgctacag agttcttgaa   3300
```

gtggtggcct aactacggct acactagaag gacagtattt ggtatctgcg ctctgctgaa 3360
gccagttacc ttcggaaaaa gagttggtag ctcttgatcc ggcaaacaaa ccaccgctgg 3420
tagcggtggt ttttttgttt gcaagcagca gattacgcgc agaaaaaaag gatctcaaga 3480
agatcctttg atcttttcta cggggtctga cgctcagtgg aacgaaaact cacgttaagg 3540
gattttggtc atgagattat caaaaaggat cttcacctag atccttttaa attaaaaatg 3600
aagttttaaa tcaatctaaa gtatatatga gtaaacttgg tctgacagtt accaatgctt 3660
aatcagtgag gcacctatct cagcgatctg tctatttcgt tcatccatag ttgcctgact 3720
ccccgtcgtg tagataacta cgatacggga gggcttacca tctggcccca gtgctgcaat 3780
gataccgcga gacccacgct caccggctcc agatttatca gcaataaacc agccagccgg 3840
aagggccgag cgcagaagtg gtcctgcaac tttatccgcc tccatccagt ctattaattg 3900
ttgccgggaa gctagagtaa gtagttcgcc agttaatagt ttgcgcaacg ttgttgccat 3960
tgctacaggc atcgtggtgt cacgctcgtc gtttggtatg gcttcattca gctccggttc 4020
ccaacgatca aggcgagtta catgatcccc catgttgtgc aaaaaagcgg ttagctcctt 4080
cggtcctccg atcgttgtca gaagtaagtt ggccgcagtg ttatcactca tggttatggc 4140
agcactgcat aattctctta ctgtcatgcc atccgtaaga tgcttttctg tgactggtga 4200
gtactcaacc aagtcattct gagaatagtg tatgcggcga ccgagttgct cttgcccggc 4260
gtcaatacgg gataataccg cgccacatag cagaacttta aaagtgctca tcattggaaa 4320
acgttcttcg gggcgaaaac tctcaaggat cttaccgctg ttgagatcca gttcgatgta 4380
acccactcgt gcacccaact gatcttcagc atcttttact ttcaccagcg tttctgggtg 4440
agcaaaaaca ggaaggcaaa atgccgcaaa aaagggaata agggcgacac ggaaatgttg 4500
aatactcata ctcttccttt ttcaatatta ttgaagcatt tatcagggtt attgtctcat 4560
gagcggatac atatttgaat gtatttagaa aaataaacaa ataggggttc cgcgcacatt 4620
tccccgaaaa gtgccac 4637

<210> SEQ ID NO 24
<211> LENGTH: 4542
<212> TYPE: DNA
<213> ORGANISM: Artificial Sequence
<220> FEATURE:
<223> OTHER INFORMATION: pSK-SCBV21-EYFP-NOS Vector - deletion F
<220> FEATURE:
<221> NAME/KEY: promoter
<222> LOCATION: (674)..(1299)
<223> OTHER INFORMATION: SCBV21 Promoter deletion F
<220> FEATURE:
<221> NAME/KEY: misc_feature
<222> LOCATION: (1302)..(2030)
<223> OTHER INFORMATION: EYFP coding sequence
<220> FEATURE:
<221> NAME/KEY: terminator
<222> LOCATION: (2040)..(2293)
<223> OTHER INFORMATION: NOS

<400> SEQUENCE: 24
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtgttgttc cagtttggaa caagagtcca ctattaaaga acgtggactc 180
caacgtcaaa gggcgaaaaa ccgtctatca gggcgatggc ccactacgtg aaccatcacc 240
ctaatcaagt tttttggggt cgaggtgccg taaagcacta aatcggaacc ctaaagggag 300

```
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tgggtaccgg    660
gcccccccctc gagagatctt ttagaagaat atgtccaaga acgaattgaa gtgttcatga    720
ttgagaactt tgacaagaaa atgggaattc aagatgtacc aagtacatca aatgctaaca    780
ttccaggaaa ttttaaatct cttgcagatt tgaagaagga taaagaagct aaagctgaat    840
atcaagacat gcttgataat catcgttcaa gcattattga cagaccaagg ccaacagatg    900
aacacttcaa gcctggatac atgtacaccg attccctgca gaagatcaag gaggactacg    960
caagcccaag acaggaggaa ccaccatgag aagacattga gttctggtta tgcaaggaag   1020
aagactacca cacagaagac ctcaatacag aagatgcagt tgatcttact gacgtaagca   1080
atgacgatca gtggaggcga tcgtaagcaa tgatgcacgg aaggacaatt atggagcgtg   1140
gaggacccat caagcactca gaacgcgaac ctcaactttc ggcgccagca ccttgtatct   1200
ttagttggtg tgtgtctttt tcggcatctg tgccacctta cctttgtcgg ccacgttgcc   1260
tatgcttagc acctacgcaa gcatagcgct cggctggtgc catggtgagc aagggcgagg   1320
agctgttcac cggggtggtg cccatcctgg tcgagctgga cggcgacgta aacggccaca   1380
agttcagcgt gtccggcgag ggcgagggcg atgccaccta cggcaagctg accctgaagt   1440
tcatctgcac caccggcaag ctgcccgtgc cctggcccac cctcgtgacc accttcggct   1500
acggcctgca gtgcttcgcc cgctaccccg accacatgaa gcagcacgac ttcttcaagt   1560
ccgccatgcc cgaaggctac gtccaggagc gcaccatctt cttcaaggac gacggcaact   1620
acaagacccg cgccgaggtg aagttcgagg gcgacaccct ggtgaaccgc atcgagctga   1680
agggcatcga cttcaaggag gacggcaaca tcctggggca caagctggag tacaactaca   1740
acagccacaa cgtctatatc atggccgaca agcagaagaa cggcatcaag gtgaacttca   1800
agatccgcca caacatcgag gacggcagcg tgcagctcgc cgaccactac cagcagaaca   1860
cccccatcgg cgacggcccc gtgctgctgc ccgacaacca ctacctgagc taccagtccg   1920
ccctgagcaa agaccccaac gagaagcgcg atcacatggt cctgctggag ttcgtgaccg   1980
ccgccgggat cactctcggc atggacgagc tgtacaagag atctatctag cgagctcgat   2040
cgttcaaaca tttggcaata aagtttctta agattgaatc ctgttgccgg tcttgcgatg   2100
attatcatat aatttctgtt gaattacgtt aagcatgtaa taattaacat gtaatgcatg   2160
acgttattta tgagatgggt ttttatgatt agagtcccgc aattatacat ttaatacgcg   2220
atagaaaaca aaatatagcg cgcaaactag gataaattat cgcgcgcggt gtcatctatg   2280
ttactagatc ggggatgggg gatccactag ttctagagcg gccgccaccg cggtggagct   2340
ccagcttttg ttccctttag tgagggttaa ttgcgcgctt ggcgtaatca tggtcatagc   2400
tgtttcctgt gtgaaattgt tatccgctca caattccaca caacatacga gccggaagca   2460
taaagtgtaa agcctggggt gcctaatgag tgagctaact cacattaatt gcgttgcgct   2520
cactgcccgc tttccagtcg ggaaacctgt cgtgccagct gcattaatga atcggccaac   2580
gcgcggggag aggcggtttg cgtattgggc gctcttccgc ttcctcgctc actgactcgc   2640
tgcgctcggt cgttcggctg cggcgagcgg tatcagctca ctcaaaggcg gtaatacggt   2700
```

tatccacaga atcaggggat aacgcaggaa agaacatgtg agcaaaaggc cagcaaaagg 2760
ccaggaaccg taaaaaggcc gcgttgctgg cgtttttcca taggctccgc ccccctgacg 2820
agcatcacaa aaatcgacgc tcaagtcaga ggtggcgaaa cccgacagga ctataaagat 2880
accaggcgtt tccccctgga agctccctcg tgcgctctcc tgttccgacc ctgccgctta 2940
ccggatacct gtccgccttt ctcccttcgg gaagcgtggc gctttctcat agctcacgct 3000
gtaggtatct cagttcggtg taggtcgttc gctccaagct gggctgtgtg cacgaacccc 3060
ccgttcagcc cgaccgctgc gccttatccg gtaactatcg tcttgagtcc aacccggtaa 3120
gacacgactt atcgccactg gcagcagcca ctggtaacag gattagcaga gcgaggtatg 3180
taggcggtgc tacagagttc ttgaagtggt ggcctaacta cggctacact agaaggacag 3240
tatttggtat ctgcgctctg ctgaagccag ttaccttcgg aaaaagagtt ggtagctctt 3300
gatccggcaa acaaaccacc gctggtagcg gtggtttttt tgtttgcaag cagcagatta 3360
cgcgcagaaa aaaaggatct caagaagatc ctttgatctt ttctacgggg tctgacgctc 3420
agtggaacga aaactcacgt taagggattt tggtcatgag attatcaaaa aggatcttca 3480
cctagatcct tttaaattaa aaatgaagtt ttaaatcaat ctaaagtata tatgagtaaa 3540
cttggtctga cagttaccaa tgcttaatca gtgaggcacc tatctcagcg atctgtctat 3600
ttcgttcatc catagttgcc tgactccccg tcgtgtagat aactacgata cgggagggct 3660
taccatctgg ccccagtgct gcaatgatac cgcgagaccc acgctcaccg gctccagatt 3720
tatcagcaat aaaccagcca gccggaaggg ccgagcgcag aagtggtcct gcaactttat 3780
ccgcctccat ccagtctatt aattgttgcc gggaagctag agtaagtagt tcgccagtta 3840
atagtttgcg caacgttgtt gccattgcta caggcatcgt ggtgtcacgc tcgtcgtttg 3900
gtatggcttc attcagctcc ggttcccaac gatcaaggcg agttacatga tcccccatgt 3960
tgtgcaaaaa agcggttagc tccttcggtc ctccgatcgt tgtcagaagt aagttggccg 4020
cagtgttatc actcatggtt atggcagcac tgcataattc tcttactgtc atgccatccg 4080
taagatgctt ttctgtgact ggtgagtact caaccaagtc attctgagaa tagtgtatgc 4140
ggcgaccgag ttgctcttgc ccggcgtcaa tacgggataa taccgcgcca catagcagaa 4200
ctttaaaagt gctcatcatt ggaaaacgtt cttcggggcg aaaactctca aggatcttac 4260
cgctgttgag atccagttcg atgtaaccca ctcgtgcacc caactgatct tcagcatctt 4320
ttactttcac cagcgtttct gggtgagcaa aaacaggaag gcaaaatgcc gcaaaaaagg 4380
gaataagggc gacacggaaa tgttgaatac tcatactctt cctttttcaa tattattgaa 4440
gcatttatca gggttattgt ctcatgagcg gatacatatt tgaatgtatt tagaaaaata 4500
aacaaatagg ggttccgcgc acatttcccc gaaaagtgcc ac 4542

<210> SEQ ID NO 25
<211> LENGTH: 1018
<212> TYPE: DNA
<213> ORGANISM: Sugarcane bacilliform virus

<400> SEQUENCE: 25
gaagaacagc atgctgaaca tctgtggaag atgctacaga tatgcaagaa gaatgggtta 60
atcttaagcc cttccaagta taaattggag taaaaagagt tgactttctt ggttcaacaa 120
ttggagataa tcagttagct gttcaagaac atatagtctc caagatagct gattttgatg 180
aagaacgtct caagaccaag gaaggactga aaagctggct ggcaacactc aattatgcca 240
gaaatcacat caaggatatg ggaaaactcc ttggaccctt atatcctaaa acttcagaaa 300
agggagcaaa aggattaaat tctgaagatt ggaaattaat cagcagaatc aagacaatgg 360
tcagaaatct gccaaatctg actattccac cagaggatgc atatattatc attgaaacag 420
atgcttgtgc aactggttgg ggtgcagttt gcaaatggaa gaaatccaag gcagacccaa 480
gaagctccga gctcatatgt cgatatgcaa gtgggaaatt tgacaaacca aaagggacat 540
gtgatgcaga aatctatgga gtaatgaatg ggctggagaa aatgagactc ttttatcttg 600
ataaaaggga aatcactgtg aggacagata gtgccgcaat agagaggttc tacaacaaga 660
gtgttgaaca taaaccctca gaaatccgtt ggataaggtt tatggactat atcactggag 720
caggaccaaa gattgtgatt gagcatatca aaggaaaaca caatggtctg gcagatatcc 780
tctcaagatt gaaagcaaaa ctggcagaat caccttcaga agaagtggtt ttacttgcga 840
aagctttaaa ggaagttgca tactatcctg aacacccgca agtgccaaaa ctaattgaat 900
ggggaaagca aattcttgat ccatttccca agttcaagaa ggacatgttt gaaaaaactg 960
aacacatcat gatggctagt caagagccta cactgctttg tggatgtaga aggcatgg 1018

<210> SEQ ID NO 26
<211> LENGTH: 811
<212> TYPE: DNA
<213> ORGANISM: Sugarcane bacilliform virus

<400> SEQUENCE: 26
aggcctgcat atcagttcac atctggcaca aaactcaacc caagcaggaa gttctataaa 60
tgtgcaatga acatgtgcca ctgctggtat tgggcagatc ttttagaaga atatgtccaa 120
gaacgaattg aagtgttcat gattgagaac tttgacaaga aaatgggaat tcaagatgta 180
ccaagtacat caaatgctaa cattccagga aattttaaat ctcttgcaga tttgaagaag 240
gataaagaag ctaaagctga atatcaagac atgcttgata atcatcgttc aagcattatt 300
gacagaccaa ggccaacaga tgaacacttc aagcctggat acatgtacac cgattccctg 360
cagaagatca aggaggacta cgcaagccca agacaggagg aaccaccatg agaagacatt 420
gagttctggt tatgcaagga agaagactac cacacagaag acctcaatac agaagatgca 480
gttgatctta ctgacgtaag caatgacgat cagtggaggc gatcgtaagc aatgatgcac 540
ggaaggacaa ttatggagcg tggaggaccc atcaagcact cagaacgcga acctcaactt 600
tcggcgccag caccttgtat ctttagttgg tgtgtgtctt tttcggcatc tgtgccacct 660
tacctttgtc ggccacgttg cctatgctta gcacctacgc aagcatagcg ctcggctggt 720
gtgtgttccc tctgcctata taaggcatgg ttgtaagact cttacactca tcggtagttc 780
accacatgat catttgagca agtttccatg g 811

<210> SEQ ID NO 27
<211> LENGTH: 716
<212> TYPE: DNA
<213> ORGANISM: Sugarcane bacilliform virus

<400> SEQUENCE: 27
agatctttta gaagaatatg tccaagaacg aattgaagtg ttcatgattg agaactttga 60
caagaaaatg ggaattcaag atgtaccaag tacatcaaat gctaacattc caggaaattt 120
taaatctctt gcagatttga agaaggataa agaagctaaa gctgaatatc aagacatgct 180
tgataatcat cgttcaagca ttattgacag accaaggcca acagatgaac acttcaagcc 240
tggatacatg tacaccgatt ccctgcagaa gatcaaggag gactacgcaa gcccaagaca 300
ggaggaacca ccatgagaag acattgagtt ctggttatgc aaggaagaag actaccacac 360
agaagacctc aatacagaag atgcagttga tcttactgac gtaagcaatg acgatcagtg 420
gaggcgatcg taagcaatga tgcacggaag gacaattatg gagcgtggag gacccatcaa 480
gcactcagaa cgcgaacctc aactttcggc gccagcacct tgtatcttta gttggtgtgt 540
gtctttttcg gcatctgtgc caccttacct ttgtcggcca cgttgcctat gcttagcacc 600
tacgcaagca tagcgctcgg ctggtgtgtg ttccctctgc ctatataagg catggttgta 660
agactcttac actcatcggt agttcaccac atgatcattt gagcaagttt ccatgg 716

<210> SEQ ID NO 28
<211> LENGTH: 727
<212> TYPE: DNA
<213> ORGANISM: Sugarcane bacilliform virus

<400> SEQUENCE: 28
aggcctgcat atcagttcac atctggcaca aaactcaacc caagcaggaa gttctataaa 60
tgtgcaatga acatgtgcca ctgctggtat tgggcagatc ttttagaaga atatgtccaa 120
gaacgaattg aagtgttcat gattgagaac tttgacaaga aaatgggaat tcaagatgta 180
ccaagtacat caaatgctaa cattccagga aattttaaat ctcttgcaga tttgaagaag 240
gataaagaag ctaaagctga atatcaagac atgcttgata atcatcgttc aagcattatt 300
gacagaccaa ggccaacaga tgaacacttc aagcctggat acatgtacac cgattccctg 360
cagaagatca aggaggacta cgcaagccca agacaggagg aaccaccatg agaagacatt 420
gagttctggt tatgcaagga agaagactac cacacagaag acctcaatac agaagatgca 480
gttgatctta ctgacgtaag caatgacgat cagtggaggc gatcgtaagc aatgatgcac 540
ggaaggacaa ttatggagcg tggaggaccc atcaagcact cagaacgcga acctcaactt 600
tcggcgccag caccttgtat ctttagttgg tgtgtgtctt tttcggcatc tgtgccacct 660
tacctttgtc ggccacgttg cctatgctta gcacctacgc aagcatagcg ctcggctggt 720
gccatgg 727

<210> SEQ ID NO 29
<211> LENGTH: 632
<212> TYPE: DNA
<213> ORGANISM: Sugarcane bacilliform virus

<400> SEQUENCE: 29
agatctttta gaagaatatg tccaagaacg aattgaagtg ttcatgattg agaactttga 60
caagaaaatg ggaattcaag atgtaccaag tacatcaaat gctaacattc caggaaattt 120
taaatctctt gcagatttga agaaggataa agaagctaaa gctgaatatc aagacatgct 180
tgataatcat cgttcaagca ttattgacag accaaggcca acagatgaac acttcaagcc 240
tggatacatg tacaccgatt ccctgcagaa gatcaaggag gactacgcaa gcccaagaca 300
ggaggaacca ccatgagaag acattgagtt ctggttatgc aaggaagaag actaccacac 360
agaagacctc aatacagaag atgcagttga tcttactgac gtaagcaatg acgatcagtg 420
gaggcgatcg taagcaatga tgcacggaag gacaattatg gagcgtggag gacccatcaa 480
gcactcagaa cgcgaacctc aactttcggc gccagcacct tgtatcttta gttggtgtgt 540
gtctttttcg gcatctgtgc caccttacct ttgtcggcca cgttgcctat gcttagcacc 600
tacgcaagca tagcgctcgg ctggtgccat gg 632

<210> SEQ ID NO 30
<211> LENGTH: 50
<212> TYPE: DNA
<213> ORGANISM: Sugarcane bacilliform virus
<220> FEATURE:
<221> NAME/KEY: misc_signal
<222> LOCATION: (41)..(41)
<223> OTHER INFORMATION: Transcription start site

<400> SEQUENCE: 30
caggaagttc tataaatgtg caatgaacat gtgccactgc tggtattggg 50

<210> SEQ ID NO 31
<211> LENGTH: 50
<212> TYPE: DNA
<213> ORGANISM: Sugarcane bacilliform virus
<220> FEATURE:
<221> NAME/KEY: misc_signal
<222> LOCATION: (41)..(41)
<223> OTHER INFORMATION: Transcription start site

<400> SEQUENCE: 31
tccctctgcc tatataaggc atggttgtaa gactcttaca ctcatcggta 50

<210> SEQ ID NO 32
<211> LENGTH: 853
<212> TYPE: DNA
<213> ORGANISM: Artificial Sequence
<220> FEATURE:
<223> OTHER INFORMATION: SCBV21 Promoter with TSS1 and TSS2
<220> FEATURE:
<221> NAME/KEY: misc_signal
<222> LOCATION: (45)..(94)
<223> OTHER INFORMATION: Transcription start site TSS1
<220> FEATURE:
<221> NAME/KEY: misc_signal
<222> LOCATION: (727)..(776)
<223> OTHER INFORMATION: Transcription start site TSS2
<220> FEATURE:
<221> NAME/KEY: misc_feature
<222> LOCATION: (806)..(845)
<223> OTHER INFORMATION: n is a, c, g, t, or absent
<220> FEATURE:
<221> NAME/KEY: misc_feature
<222> LOCATION: (846)..(849)
<223> OTHER INFORMATION: n is a, c, g, or t
<220> FEATURE:
<221> NAME/KEY: misc_feature
<222> LOCATION: (850)..(852)
<223> OTHER INFORMATION: Start codon
<220> FEATURE:
<221> NAME/KEY: misc_feature
<222> LOCATION: (853)..(853)
<223> OTHER INFORMATION: n is g or t

<400> SEQUENCE: 32
aggcctgcat atcagttcac atctggcaca aaactcaacc caagcaggaa gttctataaa 60
tgtgcaatga acatgtgcca ctgctggtat tgggcagatc ttttagaaga atatgtccaa 120
gaacgaattg aagtgttcat gattgagaac tttgacaaga aaatgggaat tcaagatgta 180
ccaagtacat caaatgctaa cattccagga aattttaaat ctcttgcaga tttgaagaag 240
gataaagaag ctaaagctga atatcaagac atgcttgata atcatcgttc aagcattatt 300
gacagaccaa ggccaacaga tgaacacttc aagcctggat acatgtacac cgattccctg 360
cagaagatca aggaggacta cgcaagccca agacaggagg aaccaccatg agaagacatt 420
gagttctggt tatgcaagga agaagactac cacacagaag acctcaatac agaagatgca 480
gttgatctta ctgacgtaag caatgacgat cagtggaggc gatcgtaagc aatgatgcac 540
ggaaggacaa ttatggagcg tggaggaccc atcaagcact cagaacgcga acctcaactt 600
tcggcgccag caccttgtat ctttagttgg tgtgtgtctt tttcggcatc tgtgccacct 660
tacctttgtc ggccacgttg cctatgctta gcacctacgc aagcatagcg ctcggctggt 720
gtgtgttccc tctgcctata taaggcatgg ttgtaagact cttacactca tcggtagttc 780
accacatgat catttgagca agtttnnnnn nnnnnnnnnn nnnnnnnnnn nnnnnnnnnn 840
nnnnnnnnna tgn 853

<210> SEQ ID NO 33
<211> LENGTH: 758
<212> TYPE: DNA
<213> ORGANISM: Sugarcane bacilliform virus
<220> FEATURE:
<221> NAME/KEY: misc_signal
<222> LOCATION: (632)..(681)
<223> OTHER INFORMATION: Transcription start site TSS2
<220> FEATURE:
<221> NAME/KEY: misc_feature
<222> LOCATION: (711)..(715)
<223> OTHER INFORMATION: n is a, t, c, or g
<220> FEATURE:
<221> NAME/KEY: misc_feature
<222> LOCATION: (716)..(718)
<223> OTHER INFORMATION: Start codon
<220> FEATURE:
<221> NAME/KEY: misc_feature
<222> LOCATION: (719)..(719)
<223> OTHER INFORMATION: n is g or t
<220> FEATURE:
<221> NAME/KEY: misc_feature
<222> LOCATION: (720)..(758)
<223> OTHER INFORMATION: n is a, t, c, g or absent

<400> SEQUENCE: 33
agatctttta gaagaatatg tccaagaacg aattgaagtg ttcatgattg agaactttga 60
caagaaaatg ggaattcaag atgtaccaag tacatcaaat gctaacattc caggaaattt 120
taaatctctt gcagatttga agaaggataa agaagctaaa gctgaatatc aagacatgct 180
tgataatcat cgttcaagca ttattgacag accaaggcca acagatgaac acttcaagcc 240
tggatacatg tacaccgatt ccctgcagaa gatcaaggag gactacgcaa gcccaagaca 300
ggaggaacca ccatgagaag acattgagtt ctggttatgc aaggaagaag actaccacac 360
agaagacctc aatacagaag atgcagttga tcttactgac gtaagcaatg acgatcagtg 420
gaggcgatcg taagcaatga tgcacggaag gacaattatg gagcgtggag gacccatcaa 480
gcactcagaa cgcgaacctc aactttcggc gccagcacct tgtatcttta gttggtgtgt 540
gtctttttcg gcatctgtgc caccttacct ttgtcggcca cgttgcctat gcttagcacc 600
tacgcaagca tagcgctcgg ctggtgtgtg ttccctctgc ctatataagg catggttgta 660
agactcttac actcatcggt agttcaccac atgatcattt gagcaagttt nnnnnatgnn 720
nnnnnnnnnn nnnnnnnnnn nnnnnnnnnn nnnnnnnn 758

<210> SEQ ID NO 34
<211> LENGTH: 33
<212> TYPE: DNA
<213> ORGANISM: Artificial Sequence
<220> FEATURE:
<223> OTHER INFORMATION: Forward PCR primer F1

<400> SEQUENCE: 34
ttactcgagg cctgcatatc agttcacatc tgg 33

<210> SEQ ID NO 35
<211> LENGTH: 37
<212> TYPE: DNA
<213> ORGANISM: Artificial Sequence
<220> FEATURE:
<223> OTHER INFORMATION: Forward PCR primer F2

<400> SEQUENCE: 35
ttactcgaga tcttttagaa gaatatgtcc aagaacg 37

<210> SEQ ID NO 36
<211> LENGTH: 42
<212> TYPE: DNA
<213> ORGANISM: Artificial Sequence
<220> FEATURE:
<223> OTHER INFORMATION: Reverse PCR primer R1

<400> SEQUENCE: 36
ttaccatgga aacttgctca aatgatcatg tggtgaacta cc 42

<210> SEQ ID NO 37
<211> LENGTH: 36
<212> TYPE: DNA
<213> ORGANISM: Artificial Sequence
<220> FEATURE:
<223> OTHER INFORMATION: Reverse PCR primer R2

<400> SEQUENCE: 37
ttaccatggc accagccgag cgctatgctt gcgtag 36

<210> SEQ ID NO 38
<211> LENGTH: 2855
<212> TYPE: DNA
<213> ORGANISM: Artificial Sequence
<220> FEATURE:
<223> OTHER INFORMATION: Expression cassette SCBV21-BvLz(m)-35S NOS
<220> FEATURE:
<221> NAME/KEY: promoter
<222> LOCATION: (1)..(1816)
<223> OTHER INFORMATION: SCBV21 Promoter
<220> FEATURE:
<221> NAME/KEY: misc_feature
<222> LOCATION: (1857)..(2300)
<223> OTHER INFORMATION: BvLz(m) coding sequence
<220> FEATURE:
<221> NAME/KEY: terminator
<222> LOCATION: (2375)..(2580)
<223> OTHER INFORMATION: 35S
<220> FEATURE:
<221> NAME/KEY: terminator
<222> LOCATION: (2603)..(2855)
<223> OTHER INFORMATION: NOS

<400> SEQUENCE: 38
gaagaacagc atgctgaaca tctgtggaag atgctacaga tatgcaagaa gaatgggtta 60
atcttaagcc cttccaagta taaattggag taaaaagagt tgactttctt ggttcaacaa 120
ttggagataa tcagttagct gttcaagaac atatagtctc caagatagct gattttgatg 180
aagaacgtct caagaccaag gaaggactga aaagctggct ggcaacactc aattatgcca 240
gaaatcacat caaggatatg ggaaaactcc ttggaccctt atatcctaaa acttcagaaa 300
agggagcaaa aggattaaat tctgaagatt ggaaattaat cagcagaatc aagacaatgg 360
tcagaaatct gccaaatctg actattccac cagaggatgc atatattatc attgaaacag 420
atgcttgtgc aactggttgg ggtgcagttt gcaaatggaa gaaatccaag gcagacccaa 480
gaagctccga gctcatatgt cgatatgcaa gtgggaaatt tgacaaacca aaagggacat 540

```
gtgatgcaga aatctatgga gtaatgaatg ggctggagaa aatgagactc ttttatcttg    600
ataaaaggga aatcactgtg aggacagata gtgccgcaat agagaggttc tacaacaaga    660
gtgttgaaca taaaccctca gaaatccgtt ggataaggtt tatggactat atcactggag    720
caggaccaaa gattgtgatt gagcatatca aaggaaaaca caatggtctg gcagatatcc    780
tctcaagatt gaaagcaaaa ctggcagaat caccttcaga agaagtggtt ttacttgcga    840
aagctttaaa ggaagttgca tactatcctg aacacccgca agtgccaaaa ctaattgaat    900
ggggaaagca aattcttgat ccatttccca agttcaagaa ggacatgttt gaaaaaactg    960
aacacatcat gatggctagt caagagccta cactgctttg tggatgtaga aggcctgcat   1020
atcagttcac atctggcaca aaactcaacc caagcaggaa gttctataaa tgtgcaatga   1080
acatgtgcca ctgctggtat tgggcagatc ttttagaaga atatgtccaa gaacgaattg   1140
aagtgttcat gattgagaac tttgacaaga aaatgggaat tcaagatgta ccaagtacat   1200
caaatgctaa cattccagga aattttaaat ctcttgcaga tttgaagaag gataaagaag   1260
ctaaagctga atatcaagac atgcttgata atcatcgttc aagcattatt gacagaccaa   1320
ggccaacaga tgaacacttc aagcctggat acatgtacac cgattccctg cagaagatca   1380
aggaggacta cgcaagccca agacaggagg aaccaccatg agaagacatt gagttctggt   1440
tatgcaagga agaagactac cacacagaag acctcaatac agaagatgca gttgatctta   1500
ctgacgtaag caatgacgat cagtggaggc gatcgtaagc aatgatgcac ggaaggacaa   1560
ttatggagcg tggaggaccc atcaagcact cagaacgcga acctcaactt tcggcgccag   1620
caccttgtat ctttagttgg tgtgtgtctt tttcggcatc tgtgccacct tacctttgtc   1680
ggccacgttg cctatgctta gcacctacgc aagcatagcg ctcggctggt gtgtgttccc   1740
tctgcctata taaggcatgg ttgtaagact cttacactca tcggtagttc accacatgat   1800
catttgagca agtttgaatc gaattcccgc ggccgccatg catctcggat ccaaacatgg   1860
cggccctggt gatcctgggc ttcctgttcc tgtccgtggc tgtgcagggc aaggtgttcg   1920
aaaggtgcga actggctagg accctgaaga agctgggcct ggatggctac aagggcgtgt   1980
ccctggctaa ctggctgtgc ctgaccaagt gggaatcctc ctacaacacc aaggctacca   2040
actacaaccc atcctccgaa tccaccgact acggcatctt ccagatcaac tccaagtggt   2100
ggtgcaacga tggcaagacc ccaaacgctg tggatggctg ccacgtgtcc tgctccgagc   2160
tgatggaaaa cgatatcgct aaggctgtgg cttgcgctaa gcacatcgtg tccgaacagg   2220
gcatcaccgc ctgggtggct tggaagtccc actgcaggga tcacgatgtg tcctcctacg   2280
tggaaggctg caccctgtga ttcgaattcg gatccccccg ggctgcagga attcgatatc   2340
aagcttatcg ataccgtcga ggggtccgca aaaatcacca gtctctctct acaaatctat   2400
ctctctctat ttttctccag aataatgtgt gagtagttcc cagataaggg aattagggtt   2460
cttatagggt ttcgctcatg tgttgagcat ataagaaacc cttagtatgt atttgtattt   2520
gtaaaatact tctatcaata aaatttctaa ttcctaaaac caaaatccag tgacctgcag   2580
gggccgctcg acgaatttcc ccgatcgttc aaacatttgg caataaagtt tcttaagatt   2640
gaatcctgtt gccggtcttg cgatgattat catataattt ctgttgaatt acgttaagca   2700
tgtaataatt aacatgtaat gcatgacgtt atttatgaga tgggttttta tgattagagt   2760
cccgcaatta tacatttaat acgcgataga aaacaaaata tagcgcgcaa actaggataa   2820
attatcgcgc gcggtgtcat ctatgttact agatc                              2855
```

<210> SEQ ID NO 39
<211> LENGTH: 2745
<212> TYPE: DNA
<213> ORGANISM: Artificial Sequence
<220> FEATURE:
<223> OTHER INFORMATION: Expression cassette MUbi(no hse)-BvLz(m)-35S
<220> FEATURE:
<221> NAME/KEY: promoter
<222> LOCATION: (1)..(1977)
<223> OTHER INFORMATION: MUbi (no hse) Promoter
<220> FEATURE:
<221> NAME/KEY: misc_feature
<222> LOCATION: (668)..(668)
<223> OTHER INFORMATION: n is a, c, g, or t
<220> FEATURE:
<221> NAME/KEY: misc_feature
<222> LOCATION: (671)..(671)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (1248)..(1248)
<223> OTHER INFORMATION: n is a, c, g, or t
<220> FEATURE:
<221> NAME/KEY: misc_feature
<222> LOCATION: (1315)..(1315)
<223> OTHER INFORMATION: n is a, c, g, or t
<220> FEATURE:
<221> NAME/KEY: misc_feature
<222> LOCATION: (1542)..(1542)
<223> OTHER INFORMATION: n is a, c, g, or t
<220> FEATURE:
<221> NAME/KEY: misc_feature
<222> LOCATION: (2032)..(2475)
<223> OTHER INFORMATION: BvLz (m) coding sequence
<220> FEATURE:
<221> NAME/KEY: terminator
<222> LOCATION: (2549)..(2745)
<223> OTHER INFORMATION: 35S

<400> SEQUENCE: 39
aagcttgcat gcctgcagtg cagcgtgacc cggtcgtgcc cctctctaga gataatgagc 60
attgcatgtc taagttataa aaaattacca catatttttt ttgtcacact tgtttgaagt 120
gcagtttatc tatctttata catatattta aactttactc tacgaataat ataatctata 180
gtactacaat aatatcagtg ttttagagaa tcatataaat gaacagttag acatggtcta 240
aaggacaatt gagtattttg acaacaggac tctacagttt tatcttttta gtgtgcatgt 300
gttctccttt ttttttgcaa atagcttcac ctatataata cttcatccat tttattagta 360
catccattta gggtttaggg ttaatggttt ttatagacta atttttttag tacatctatt 420
ttattctatt ttagcctcta aattaagaaa actaaaactc tattttagtt tttttattta 480
ataatttaga tataaaatag aataaaataa agtgactaaa aattaaacaa ataccettta 540 agaaattaaa aaaactaagg aaacattttt cttgtttcga gtagataatg ccagcctgtt 600
aaacgccgtc gacgagtcta acggacacca accagcgaac cagcagcgtc gcgtcgggcc 660
aagcgaanca nacggcacgg natctctgtc gctgcctcca ccgttggact tgctccgctg 720
tcggcatcca gaaattgcgt ggcggcaggc agacgtgagc cggcacgagg cggcctcctc 780
ctcctctcac ggcacggcag ctacggggga ttcctttccc accgctcctt cgctttccct 840
tcctcgcccg ccgtaataaa tagacacccc ctccacaccc tctttcccca acctcgtgtt 900
gttcggagcg cacacacaca caaccagatc tcccccaaat ccacccgtcg gcacctccgc 960
ttcaaggtac gccgctcgtc ctcccccccc ccccctctct accttctcta gatcggcgtt 1020
ccggtccatg gttagggccc ggtagttcta cttctgttca tgtttgtgtt agatccgtgt 1080
ttgtgttaga tccgtgctgc tagcgttcgt acacggatgc gacctgtacg tcagacacgt 1140
tctgattgct aacttgccag tgtttctctt tggggaatcc tgggatggct ctagccgttc 1200
cgcagacggg atcgatttca tgattttttt tgtttcgttg catagggntt ggtttgccct 1260
tttcctttat ttcaatatat gccgtgccac ttgtttgtcg ggtcatcttt tcatngcttt 1320
tttttgtctt ggttgtgatg atgtggtctg gttgggcggt cgttctagat cggagtagaa 1380
ttctgtttca aactacctgg tggatttatt aattttggat ctgtatgtgt gtgccataca 1440
tattcatagt tacgaattga agatgatgga tggaaatatc gatctaggat aggtatacat 1500
gttgatgcgg gttttactga tgcatataca gagatgcttt tnttcgcttg gttgtgatga 1560
tgtggtgtgg ttgggcggtc gttcattcgt tctagatcgg agtagaatac tgtttcaaac 1620
tacctggtgt atttattaat tttggaactg tatgtgtgtg tcatacatct tcatagttac 1680
gagtttaaga tggatggaaa tatcgatcta ggataggtat acatgttgat gtgggtttta 1740
ctgatgcata tacatgatgg catatgcagc atctattcat atgctctaac cttgagtacc 1800
tatctattat aataaacaag tatgttttat aattattttg atcttgatat acttggatga 1860
tggcatatgc agcagctata tgtggatttt tttagccctg ccttcatacg ctatttattt 1920
gcttggtact gtttcttttg tcgatgctca ccctgttgtt tggtgttact tctgcaggtc 1980
gactctagag gatctgatat ctgatcagaa gacaccatct cggatccaaa catggcggcc 2040
ctggtgatcc tgggcttcct gttcctgtcc gtggctgtgc agggcaaggt gttcgaaagg 2100
tgcgaactgg ctaggaccct gaagaagctg ggcctggatg gctacaaggg cgtgtccctg 2160
gctaactggc tgtgcctgac caagtgggaa tcctcctaca acaccaaggc taccaactac 2220
aacccatcct ccgaatccac cgactacggc atcttccaga tcaactccaa gtggtggtgc 2280
aacgatggca agaccccaaa cgctgtggat ggctgccacg tgtcctgctc cgagctgatg 2340
gaaaacgata tcgctaaggc tgtggcttgc gctaagcaca tcgtgtccga acagggcatc 2400
accgcctggg tggcttggaa gtcccactgc agggatcacg atgtgtcctc ctacgtggaa 2460
ggctgcaccc tgtgattcga attcggatcc cccgggctgc aggaattcga tatcaagctt 2520
atcgataccg tcgaggggtc cgcaaaaatc accagtctct ctctacaaat ctatctctct 2580
ctatttttct ccagaataat gtgtgagtag ttcccagata agggaattag ggttcttata 2640
gggtttcgct catgtgttga gcatataaga aacccttagt atgtatttgt atttgtaaaa 2700
tacttctatc aataaaattt ctaattccta aaaccaaaat ccagt 2745

<210> SEQ ID NO 40
<211> LENGTH: 2977
<212> TYPE: DNA
<213> ORGANISM: Artificial Sequence
<220> FEATURE:
<223> OTHER INFORMATION: Expression cassette MUbi(no hse)-BvLz(m)-3'SrMV UTR-35S
<220> FEATURE:
<221> NAME/KEY: promoter
<222> LOCATION: (1)..(1977)
<223> OTHER INFORMATION: MUbi (no hse) Promoter
<220> FEATURE:
<221> NAME/KEY: misc_feature
<222> LOCATION: (668)..(668)
<223> OTHER INFORMATION: n is a, c, g, or t
<220> FEATURE:
<221> NAME/KEY: misc_feature
<222> LOCATION: (671)..(671)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (1248)..(1248)
<223> OTHER INFORMATION: n is a, c, g, or t
<220> FEATURE:
<221> NAME/KEY: misc_feature
<222> LOCATION: (1315)..(1315)
<223> OTHER INFORMATION: n is a, c, g, or t
<220> FEATURE:
<221> NAME/KEY: misc_feature
<222> LOCATION: (1542)..(1542)
<223> OTHER INFORMATION: n is a, c, g, or t
<220> FEATURE:
<221> NAME/KEY: misc_feature
<222> LOCATION: (2032)..(2475)
<223> OTHER INFORMATION: BvLz (m) coding sequence
<220> FEATURE:
<221> NAME/KEY: misc_feature
<222> LOCATION: (2494)..(2720)
<223> OTHER INFORMATION: 3' Untranslated Region of SrMV
<220> FEATURE:
<221> NAME/KEY: terminator
<222> LOCATION: (2781)..(2977)
<223> OTHER INFORMATION: 35S terminator

<400> SEQUENCE: 40
aagcttgcat gcctgcagtg cagcgtgacc cggtcgtgcc cctctctaga gataatgagc 60
attgcatgtc taagttataa aaaattacca catatttttt ttgtcacact tgtttgaagt 120
gcagtttatc tatctttata catatattta aactttactc tacgaataat ataatctata 180
gtactacaat aatatcagtg ttttagagaa tcatataaat gaacagttag acatggtcta 240
aaggacaatt gagtattttg acaacaggac tctacagttt tatctttttta gtgtgcatgt 300 gttctccttt ttttttgcaa atagcttcac ctatataata cttcatccat tttattagta 360
catccattta gggtttaggg ttaatggttt ttatagacta atttttttag tacatctatt 420
ttattctatt ttagcctcta aattaagaaa actaaaactc tattttagtt tttttattta 480
ataatttaga tataaaatag aataaaataa agtgactaaa aattaaacaa ataccctttta 540 agaaattaaa aaaactaagg aaacattttt cttgtttcga gtagataatg ccagcctgtt 600
aaacgccgtc gacgagtcta acggacacca accagcgaac cagcagcgtc gcgtcgggcc 660
aagcgaanca nacggcacgg natctctgtc gctgcctcca ccgttggact tgctccgctg 720
tcggcatcca gaaattgcgt ggcggcaggc agacgtgagc cggcacgagg cggcctcctc 780
ctcctctcac ggcacggcag ctacgggga ttcctttccc accgctcctt cgctttccct 840
tcctcgcccg ccgtaataaa tagacacccc ctccacaccc tctttcccca acctcgtgtt 900
gttcggagcg cacacacaca caaccagatc tcccccaaat ccacccgtcg gcacctccgc 960
ttcaaggtac gccgctcgtc ctcccccccc cccctctct accttctcta gatcggcgtt 1020
ccggtccatg gttagggccc ggtagttcta cttctgttca tgtttgtgtt agatccgtgt 1080
ttgtgttaga tccgtgctgc tagcgttcgt acacggatgc gacctgtacg tcagacacgt 1140
tctgattgct aacttgccag tgtttctctt tggggaatcc tgggatggct ctagccgttc 1200
cgcagacggg atcgatttca tgattttttt tgtttcgttg catagggntt ggtttgccct 1260
tttcctttat ttcaatatat gccgtgccac ttgtttgtcg ggtcatcttt tcatngcttt 1320
tttttgtctt ggttgtgatg atgtggtctg gttgggcggt cgttctagat cggagtagaa 1380
ttctgtttca aactacctgg tggatttatt aattttggat ctgtatgtgt gtgccataca 1440

```
tattcatagt tacgaattga agatgatgga tggaaatatc gatctaggat aggtatacat   1500

gttgatgcgg gttttactga tgcatataca gagatgcttt tnttcgcttg gttgtgatga   1560

tgtggtgtgg ttgggcggtc gttcattcgt tctagatcgg agtagaatac tgtttcaaac   1620

tacctggtgt atttattaat tttggaactg tatgtgtgtg tcatacatct tcatagttac   1680

gagtttaaga tggatggaaa tatcgatcta ggataggtat acatgttgat gtgggtttta   1740

ctgatgcata tacatgatgg catatgcagc atctattcat atgctctaac cttgagtacc   1800

tatctattat aataaacaag tatgttttat aattattttg atcttgatat acttggatga   1860

tggcatatgc agcagctata tgtggatttt tttagccctg ccttcatacg ctatttattt   1920

gcttggtact gtttcttttg tcgatgctca ccctgttgtt tggtgttact tctgcaggtc   1980

gactctagag gatctgatat ctgatcagaa gacaccatct cggatccaaa catggcggcc   2040

ctggtgatcc tgggcttcct gttcctgtcc gtggctgtgc agggcaaggt gttcgaaagg   2100

tgcgaactgg ctaggaccct gaagaagctg ggcctggatg gctacaaggg cgtgtccctg   2160

gctaactggc tgtgcctgac caagtgggaa tcctcctaca acaccaaggc taccaactac   2220

aacccatcct ccgaatccac cgactacggc atcttccaga tcaactccaa gtggtggtgc   2280

aacgatggca agaccccaaa cgctgtggat ggctgccacg tgtcctgctc cgagctgatg   2340

gaaaacgata tcgctaaggc tgtggcttgc gctaagcaca tcgtgtccga acagggcatc   2400

accgcctggg tggcttggaa gtcccactgc agggatcacg atgtgtcctc ctacgtggaa   2460

ggctgcaccc tgtgattcga attcggatcc cccgatcttc attgcagttt ttaaagtatt   2520

ttatatattt actatttcag tgagggtctc cctccttagt attatatatg tacttcagaa   2580

atagtagtca ttctgcaggg gagtgaggtt cacctccaac cctatggtta ctatttctta   2640

ctagcgtcga actacattac ggacaccctg ttgtgtggtt ctaccacgag tcaggagctg   2700

cgagtattgt agcaagagaa gaattgggct gcaggaattc gatatcaagc ttatcgatac   2760

cgtcgagggg tccgcaaaaa tcaccagtct ctctctacaa atctatctct ctctattttt   2820

ctccagaata atgtgtgagt agttcccaga taagggaatt agggttctta tagggtttcg   2880

ctcatgtgtt gagcatataa gaaaccctta gtatgtattt gtatttgtaa aatacttcta   2940

tcaataaaat ttctaattcc taaaaccaaa atccagt                            2977
```

```
<210> SEQ ID NO 41
<211> LENGTH: 3114
<212> TYPE: DNA
<213> ORGANISM: Artificial Sequence
<220> FEATURE:
<223> OTHER INFORMATION: Expression cassette MUbi(no hse)-5'SrMV
      UTR-BvLz(sc)-3'SrMV UTR-35S
<220> FEATURE:
<221> NAME/KEY: promoter
<222> LOCATION: (1)..(1977)
<223> OTHER INFORMATION: MUbi(no hse) Promoter
<220> FEATURE:
<221> NAME/KEY: misc_feature
<222> LOCATION: (668)..(668)
<223> OTHER INFORMATION: n is a, c, g, or t
<220> FEATURE:
<221> NAME/KEY: misc_feature
<222> LOCATION: (671)..(671)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (1248)..(1248)
```

-continued

<223> OTHER INFORMATION: n is a, c, g, or t
<220> FEATURE:
<221> NAME/KEY: misc_feature
<222> LOCATION: (1315)..(1315)
<223> OTHER INFORMATION: n is a, c, g, or t
<220> FEATURE:
<221> NAME/KEY: misc_feature
<222> LOCATION: (1542)..(1542)
<223> OTHER INFORMATION: n is a, c, g, or t
<220> FEATURE:
<221> NAME/KEY: misc_feature
<222> LOCATION: (2028)..(2168)
<223> OTHER INFORMATION: 5' Untranslated Region of SrMV
<220> FEATURE:
<221> NAME/KEY: misc_feature
<222> LOCATION: (2169)..(2612)
<223> OTHER INFORMATION: BvLz (sc) coding sequence
<220> FEATURE:
<221> NAME/KEY: misc_feature
<222> LOCATION: (2613)..(2847)
<223> OTHER INFORMATION: 3' Untranslated Region of SrMV
<220> FEATURE:
<221> NAME/KEY: terminator
<222> LOCATION: (2918)..(3114)
<223> OTHER INFORMATION: 35S

<400> SEQUENCE: 41
aagcttgcat gcctgcagtg cagcgtgacc cggtcgtgcc cctctctaga gataatgagc 60
attgcatgtc taagttataa aaaattacca catatttttt ttgtcacact tgtttgaagt 120
gcagtttatc tatctttata catatattta aactttactc tacgaataat ataatctata 180
gtactacaat aatatcagtg ttttagagaa tcatataaat gaacagttag acatggtcta 240
aaggacaatt gagtattttg acaacaggac tctacagttt tatcttttta gtgtgcatgt 300
gttctccttt ttttttgcaa atagcttcac ctatataata cttcatccat tttattagta 360
catccattta gggtttaggg ttaatggttt ttatagacta atttttttag tacatctatt 420
ttattctatt ttagcctcta aattaagaaa actaaaactc tattttagtt tttttattta 480
ataatttaga tataaaatag aataaaataa agtgactaaa aattaaacaa atacccttta 540
agaaattaaa aaaactaagg aaacattttt cttgtttcga gtagataatg ccagcctgtt 600
aaacgccgtc gacgagtcta acggacacca accagcgaac cagcagcgtc gcgtcgggcc 660
aagcgaanca nacggcacgg natctctgtc gctgcctcca ccgttggact tgctccgctg 720
tcggcatcca gaaattgcgt ggcggcaggc agacgtgagc cggcacgagg cggcctcctc 780
ctcctctcac ggcacggcag ctacggggga ttcctttccc accgctcctt cgctttccct 840
tcctcgcccg ccgtaataaa tagacacccc ctccacaccc tctttcccca acctcgtgtt 900
gttcggagcg cacacacaca caaccagatc tcccccaaat ccacccgtcg gcacctccgc 960
ttcaaggtac gccgctcgtc ctcccccccc ccccctctct accttctcta gatcggcgtt 1020
ccggtccatg gttagggccc ggtagttcta cttctgttca tgtttgtgtt agatccgtgt 1080
ttgtgttaga tccgtgctgc tagcgttcgt acacggatgc gacctgtacg tcagacacgt 1140
tctgattgct aacttgccag tgtttctctt tggggaatcc tgggatggct ctagccgttc 1200
cgcagacggg atcgatttca tgattttttt tgtttcgttg catagggntt ggtttgccct 1260
tttcctttat ttcaatatat gccgtgccac ttgtttgtcg ggtcatcttt tcatngcttt 1320
tttttgtctt ggttgtgatg atgtggtctg gttgggcggt cgttctagat cggagtagaa 1380
ttctgtttca aactacctgg tggatttatt aattttggat ctgtatgtgt gtgccataca 1440
tattcatagt tacgaattga agatgatgga tggaaatatc gatctaggat aggtatacat 1500
gttgatgcgg gttttactga tgcatataca gagatgcttt tnttcgcttg gttgtgatga 1560

```
tgtggtgtgg ttgggcggtc gttcattcgt tctagatcgg agtagaatac tgtttcaaac   1620
tacctggtgt atttattaat tttggaactg tatgtgtgtg tcatacatct tcatagttac   1680
gagtttaaga tggatggaaa tatcgatcta ggataggtat acatgttgat gtgggtttta   1740
ctgatgcata tacatgatgg catatgcagc atctattcat atgctctaac cttgagtacc   1800
tatctattat aataaacaag tatgttttat aattattttg atcttgatat acttggatga   1860
tggcatatgc agcagctata tgtggatttt tttagccctg ccttcatacg ctatttattt   1920
gcttggtact gtttcttttg tcgatgctca ccctgttgtt tggtgttact tctgcaggtc   1980
gactctagag gatctgatat ctgatcagaa gacaccatct cggatccaaa acaacaagac   2040
tcaacacaac acaacaagac acagcaaagc aacttatatt gcaacgcatc gtcagcacat   2100
tccaaatcga agttcacggt tcaagagcaa ggtgccttga tcgaactctt tggagaattt   2160
cagcaaacat ggcggctctc gtcatcctgg gattcctttt cctgtcggtt gcggtgcaag   2220
gaaaggtttt cgagcgctgc gagcttgccc ggacgctgaa gaaactgggg ctggacggtt   2280
acaagggtgt ttcccttgct aactggctgt gccttaccaa gtgggagtcc tcctacaaca   2340
ccaaggccac gaactataac ccctcctccg agtctaccga ttacgggatc ttccagatta   2400
actccaagtg gtggtgcaac gacggaaaga cccctaacgc ggtggacggt tgccacgtgt   2460
cctgctccga gcttatggag aacgatattg ccaaggcggt tgcgtgcgcc aagcatattg   2520
tgtccgagca gggtatcacc gcgtgggtcg cctggaagag ccactgcagg gaccacgatg   2580
tgagcagcta cgtggagggc tgcaccctct gatgtactga gatcttcatt gcagttttta   2640
aagtatttta tatatttact atttcagtga gggtctccct ccttagtatt atatatgtac   2700
ttcagaaata gtagtcattc tgcaggggag tgaggttcac ctccaaccct atggttacta   2760
tttcttacta gcgtcgaact acattacgga caccctgttg tgtggttcta ccacgagtca   2820
ggagctgcga gtattgtagc aagagaagaa ttcggatccc ccgggctgca ggaattcgat   2880
atcaagctta tcgataccgt cgaggggtcc gcaaaaatca ccagtctctc tctacaaatc   2940
tatctctctc tatttttctc cagaataatg tgtgagtagt tcccagataa gggaattagg   3000
gttcttatag ggtttcgctc atgtgttgag catataagaa acccttagta tgtatttgta   3060
tttgtaaaat acttctatca ataaaatttc taattcctaa aaccaaaatc cagt         3114
```

```
<210> SEQ ID NO 42
<211> LENGTH: 3020
<212> TYPE: DNA
<213> ORGANISM: Artificial Sequence
<220> FEATURE:
<223> OTHER INFORMATION: Expression cassette MUbi(no hse)-BvLz(m)-35S
      NOS
<220> FEATURE:
<221> NAME/KEY: promoter
<222> LOCATION: (1)..(1977)
<223> OTHER INFORMATION: MUbi(no hse) Promoter
<220> FEATURE:
<221> NAME/KEY: misc_feature
<222> LOCATION: (668)..(668)
<223> OTHER INFORMATION: n is a, c, g, or t
<220> FEATURE:
<221> NAME/KEY: misc_feature
<222> LOCATION: (671)..(671)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
```

<222> LOCATION: (1248)..(1248)
<223> OTHER INFORMATION: n is a, c, g, or t
<220> FEATURE:
<221> NAME/KEY: misc_feature
<222> LOCATION: (1315)..(1315)
<223> OTHER INFORMATION: n is a, c, g, or t
<220> FEATURE:
<221> NAME/KEY: misc_feature
<222> LOCATION: (1542)..(1542)
<223> OTHER INFORMATION: n is a, c, g, or t
<220> FEATURE:
<221> NAME/KEY: misc_feature
<222> LOCATION: (2032)..(2475)
<223> OTHER INFORMATION: BvLz (m) coding sequence
<220> FEATURE:
<221> NAME/KEY: terminator
<222> LOCATION: (2549)..(2745)
<223> OTHER INFORMATION: 35S
<220> FEATURE:
<221> NAME/KEY: terminator
<222> LOCATION: (2768)..(3020)
<223> OTHER INFORMATION: NOS

<400> SEQUENCE: 42
aagcttgcat gcctgcagtg cagcgtgacc cggtcgtgcc cctctctaga gataatgagc 60
attgcatgtc taagttataa aaaattacca catatttttt ttgtcacact tgtttgaagt 120
gcagtttatc tatctttata catatattta aactttactc tacgaataat ataatctata 180
gtactacaat aatatcagtg ttttagagaa tcatataaat gaacagttag acatggtcta 240
aaggacaatt gagtattttg acaacaggac tctacagttt tatcttttta gtgtgcatgt 300
gttctccttt ttttttgcaa atagcttcac ctatataata cttcatccat tttattagta 360
catccattta gggtttaggg ttaatggttt ttatagacta attttttag tacatctatt 420 ttattctatt ttagcctcta aattaagaaa actaaaactc tattttagtt tttttattta 480
ataatttaga tataaaatag aataaaataa agtgactaaa aattaaacaa ataccottta 540 agaaattaaa aaaactaagg aaacattttt cttgtttcga gtagataatg ccagcctgtt 600
aaacgccgtc gacgagtcta acggacacca accagcgaac cagcagcgtc gcgtcgggcc 660
aagcgaanca nacggcacgg natctctgtc gctgcctcca ccgttggact tgctccgctg 720
tcggcatcca gaaattgcgt ggcggcaggc agacgtgagc cggcacgagg cggcctcctc 780
ctcctctcac ggcacggcag ctacggggga ttcctttccc accgctcctt cgctttccct 840
tcctcgcccg ccgtaataaa tagacacccc ctccacaccc tctttcccca acctcgtgtt 900
gttcggagcg cacacacaca caaccagatc tcccccaaat ccacccgtcg gcacctccgc 960
ttcaaggtac gccgctcgtc ctcccccccc cccctctct accttctcta gatcggcgtt 1020
ccggtccatg gttagggccc ggtagttcta cttctgttca tgtttgtgtt agatccgtgt 1080
ttgtgttaga tccgtgctgc tagcgttcgt acacggatgc gacctgtacg tcagacacgt 1140
tctgattgct aacttgccag tgtttctctt tggggaatcc tgggatggct ctagccgttc 1200
cgcagacggg atcgatttca tgattttttt tgtttcgttg catagggntt ggtttgccct 1260
tttcctttat ttcaatatat gccgtgccac ttgtttgtcg ggtcatcttt tcatngcttt 1320
tttttgtctt ggttgtgatg atgtggtctg gttgggcggt cgttctagat cggagtagaa 1380
ttctgtttca aactacctgg tggatttatt aattttggat ctgtatgtgt gtgccataca 1440
tattcatagt tacgaattga agatgatgga tggaaatatc gatctaggat aggtatacat 1500
gttgatgcgg gttttactga tgcatataca gagatgcttt tnttcgcttg gttgtgatga 1560
tgtggtgtgg ttgggcggtc gttcattcgt tctagatcgg agtagaatac tgtttcaaac 1620

```
tacctggtgt atttattaat tttggaactg tatgtgtgtg tcatacatct tcatagttac   1680

gagtttaaga tggatggaaa tatcgatcta ggataggtat acatgttgat gtgggtttta   1740

ctgatgcata tacatgatgg catatgcagc atctattcat atgctctaac cttgagtacc   1800

tatctattat aataaacaag tatgttttat aattattttg atcttgatat acttggatga   1860

tggcatatgc agcagctata tgtggatttt tttagccctg ccttcatacg ctatttattt   1920

gcttggtact gtttcttttg tcgatgctca ccctgttgtt tggtgttact tctgcaggtc   1980

gactctagag gatctgatat ctgatcagaa gacaccatct cggatccaaa catggcggcc   2040

ctggtgatcc tgggcttcct gttcctgtcc gtggctgtgc agggcaaggt gttcgaaagg   2100

tgcgaactgg ctaggaccct gaagaagctg ggcctggatg gctacaaggg cgtgtccctg   2160

gctaactggc tgtgcctgac caagtgggaa tcctcctaca acaccaaggc taccaactac   2220

aacccatcct ccgaatccac cgactacggc atcttccaga tcaactccaa gtggtggtgc   2280

aacgatggca agaccccaaa cgctgtggat ggctgccacg tgtcctgctc cgagctgatg   2340

gaaaacgata tcgctaaggc tgtggcttgc gctaagcaca tcgtgtccga acagggcatc   2400

accgcctggg tggcttggaa gtcccactgc agggatcacg atgtgtcctc ctacgtggaa   2460

ggctgcaccc tgtgattcga attcggatcc cccgggctgc aggaattcga tatcaagctt   2520

atcgataccg tcgaggggtc cgcaaaaatc accagtctct ctctacaaat ctatctctct   2580

ctatttttct ccagaataat gtgtgagtag ttcccagata agggaattag ggttcttata   2640

gggtttcgct catgtgttga gcatataaga aacccttagt atgtatttgt atttgtaaaa   2700

tacttctatc aataaaattt ctaattccta aaaccaaaat ccagtgggcc gctcgacgaa   2760

tttccccgat cgttcaaaca tttggcaata aagtttctta agattgaatc ctgttgccgg   2820

tcttgcgatg attatcatat aatttctgtt gaattacgtt aagcatgtaa taattaacat   2880

gtaatgcatg acgttattta tgagatgggt ttttatgatt agagtcccgc aattatacat   2940

ttaatacgcg atagaaaaca aaatatagcg cgcaaactag gataaattat cgcgcgcggt   3000

gtcatctatg ttactagatc                                               3020
```

<210> SEQ ID NO 43
<211> LENGTH: 4020
<212> TYPE: DNA
<213> ORGANISM: Artificial Sequence
<220> FEATURE:
<223> OTHER INFORMATION: Expression cassette SPRP(no 5'UTR)-5'SrMV UTR-BvLz(sc)-3'SrMV UTR-35S
<220> FEATURE:
<221> NAME/KEY: promoter
<222> LOCATION: (1)..(2900)
<223> OTHER INFORMATION: SPRP(no 5'UTR) promoter
<220> FEATURE:
<221> NAME/KEY: misc_feature
<222> LOCATION: (2934)..(3074)
<223> OTHER INFORMATION: 5' Untranslated Region of SrMV
<220> FEATURE:
<221> NAME/KEY: misc_feature
<222> LOCATION: (3075)..(3518)
<223> OTHER INFORMATION: BvLz (sc) coding sequence
<220> FEATURE:
<221> NAME/KEY: misc_feature
<222> LOCATION: (3519)..(3753)
<223> OTHER INFORMATION: 3' Untranslated Region of SrMV
<220> FEATURE:
<221> NAME/KEY: terminator
<222> LOCATION: (3824)..(4020)
<223> OTHER INFORMATION: 35S

<400> SEQUENCE: 43

-continued

```
atatttgcta gagatgttca aagtgatcat ctcagagcaa tatacggaaa gatgtttgaa     60
aaaatacttt cataagtgtt tggtattgac caagcaatga cccgatacat gtatcgccct    120
tagaacaaat atgaccgatg tatacatcgc ccttagttgc tgattagccg atgagttggg    180
tattgttgct tttcagtttt gaattgtgtt tttagattca tgcattattc acttgaaaac    240
agggagcata tattgacact caaattgggc ctctgcctat ttaaataggc ccatgacagt    300
tctggcacaa tctaaggaag actctataaa gcaacatgat aatagtacca tattggtttt    360
cctataggat aagaccaccc ctactcctta taaaataagg ggtatatgac tgattgagtt    420
tccaactatc taatcgataa aaatagatct actacctagt tttacctttt tccaactctc    480
ttgctgtttg ttgcatctct ttgcgagatt catcggcgtt ctaggcggcc ttgctggtcc    540
tagaataaca ctaggcgtgc tcctcgacgg gtcctctcga gaggcattcc caagcttttg    600
cggcgttgaa tgagttcaag atcggcctaa ccgttctcta gatcggttta gtcggtctta    660
gagttgtttg ctacgtgttt aaagttgtgt gcagcctagg gcgagctagc ccttgctgac    720
gtgtgactta gatcacaatc taacgtctaa cagctggctt gactttgcat taaaaaaaaa    780
gagtagtgtg caagtgtgga agcgtcgttt ttttatttga aaaaacaaaa aaatgcgcag    840
tatattaagg gacatcctaa ttaagaggct aagagcaaat gcacaacagt gtactccacg    900
agagattggt cctgtaagtt gtggatgcat gttagcacag gcacaacagg ccagtagttg    960
gggcgtcagt gtcaacgatg tcgggtcggt ggcaggagag ggtgggaaaa catccacgag   1020
cagaaaagga catcgccgtt ggaacaaggg acgagtgcac cactccggcc acgccgtacc   1080
gtacgcctca gaccccgcca cagcgcgttc gctagctgct gctgagcctg atgcctgaac   1140
acggtcgggt cgccaccaca ctgtccatca tctatccgtt cattcatcca cgactgtgct   1200
tgcacagcca tacactgccg aacctagctc gtgtttagat gcaatttttt tttacaaaat   1260
gctcctgtag cacttttttta ttgttatttg gaaattagtg tctaatcgtg aactaattag   1320
gcttaaaaga ttcatctcgt gaatttcatc taaactgtgt aattagtttt atttttttatc   1380
tatatttaat gcttcatgca tgtgtctaaa gattcgatgt gatgggaaat attgaaaatt   1440
tttgcaaaat tttttgcatc taaactgagc cctacacctc ggtcccagac cgttcgtcga   1500
tgaatctgga caactacctg tccagatttt tattcctata ccaacagttt tttgaatgga   1560
gggagtacga agtcgccagt acgtgtccct tttaacctgt agtgataaaa ctgtgaattt   1620
ctagataaac ttttgggatg aggccctatt tatctggctt ataatccgtc ttatttagct   1680
tgttttttca gccggaacag tatttttctc tcacaaaaaa tcagccaaca gtgtttttca   1740
gccggcttat aaacttttgg gatgcaacca tttttgaacc acttttcttt ttttaacgta   1800
ttttctacca cttttcaacc acgcactgac gcacgctatg catgtaattc aacaagtact   1860
cttattactt actttgtcta attgactggt ttaccatcac cctggacctg caggcaaagc   1920
aagatgtgga cactgccgtg tcggtcacgc aggaaatcaa agttctacga cgacatttgt   1980
acggcgcgcg gtacgcatct tagcgtcctc actctcatct tctccggcca gcacagccgc   2040
aatacacgca cacacgtact ctcggaacgg tcactacaca gtctgatgtg ctgcaccgta   2100
ccggcctgca atgcaaccat gcatatcatc gatcatgtgt ctcacagtgc cgtctgtgtc   2160
ctttccctta ggcgatcctg atcttgagct tcacgagctg agtgcccgcc agccatgcat   2220
gcatgatgtc caccagacat gcatgcatgg cacacctagc agctcgccat gcataggact   2280
agctagctat aggacgatga tgatctgagc tccatccagg accatgtgca tgcaacagcg   2340
cgcgacagat gaagatgaca attgctagcc tggtcatcca tcgtccacac aaaaatatct   2400
```

```
ttgctacctc aaagcaagga ggaaacctac acagataaca actgactagc ctgcagggga   2460

tgaatcttca tacatactcc agtacatagc tcgctcgctg gtcatttggt caacagcggc   2520

agcatgcgtc gtcaaacaca agctaaatgc cttttacccg tcccgtgtat catcaaaagt   2580

taacaaacct acctgtcagg cagcagcgta tatgtgaaac aagaaatgga tggaagagtc   2640

cgtgagaaag taaaggtgaa agatacgtgc tactgctatc cgttgaatag caataaacac   2700

gggcttagct gttacctacc cgttgatacg gcggaggcca aacgtgtaaa gcagcttatt   2760

tttttaatg agagagtgta aagcagctac ttagctgggc agacagccca tccacgcgtc   2820

caaagctgct tggctctcgc gcgctataaa tccgacccat ggccacaccc cgtcatccac   2880

atccacacac acaacagaga gaagacgaat tcaatcacta gcatctcgga tccaaaacaa   2940

caagactcaa cacaacacaa caagacacag caaagcaact tatattgcaa cgcatcgtca   3000

gcacattcca aatcgaagtt cacggttcaa gagcaaggtg ccttgatcga actctttgga   3060

gaatttcagc aaacatggcg gctctcgtca tcctgggatt ccttttcctg tcggttgcgg   3120

tgcaaggaaa ggttttcgag cgctgcgagc ttgcccggac gctgaagaaa ctggggctgg   3180

acggttacaa gggtgtttcc cttgctaact ggctgtgcct taccaagtgg gagtcctcct   3240

acaacaccaa ggccacgaac tataacccct cctccgagtc taccgattac gggatcttcc   3300

agattaactc caagtggtgg tgcaacgacg gaaagacccc taacgcggtg gacggttgcc   3360

acgtgtcctg ctccgagctt atggagaacg atattgccaa ggcggttgcg tgcgccaagc   3420

atattgtgtc cgagcagggt atcaccgcgt gggtcgcctg gaagagccac tgcagggacc   3480

acgatgtgag cagctacgtg gagggctgca ccctctgatg tactgagatc ttcattgcag   3540

tttttaaagt attttatata tttactattt cagtgagggt ctccctcctt agtattatat   3600

atgtacttca gaaatagtag tcattctgca ggggagtgag gttcacctcc aaccctatgg   3660

ttactatttc ttactagcgt cgaactacat tacggacacc ctgttgtgtg gttctaccac   3720

gagtcaggag ctgcgagtat tgtagcaaga gaagaattcg gatcccccgg gctgcaggaa   3780

ttcgatatca agcttatcga taccgtcgag ggtccgcaa aaatcaccag tctctctcta   3840

caaatctatc tctctctatt tttctccaga ataatgtgtg agtagttccc agataaggga   3900

attagggttc ttatagggtt tcgctcatgt gttgagcata taagaaaccc ttagtatgta   3960

tttgtatttg taaaatactt ctatcaataa aatttctaat tcctaaaacc aaaatccagt   4020
```

<210> SEQ ID NO 44
<211> LENGTH: 3993
<212> TYPE: DNA
<213> ORGANISM: Artificial Sequence
<220> FEATURE:
<223> OTHER INFORMATION: Expression cassette SPRP-BvLz(m)-3'SrMV UTR-35S
<220> FEATURE:
<221> NAME/KEY: promoter
<222> LOCATION: (1)..(3016)
<223> OTHER INFORMATION: SPRP Promoter
<220> FEATURE:
<221> NAME/KEY: misc_feature
<222> LOCATION: (3048)..(3491)
<223> OTHER INFORMATION: BvLz (m) coding sequence
<220> FEATURE:
<221> NAME/KEY: misc_feature
<222> LOCATION: (3510)..(3736)
<223> OTHER INFORMATION: 3' Untranslated Region of SrMV
<220> FEATURE:
<221> NAME/KEY: terminator
<222> LOCATION: (3797)..(3993)
<223> OTHER INFORMATION: 35S

<400> SEQUENCE: 44

```
atatttgcta gagatgttca aagtgatcat ctcagagcaa tatacggaaa gatgtttgaa     60
aaaatacttt cataagtgtt tggtattgac caagcaatga cccgatacat gtatcgccct    120
tagaacaaat atgaccgatg tatacatcgc ccttagttgc tgattagccg atgagttggg    180
tattgttgct tttcagtttt gaattgtgtt tttagattca tgcattattc acttgaaaac    240
agggagcata tattgacact caaattgggc ctctgcctat ttaaataggc ccatgacagt    300
tctggcacaa tctaaggaag actctataaa gcaacatgat aatagtacca tattggtttt    360
cctataggat aagaccaccc ctactcctta taaaataagg ggtatatgac tgattgagtt    420
tccaactatc taatcgataa aaatagatct actacctagt tttacctttt tccaactctc    480
ttgctgtttg ttgcatctct ttgcgagatt catcggcgtt ctaggcggcc ttgctggtcc    540
tagaataaca ctaggcgtgc tcctcgacgg gtcctctcga gaggcattcc caagcttttg    600
cggcgttgaa tgagttcaag atcggcctaa ccgttctcta gatcggttta gtcggtctta    660
gagttgtttg ctacgtgttt aaagttgtgt gcagcctagg gcgagctagc ccttgctgac    720
gtgtgactta gatcacaatc taacgtctaa cagctggctt gactttgcat taaaaaaaaa    780
gagtagtgtg caagtgtgga agcgtcgttt ttttatttga aaaaacaaaa aaatgcgcag    840
tatattaagg gacatcctaa ttaagaggct aagagcaaat gcacaacagt gtactccacg    900
agagattggt cctgtaagtt gtggatgcat gttagcacag gcacaacagg ccagtagttg    960
gggcgtcagt gtcaacgatg tcgggtcggt ggcaggagag ggtgggaaaa catccacgag   1020
cagaaaagga catcgccgtt ggaacaaggg acgagtgcac cactccggcc acgccgtacc   1080
gtacgcctca gaccccgcca cagcgcgttc gctagctgct gctgagcctg atgcctgaac   1140
acggtcgggt cgccaccaca ctgtccatca tctatccgtt cattcatcca cgactgtgct   1200
tgcacagcca tacactgccg aacctagctc gtgtttagat gcaatttttt tttacaaaat   1260
gctcctgtag cactttttta ttgttatttg gaaattagtg tctaatcgtg aactaattag   1320
gcttaaaaga ttcatctcgt gaatttcatc taaactgtgt aattagtttt atttttatc    1380
tatatttaat gcttcatgca tgtgtctaaa gattcgatgt gatgggaaat attgaaaatt   1440
tttgcaaaat tttttgcatc taaactgagc cctacacctc ggtcccagac cgttcgtcga   1500
tgaatctgga caactacctg tccagatttt tattcctata ccaacagttt tttgaatgga   1560
gggagtacga agtcgccagt acgtgtccct tttaacctgt agtgataaaa ctgtgaattt   1620
ctagataaac ttttgggatg aggccctatt tatctggctt ataatccgtc ttatttagct   1680
tgtttttca gccggaacag tatttttctc tcacaaaaaa tcagccaaca gtgtttttca    1740
gccggcttat aaactttgg gatgcaacca tttttgaacc acttttcttt ttttaacgta    1800
ttttctacca cttttcaacc acgcactgac gcacgctatg catgtaattc aacaagtact   1860
cttattactt actttgtcta attgactggt ttaccatcac cctggacctg caggcaaagc   1920
aagatgtgga cactgccgtg tcggtcacgc aggaaatcaa agttctacga cgacatttgt   1980
acggcgcgcg gtacgcatct tagcgtcctc actctcatct tctccggcca gcacagccgc   2040
aatacacgca cacacgtact ctcggaacgg tcactacaca gtctgatgtg ctgcaccgta   2100
ccggcctgca atgcaaccat gcatatcatc gatcatgtgt ctcacagtgc cgtctgtgtc   2160
ctttccctta ggcgatcctg atcttgagct tcacgagctg agtgcccgcc agccatgcat   2220
gcatgatgtc caccagacat gcatgcatgg cacacctagc agctcgccat gcataggact   2280
agctagctat aggacgatga tgatctgagc tccatccagg accatgtgca tgcaacagcg   2340
```

```
cgcgacagat gaagatgaca attgctagcc tggtcatcca tcgtccacac aaaaatatct   2400

ttgctacctc aaagcaagga ggaaacctac acagataaca actgactagc ctgcagggga   2460

tgaatcttca tacatactcc agtacatagc tcgctcgctg gtcatttggt caacagcggc   2520

agcatgcgtc gtcaaacaca agctaaatgc cttttacccg tcccgtgtat catcaaaagt   2580

taacaaacct acctgtcagg cagcagcgta tatgtgaaac aagaaatgga tggaagagtc   2640

cgtgagaaag taaaggtgaa agatacgtgc tactgctatc cgttgaatag caataaacac   2700

gggcttagct gttacctacc cgttgatacg gcggaggcca aacgtgtaaa gcagcttatt   2760

tttttaatg agagagtgta aagcagctac ttagctgggc agacagccca tccacgcgtc   2820

caaagctgct tggctctcgc gcgctataaa tccgacccat ggccacaccc cgtcatccac   2880

atccacacac acaacagaga ctactcgggc actaccaaca gctgctctag agaaagagag   2940

agagaggcag agagctagca acacacagca gagagagaac tagcaggcga acttgttgga   3000

ggagcagcgg ctagccgaat tcctgcagcc ccatctcgga tccaaacatg gcggccctgg   3060

tgatcctggg cttcctgttc ctgtccgtgg ctgtgcaggg caaggtgttc gaaaggtgcg   3120

aactggctag gaccctgaag aagctgggcc tggatggcta caagggcgtg tccctggcta   3180

actggctgtg cctgaccaag tgggaatcct cctacaacac caaggctacc aactacaacc   3240

catcctccga atccaccgac tacggcatct tccagatcaa ctccaagtgg tggtgcaacg   3300

atggcaagac cccaaacgct gtggatggct gccacgtgtc ctgctccgag ctgatggaaa   3360

acgatatcgc taaggctgtg gcttgcgcta agcacatcgt gtccgaacag ggcatcaccg   3420

cctgggtggc ttggaagtcc cactgcaggg atcacgatgt gtcctcctac gtggaaggct   3480

gcaccctgtg attcgaattc ggatcccccg atcttcattg cagtttttaa agtattttat   3540

atatttacta tttcagtgag ggtctccctc cttagtatta tatatgtact tcagaaatag   3600

tagtcattct gcaggggagt gaggttcacc tccaacccta tggttactat ttcttactag   3660

cgtcgaacta cattacggac accctgttgt gtggttctac cacgagtcag gagctgcgag   3720

tattgtagca agagaagaat tgggctgcag gaattcgata tcaagcttat cgataccgtc   3780

gaggggtccg caaaaatcac cagtctctct ctacaaatct atctctctct atttttctcc   3840

agaataatgt gtgagtagtt cccagataag ggaattaggg ttcttatagg gtttcgctca   3900

tgtgttgagc atataagaaa cccttagtat gtatttgtat ttgtaaaata cttctatcaa   3960

taaaatttct aattcctaaa accaaaatcc agt                                3993
```

<210> SEQ ID NO 45
<211> LENGTH: 4045
<212> TYPE: DNA
<213> ORGANISM: Artificial Sequence
<220> FEATURE:
<223> OTHER INFORMATION: Expression cassette SPRP-BvLz(m)-35S NOS
<220> FEATURE:
<221> NAME/KEY: promoter
<222> LOCATION: (1)..(3016)
<223> OTHER INFORMATION: SPRP Promoter
<220> FEATURE:
<221> NAME/KEY: misc_feature
<222> LOCATION: (3048)..(3491)
<223> OTHER INFORMATION: BvLz (m) coding sequence
<220> FEATURE:
<221> NAME/KEY: terminator
<222> LOCATION: (3565)..(3761)
<223> OTHER INFORMATION: 35SExp
<220> FEATURE:
<221> NAME/KEY: terminator
<222> LOCATION: (3793)..(4045)

<223> OTHER INFORMATION: NOS

<400> SEQUENCE: 45

```
atatttgcta gagatgttca aagtgatcat ctcagagcaa tatacggaaa gatgtttgaa     60
aaaatacttt cataagtgtt tggtattgac caagcaatga cccgatacat gtatcgccct    120
tagaacaaat atgaccgatg tatacatcgc ccttagttgc tgattagccg atgagttggg    180
tattgttgct tttcagtttt gaattgtgtt tttagattca tgcattattc acttgaaaac    240
agggagcata tattgacact caaattgggc ctctgcctat ttaaataggc ccatgacagt    300
tctggcacaa tctaaggaag actctataaa gcaacatgat aatagtacca tattggtttt    360
cctataggat aagaccaccc ctactcctta taaaataagg ggtatatgac tgattgagtt    420
tccaactatc taatcgataa aaatagatct actacctagt tttacctttt tccaactctc    480
ttgctgtttg ttgcatctct ttgcgagatt catcggcgtt ctaggcggcc ttgctggtcc    540
tagaataaca ctaggcgtgc tcctcgacgg gtcctctcga gaggcattcc caagcttttg    600
cggcgttgaa tgagttcaag atcggcctaa ccgttctcta gatcggttta gtcggtctta    660
gagttgtttg ctacgtgttt aaagttgtgt gcagcctagg gcgagctagc ccttgctgac    720
gtgtgactta gatcacaatc taacgtctaa cagctggctt gactttgcat taaaaaaaaa    780
gagtagtgtg caagtgtgga agcgtcgttt ttttatttga aaaaacaaaa aaatgcgcag    840
tatattaagg gacatcctaa ttaagaggct aagagcaaat gcacaacagt gtactccacg    900
agagattggt cctgtaagtt gtggatgcat gttagcacag gcacaacagg ccagtagttg    960
gggcgtcagt gtcaacgatg tcgggtcggt ggcaggagag ggtgggaaaa catccacgag   1020
cagaaaagga catcgccgtt ggaacaaggg acgagtgcac cactccggcc acgccgtacc   1080
gtacgcctca gaccccgcca cagcgcgttc gctagctgct gctgagcctg atgcctgaac   1140
acggtcgggt cgccaccaca ctgtccatca tctatccgtt cattcatcca cgactgtgct   1200
tgcacagcca tacactgccg aacctagctc gtgtttagat gcaatttttt tttacaaaat   1260
gctcctgtag cactttttta ttgttatttg gaaattagtg tctaatcgtg aactaattag   1320
gcttaaaaga ttcatctcgt gaatttcatc taaactgtgt aattagtttt attttttatc   1380
tatatttaat gcttcatgca tgtgtctaaa gattcgatgt gatgggaaat attgaaaatt   1440
tttgcaaaat tttttgcatc taaactgagc cctacacctc ggtcccagac cgttcgtcga   1500
tgaatctgga caactacctg tccagatttt tattcctata ccaacagttt tttgaatgga   1560
gggagtacga agtcgccagt acgtgtccct tttaacctgt agtgataaaa ctgtgaattt   1620
ctagataaac ttttgggatg aggccctatt tatctggctt ataatccgtc ttatttagct   1680
tgtttttttca gccggaacag tatttttctc tcacaaaaaa tcagccaaca gtgtttttca   1740
gccggcttat aaacttttgg gatgcaacca tttttgaacc acttttcttt ttttaacgta   1800
ttttctacca cttttcaacc acgcactgac gcacgctatg catgtaattc aacaagtact   1860
cttattactt actttgtcta attgactggt ttaccatcac cctggacctg caggcaaagc   1920
aagatgtgga cactgccgtg tcggtcacgc aggaaatcaa agttctacga cgacatttgt   1980
acggcgcgcg gtacgcatct tagcgtcctc actctcatct tctccggcca gcacagccgc   2040
aatacacgca cacacgtact ctcggaacgg tcactacaca gtctgatgtg ctgcaccgta   2100
ccggcctgca atgcaaccat gcatatcatc gatcatgtgt ctcacagtgc cgtctgtgtc   2160
ctttccctta ggcgatcctg atcttgagct tcacgagctg agtgcccgcc agccatgcat   2220
gcatgatgtc caccagacat gcatgcatgg cacacctagc agctcgccat gcataggact   2280
```

```
agctagctat aggacgatga tgatctgagc tccatccagg accatgtgca tgcaacagcg   2340
cgcgacagat gaagatgaca attgctagcc tggtcatcca tcgtccacac aaaaatatct   2400
ttgctacctc aaagcaagga ggaaacctac acagataaca actgactagc ctgcagggga   2460
tgaatcttca tacatactcc agtacatagc tcgctcgctg gtcatttggt caacagcggc   2520
agcatgcgtc gtcaaacaca agctaaatgc cttttacccg tcccgtgtat catcaaaagt   2580
taacaaacct acctgtcagg cagcagcgta tatgtgaaac aagaaatgga tggaagagtc   2640
cgtgagaaag taaaggtgaa agatacgtgc tactgctatc cgttgaatag caataaacac   2700
gggcttagct gttacctacc cgttgatacg gcggaggcca aacgtgtaaa gcagcttatt   2760
ttttttaatg agagagtgta aagcagctac ttagctgggc agacagccca tccacgcgtc   2820
caaagctgct tggctctcgc gcgctataaa tccgacccat ggccacaccc cgtcatccac   2880
atccacacac acaacagaga ctactcgggc actaccaaca gctgctctag agaaagagag   2940
agagaggcag agagctagca acacacagca gagagagaac tagcaggcga acttgttgga   3000
ggagcagcgg ctagccgaat tcctgcagcc ccatctcgga tccaaacatg gcggccctgg   3060
tgatcctggg cttcctgttc ctgtccgtgg ctgtgcaggg caaggtgttc gaaaggtgcg   3120
aactggctag gaccctgaag aagctgggcc tggatggcta caagggcgtg tccctggcta   3180
actggctgtg cctgaccaag tgggaatcct cctacaacac caaggctacc aactacaacc   3240
catcctccga atccaccgac tacggcatct tccagatcaa ctccaagtgg tggtgcaacg   3300
atggcaagac cccaaacgct gtggatggct gccacgtgtc ctgctccgag ctgatggaaa   3360
acgatatcgc taaggctgtg gcttgcgcta agcacatcgt gtccgaacag ggcatcaccg   3420
cctgggtggc ttggaagtcc cactgcaggg atcacgatgt gtcctcctac gtggaaggct   3480
gcaccctgtg attcgaattc ggatcccccg ggctgcagga attcgatatc aagcttatcg   3540
ataccgtcga ggggtccgca aaaatcacca gtctctctct acaaatctat ctctctctat   3600
ttttctccag aataatgtgt gagtagttcc cagataaggg aattagggtt cttatagggt   3660
ttcgctcatg tgttgagcat ataagaaacc cttagtatgt atttgtattt gtaaaatact   3720
tctatcaata aaatttctaa ttcctaaaac caaaatccag tgacctgcag ggccgctcg    3780 acgaatttcc ccgatcgttc aaacatttgg caataaagtt tcttaagatt gaatcctgtt   3840
gccggtcttg cgatgattat catataattt ctgttgaatt acgttaagca tgtaataatt   3900
aacatgtaat gcatgacgtt atttatgaga tgggttttta tgattagagt cccgcaatta   3960
tacatttaat acgcgataga aaacaaaata tagcgcgcaa actaggataa attatcgcgc   4020
gcggtgtcat ctatgttact agatc                                         4045
```

```
<210> SEQ ID NO 46
<211> LENGTH: 2936
<212> TYPE: DNA
<213> ORGANISM: Artificial Sequence
<220> FEATURE:
<223> OTHER INFORMATION: Expression cassette SEF1alpha-BvLz(m)-3'SrMV
      UTR-35S
<220> FEATURE:
<221> NAME/KEY: promoter
<222> LOCATION: (1)..(1959)
<223> OTHER INFORMATION: SEF1alpha Promoter
<220> FEATURE:
<221> NAME/KEY: misc_feature
<222> LOCATION: (1991)..(2434)
<223> OTHER INFORMATION: BvLz (m) coding sequence
<220> FEATURE:
<221> NAME/KEY: misc_feature
```

<222> LOCATION: (2453)..(2679)
<223> OTHER INFORMATION: 3' Untranslated Region of SrMV
<220> FEATURE:
<221> NAME/KEY: terminator
<222> LOCATION: (2740)..(2936)
<223> OTHER INFORMATION: 35S

<400> SEQUENCE: 46
ataaactcaa gctttcacca atactttctc cgtttcaaat tataagatgt tttagttttt 60
ttagatacat tatttttact atgtatcaag acattgtata tttttaagtg cgtaccaaaa 120
gtcataaatc taaaaaagtc aaacgtctta taatttaaaa tggagggagg actttctaac 180
tcataccact tgttcccttg ctggttatta attactacat acaaagacca aaattgaata 240
gccaaacttg attctcaaac caactatttt atcaaaatct atgcttttgt ccatttccaa 300
gcaagggaaa ttagttgtga acgtgcaaag tagtaaagga ccccttcca aaagggagac 360 gagcccacat tgttaggaca aaaaaatctt tagtatatta gttctttatt taaagtctat 420
ataattctac tccatatatg acattaaagt gtaactggta tctaaagatc taagagcata 480
acaagcataa aattcaaact tattaaatct aggatccccg tacctcccaa ctctttctgc 540
agtttaattc gctcacaacg cctccttctt tgatgttttt ttccgctgta cctgtgccag 600
tataccaaaa ttttaatttt tttgagcgac caaaatacct tttcgaattt aattttcatg 660
tttcatttta gttttactac gtggtatcca ccatatacta cgtatacaag agcaactcca 720
agagatttgg taaaattaga tgctaaattg tgagatttag ccattatgta aaatagaaag 780
tctatctaaa atgtagaatt ttaaaaccag cctaactaaa ttggaaaaca caaatagcaa 840
gtaggactcg ctagggaaat atggccagcg agaatggtag gatagccagc tagaaaaaat 900
aaaaaccaat atagacagct gttgtaatgt ttttttaaag aacattagct gtaaatcgct 960
ttactaatac attttgctca tggccacgag gcaggggtcg ggtcttgggt cttttttttt 1020
ttgaaacttg gtaaaacttc attactcggc taacaaatcg ttagcaacgg agtctatcca 1080
tataaaaaac aatagtatgt gtaggtcgaa tgctgttttt gttcatttgt ggcccatgaa 1140
gtgttttttt tgggcccaat agcccattca tccatgcctg aaccctaggg cgtcttcctt 1200
ataaaaacct agctccattc tgttctcaaa ccccaacacg cagtcggccg ccgcagaccg 1260
ggagtagccg acgcgccgtc accgtatcct cagatcagcg gcgagccgta accaagcaac 1320
tctgctgacg cccgacgagg tactccgccg cacgcgcgcg cgcttctctt ccttttcttt 1380
tcgctgtgct ttgagcctgt ttgtttgatg actagatcta ctgggtttgt cgtctatgtg 1440
tgatgagacg agccgattca tgcactggat ttctaatcaa gtgttgtttc cgccgctgct 1500
acctctattt agtgtctatg tatgaatttg gttgcagttt acaactgatt tgtcgagcca 1560
taaattataa ccgtttggtg gttctagact agatccagtt tccgatctat gatattacgt 1620
ggctgaggca cttaactctg ttttgtgtgt aagaactgag ccgattcatg tgctggagta 1680
ctaatccaag ttttcctttc gcctcgtcta actctagtat gtactccgta tataaacttg 1740
attgcagttt gcaactgatt ctcggccata gattattact gttgcgttgt tcattagatc 1800
cagtttccga tctctgattt acctgcgtag ggtacttcgt ctttggattt tcctgtcctt 1860
gttgattgtt tgattactgg tttatttcca tatatttatt tctaactgtt tttatctgct 1920
attttgatgt aagcagcagt gtagcgtttc ccttcagccg aattcctgca gccccatctc 1980
ggatccaaac atggcggccc tggtgatcct gggcttcctg ttcctgtccg tggctgtgca 2040
gggcaaggtg ttcgaaaggt gcgaactggc taggaccctg aagaagctgg gcctggatgg 2100
ctacaagggc gtgtccctgg ctaactggct gtgcctgacc aagtgggaat cctcctacaa 2160
caccaaggct accaactaca acccatcctc cgaatccacc gactacggca tcttccagat 2220
caactccaag tggtggtgca acgatggcaa gaccccaaac gctgtggatg gctgccacgt 2280
gtcctgctcc gagctgatgg aaaacgatat cgctaaggct gtggcttgcg ctaagcacat 2340
cgtgtccgaa cagggcatca ccgcctgggt ggcttggaag tcccactgca gggatcacga 2400
tgtgtcctcc tacgtggaag gctgcaccct gtgattcgaa ttcggatccc ccgatcttca 2460
ttgcagtttt taaagtattt tatatattta ctatttcagt gagggtctcc ctccttagta 2520
ttatatatgt acttcagaaa tagtagtcat tctgcagggg agtgaggttc acctccaacc 2580
ctatggttac tatttcttac tagcgtcgaa ctacattacg gacaccctgt tgtgtggttc 2640
taccacgagt caggagctgc gagtattgta gcaagagaag aattgggctg caggaattcg 2700
atatcaagct tatcgatacc gtcgaggggt ccgcaaaaat caccagtctc tctctacaaa 2760
tctatctctc tctatttttc tccagaataa tgtgtgagta gttcccagat aagggaatta 2820
gggttcttat agggtttcgc tcatgtgttg agcatataag aaacccttag tatgtatttg 2880
tatttgtaaa atacttctat caataaaatt tctaattcct aaaaccaaaa tccagt 2936

<210> SEQ ID NO 47
<211> LENGTH: 2988
<212> TYPE: DNA
<213> ORGANISM: Artificial Sequence
<220> FEATURE:
<223> OTHER INFORMATION: Expression cassette SEF1alpha-BvLz(m)-35S NOS
<220> FEATURE:
<221> NAME/KEY: promoter
<222> LOCATION: (1)..(1959)
<223> OTHER INFORMATION: SEF1alpha Promoter
<220> FEATURE:
<221> NAME/KEY: misc_feature
<222> LOCATION: (1991)..(2434)
<223> OTHER INFORMATION: BvLz (m) coding sequence
<220> FEATURE:
<221> NAME/KEY: terminator
<222> LOCATION: (2508)..(2704)
<223> OTHER INFORMATION: 35S
<220> FEATURE:
<221> NAME/KEY: terminator
<222> LOCATION: (2736)..(2988)
<223> OTHER INFORMATION: NOS

<400> SEQUENCE: 47
ataaactcaa gctttcacca atactttctc cgtttcaaat tataagatgt tttagttttt 60
ttagatacat tatttttact atgtatcaag acattgtata tttttaagtg cgtaccaaaa 120
gtcataaatc taaaaaagtc aaacgtctta taatttaaaa tggagggagg actttctaac 180
tcataccact tgttcccttg ctggttatta attactacat acaaagacca aaattgaata 240
gccaaacttg attctcaaac caactatttt atcaaaatct atgcttttgt ccatttccaa 300
gcaagggaaa ttagttgtga acgtgcaaag tagtaaagga ccccttttcca aaagggagac 360 gagcccacat tgttaggaca aaaaaatctt tagtatatta gttctttatt taaagtctat 420
ataattctac tccatatatg acattaaagt gtaactggta tctaaagatc taagagcata 480
acaagcataa aattcaaact tattaaatct aggatccccg tacctcccaa ctctttctgc 540
agtttaattc gctcacaacg cctccttctt tgatgttttt ttccgctgta cctgtgccag 600
tataccaaaa ttttaatttt tttgagcgac caaaatacct tttcgaattt aattttcatg 660
tttcatttta gttttactac gtggtatcca ccatatacta cgtatacaag agcaactcca 720
agagatttgg taaaattaga tgctaaattg tgagatttag ccattatgta aaatagaaag 780

```
tctatctaaa atgtagaatt ttaaaaccag cctaactaaa ttggaaaaca caaatagcaa    840
gtaggactcg ctagggaaat atggccagcg agaatggtag gatagccagc tagaaaaaat    900
aaaaaccaat atagacagct gttgtaatgt ttttttaaag aacattagct gtaaatcgct    960
ttactaatac attttgctca tggccacgag gcaggggtcg ggtcttgggt cttttttttt   1020
ttgaaacttg gtaaaacttc attactcggc taacaaatcg ttagcaacgg agtctatcca   1080
tataaaaaac aatagtatgt gtaggtcgaa tgctgttttt gttcatttgt ggcccatgaa   1140
gtgttttttt tgggcccaat agcccattca tccatgcctg aaccctaggg cgtcttcctt   1200
ataaaaacct agctccattc tgttctcaaa ccccaacacg cagtcggccg ccgcagaccg   1260
ggagtagccg acgcgccgtc accgtatcct cagatcagcg gcgagccgta accaagcaac   1320
tctgctgacg cccgacgagg tactccgccg cacgcgcgcg cgcttctctt ccttttcttt   1380
tcgctgtgct ttgagcctgt ttgtttgatg actagatcta ctgggtttgt cgtctatgtg   1440
tgatgagacg agccgattca tgcactggat ttctaatcaa gtgttgtttc cgccgctgct   1500
acctctattt agtgtctatg tatgaatttg gttgcagttt acaactgatt tgtcgagcca   1560
taaattataa ccgtttggtg gttctagact agatccagtt tccgatctat gatattacgt   1620
ggctgaggca cttaactctg ttttgtgtgt aagaactgag ccgattcatg tgctggagta   1680
ctaatccaag ttttcctttc gcctcgtcta actctagtat gtactccgta tataaacttg   1740
attgcagttt gcaactgatt ctcggccata gattattact gttgcgttgt tcattagatc   1800
cagtttccga tctctgattt acctgcgtag ggtacttcgt ctttggattt tcctgtcctt   1860
gttgattgtt tgattactgg tttatttcca tatatttatt tctaactgtt tttatctgct   1920
attttgatgt aagcagcagt gtagcgtttc ccttcagccg aattcctgca gccccatctc   1980
ggatccaaac atggcggccc tggtgatcct gggcttcctg ttcctgtccg tggctgtgca   2040
gggcaaggtg ttcgaaaggt gcgaactggc taggaccctg aagaagctgg gcctggatgg   2100
ctacaagggc gtgtccctgg ctaactggct gtgcctgacc aagtgggaat cctcctacaa   2160
caccaaggct accaactaca acccatcctc cgaatccacc gactacggca tcttccagat   2220
caactccaag tggtggtgca acgatggcaa gaccccaaac gctgtggatg gctgccacgt   2280
gtcctgctcc gagctgatgg aaaacgatat cgctaaggct gtggcttgcg ctaagcacat   2340
cgtgtccgaa cagggcatca ccgcctgggt ggcttggaag tcccactgca gggatcacga   2400
tgtgtcctcc tacgtggaag gctgcaccct gtgattcgaa ttcggatccc ccgggctgca   2460
ggaattcgat atcaagctta tcgataccgt cgaggggtcc gcaaaaatca ccagtctctc   2520
tctacaaatc tatctctctc tatttttctc cagaataatg tgtgagtagt tcccagataa   2580
gggaattagg gttcttatag ggtttcgctc atgtgttgag catataagaa acccttagta   2640
tgtatttgta tttgtaaaat acttctatca ataaaatttc taattcctaa aaccaaaatc   2700
cagtgacctg caggggccgc tcgacgaatt tccccgatcg ttcaaacatt tggcaataaa   2760
gtttcttaag attgaatcct gttgccggtc ttgcgatgat tatcatataa tttctgttga   2820
attacgttaa gcatgtaata attaacatgt aatgcatgac gttatttatg agatgggttt   2880
ttatgattag agtcccgcaa ttatacattt aatacgcgat agaaaacaaa atatagcgcg   2940
caaactagga taaattatcg cgcgcggtgt catctatgtt actagatc                2988
```

<210> SEQ ID NO 48
<211> LENGTH: 3621
<212> TYPE: DNA

<213> ORGANISM: Artificial Sequence
<220> FEATURE:
<223> OTHER INFORMATION: Expression cassette JAS-BvLz(m)-35S
<220> FEATURE:
<221> NAME/KEY: promoter
<222> LOCATION: (54)..(2681)
<223> OTHER INFORMATION: JAS Promoter
<220> FEATURE:
<221> NAME/KEY: misc_feature
<222> LOCATION: (2692)..(3135)
<223> OTHER INFORMATION: BvLz (m) coding sequence
<220> FEATURE:
<221> NAME/KEY: terminator
<222> LOCATION: (3425)..(3621)
<223> OTHER INFORMATION: 35S

<400> SEQUENCE: 48

```
tctagataat acgactcact atagggcacg cgtggtcgac ggcccgggct ggtctgcgac     60

agctagaggc gccaccgcgt cctagcttcc tccaacttct cgtcggagat cccttcaggg    120

atgcccaatg ccaccgcccc taagtcaacc tgcgggagct ggagcttcgc cagggtcaga    180

gctgcggcag caccctggta gaccgcattc ctgatgaccc gcggggtgcg ctccatgaag    240

aagtgcattc gcccaaccaa gtcgagtggg tcgcctggag ggggcgggga agcaaaacgt    300

tgcatgcacc tagcgccctg gcagcgagct cctgtagtat cacctgcgtc gcctccagct    360

catgctcgca agcctccagg gcggcccggc agtgctccaa cactttcgcc tcctcctaca    420

gctccttcca catgcagtcg tgctccgcac gcaccttctc caccttttta ctcttttctt    480

tctcttttct tggcccatct ttggtatttt cacaaatgtc cccctacaaa tgataaatca    540

ccaaaactca tggagcttgc tagttataaa ctctaattct aagtttggtg tttatttgag    600

tggattttgt gtgaaagttg gtggttagaa ataggagtta aggaccgcca acaagatccc    660

ccacacttag ccctttgctc atcctcgagt aaagttcaag gactaaggtg gaacatctcc    720

tcaaatggta cgatgcctgc atataagtta ttccaagcct cacctataca tgtgaacttt    780

gaagtgtcta ccacgccatc ttgggtggtt gagaaatgga acagatcaga atccagtcat    840

ctttacctct cttgcttaga taacttgggt ttttgtaagg ttttcaaatt taaaacatag    900

tcttgctcct caaatgattc tctcatatag ctcaatgtgt atggtttctc accaaggcaa    960

tgttttgcct cttttcatcc tacttctaat atttcttttg tggagcttag ggtagggaat   1020

gaaaaggaag catacttgca ttgcatatgt tactaagtca aaaaccaaat ctgaggagaa   1080

gcaagtcata caatctgatc aagatgtgca agtgtgtgga tatgtggatt aagataactc   1140

ctgtttattc atgctctcct ccttaataaa ctttagaggg catggcaatc tttgcatggg   1200

ccttcatgag ctcatcgtat gtctaagcat ggagctcatc atttatataa gcatggtgat   1260

accaaaatta ctccttttga gcatgtttat atttaggagg acgttttacc tgttgaggta   1320

aatctgaacg ctaataaatc ggctaagcaa aataatttat cacctgttga ttctaacaat   1380

ttgatgatgg acaatattga tgaggtgact gacaaatgat tgaaggcttt aaaggagatt   1440

gagaaggata aatctacaat aaaaatgtaa agaagaaagc attcaaagtg tgagatctgg   1500

tgtggaagac tattttgcct cttgggggta aaagacaaca agtttagtaa gtggcctcaa   1560

aattgggagg gcccatgcaa gattgttaaa gtaattgttt tggattgacg gaggcatttc   1620

aaggtgatca tctacctaga gctctcaatg ggaggtgctc gaagacatat tacccatgtg   1680

tatggcaaga tgtttagcta gtaactgact gatagtgtaa acgatctcca atggggcaag   1740

acatattacc taaggccagg ctggtttttg caagttcgag taggatatag agattctcgt   1800

gcgagttgta aacgatctcc aatggggcaa gacatcctac cctatatata gtgaaggggc   1860
```

```
agtagctgat tgagaatcaa tcaatcaagc acaatataat ttattaattt tttattcaaa   1920
cccaattttt ttccttttcc aaccctaatt atagttttcc ttttgcctct aggacaaatt   1980
gacgtgttcc gggtatcctg ctgaattaag aacaacccta ggtgcacctg tcccgataga   2040
gtcccacctg ggtaggcatt catagggatt cgtgtatttc ctgcaaaaaa gcgattaagc   2100
tggcttctaa aactggctag gccggattct gtggccttca ctaccaggtg attttcatgt   2160
gatccgtgca ttctagcact ttgctatgta acccaaactt aagtcgacaa ctataaatat   2220
gctacttgca ggatgttatc acgacacaac tcctaatcta cggaagccta agtttagttt   2280
tgctcggaga caagcaattg tggccagtca ctatagctac gtcagagggt agtgggagca   2340
gttgcgtcgt tggattgaaa acaggtggat cgtatcagat attatgcatt cacatggaca   2400
gtaaatgtgg tacagtaact tcgcaaacaa taaaatctgt cacaatttat tagtgcactc   2460
ctctgacgta aatgcttcta cgtcagagga tttgattccg agggccgctg cacccatcac   2520
taatgacggt ctttacccat catcatggac cattgttcac atccatgcta tcactgtcgt   2580
cctgtccatg cactgcagcc ctctataaat actggcatcc ctcccccgtt cacagatcac   2640
acaacacaag caagaaataa acggtagctg ccataactag tggatccaaa catggcggcc   2700
ctggtgatcc tgggcttcct gttcctgtcc gtggctgtgc agggcaaggt gttcgaaagg   2760
tgcgaactgg ctaggaccct gaagaagctg ggcctggatg gctacaaggg cgtgtccctg   2820
gctaactggc tgtgcctgac caagtgggaa tcctcctaca acaccaaggc taccaactac   2880
aacccatcct ccgaatccac cgactacggc atcttccaga tcaactccaa gtggtggtgc   2940
aacgatggca agaccccaaa cgctgtggat ggctgccacg tgtcctgctc cgagctgatg   3000
gaaaacgata tcgctaaggc tgtggcttgc gctaagcaca tcgtgtccga acagggcatc   3060
accgcctggg tggcttggaa gtcccactgc agggatcacg atgtgtcctc ctacgtggaa   3120
ggctgcaccc tgtgattcga attcggatcc gaattgatct tcattgcagt ttttaaagta   3180
ttttatatat ttactatttc agtgagggtc tccctcctta gtattatata tgtacttcag   3240
aaatagtagt cattctgcag gggagtgagg ttcacctcca accctatggt tactatttct   3300
tactagcgtc gaactacatt acggacaccc tgttgtgtgg ttctaccacg agtcaggagc   3360
tgcgagtatt gtagcaagag aagaattatc aagcttatcg ataccgtcga ggggtccgca   3420
aaaatcacca gtctctctct acaaatctat ctctctctat tttctccag aataatgtgt    3480
gagtagttcc cagataaggg aattagggtt cttatagggt ttcgctcatg tgttgagcat   3540
ataagaaacc cttagtatgt atttgtattt gtaaaatact tctatcaata aaatttctaa   3600
ttcctaaaac caaaatccag t                                             3621
```

<210> SEQ ID NO 49
<211> LENGTH: 3855
<212> TYPE: DNA
<213> ORGANISM: Artificial Sequence
<220> FEATURE:
<223> OTHER INFORMATION: Expression cassette JAS-BvLz(m)-3'SrMV UTR-35S
<220> FEATURE:
<221> NAME/KEY: promoter
<222> LOCATION: (54)..(2681)
<223> OTHER INFORMATION: JAS Promoter
<220> FEATURE:
<221> NAME/KEY: misc_feature
<222> LOCATION: (2694)..(3137)
<223> OTHER INFORMATION: BvLz (m) coding sequence
<220> FEATURE:
<221> NAME/KEY: misc_feature
<222> LOCATION: (3158)..(3384)

<223> OTHER INFORMATION: 3' Untranslated Region of SrMV
<220> FEATURE:
<221> NAME/KEY: terminator
<222> LOCATION: (3659)..(3855)
<223> OTHER INFORMATION: 35S

<400> SEQUENCE: 49
tctagataat acgactcact atagggcacg cgtggtcgac ggcccgggct ggtctgcgac 60
agctagaggc gccaccgcgt cctagcttcc tccaacttct cgtcggagat cccttcaggg 120
atgcccaatg ccaccgcccc taagtcaacc tgcgggagct ggagcttcgc cagggtcaga 180
gctgcggcag caccctggta gaccgcattc ctgatgaccc gcggggtgcg ctccatgaag 240
aagtgcattc gcccaaccaa gtcgagtggg tcgcctggag ggggcgggga agcaaaacgt 300
tgcatgcacc tagcgccctg gcagcgagct cctgtagtat cacctgcgtc gcctccagct 360
catgctcgca agcctccagg gcggcccggc agtgctccaa cactttcgcc tcctcctaca 420
gctccttcca catgcagtcg tgctccgcac gcaccttctc cacctttta ctcttttctt 480 tctcttttct tggcccatct ttggtatttt cacaaatgtc cccctacaaa tgataaatca 540
ccaaaactca tggagcttgc tagttataaa ctctaattct aagtttggtg tttatttgag 600
tggattttgt gtgaaagttg gtggttagaa ataggagtta aggaccgcca acaagatccc 660
ccacacttag ccctttgctc atcctcgagt aaagttcaag gactaaggtg gaacatctcc 720
tcaaatggta cgatgcctgc atataagtta ttccaagcct cacctataca tgtgaacttt 780
gaagtgtcta ccacgccatc ttgggtggtt gagaaatgga acagatcaga atccagtcat 840
ctttacctct cttgcttaga taacttgggt ttttgtaagg ttttcaaatt taaaacatag 900
tcttgctcct caaatgattc tctcatatag ctcaatgtgt atggtttctc accaaggcaa 960
tgttttgcct cttttcatcc tacttctaat atttcttttg tggagcttag ggtagggaat 1020
gaaaaggaag catacttgca ttgcatatgt tactaagtca aaaaccaaat ctgaggagaa 1080
gcaagtcata caatctgatc aagatgtgca agtgtgtgga tatgtggatt aagataactc 1140
ctgtttattc atgctctcct ccttaataaa ctttagaggg catggcaatc tttgcatggg 1200
ccttcatgag ctcatcgtat gtctaagcat ggagctcatc atttatataa gcatggtgat 1260
accaaaatta ctccttttga gcatgtttat atttaggagg acgttttacc tgttgaggta 1320
aatctgaacg ctaataaatc ggctaagcaa aataatttat cacctgttga ttctaacaat 1380
ttgatgatgg acaatattga tgaggtgact gacaaatgat tgaaggcttt aaaggagatt 1440
gagaaggata aatctacaat aaaaatgtaa agaagaaagc attcaaagtg tgagatctgg 1500
tgtggaagac tattttgcct cttgggggta aaagacaaca agtttagtaa gtggcctcaa 1560
aattgggagg gcccatgcaa gattgttaaa gtaattgttt tggattgacg gaggcatttc 1620
aaggtgatca tctacctaga gctctcaatg ggaggtgctc gaagacatat tacccatgtg 1680
tatggcaaga tgtttagcta gtaactgact gatagtgtaa acgatctcca atggggcaag 1740
acatattacc taaggccagg ctggtttttg caagttcgag taggatatag agattctcgt 1800
gcgagttgta aacgatctcc aatggggcaa gacatcctac cctatatata gtgaaggggc 1860
agtagctgat tgagaatcaa tcaatcaagc acaatataat ttattaattt tttattcaaa 1920
cccaattttt ttcctttcc aaccctaatt atagttttcc ttttgcctct aggacaaatt 1980
gacgtgttcc gggtatcctg ctgaattaag aacaacccta ggtgcacctg tcccgataga 2040
gtcccacctg ggtaggcatt catagggatt cgtgtatttc ctgcaaaaaa gcgattaagc 2100
tggcttctaa aactggctag gccggattct gtggccttca ctaccaggtg attttcatgt 2160

```
gatccgtgca ttctagcact ttgctatgta acccaaactt aagtcgacaa ctataaatat   2220

gctacttgca ggatgttatc acgacacaac tcctaatcta cggaagccta agtttagttt   2280

tgctcggaga caagcaattg tggccagtca ctatagctac gtcagagggt agtgggagca   2340

gttgcgtcgt tggattgaaa acaggtggat cgtatcagat attatgcatt cacatggaca   2400

gtaaatgtgg tacagtaact tcgcaaacaa taaaatctgt cacaatttat tagtgcactc   2460

ctctgacgta aatgcttcta cgtcagagga tttgattccg agggccgctg cacccatcac   2520

taatgacggt ctttacccat catcatggac cattgttcac atccatgcta tcactgtcgt   2580

cctgtccatg cactgcagcc ctctataaat actggcatcc ctcccccgtt cacagatcac   2640

acaacacaag caagaaataa acggtagctg ccataactag tccggatcca aacatggcgg   2700

ccctggtgat cctgggcttc ctgttcctgt ccgtggctgt gcagggcaag gtgttcgaaa   2760

ggtgcgaact ggctaggacc ctgaagaagc tgggcctgga tggctacaag ggcgtgtccc   2820

tggctaactg gctgtgcctg accaagtggg aatcctccta caacaccaag gctaccaact   2880

acaacccatc ctccgaatcc accgactacg gcatcttcca gatcaactcc aagtggtggt   2940

gcaacgatgg caagacccca aacgctgtgg atggctgcca cgtgtcctgc tccgagctga   3000

tggaaaacga tatcgctaag gctgtggctt gcgctaagca catcgtgtcc gaacagggca   3060

tcaccgcctg ggtggcttgg aagtcccact gcagggatca cgatgtgtcc tcctacgtgg   3120

aaggctgcac cctgtgattc gaaaattcgg atccgatgat cttcattgca gtttttaaag   3180

tattttatat atttactatt tcagtgaggg tctccctcct tagtattata tatgtacttc   3240

agaaatagta gtcattctgc aggggagtga ggttcacctc caaccctatg gttactattt   3300

cttactagcg tcgaactaca ttacggacac cctgttgtgt ggttctacca cgagtcagga   3360

gctgcgagta ttgtagcaag agaagaattg atcttcattg cagtttttaa agtattttat   3420

atatttacta tttcagtgag ggtctccctc cttagtatta tatatgtact tcagaaatag   3480

tagtcattct gcaggggagt gaggttcacc tccaacccta tggttactat ttcttactag   3540

cgtcgaacta cattacggac accctgttgt gtggttctac cacgagtcag gagctgcgag   3600

tattgtagca agagaagaat tatcaagctt atcgataccg tcgaggggtc cgcaaaaatc   3660

accagtctct ctctacaaat ctatctctct ctatttttct ccagaataat gtgtgagtag   3720

ttcccagata agggaattag ggttcttata gggtttcgct catgtgttga gcatataaga   3780

aacccttagt atgtatttgt atttgtaaaa tacttctatc aataaaattt ctaattccta   3840

aaaccaaaat ccagt                                                    3855
```

<210> SEQ ID NO 50
<211> LENGTH: 2854
<212> TYPE: DNA
<213> ORGANISM: Artificial Sequence
<220> FEATURE:
<223> OTHER INFORMATION: Expression cassette SCBV21-BvLz(m)-35S NOS
<220> FEATURE:
<221> NAME/KEY: promoter
<222> LOCATION: (1)..(1816)
<223> OTHER INFORMATION: SCBV21 Promoter
<220> FEATURE:
<221> NAME/KEY: misc_feature
<222> LOCATION: (1857)..(2300)
<223> OTHER INFORMATION: BvLz (m) coding sequence
<220> FEATURE:
<221> NAME/KEY: terminator
<222> LOCATION: (2374)..(2570)
<223> OTHER INFORMATION: 35S
<220> FEATURE:

<221> NAME/KEY: terminator
<222> LOCATION: (2602)..(2854)
<223> OTHER INFORMATION: NOS

<400> SEQUENCE: 50
gaagaacagc atgctgaaca tctgtggaag atgctacaga tatgcaagaa gaatgggtta 60
atcttaagcc cttccaagta taaattggag taaaaagagt tgactttctt ggttcaacaa 120
ttggagataa tcagttagct gttcaagaac atatagtctc caagatagct gattttgatg 180
aagaacgtct caagaccaag gaaggactga aaagctggct ggcaacactc aattatgcca 240
gaaatcacat caaggatatg ggaaaactcc ttggaccctt atatcctaaa acttcagaaa 300
agggagcaaa aggattaaat tctgaagatt ggaaattaat cagcagaatc aagacaatgg 360
tcagaaatct gccaaatctg actattccac cagaggatgc atatattatc attgaaacag 420
atgcttgtgc aactggttgg ggtgcagttt gcaaatggaa gaaatccaag gcagacccaa 480
gaagctccga gctcatatgt cgatatgcaa gtgggaaatt tgacaaacca aaagggacat 540
gtgatgcaga aatctatgga gtaatgaatg ggctggagaa aatgagactc ttttatcttg 600
ataaaaggga aatcactgtg aggacagata gtgccgcaat agagaggttc tacaacaaga 660
gtgttgaaca taaaccctca gaaatccgtt ggataaggtt tatggactat atcactggag 720
caggaccaaa gattgtgatt gagcatatca aaggaaaaca caatggtctg gcagatatcc 780
tctcaagatt gaaagcaaaa ctggcagaat caccttcaga agaagtggtt ttacttgcga 840
aagctttaaa ggaagttgca tactatcctg aacacccgca agtgccaaaa ctaattgaat 900
ggggaaagca aattcttgat ccatttccca agttcaagaa ggacatgttt gaaaaaactg 960
aacacatcat gatggctagt caagagccta cactgctttg tggatgtaga aggcctgcat 1020
atcagttcac atctggcaca aaactcaacc caagcaggaa gttctataaa tgtgcaatga 1080
acatgtgcca ctgctggtat tggcagatc ttttagaaga atatgtccaa gaacgaattg 1140
aagtgttcat gattgagaac tttgacaaga aaatgggaat tcaagatgta ccaagtacat 1200
caaatgctaa cattccagga aattttaaat ctcttgcaga tttgaagaag gataaagaag 1260
ctaaagctga atatcaagac atgcttgata atcatcgttc aagcattatt gacagaccaa 1320
ggccaacaga tgaacacttc aagcctggat acatgtacac cgattccctg cagaagatca 1380
aggaggacta cgcaagccca agacaggagg aaccaccatg agaagacatt gagttctggt 1440
tatgcaagga agaagactac cacacagaag acctcaatac agaagatgca gttgatctta 1500
ctgacgtaag caatgacgat cagtggaggc gatcgtaagc aatgatgcac ggaaggacaa 1560
ttatggagcg tggaggaccc atcaagcact cagaacgcga acctcaactt tcggcgccag 1620
caccttgtat ctttagttgg tgtgtgtctt tttcggcatc tgtgccacct tacctttgtc 1680
ggccacgttg cctatgctta gcacctacgc aagcatagcg ctcggctggt gtgtgttccc 1740
tctgcctata taaggcatgg ttgtaagact cttacactca tcggtagttc accacatgat 1800
catttgagca agtttgaatc gaattcccgc ggccgccatg catctcggat ccaaacatgg 1860
cggccctggt gatcctgggc ttcctgttcc tgtccgtggc tgtgcagggc aaggtgttcg 1920
aaaggtgcga actggctagg accctgaaga agctgggcct ggatggctac aagggcgtgt 1980
ccctggctaa ctggctgtgc ctgaccaagt gggaatcctc ctacaacacc aaggctacca 2040
actacaaccc atcctccgaa tccaccgact acggcatctt ccagatcaac tccaagtggt 2100
ggtgcaacga tggcaagacc ccaaacgctg tggatggctg ccacgtgtcc tgctccgagc 2160
tgatggaaaa cgatatcgct aaggctgtgg cttgcgctaa gcacatcgtg tccgaacagg 2220

```
gcatcaccgc ctgggtggct tggaagtccc actgcaggga tcacgatgtg tcctcctacg    2280

tggaaggctg caccctgtga ttcgaattcg gatcccccgg gctgcaggaa ttcgatatca    2340

agcttatcga taccgtcgag gggtccgcaa aaatcaccag tctctctcta caaatctatc    2400

tctctctatt tttctccaga ataatgtgtg agtagttccc agataaggga attagggttc    2460

ttatagggtt tcgctcatgt gttgagcata taagaaaccc ttagtatgta tttgtatttg    2520

taaaatactt ctatcaataa aatttctaat tcctaaaacc aaaatccagt gacctgcagg    2580

ggccgctcga cgaatttccc cgatcgttca aacatttggc aataaagttt cttaagattg    2640

aatcctgttg ccggtcttgc gatgattatc atataatttc tgttgaatta cgttaagcat    2700

gtaataatta acatgtaatg catgacgtta tttatgagat gggtttttat gattagagtc    2760

ccgcaattat acatttaata cgcgatagaa aacaaaatat agcgcgcaaa ctaggataaa    2820

ttatcgcgcg cggtgtcatc tatgttacta gatc                                2854
```

COMPOSITIONS, ORGANISMS, SYSTEMS, AND METHODS FOR EXPRESSING A GENE PRODUCT IN PLANTS

RELATED APPLICATIONS

This application is a continuation of U.S. application Ser. No. 13/104,158, filed May 10, 2011, which claims priority to U.S. Provisional Application No. 61/395,197 filed May 10, 2010 and U.S. Provisional Application No. 61/400,976 filed Aug. 5, 2010. The entire contents of each of the above applications are hereby incorporated in their entirety by this reference.

FIELD OF THE DISCLOSURE

The present disclosure relates, in some embodiments, to compositions, organisms, systems, and methods for expressing a gene product in a plant using a promoter operable in monocots, dicots, or both monocots and dicots.

BACKGROUND OF THE DISCLOSURE

Biotechnology promises to revolutionize everything from agriculture to modern medicine. For example, methods of genetically engineering plants are being explored to increase productivity through greater drought and insect resistance as well as increased yields. In addition, plants are being examined as potential biofactories for the production of proteins (e.g., antibodies) and other compounds for use in human and veterinary medicine. However, a limited number of promoters exist for driving expression of a gene product of interest in plants. Some of these are effective at driving expression in only some plants. Others are effective at driving expression in some tissues and/or cells, but not others.

SUMMARY

Accordingly, a need has arisen for promoters operable in plants including promoters that are operable monocots, dicots, or both monocots and dicots and/or promoters that are operable in multiple tissues and/or cells.

The present disclosure relates, in some embodiments, to compositions, organisms, systems, and methods for expressing a gene product in a plant using a promoter operable in monocots, dicots, or both monocots and dicots. For example, a composition may comprise a nucleic acid (e.g., an isolated and/or purified nucleic acid) comprising an expression control sequence (e.g., a promoter). In some embodiments, an expression control sequence may comprise a nucleic acid sequence at least about 85% identical to a sequence selected from (a) nucleotides 1-1786 of SEQ ID NO: 1, (b) nucleotides 1450-1786 of SEQ ID NO: 1, (c) SEQ ID NO: 1, (d) SEQ ID NO: 17, (e) SEQ ID NO: 18, (f) SEQ ID NO: 26, (g) SEQ ID NO: 27, (h) SEQ ID NO: 32, and/or (i) SEQ ID NO: 33; wherein the expression control sequence has promoter activity in at least one monocot and at least one dicot. An expression control sequence may have promoter activity in at least two monocots and at least two dicots according to some embodiments. A nucleic acid may comprise, in some embodiments, a expression control sequence (e.g., SEQ ID NO: 1) and an exogenous nucleic acid, wherein the expression control sequence is operable to drive transcription of the exogenous nucleic acid in at least one monocot and at least one dicot. According to some embodiments, an isolated nucleic acid according to claim 3, wherein the exogenous nucleic acid comprises a transgene. An isolated nucleic acid may comprise an exogenous nucleic acid that (a) alters carbon metabolism in the plant cell when expressed or transcribed and/or (b) encodes an insecticide effective against at least one stem-boring insect, in some embodiments.

According to some embodiments, the present disclosure relates to an expression vector. For example, an expression vector may comprise, in a 5' to 3' direction, a sugarcane bacilliform virus (SCBV) promoter (e.g., (a) nucleotides 1-1786 of SEQ ID NO: 1, (b) nucleotides 1450-1786 of SEQ ID NO: 1, (c) SEQ ID NO: 1, (d) SEQ ID NO: 17, (e) SEQ ID NO: 18, (f) SEQ ID NO: 26, (g) SEQ ID NO: 27, (h) SEQ ID NO: 32, and/or (i) SEQ ID NO: 33); an exogenous nucleic acid (e.g., a transgene); and a 3' termination sequence, wherein the SCBV promoter has promoter activity sufficient to express the exogenous nucleic acid in at least one monocot and at least one dicot. An expression vector may be located in a cell (e.g., a bacterial cell, a yeast cell, a plant cell, an insect cell, a mammalian cell) according to some embodiments. An expression vector may comprise, according to some embodiments, the nucleotide sequence of AAAATGG at positions −3 to +4 (e.g., at nucleotides 1858-1864 of SEQ ID NO; 18). In some embodiments, an expression vector may comprise a linker (e.g., between the expression control sequence and the exogenous nucleic acid) having a length of from about 1 to about 200 nucleotides.

The present disclosure further relates, in some embodiments, to a cell (e.g., a bacterial cell, a yeast cell, a plant cell, an insect cell, a mammalian cell) comprising an expression vector comprising an expression control sequence (e.g., an SCBV promoter). For example, a cell may comprise an expression vector having an SCBV promoter (e.g., having a nucleotide sequence at least about 85% identical to SEQ ID NO: 1); an exogenous nucleic acid; and a 3' termination sequence, wherein the SCBV promoter has promoter activity sufficient to express the exogenous nucleic acid in at least one monocot and at least one dicot. An exogenous nucleic acid may comprise a transgene in some embodiments. For example, an exogenous nucleic acid may (a) alter carbon metabolism in the plant cell when expressed or transcribed and/or (b) encode an insecticide effective against at least one stem-boring insect. A cell, in some embodiments, may be a plant cell (e.g., located in a plant). A cell may comprise a plant cell (or plant) selected from a monocot cell and a dicot cell. A monocot may be selected from sugarcane, *miscanthus*, a *miscanthus*×sugarcane hybrid, switch grass, oats, wheat, barley, maize, rice, banana, *yucca*, onion, asparagus, sorghum and hybrids thereof. A dicot may be selected from coffee, tomato, pepper, tobacco, lima bean, *Arabidopsis*, rubber, orange, grapefruit, potato, squash, peas, and sugar beet. A plant, in some embodiments, may comprise an expression vector having a promoter (e.g., having a nucleotide sequence at least about 85% identical to SEQ ID NO: 1), an exogenous nucleic acid operably linked to the promoter, and a 3' termination sequence, wherein the promoter has promoter activity sufficient to express the exogenous nucleic acid in at least one monocot and at least one dicot.

The present disclosure relates, in some embodiments, to methods for constitutively expressing an exogenous nucleic acid in a plant. For example, a method may comprise contacting an expression cassette or expression vector with the cytosol of a cell of the plant, wherein the expression cassette or expression vector comprises (i) the exogenous nucleic acid, (ii) an expression control sequence (e.g., a SCBV promoter having a nucleotide sequence at least about 85% identical to SEQ ID NO: 1) operable to drive expression of the exogenous nucleic acid, and (iii) a 3' termination sequence operably linked to the exogenous nucleic acid, and wherein the plant is selected from the group consisting of a monocot and a dicot. Contacting, according to some embodiments, may comprise biolistically bombarding the cell with a particle comprising the expression cassette and/or co-cultivating the cell with a *Agrobacterium* cell comprising the expression cassette.

In some embodiments, the present disclosure relates to methods directing constitutive expression of a nucleic acid in a plant. For example, a method may comprise transforming a plant (e.g., a plant, a plant cell, a leaf disc, an embryonic callus) with an expression nucleic acid, the expression nucleic acid (e.g., an expression vector) comprising an expression control sequence (e.g., a promoter having a nucleotide sequence at least about 85% identical to SEQ ID NO: 1), an exogenous nucleic acid and a 3' termination sequence, wherein the plant is selected from the group consisting of a monocot and a dicot. Transforming may comprise, according to some embodiments, biolistically bombarding the plant with a particle comprising the expression cassette and/or co-cultivating the plant with a *Agrobacterium* cell comprising the expression cassette. A method may comprise, in some embodiments, regenerating a plant from a transformed cell (e.g., embryonic callus) to form one or more progeny of the transformed cell. A method may comprise cultivating and/or breeding progeny of a transformed cell according to some embodiments.

The present disclosure relates, according to some embodiments, to an isolated nucleic acid (e.g., an isolated and/or purified nucleic acid) comprising an expression control sequence. An expression control sequence may comprise, for example, the sequence of nucleotides 632-716 of SEQ ID NO: 33; wherein the expression control sequence has promoter activity in at least one monocot and at least one dicot. In some embodiments, an expression control sequence may have sufficient length (e.g., more than about 0.3 kb, more than about 0.4 kb, more than about 0.5 kb, more than about 0.6 kb, more than about 0.7 kb, and/or more than about 0.8 kb) to be operable as an expression control sequence in at least one monocot and at least one dicot. For example, an expression control sequence may be at least about 0.75 kb. In some embodiments, a nucleic acid (e.g., an isolated and/or purified nucleic acid) may comprise an expression control sequence having a sequence selected from the group consisting of SEQ ID NO: 30, SEQ ID NO: 31, SEQ ID NO: 32, SEQ ID NO: 33 and combinations thereof; wherein the expression control sequence has promoter activity in at least one monocot and at least one dicot. For example, a nucleic acid may comprise (e.g., in a 5' to 3' direction) an expression control sequence comprising the sequence of SEQ ID NO:30 and the sequence of SEQ ID NO:31 separated by a spacer of about 630 nucleotides, a linker of from about 1 to about 75 nucleotides in length, and a start codon, wherein the expression control sequence has promoter activity in at least one monocot and at least one dicot. A linker may have, in some embodiments, at least about 85%, at least about 90%, at least about 95%, at least about 98%, and/or at least about 99% identity to the sequence of nucleotides 778-805 of SEQ ID NO:32. According to some embodiments, a spacer may have at least about 85%, at least about 90%, at least about 95%, at least about 98%, and/or at least about 99% identity to sequence of nucleotides 96-726 of SEQ ID NO:32. An expression control sequence may comprise at its 5' end a sequence having at least about 85%, at least about 90%, at least about 95%, at least about 98%, and/or at least about 99% identity to the sequence of nucleotides 1-44 of SEQ ID NO:32.

The present disclosure further relates, in some embodiments, to expression systems for expressing desirable amounts of a gene product (e.g., protein) of interest. An expression system may comprise, for example, nucleic acids, expression cassettes, cells, and/or plants comprising two or more expression control sequences, each operably linked to a coding sequence (e.g., transgene) encoding a gene product (e.g., protein) of interest. An expression system may comprise, according to some embodiments, a plant having two or more expression cassettes, each comprising an expression control sequence (e.g., promoter), a coding sequence encoding the gene product (e.g., protein) of interest, and/or one or more terminators, wherein each expression control sequence (e.g., promoter) is different from the other(s) and/or each copy of the coding sequence encoding the gene product (e.g., protein) of interest is substantially identical and/or identical to the other(s). An expression control sequence (e.g., promoter) may comprise any promoter operative in a plant including, for example, a maize ubiquitin 1 promoter (with or without a heat shock element), a sugarcane proline-rich protein promoter, a sugarcane elongation factor 1α promoter, a sugarcane jasmonate-inducible promoter, a sugarcane bacilliform virus promoter, a sugarcane O-methyltranserase promoter, and/or combinations thereof. An expression system may comprise a plant having 2, 3, 4, 5, or more promoters, each independently selected from the group consisting of a maize ubiquitin 1 promoter (with or without a heat shock element), a sugarcane proline-rich protein promoter, a sugarcane elongation factor 1α promoter, a sugarcane jasmonate-inducible promoter, a sugarcane bacilliform virus promoter, a sugarcane O-methyltransferase promoter, and/or combinations thereof, and each operably linked (e.g., in trans) to a coding sequence (e.g., transgene) encoding a gene product (e.g., protein) of interest, wherein each copy of the coding sequence encoding the gene product (e.g., protein) of interest is substantially identical and/or identical to the other(s). A coding sequence of interest may include, in some embodiments, any of the coding sequences cited in the present disclosure.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

Some embodiments of the disclosure may be understood by referring, in part, to the present disclosure and the accompanying drawings, wherein.

BRIEF DESCRIPTION OF THE SEQUENCE LISTING

Figure 1:
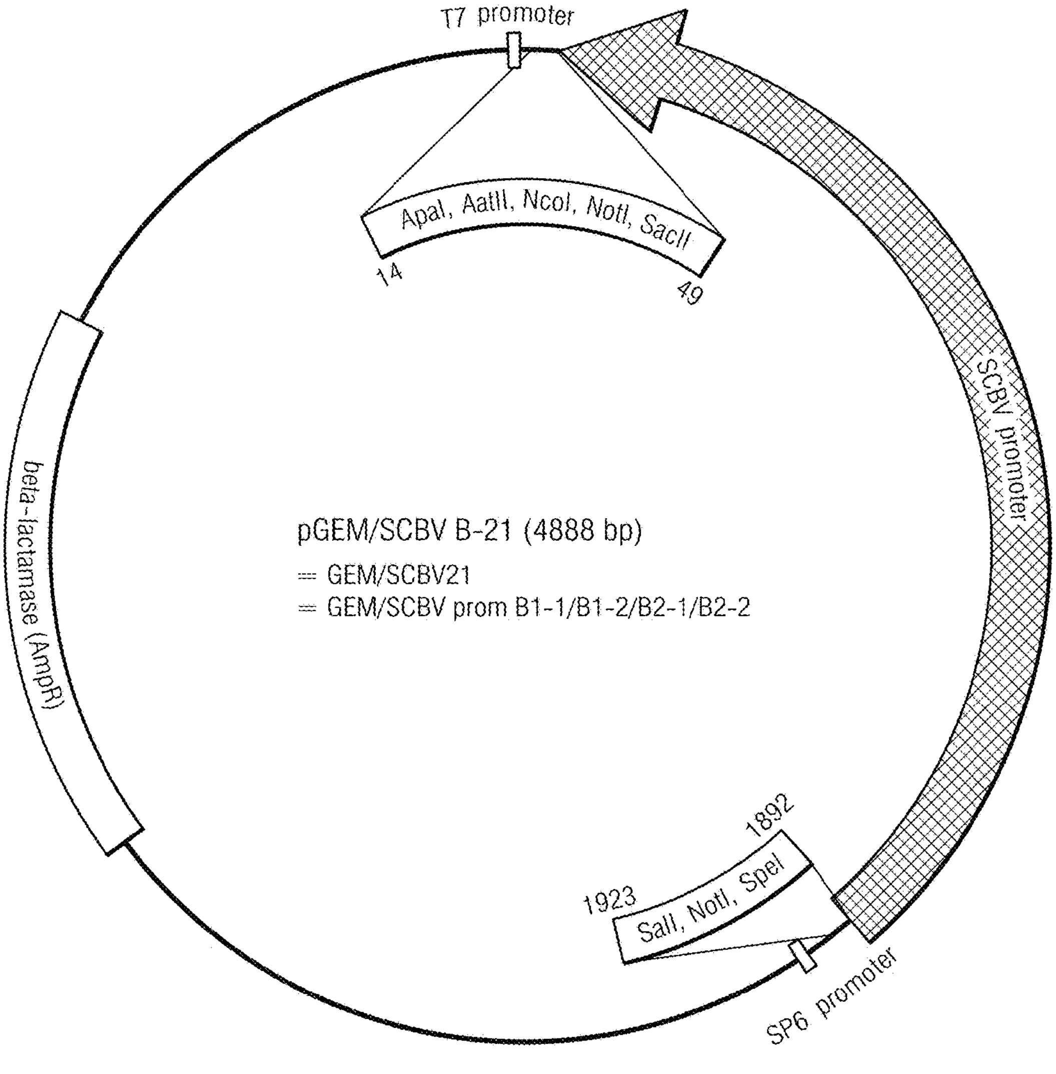
FIG. 1 illustrates a vector for a promoter according to a specific example embodiment of the disclosure.

Some embodiments of the disclosure may be understood by referring, in part, to the present disclosure and the accompanying sequence listing, wherein:

SEQ ID NO: 1 illustrates a sugarcane bacilliform virus promoter according to a specific example embodiment of the disclosure;

SEQ ID NO: 2 illustrates an expression cassette according to a specific example embodiment of the disclosure comprising a sugarcane bacilliform virus promoter, a GUS coding sequence, and a NOS terminator;

SEQ ID NO: 3 illustrates an expression cassette according to a specific example embodiment of the disclosure comprising a sugarcane bacilliform virus promoter, an enhanced YFP coding sequence, and a NOS terminator;

SEQ ID NO: 4 illustrates an expression cassette according to a specific example embodiment of the disclosure comprising a 35S promoter, a GUS coding sequence, and a NOS terminator;

SEQ ID NO: 5 illustrates an expression cassette according to a specific example embodiment of the disclosure comprising a 35S promoter, an enhanced YFP coding sequence, and a NOS terminator;

SEQ ID NO: 6 illustrates an expression cassette according to a specific example embodiment of the disclosure comprising an E35S promoter, an enhanced YFP coding sequence, and a NOS terminator;

SEQ ID NO: 7 illustrates an expression cassette according to a specific example embodiment of the disclosure comprising a maize ubiquitin promoter (mUbi1 no hse), a GUS coding sequence, and a NOS terminator;

SEQ ID NO: 8 illustrates an expression cassette according to a specific example embodiment of the disclosure comprising a maize ubiquitin promoter (mUbi1 no hse), an enhanced YFP coding sequence, and a NOS terminator;

SEQ ID NO: 9 illustrates an expression cassette according to a specific example embodiment of the disclosure comprising a maize ubiquitin promoter, a GUS coding sequence, and a NOS terminator;

SEQ ID NO: 10 illustrates an expression cassette according to a specific example embodiment of the disclosure comprising a ubiquitin promoter, an enhanced YFP coding sequence, and a NOS terminator;

SEQ ID NO: 11 illustrates a P-2 PCR primer according to a specific example embodiment of the disclosure;

SEQ ID NO: 12 illustrates a P-W3F PCR primer according to a specific example embodiment of the disclosure;

SEQ ID NO: 13 illustrates a P-W4F PCR primer according to a specific example embodiment of the disclosure;

SEQ ID NO: 14 illustrates a P-W1R PCR primer according to a specific example embodiment of the disclosure;

SEQ ID NO: 15 illustrates a SCBV/Prom/F PCR primer according to a specific example embodiment of the disclosure;

SEQ ID NO: 16 illustrates a SCBV/Prom/R PCR primer according to a specific example embodiment of the disclosure;

SEQ ID NO: 17 illustrates a sugarcane bacilliform virus promoter according to a specific example embodiment of the disclosure;

SEQ ID NO: 18 illustrates a sugarcane bacilliform virus promoter according to a specific example embodiment of the disclosure;

SEQ ID NO: 19 illustrates a vector (wild type pSK-SCBV21-EYFP-Nos) with a promoter according to a specific example embodiment of the disclosure;

SEQ ID NO: 20 illustrates a vector with a promoter (deletion mutant B) according to a specific example embodiment of the disclosure;

SEQ ID NO: 21 illustrates a vector with a promoter (deletion mutant C) according to a specific example embodiment of the disclosure;

SEQ ID NO: 22 illustrates a vector with a promoter (deletion mutant D) according to a specific example embodiment of the disclosure;

SEQ ID NO: 23 illustrates a vector with a promoter (deletion mutant E) according to a specific example embodiment of the disclosure;

SEQ ID NO: 24 illustrates a vector with a promoter (deletion mutant F) according to a specific example embodiment of the disclosure;

SEQ ID NO: 25 illustrates a sugarcane bacilliform virus promoter (deletion B) according to a specific example embodiment of the disclosure;

SEQ ID NO: 26 illustrates a sugarcane bacilliform virus promoter (deletion C) according to a specific example embodiment of the disclosure;

SEQ ID NO: 27 illustrates a sugarcane bacilliform virus promoter (deletion D) according to a specific example embodiment of the disclosure;

SEQ ID NO: 28 illustrates a sugarcane bacilliform virus promoter (deletion E) according to a specific example embodiment of the disclosure;

SEQ ID NO: 29 illustrates a sugarcane bacilliform virus promoter (deletion F) according to a specific example embodiment of the disclosure;

SEQ ID NO: 30 illustrates a transcription start site (TSS1) according to a specific example embodiment of the disclosure;

SEQ ID NO: 31 illustrates a transcription start site (TSS2) according to a specific example embodiment of the disclosure;

SEQ ID NO: 32 illustrates a sugarcane bacilliform virus promoter with TSS1 and TSS2 according to a specific example embodiment of the disclosure;

SEQ ID NO: 33 illustrates a sugarcane bacilliform virus promoter with TSS2 according to a specific example embodiment of the disclosure;

SEQ ID NO: 34 illustrates a Forward PCR primer F1 according to a specific example embodiment of the disclosure;

SEQ ID NO: 35 illustrates a Forward PCR primer F2 according to a specific example embodiment of the disclosure;

SEQ ID NO: 36 illustrates a Reverse PCR primer R1 according to a specific example embodiment of the disclosure;

SEQ ID NO: 37 illustrates a Reverse PCR primer R2 according to a specific example embodiment of the disclosure;

SEQ ID NO: 38 illustrates an expression cassette according to a specific example embodiment of the disclosure comprising a sugarcane bacilliform virus promoter, a bovine lysozyme coding sequence, a 35S terminator, and a NOS terminator;

SEQ ID NO: 39 illustrates an expression cassette according to a specific example embodiment of the disclosure comprising a maize ubiquitin promoter (with no heat shock element), a bovine lysozyme coding sequence, and a 35S terminator;

SEQ ID NO: 40 illustrates an expression cassette according to a specific example embodiment of the disclosure comprising a maize ubiquitin promoter (with no heat shock element), a bovine lysozyme coding sequence, a 3' untranslated region of Sorghum mosaic virus protein, and a 35S terminator;

SEQ ID NO: 41 illustrates an expression cassette according to a specific example embodiment of the disclosure comprising a maize ubiquitin promoter (with no heat shock element), a 5' untranslated region of Sorghum mosaic virus protein, a bovine lysozyme coding sequence, a 3' untranslated region of Sorghum mosaic virus protein, and a 35S terminator;

SEQ ID NO: 42 illustrates an expression cassette according to a specific example embodiment of the disclosure comprising a maize ubiquitin promoter (with no heat shock element), a bovine lysozyme coding sequence, a 35S terminator, and a NOS terminator;

SEQ ID NO: 43 illustrates an expression cassette according to a specific example embodiment of the disclosure comprising a sugarcane proline rich promoter (with no 5'

UTR), a bovine lysozyme coding sequence, a 3' untranslated region of Sorghum mosaic virus protein, and a 35S terminator;

SEQ ID NO: 44 illustrates an expression cassette according to a specific example embodiment of the disclosure comprising a sugarcane proline rich promoter (with no 5' UTR), a 5' untranslated region of Sorghum mosaic virus protein, a bovine lysozyme coding sequence, a 3' untranslated region of Sorghum mosaic virus protein, and a 35S terminator;

SEQ ID NO: 45 illustrates an expression cassette according to a specific example embodiment of the disclosure comprising a sugarcane proline rich promoter (with no 5'UTR), a bovine lysozyme coding sequence, a 35S terminator, and a NOS terminator;

SEQ ID NO: 46 illustrates an expression cassette according to a specific example embodiment of the disclosure comprising a sugarcane elongation factor 1α promoter, a bovine lysozyme coding sequence, a 3' untranslated region of Sorghum mosaic virus protein, and a 35S terminator;

SEQ ID NO: 47 illustrates an expression cassette according to a specific example embodiment of the disclosure comprising a sugarcane elongation factor 1α promoter, a bovine lysozyme coding sequence, a 35S terminator, and a NOS terminator;

SEQ ID NO: 48 illustrates an expression cassette according to a specific example embodiment of the disclosure comprising a jasmonate responsive promoter, a bovine lysozyme coding sequence, and a 35S terminator;

SEQ ID NO: 49 illustrates an expression cassette according to a specific example embodiment of the disclosure comprising a jasmonate responsive promoter, a bovine lysozyme coding sequence, a 3' untranslated region of Sorghum mosaic virus protein, and a 35S terminator; and SEQ ID NO: 50 illustrates an expression cassette according to a specific example embodiment of the disclosure comprising a sugarcane bacilliform virus promoter, a bovine lysozyme coding sequence, a 35S terminator, and a NOS terminator.

DETAILED DESCRIPTION

The present disclosure relates, in some embodiments, to compositions, organisms, systems, and methods for expressing a gene product in a plant using a promoter operable in monocots, dicots, or both monocots and dicots. For example, the present disclosure relates to expression control sequences (e.g., promoters), expression cassettes, expression vectors, microorganisms, and/or plants comprising a sugarcane bacilliform virus (SCBV) promoter. An expression control sequence, according to some embodiments, may be constitutively active or conditionally active in (a) an organ selected from root, leaf, stem, flower, seed, fruit, and/or tuber and/or (b) active in a tissue selected from epidermis, periderm, parenchyma, collenchyma, sclerenchyma, xylem, phloem, and/or secretory structures.

In some embodiments, an expression control sequence may be included in methods, compositions, systems, and/or organisms to alter carbon metabolism (e.g., in a sucrose accumulating tissue) and/or to express a protein (e.g., an insecticidal protein) in a plant (e.g., in sugarcane). An expression control sequence may be included, according to some embodiments, in methods, compositions, systems, and/or organisms to improve pest and/or disease tolerance and/or disease resistance (e.g., rice plants).

Sugarcane bacilliform virus (SCBV) belongs to the genus Badnavirus in the family Caulimoviridae. The virions of those species that belong to the genus Badnavirus have non-enveloped bacilliform particles. SCBV is serologically related to Banana streak virus (BSV). The genome of SCBV consists of a single double-stranded DNA of ~7600 bp in size encoding three open reading frames whose transcription is directed by a single promoter residing in between the 3' portion of ORF3 and near the 5' end of ORF1.

The promoter of SCBV Mor isolate may be active both in monocots and dicots. The promoters from other badnaviruses, including Rice tungro bacilliform virus, Commelina yellow mosaic virus, Banana streak virus and Taro bacilliform virus, have also been tested for foreign gene expression. In some embodiments, promoters from these viruses may be useful for transgene expression in monocots since the aforementioned badnaviruses infect monocots. While it seems that the promoters from RTBV, CoYMV and TaBV are typically active in vascular tissues, the promoters from SCBV and BSV direct constitutive expression of foreign genes.

SCBV is closely related to BSV and may display considerable sequence variation among different SCBV isolates. Similar sequence variations may be present in SCBV promoter regions cloned from SCB V-infected *Saccharum officinarum* species. While the PCR-derived promoter sequence cloned from *S. officinarum* Ireng Maleng showed only ~53% sequence homology with the promoter sequence of another SCBV Ireng Maleng isolate (SCBVIM-12), this PCR-derived promoter showed ~74% sequence homology with BSV promoter regions.

Preliminary screening for SCBV incidence in sugarcane fields located in the Mid R10 Grande Valley, Tex. Confirmed that SCBV is prevalent in the sugarcane fields in this region. A SCBV promoter from the SCBV-positive commercial sugarcane hybrid CP72-1210 has been isolated, purified, and cloned. Its promoter activity has been confirmed in various monocot and dicot plants and in transgenic sugarcane plants.

Expression Control Sequences

In some embodiments, an expression control sequence may comprise one or more promoters, one or more operators, one or more enhancers, one or more ribosome binding sites, and/or combinations thereof. An expression control sequence may comprise, for example, a nucleic acid having (a) promoter activity in a monocot, a dicot, or both a monocot and a dicot and (b) a nucleotide sequence more than about 70% identical to SEQ ID NO: 1, more than about 75% identical to SEQ ID NO: 1, more than about 80% identical to SEQ ID NO: 1, more than about 81% identical to SEQ ID NO: 1, more than about 82% identical to SEQ ID NO: 1, more than about 83% identical to SEQ ID NO: 1, more than about 84% identical to SEQ ID NO: 1, more than about 85% identical to SEQ ID NO: 1, more than about 86% identical to SEQ ID NO: 1, more than about 87% identical to SEQ ID NO: 1, more than about 88% identical to SEQ ID NO: 1, more than about 89% identical to SEQ ID NO: 1, more than about 90% identical to SEQ ID NO: 1, more than about 92% identical to SEQ ID NO: 1, more than about 94% identical to SEQ ID NO: 1, more than about 96% identical to SEQ ID NO: 1, more than about 98% identical to SEQ ID NO: 1, and/or more than about 99% identical to SEQ ID NO: 1. According to some embodiments, sequences that are not 100% identical over the full length of SEQ ID NO: 1 may have points and/or regions of variation that are dispersed (e.g., uniformly, haphazardly) over the length of the subject nucleic acid. For example, an expression control sequence may comprise one or more regions of sequence that are 100% identical to SEQ ID NO: 1 (e.g., in or near a TATA-box, a CCAAT-box, and/or a TSS-motif) and one or more regions that are less than 100% identical length and/or sequence. An expression control sequence may comprise, for example, a region that is about 95% identical to nucleotides 1-1450 of SEQ ID NO: 1 (in length and/or sequence) and a region that is 100% identical to nucleotides 1450-1786 of SEQ ID NO: 1.

According to some embodiments, an expression control sequence may share similarity (e.g., from more than about 70% to 100% identity as disclosed above) to (a) nucleotides 1-1786 of SEQ ID NO: 1, (b) SEQ ID NO: 17, (c) SEQ ID NO: 18, (d) SEQ ID NO: 26, (e) SEQ ID NO: 27, (f) SEQ ID NO: 32, and/or (g) SEQ ID NO: 33). For example, an expression control sequence may be more than about 85% identical to SEQ ID NO: 26, SEQ ID NO: 27, SEQ ID NO: 32, and/or SEQ ID NO: 33; more than about 95% identical to SEQ ID NO: 26, SEQ ID NO: 27, SEQ ID NO: 32, and/or SEQ ID NO: 33; and/or more than about 98% identical to SEQ ID NO: 26, SEQ ID NO: 27, SEQ ID NO: 32, and/or SEQ ID NO: 33.

An expression control sequence, in some embodiments, may comprise TSS1 (SEQ ID NO:30), TSS2 (SEQ ID NO: 31), or both TSS1 and TSS2. For example, an expression control sequence may be at least about 0.76 kb in length with the 5' end of TSS1, if present, within 100 nucleotides of the −760 position and the 5' end of TSS2, if present, within 100 nucleotides of the −80 position. An expression control sequence, for example, may be at least about 0.7 kb in length with the 5' end of TSS1, if present, within 100 nucleotides of the 5' end of the expression control sequence and the 5' end of TSS2, if present, within 100 nucleotides of the −80 position. In some embodiments, TSS2, if present, may be positioned such that it does not extend beyond the start codon. In some embodiments, TSS1 may be 5' of TSS2. An expression control sequence may comprise, in some embodiments, TSS1 and TSS2 separated by a spacer (e.g., more than about 500 nucleotides, more than about 550 nucleotides, more than about 600 nucleotides, and/or more than about 650 nucleotides), a linker of from about 1 to about 75 nucleotides in length, and/or a start codon. A spacer may have, for example, more than about 85% identity, more than about 90% identity, more than about 95% identity, and/or more than about 98% identity to the sequence of nucleotides 96-726 of SEQ ID NO:32. A linker may have, for example, more than about 85% identity, more than about 90% identity, more than about 95% identity, and/or more than about 98% identity to the sequence of nucleotides 778-805 of SEQ ID NO:32. An expression control sequence may further comprise (e.g., 5' of TSS1) a sequence having more than about 85% identity to the sequence of nucleotides 1-44 of SEQ ID NO:32.

An expression control sequence may comprise a fragment of SEQ ID NO: 1 according to some embodiments. For example, an expression control sequence may comprise the portion of SEQ ID NO: 1 that is upstream of a transcription start site (e.g., upstream of nucleotide 1787). In some embodiments, an expression control sequence may comprise a nucleic acid having at least 70% identity to nucleotides 1-1786 of SEQ ID NO: 1.

According to some embodiments, an expression control sequence may comprise a sequence of a nucleic acid found in virus (e.g., a plant virus). For example, an expression control sequence may comprise, according to some embodiments, an SCBV promoter, a Rice tungro bacilliform virus promoter, a Commelina yellow mosaic virus promoter, a Banana streak virus promoter, a Taro bacilliform virus promoter, and/or combinations thereof. In some embodiments, an expression control sequence may comprise a nucleic acid having the nucleotide sequence of SEQ ID NO: 1.

An expression control sequence, according to some embodiments, may be operable to drive higher expression of a nucleic acid sequence (e.g., a coding sequence) in a cell compared to the 35S promoter (e.g., from about 5% higher to about 50% higher, from about 50% higher to about 500% higher). Metrics for expression may include, for example, rate of appearance and/or accumulation of a gene product (e.g., RNA and/or protein) and/or total accumulation of a gene product as of one or more time points (e.g., elapsed time after a starting point and/or a stage of development). Comparative assays for gene products may be qualitative, semi-quantitative, and/or quantitative in some embodiments. Comparative assays may indirectly and/or directly assess the presence and/or amount of gene product. In some embodiments, an expression control sequence may be sensitive to one or more stimuli (e.g., one or more small molecules, one or more plant defense-inducing agents, mechanical damage, temperature, pressure). For example, activity of an expression control sequence may be enhanced or suppressed upon infection with a virus (e.g., a bacilliform virus). An expression control sequence may comprise, in some embodiments, a light responsive element, a copper responsive element, a salicylic acid responsive element, an auxin responsive element, a sulfur responsive element, and/or a dehydration responsive element. Identification of motifs may be informed by available motif prediction software (e.g., PLACE database of the National Institute of Agrobiological Sciences, Japan) and/or experimental data.

The present disclosure relates, according to some embodiments, to one or more expression control sequences like a nucleotide sequence of nucleotides −1816 to −1 of SCBV21 (e.g., nucleotides 1-1816 of SEQ ID NO:1) SEQ ID NO:1 and/or operable to direct expression in at least one monocot and/or at least one dicot. For example, an expression control sequence may include a nucleic acid sequence that differs from SEQ ID NO: 1 at one or more positions. Examples of expression control sequences that differ from SEQ ID NO: 1 may include, in some embodiments, a promoter from one or more bacilliform virus isolates. An expression control sequence, according to some embodiments, may hybridize to a nucleic acid having the nucleotide sequence of SEQ ID NO: 1 under stringent conditions. Stringent conditions may include, for example, (a) 4×SSC at 65° C. followed by 0.1×SSC at 65° for 60 minutes and/or (b) 50% formamide, 4×SSC at 65° C. An expression control sequence may comprise a deletion fragment of a nucleic acid having a sequence of SEQ ID NO: 1 and having the capacity to direct expression in at least one monocot and/or at least one dicot, in some embodiments. One of ordinary skill in the art having the benefit of the present disclosure may prepare one or more deletion fragments of a nucleic acid having a sequence of SEQ ID NO: 1.

An expression control sequence having a sequence like SEQ ID NO: 1 may be identified by database searches using the promoter or elements thereof as the query sequence using the Gapped BLAST algorithm (Altschul et al., 1997 *Nucl. Acids Res.* 25:3389-3402) with the BLOSUM62 Matrix, a gap cost of 11 and persistence cost of 1 per residue and an E value of 10. Sequence identity may be assessed by any available method according to some embodiments. For example, two sequences may be compared with either ALIGN (Global alignment) or LALIGN (Local homology alignment) in the FASTA suite of applications (Pearson and Lipman, 1988 *Proc. Nat. Acad. Sci.* 85:2444-24448; Pearson, 1990 *Methods in Enzymology* 183:63-98) with the BLOSUM50 matrix and gap penalties of −16, −4. Sequence similarity may be assessed according to ClustalW (Larkin et al., 2007, *Bioinformatics* 23(21): 2947-2948), BLAST, FASTA or similar algorithm.

Expression Cassettes and Vectors

The disclosure relates, in some embodiments, to expression vectors and/or expression cassettes for expressing a nucleic acid sequence (e.g., a coding sequence) in a cell and comprising an expression control sequence and the nucleic acid sequence operably linked to the expression control sequence. A cassette, in some embodiments, may include a nucleotide sequence capable of expressing a particular coding sequence inserted so as to be operably linked to one or more expression control sequences present in the nucleotide sequence. Thus, for example, an expression cassette may include a heterologous coding sequence which is desired to be expressed in a plant seed according to some embodiments.

The disclosure relates, in some embodiments, to an expression vector which may comprise, for example, a nucleic acid having an expression control sequence and a coding sequence operably linked to the expression control sequence. An expression vector may be contacted with a cell (e.g., a plant cell) under conditions that permit expression (e.g., transcription) of the coding sequence. An expression control sequence may be contacted with a plant cell (e.g., an embryonic cell, a stem cell, a callous cell) under conditions that permit expression of the coding sequence in the cell and/or cells derived from the plant cell according to some embodiments. An expression vector may be contacted with a cell (e.g., a plant cell), in some embodiments, under conditions that permit inheritance of at least a portion of the expression vector in the cell's progeny. Examples of expression vectors may include, without limitation the vectors shown in FIG. 1, FIG. 2, FIG. 5, and FIG. 9. According to some embodiments, an expression vector may include one or more selectable markers. For example, an expression vector may include a marker for selection when the vector is in a bacterial host, a yeast host, and/or a plant host.

According to some embodiments, the disclosure relates to an expression cassette which may comprise, for example, a nucleic acid having an expression control sequence and a coding sequence operably linked to the expression control sequence. An expression cassette may be comprised in an expression vector. A coding sequence, in some embodiments, may comprise any coding sequence expressible in at least one plant cell. For example, a coding sequence may comprise a human sequence (e.g., an antibody sequence), a non-human animal sequence, a plant sequence, a yeast sequence, a bacterial sequence, a viral sequence (e.g., plant virus, animal virus, and/or vaccine sequence), an artificial sequence, an antisense sequence thereof, a fragment thereof, a variant thereof, and/or combinations thereof. According to some embodiments, a coding sequence may comprise, a sugar transport gene and/or a sugar accumulation gene. Examples of sugar transport genes may include, without limitation, a disaccharide transporter (e.g., a sucrose transporter) and/or a monosaccharide transporter. A coding sequence may comprise, in some embodiments, a sequence encoding one or more gene products with insecticidal, antimicrobial, and/or antiviral activity. Examples of gene products that may have insecticidal activity, antimicrobial activity, and/or antiviral activity may include, without limitation, avidin, vegetative insecticidal proteins (e.g., Vip3A), insecticidal crystal proteins from *Bacillus thuringiensis* (e.g., Cry1, Cry1Ab, Cry2, Cry9), pea albumin (e.g., PA1b), hirsutellin A, lectins (e.g., smow drop lily lectin, garlic lectin, onion lectin), amylase inhibitors (e.g., alpha amylase inhibitor), arcelins (e.g., arcelins from beans), proteinase inhibitors, lysozymes (e.g., bovine lysozyme, human lysozyme, mollusk lysozyme), defensin, chitinase, β-1,3-glucanase, variants thereof, and/or combinations thereof. A coding sequence may comprise an enzyme for forming and/or modifying a polymer according to some embodiments. Examples of enzymes for forming and/or modifying a polymer may include, without limitation, a polyhydroxyalkanoate synthases, 4-hydroxybutyryl-CoA transferases, variants thereof, and/or combinations thereof. In some embodiments, a coding sequence may comprise a sequence encoding one or more enzymes that hydrolyzes cellulose. Examples of enzymes that hydrolyze cellulose include, without limitation, cellulase, endoglucanases (e.g., endo β-1,4 glucanases), glucosidases (e.g., β glucosidase), hydrolases (e.g., β-1,4-glucan cellobiohydrolase), exocellulases, variants thereof, and/or combinations thereof. In some embodiments, a coding sequence may comprise a sequence encoding one or more enzymes that form and/or modify a sugar (e.g., sucrose, trehalose, sorbitol, fructan, fructose, tagatose, sucralose). Examples of enzymes that form and/or modify a sugar may include, without limitation, trehalose-6-phosphate synthase (TPS) and trehalose-6-phosphate phosphatase (TPP). According to some embodiments, a coding sequence may comprise a sequence encoding an enzyme for forming or modifying glycine betaine, a polyamine, proline, threhalose, a variant thereof, and/or combinations thereof. A coding sequence may comprise, in some embodiments, a start codon, an intron, and/or a translation termination sequence. According to some embodiments, a coding sequence may comprise one or more natural or artificial coding sequences (e.g., encoding a single protein or a chimera). According to some embodiments, an expression cassette may optionally comprise a termination sequence.

An expression control sequence may be used, in some embodiments, to construct an expression cassette comprising, in the 5' to 3' direction, (a) the expression control sequence (e.g., a SCBV promoter), (b) a heterologous gene or a coding sequence, or sequence complementary to a native plant gene under control of the expression control sequence, and/or (c) a 3' termination sequence (e.g., a termination sequence comprising a polyadenylation site). Examples of expression cassettes may include, in some embodiments, SEQ ID NO: 2, SEQ ID NO:3, nucleotides 710-3538 of SEQ ID NO:19, nucleotides 674-2472 of SEQ ID NO:21, nucleotides 674-2377 of SEQ ID NO:22, SEQ ID NO:38, SEQ ID NO:50, and/or sequences having at least about 98% and/or at least about 99% identity thereto. An expression cassette may be incorporated into a variety of autonomously replicating vectors in order to construct an expression vector. An expression cassette may be constructed, for example, by ligating an expression control sequence to a sequence to be expressed (e.g., a coding sequence).

Some techniques for construction of expression cassettes are well known to those of ordinary skill in the art. For example, a variety of strategies are available for ligating fragments of DNA, the choice of which depends on the nature of the termini of the DNA fragments. Restriction and/or deletion fragments that contain a subject promoter TATA box may be ligated in a forward orientation to a promoterless heterologous gene or coding sequence such as the coding sequence of GUS. An expression control sequence and/or portions thereof may be provided by other means, for example chemical or enzymatic synthesis as artisan of ordinary skill having the benefit of the present disclosure may appreciate.

A nucleic acid may comprise, in a 5' to 3' direction, an expression control sequence, a linker (optional), and a coding sequence according to some embodiments. A linker may be, in some embodiments, from about 1 nucleotide to about 200 nucleotides in length and/or may comprise one or more restriction sites. Expression level of a nucleic acid sequence (e.g., a coding sequence) operably linked to an expression control sequence may be influenced by the length and/or sequence of a linker and/or the 5' sequence of the coding sequence. For example, expression level may be influenced by the junction sequence from about the −4 position to about the +4 position, in which the −1 position defines the 3' end of the junction sequence and the +1 position defines the 5' end of the coding sequence. In some embodiments, a nucleic acid may comprise, in a 5' to 3' direction, an expression control sequence, a linker, and a coding sequence, wherein the junction sequence, from positions −4 to +4 comprises a sequence selected from the sequences shown in Table 1. A nucleic acid may comprise, in a 5' to 3' direction, an expression control sequence and a coding sequence, wherein the junction sequence comprises a sequence selected from the sequences shown in Table 1 according to some embodiments. In some embodiments, a −3 to −1 sequence of AAA may be associated with higher (e.g., the highest) expression levels than other −3 to −1 sequences. A +1 to +4 sequence of ATGG may be associated with higher (e.g., the highest) expression levels than other +1 to +4 sequences (e.g., ATGC, ATGA, ATGT).

TABLE 1

| | Optional Junction Sequences | | | | | | | |
|---|---|---|---|---|---|---|---|---|
| | −4 | −3 | −2 | −1 | +1 | +2 | +3 | +4 |
| 1 | N | N | N | N | A | T | G | G/T |
| 2 | N | A/C | A/C | A/C | A | T | G | G |
| 3 | A/C | A/C | A/C | A/C | A | T | G | G |
| 4 | N | A | A | A | A | T | G | G |
| 5 | N | A | A | C | A | T | G | G |
| 6 | N | A | C | A | A | T | G | G |
| 7 | N | A | C | C | A | T | G | G |
| 8 | N | C | A | A | A | T | G | G |
| 9 | N | C | A | C | A | T | G | G |
| 10 | N | C | C | A | A | T | G | G |
| 11 | N | C | C | C | A | T | G | G |
| 12 | N | A | A | T | A | T | G | G |
| 13 | N | A | T | A | A | T | G | G |
| 14 | N | A | T | T | A | T | G | G |
| 15 | N | T | A | A | A | T | G | G |
| 16 | N | T | A | T | A | T | G | G |
| 17 | N | T | T | A | A | T | G | G |
| 18 | N | T | T | T | A | T | G | G |
| 19 | N | C | T | T | A | T | G | G |
| 20 | N | T | C | T | A | T | G | G |
| 21 | N | T | T | C | A | T | G | G |
| 22 | C | A | C | C | A | T | G | G |
| 23 | N | N | C | C | A | T | G | G |
| 24 | C | G | C | C | A | T | G | G |
| 25 | N | A/C | A/C | A/C | A | T | G | G |
| 26 | A/C | A/C | A/C | A/C | A | T | G | G |
| 27 | N | A | A | A | A | T | G | G |
| 28 | N | A | A | C | A | T | G | G |
| 29 | N | A | C | A | A | T | G | G |
| 30 | N | A | C | C | A | T | G | G |
| 31 | N | C | A | A | A | T | G | G |
| 32 | N | C | A | C | A | T | G | G |
| 33 | N | C | C | A | A | T | G | G |
| 34 | N | C | C | C | A | T | G | G |
| 35 | N | A | A | T | A | T | G | G |
| 36 | N | A | T | A | A | T | G | G |

TABLE 1-continued

| | Optional Junction Sequences | | | | | | | |
|---|---|---|---|---|---|---|---|---|
| | −4 | −3 | −2 | −1 | +1 | +2 | +3 | +4 |
| 37 | N | A | T | T | A | T | G | G |
| 38 | N | T | A | A | A | T | G | G |
| 39 | N | T | A | T | A | T | G | G |
| 40 | N | T | T | A | A | T | G | G |
| 41 | N | T | T | T | A | T | G | G |
| 42 | N | C | T | T | A | T | G | G |
| 43 | N | T | C | T | A | T | G | G |
| 44 | N | T | T | C | A | T | G | G |
| 45 | C | A | C | C | A | T | G | G |
| 46 | N | N | C | C | A | T | G | G |
| 47 | C | G | C | C | A | T | G | G |

In some embodiments, the 3' end of a heterologous coding sequence may be operably linked to a termination sequence including, for example, a polyadenylation site, exemplified by, but not limited to, a nopaline synthase polyadenylation site and/or a octopine T-DNA gene 7 polyadenylation site. A polyadenylation site may be provided by the heterologous gene or coding sequence according to some embodiments. A nucleic acid, according to some embodiments, may comprise a 5' untranslated region (5' UTR), a 3' untranslated region (3' UTR), and/or combinations thereof. For example, a nucleic acid may comprise (e.g., in a 5' to 3' direction) an expression control sequence, a 5' UTR, a coding sequence (e.g., a transgene), a 3' UTR, and/or a termination sequence.

Microorganisms

The present disclosure relates, in some embodiments, to a microorganism comprising an expression control sequence. For example, a microorganism may comprise a bacterium, a yeast, and/or a virus. In some embodiments, an expression control sequence may comprise a SCBV promoter. A microorganism may comprise an expression control sequence and a coding sequence operably linked to the expression control sequence. Examples of microorganisms may include, without limitation, *Agrobacterium tumefaciens, Escherichia coli*, a lepidopteran cell line, a Rice tungro bacilliform virus, a Commelina yellow mosaic virus, a Banana streak virus, a Taro bacilliform virus, and/or baculovirus. An expression control sequence may be present on a genomic nucleic acid and/or an extra-genomic nucleic acid.

Plants

The present disclosure relates, in some embodiments, to a plant cell (e.g., an embryonic cell, a stem cell, a callous cell), a tissue, and/or a plant comprising an expression control sequence. A plant and/or plant cell may be selected from a monocot and/or a dicot in some embodiments. Examples of a monocot may include, without limitation, sugarcane, *miscanthus*, a *miscanthus*×sugarcane hybrid, switch grass, oats, wheat, barley, maize, rice, banana, *yucca*, onion, asparagus, and/or sorghum. Examples of a dicot may include, without limitation, coffee, tomato, pepper, tobacco, lima bean, *Arabidopsis*, rubber, orange, grapefruit, potato, grapefruit, potato, squash, peas, and/or sugar beet. A plant cell may be included in a plant tissue, a plant organ, and/or a whole plant in some embodiments. A plant cell in a tissue, organ, and/or whole plant may be adjacent, according to some embodiments, to one or more isogenic cells and/or one or more heterogenic cells. In some embodiments, a plant may include primary transformants and/or progeny thereof. A plant comprising an expression control sequence may further comprise a transgene (e.g., promotorless heterologous gene, a coding sequence) operably linked to the expression control sequence, in some embodiments. A transgene may be expressed, according to some embodiments, in a plant comprising an expression control sequence in all (e.g., substantially all) organs, tissues, and/or cell types including, without limitation, stalks, leaves, roots, seeds, flowers, fruit, meristem, parenchyma, storage parenchyma, collenchyma, sclerenchyma, epidermis, mesophyll, bundle sheath, guard cells, protoxylem, metaxylem, phloem, phloem companion, and/or combinations thereof. In some embodiments, a transgene and/or its gene product may be located in and/or translocated to one or more organelles (e.g., vacuoles, chloroplasts, mitochondria, plastids).

Expression Systems

The present disclosure relates, according to some embodiments, to a system for expression of (e.g., to high levels) of a nucleic acid sequence (e.g., comprising one or more coding sequences). For example, an expression system may be comprised in plants to be used as a biofactory for high-value proteins. Without being limited to any particular mechanism of action, an expression system may benefit from additive and/or synergistic expression control sequence activities, transcriptional synergism, and/or reduced silencing of an introduced coding sequence (e.g., transgene), a phenomenon frequently observed in plants when the same promoters are used to express the same or different transgenes, and constituting a major risk for the economic exploitation of plants as biofactories. Plants comprising an expression system may retain desirable (e.g., high) expression levels through one or more consecutive generations of transgenic plants.

In some embodiments, an expression system may comprise two or more expression control sequences (e.g., promoters) each operably linked to a respective number of clones of a single coding sequence. According to some embodiments, two, three, four, five, or more expression control sequences (e.g., promoters) may be operably linked to two, three, four, five, or more clones of a single coding sequence. Each expression control sequence independently may be constitutive and/or regulated (e.g., tissue-specific expression, developmentally-inducible expression, stress-inducible expression, defense-inducible expression, and/or drought-inducible expression) according to some embodiments. In some embodiments, each clone of a coding sequence may be identical to one or more of the other clones. Copies of a coding sequence, according to some embodiments, may differ from one another somewhat, for example, where one copy may be codon optimized for one family, genus, and/or species while another may be optimized for a different family, genus, and/or species, or not codon optimized at all. Each expression control sequence-coding sequence clone independently may be present (e.g., in a microorganism and/or plant) on an expression vector, on a genomic nucleic acid, and/or on an extra-genomic nucleic acid in some embodiments. Each expression control sequence-coding sequence clone independently, in some embodiments, may further comprise one or more terminators.

The present disclosure relates, according to some embodiments, to transgenic plants of sugarcane, a high biomass producer and sugar accumulator, which are generated from explants transformed with an expression system (e.g., a multiple promoter-one transgene system). Transgenic sugarcane plants according to some embodiments of the disclosure were observed expressing high levels (up to 6.0 mg per kg of total stalk fresh weight, which corresponds to about 1% total soluble protein or TSP) of extractable active bovine stomach lyzozyme (BvLz)) an antimicrobial protein. The high BvLz expression levels are stable in consecutive generations of transgenic plants, allowing for the economic production and purification of the corresponding protein.

The present disclosure relates, in some embodiments, to methods for producing the multiple promoter-one transgene expression vectors and the transgenic plants. Methods may be used, for example, to transform different varieties of sugarcane by co-bombarding a target explant tissue (e.g., embryogenic callus or leaf roll disc) with the BvLz transgene encoding a protein normally present in bovine stomach and that is codon optimized for expression in monocotyledonous plants, under the control of multiple promoters from separate vectors.

Methods

According to some embodiments, the present disclosure relates to methods for transforming and/or transfecting a plant with a nucleic acid comprising an expression control sequence. For example, a method may comprise contacting a cell (e.g., a yeast cell and/or a plant cell) with a nucleic acid comprising an expression control sequence. Contacting a nucleic acid with a cell may comprise, in some embodiments, co-cultivating the target cell with a bacteria (e.g., *Agrobacterium*) comprising the nucleic acid (e.g., in a binary vector), electroporating the cell in the presence of the nucleic acid, infecting the cell with a virus (baculovirus) comprising the nucleic acid, bombarding the cell (e.g., a cell in a leaf, stem, and/or callus) with particles comprising the nucleic acid, agitating the cell in a solution comprising the nucleic acid and one or more whiskers (e.g., silicone carbide whiskers), and/or chemically inducing the cell to take up extracellular DNA. In some embodiments, contacting a nucleic acid with a cell may comprise contacting the nucleic acid with a plant leaf disc and/or a plant protoplast.

The disclosure relates, in some embodiments, to methods for expressing a nucleic acid sequence (e.g., comprising one or more coding sequences) in a cell. For example, a method may comprise contacting a cell (e.g., a yeast cell and/or a plant cell) with a nucleic acid comprising an expression control sequence and a coding sequence operably linked to the expression control sequence under conditions that permit expression of the coding sequence. Expression, according to some embodiments, may be constitutive, conditional, native (e.g., in the normal time and/or tissue), and/or ectopic. In some embodiments, a method may further comprise expressing a nucleic acid sequence in a plant (e.g., a monocot and/or a dicot). A method may include harvesting (e.g., partially purifying) from a plant a gene product of a nucleic acid sequence (e.g., an exogenous sequence) expressed in the plant, according to some embodiments.

In some embodiments, the present disclosure relates to methods for isolating an expression control sequence operable in at least one monocot and/or at least one dicot. For example, a method may comprise screening a library (e.g., a plant genomic library, a bacterial artificial chromosome library, a plant virus genomic library) with a probe comprising a nucleic acid having a nucleic acid sequence of SEQ ID NO: 1, a complement thereof, and/or a portion thereof (e.g., under stringent hybridization conditions). A method may comprise amplifying an expression control sequence from a library (e.g., using a polymerase chain reaction) using one or more primers derived from a nucleic acid sequence of SEQ ID NO: 1, a complement thereof, and/or a portion thereof. Operability of a candidate expression control sequence in at least one monocot and/or at least one dicot may be confirmed, in some embodiments, by forming a transcriptional and/or translational fusion of a candidate expression control sequence with a coding sequence expressible in the at least one monocot and/or the at least one dicot to form an expression cassette, transferring the expression cassette into the at least one monocot and/or the at least one dicot, and/or detecting expression of the coding sequence. An assay for detecting expression of the coding sequence may depend on the nature of the coding sequence. For example, a coding sequence may comprise a reporter gene (e.g., an autofluorescent protein, chloramphenicol acetyl transferase and β-glucuronidase (GUS)). Standard assays are available to sensitively detect a reporter enzyme in a transgenic organism.

The present disclosure relates, according to some embodiments, to methods for isolating an expression control sequence operable in at least one monocot and/or at least one dicot. For example, a method may comprise selecting one or more primers from about 15 to about 40 nucleotides in length and corresponding to (but not necessarily identical to) sequences at or near the 5' and/or 3' ends of SEQ ID NO: 1, contacting the one or more primers with an amplification library (e.g., a partial or complete viral genomic library, a partial or complete plant genomic library) and a nucleic acid polymerase under conditions that permit amplification of an expression control sequence. A plant genomic library, according to some embodiments, may comprise nucleic acids isolated from a virus-infected and/or virus-free plant. In some embodiments, a method may comprise screening a library with a probe comprising SEQ ID NO:1 or a fragment thereof. One or more candidate expression control sequences (e.g., amplification products) may be cloned into an expression vector in a position to drive expression of a coding sequence (e.g., GUS, an autofluorescent protein). Operability of the amplification products may be assessed, for example, by contacting a plant cell with such expression vectors under conditions that permit expression of the coding sequence (e.g., microprojectile bombardment, *Agrobacterium*-mediated transformation) and examining the plant cell for the appearance of a gene product of the coding sequence (e.g., the encoded protein).

The present disclosure, in some embodiments, relates to methods of increasing expression levels of a coding sequence in at least one monocot and/or at least one dicot. For example, an expression cassette and/or expression vector may be introduced into a plant in order to effect expression of a coding sequence. According to some embodiments, a method of producing a plant with increased levels of a product of a sucrose accumulating gene and/or a defense gene may comprise transforming a plant cell with an expression vector and/or expression cassette comprising an expression control sequence operably linked to a sucrose accumulating gene or a defense gene and regenerating a plant with increased levels of the product of the sucrose accumulating gene or defense gene. In some embodiments of the present disclosure, a transgenic sugarcane line may be produced in which sugar metabolism is altered to increase stem dry weight (e.g., more than about 50% sucrose, more than about 60% sucrose, more than about 70% sucrose). A transgenic sugarcane line may be produced, according to some embodiments, with enhanced bioinsecticidal activity (e.g., for protection against stem boring insects, which may be the most destructive pests).

The present disclosure, in some embodiments, relates to methods of decreasing expression levels of a coding sequence (e.g., a native plant sequence, a viral sequence) in at least one monocot and/or at least one dicot. For example, a method may comprise contacting at least one monocot cell and/or at least one dicot cell with an expression vector comprising an expression control sequence and an antisense sequence that is complementary to at least a portion of the coding sequence and operably linked to the expression control sequence. In some embodiments, a method may comprise contacting at least one monocot cell and/or at least one dicot cell with an RNA interference (RNAi) expression vector comprising an expression control sequence and a nucleic acid sequence which is an inverted repeat of the native plant gene, the expression level of which is to be reduced and/or silenced, and operably linked to the expression control sequence. A method may comprise, in some embodiments, contacting at least one monocot cell and/or at least one dicot cell with a cosuppression expression vector comprising an expression control sequence and a nucleic acid sequence coding for the native plant gene operably linked to the expression control sequence.

Embryonic calli and other susceptible tissues, in some embodiments, may be inoculated with a "disarmed" foreign DNA-containing *A. tumefaciens*, cultured for a number of days, and transferred to antibiotic-containing medium. Transformed shoots may be selected after rooting in medium containing the appropriate antibiotic, and transferred to soil. Transgenic plants may be pollinated and seeds from these plants may be collected and grown on antibiotic selection medium.

Expression of a heterologous or reporter gene in tissues, developing seeds, young seedlings and mature plants may be monitored, according to some embodiments, by immunological, histochemical, mRNA expression or activity assays. Choice of expression assay for the expression cassette may depend upon the nature of the heterologous coding sequence. For example, RNA gel blot analysis may be used to assess transcription if appropriate nucleotide probes are available. If antibodies to the polypeptide encoded by the heterologous gene (e.g., coding sequence) are available, western analysis and immunohistochemical localization may be used to assess the production and localization of the polypeptide. Depending upon the heterologous gene, appropriate biochemical assays may be used.

The present disclosure further relates to methods for isolating and/or purifying ("purifying") a gene product (e.g., a nucleic acid and/or a protein) from a plant. For example, a method may comprise providing a plant comprising a nucleic acid having an expression control sequence and a coding sequence operably linked to the expression control sequence, wherein the coding sequence encodes a gene product of interest. A method may comprise, according to some embodiments, producing a transgenic protein in a plant, extracting juice containing the transgenic protein from the plant, cleaning the juice to remove particulate matter, and/or transmitting the juice through at least one membrane to produce two fractions, one of the fractions containing the transgenic protein. In some embodiments, a transgenic protein may comprise a lectin, an enzyme, a vaccine, a bacterial lytic peptide, a bacterial lytic protein, an antimicrobial peptide, an antimicrobial peptide protein, an antiviral peptide, an antiviral protein, an insecticidal peptide, an insecticidal protein, a therapeutic peptide, and a therapeutic protein.

As will be understood by those skilled in the art who have the benefit of the instant disclosure, other equivalent or alternative compositions, devices, methods, and systems for expressing a nucleic acid sequence in at least one monocot and/or at least on dicot can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. For example, the position and number of expression control sequences may be varied. Each disclosed method and method step may be performed in association with any other disclosed method or method step and in any order. Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to 50 may include 55, but not 60 or 75. In addition, it may be desirable, in some embodiments, to mix and match range endpoints. Also, in some embodiments, each figure disclosed (e.g., in one or more of the Examples and/or Drawings) may form the basis of a range (e.g., disclosed value±about 10%, disclosed value ±about 100%) and/or a range endpoint. Persons skilled in the art may make various changes in methods of preparing and using a composition, device, and/or system of the disclosure. For example, a composition, device, and/or system may be prepared and or used as appropriate for animal and/or human use (e.g., with regard to sanitary, infectivity, safety, toxicity, biometric, and other considerations).

These equivalents and alternatives along with obvious changes and modifications are intended to be included within the scope of the present disclosure. Accordingly, the foregoing disclosure is intended to be illustrative, but not limiting, of the scope of the disclosure as illustrated by the following claims.

EXAMPLES

Some specific example embodiments of the disclosure may be illustrated by one or more of the examples provided herein.

Example 1: SCBV Infection in Sugarcane Fields in the Mid Rio Grande Valley, Tex.

Leaves were harvested from haphazardly selected sugarcane plants in fields in the mid Rio Grande Valley of Texas. The incidence of SCBV infection was examined by Southern blotting after DNA extraction from the harvested sugarcane leaves (Table 2). The $^{32}$P-dCTP-labelled DNA probe for Southern blots was prepared from the SCBV fragment of ~1.4 Kb encompassing SCBV ORF1, ORF2 and the 5' 450 nt of ORF3, which was cloned by PCR using sugarcane DNA prepared from CP72-1210. The Southern results showed that of fourteen sugarcane varieties/clones tested, eleven varieties/clones were SCBV positive, which indicates that SCBV infection is prevalent in the fields in the Mid Rio Grande Valley.

TABLE 2

SCBV incidence in commercial sugarcane varieties.

| Variety/ clone | Infec- tivity* | Plants that tested positive for SCBV/ total plants tested |
|---|---|---|
| CP72-1210 | 100% | (6/6) |
| TCP87-3308 | 100% | (6/6) |
| TCP89-3505 | 100% | (6/6) |
| TCP04-4688 | 83.30% | (5/6) |
| TCP05-4732 | 100% | (6/6) |
| TCP05-4738 | 100% | (6/6) |
| TCP05-4747 | 100% | (6/6) |
| TCP05-4760 | 16.70% | (1/6) |
| TCP05-4784 | 100% | (6/6) |
| TCP98-4454 | 0% | (0/6) |
| NCO310 | 0% | (0/6) |
| 91 | 0% | (0/6) |
| 385 | 100% | (6/6) |
| 1903 | 100% | (6/6) |

*The results are based on Southern blot hybridizations.

Example 2: Cloning and Sequencing of a SCBV Promoter (SCBV21)

Total genomic DNA was isolated from the leaf tissue of SCBV-positive sugarcane cultivar CP72-1210. The DNA concentration was adjusted to ~100 ng/ul, and ~250 ng of DNA was used for PCR reactions. The primer sequence information was provided by Dr. Guohui Zhou from Southern China Agricultural University, Guangzhou, China, who has cloned a Southern China isolate of SCBV. Primer names and sequences are as follows: P-2 (5'-acg cgg taa cac gta gtc cta agg t-3'; SEQ ID NO: 11), P-W3F (5'-gac atc aaa tgg ttg tat cc-3'; SEQ ID NO: 12), P-W4F (5'-aca ccg cat tca gag tga ag-3'; SEQ ID NO: 13) and P-W1R (5-ccg cat taa cgt tct α-3'; SEQ ID NO: 14). All PCR reactions were performed in 20 μl of reaction mixture using Taq DNA polymerase (NEB) following the manufacturer's recommendation. The primer set, P-2 and P-W3F, was used for the first PCR reaction using the following PCR parameters for pre-amplification of SCBV genome containing its promoter sequence: 1 cycle at 94° C. for 4 min, 10 cycles each at 94° C. for 30 sec, at 48° C. for 30 sec, and at 72° C. for 5 min. Then, 5 μl of the first PCR reaction mixture was used as a template for the second PCR reaction with a primer set, P-W1R and P-W4F by the following PCR program: 1 cycle at 94° C. for 4 min, 35 cycles each at 94° C. for 30 sec, at 52° C. for 30 sec, and at 72° C. for 4 min, and 1 cycle at 72° C. for 5 min. The PCR reaction mixture was analyzed by electrophoresis on 1% agarose gels. The size of the obtained PCR product was ~2 kb which was cloned into the pGEM T-Easy vector (Promega). The nucleotide sequence of the cloned product was analyzed by sequencing, which confirmed that the cloned fragment has homology with SCBV ORF3. After the sequence alignment with other SCBV promoter sequences, two primers, SCBV/Prom/F (5'-GAA GAA CAG CAT GCT GAA CAT CTG TGG AAG ATG C-3'; SEQ ID NO: 15) and SCBV/Prom/R (5'-CAA ACT TGC TCA AAT GAT CAT GTG GTG AAC TAC CGA TG-3'; SEQ ID NO: 16) were designed from the conserved regions. The PCR condition with these two primers was: 1 cycle at 94° C. for 4 min, 35 cycles each at 94° C. for 30 sec, at 52° C. for 30 sec and at 72° C. for 2 min, and 1 cycle at 72° C. for 5 min. The PCR product was analyzed on 1% agarose gels, and the PCR product was cloned into pGEM T-Easy, and the cloned sequence was confirmed by sequencing. The cloned PCR product was named as pGEM/SCBV21 (FIG. 1).

Example 3: SCBV21 Promoter Activity

Figure 2:
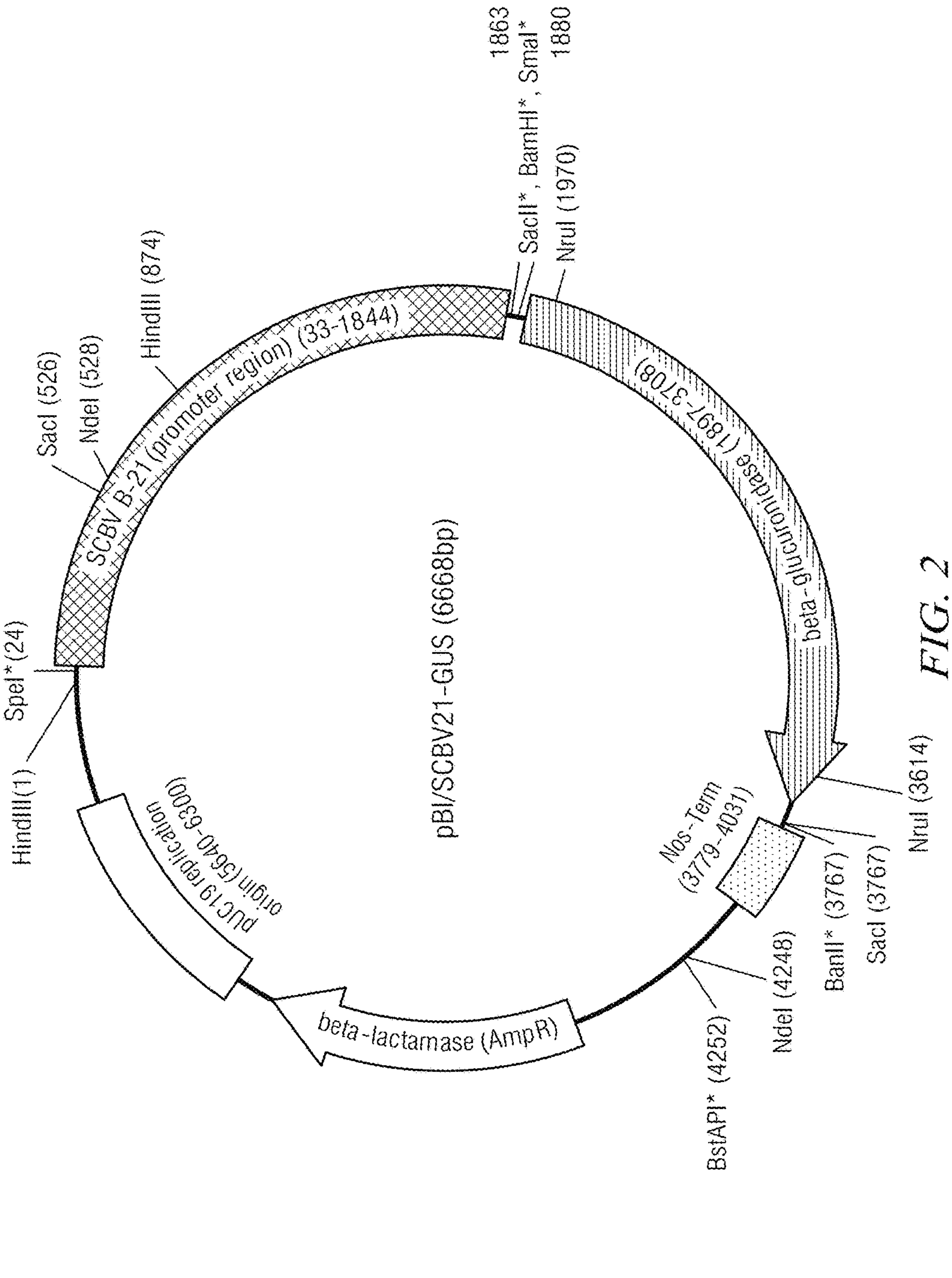
FIG. 2 illustrates a vector with a promoter according to a specific example embodiment of the disclosure.
Figure 3:
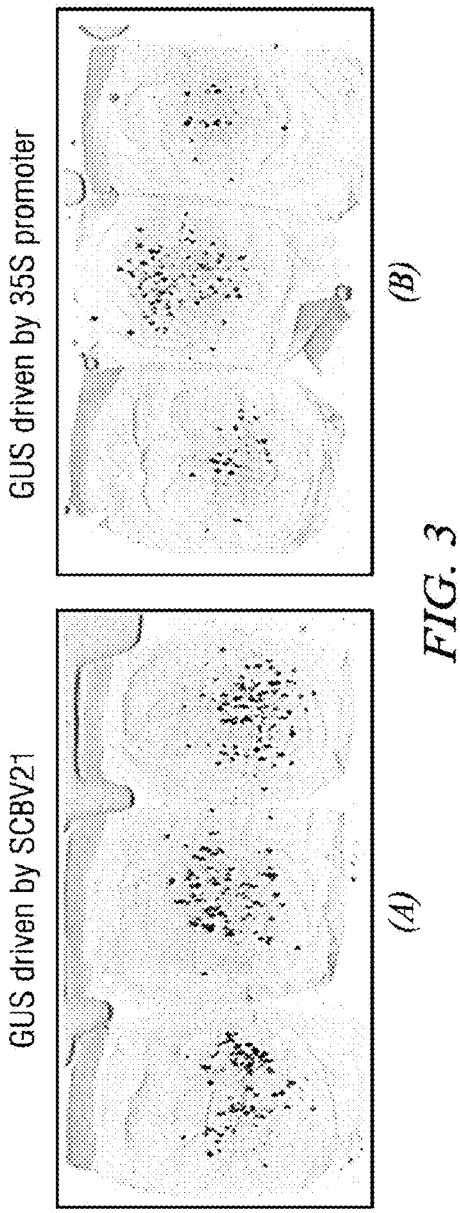
FIGS. 3A and 3B illustrate GUS expression under the control of a promoter according to a specific example embodiment of the disclosure compared to a 35S promoter.

To test the promoter activity of the cloned SCBV21, it was subcloned upstream of the β-glucuronidase (GUS) gene to construct pBI/SCBV21-GUS. (FIG. 2). The promoter activity of SCBV21 was tested by bombarding DNA-coated tungsten particles onto the onion epidermal layers using a gene gun. GUS expression was confirmed by histochemical GUS assays 2 days after bombardment (FIG. 3).

Example 4: Sequence Comparison of SCBV Promoters from Different SCBV Isolates

The sequence of SCBV21 was compared with two SCBV isolates, SCBV Ireng Maleng (IM) and SCBV Morocco (Mor). Table 3 shows that SCBV21 has 87% and 71% identity with SCBV-IM and SCBV-Mor isolates, respectively.

TABLE 3

Sequence comparisons of SCBV21 to two other SCBV isolates

| | SCBV-IM-AJ277091* | SCBV-Mor M89923* |
|---|---|---|
| SCBV21 | 87% | 71% |

*NCBI Genebank accession number.

Figure 4:
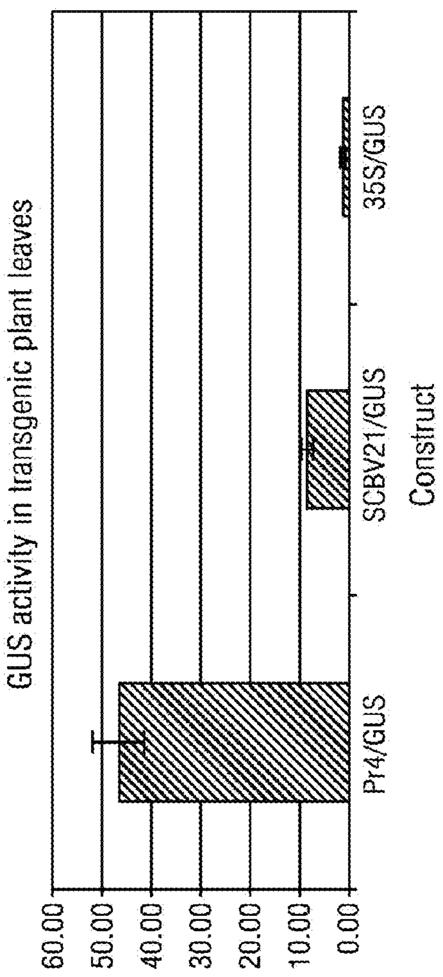
FIG. 4 illustrates a bar graph showing GUS activity in transgenic plant leaves according to a specific example embodiment of the disclosure.
Figure 5:
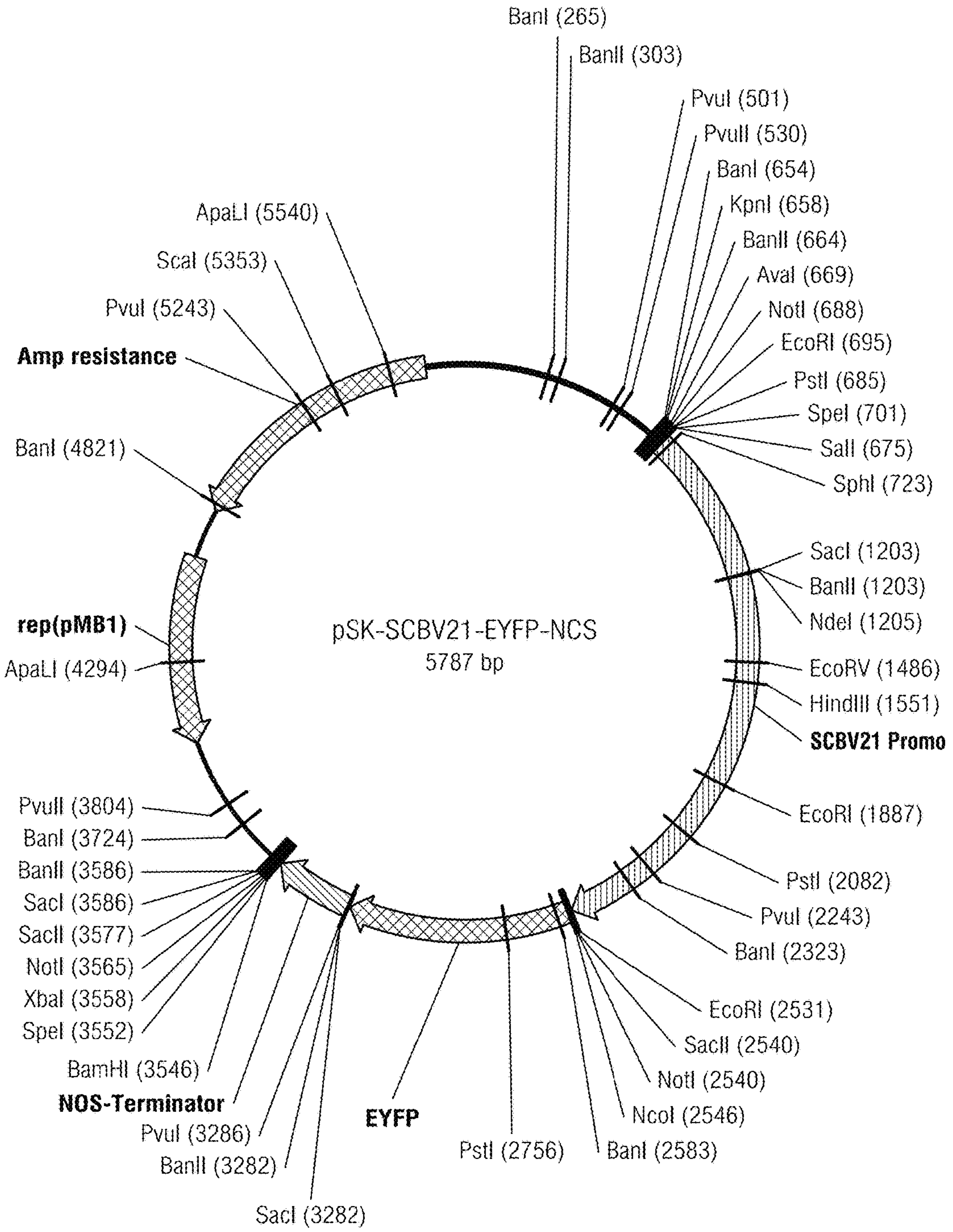
FIG. 5 illustrates a vector with a promoter according to a specific example embodiment of the disclosure.

Sequence identity (%): The sequence identity (%) was obtained by BLASTn search with SCBV21 in NCBI GeneBank Example 5: SCBV21-Driven GUS Transgene Expression in Transgenic Sugarcane Transgenic sugarcane was generated with the DNA construct, pBI/SCBV21-GUS (FIG. 1), and the GUS transgene expression level of this transgenic line was compared with other transgenic lines of which GUS transgene expression was driven by CaMV 35S promoter or a modified maize Ubi promoter that lacks a heat shock element (mUbi1-no hse) (FIG. 4). GUS expression levels in SCBV21/GUS transgenic lines is about four to six times higher than in 35S/GUS transgenic lines, while mUbi1-no hse/GUS transgenic lines displayed the highest GUS expression level which is six to ten times more than that of the SCBV21/GUS lines (FIG. 4**).

Example 6: SCBV21 Directs GUS Expression in Sorghum, Tobacco and Lima Bean Seed

Figure 6:
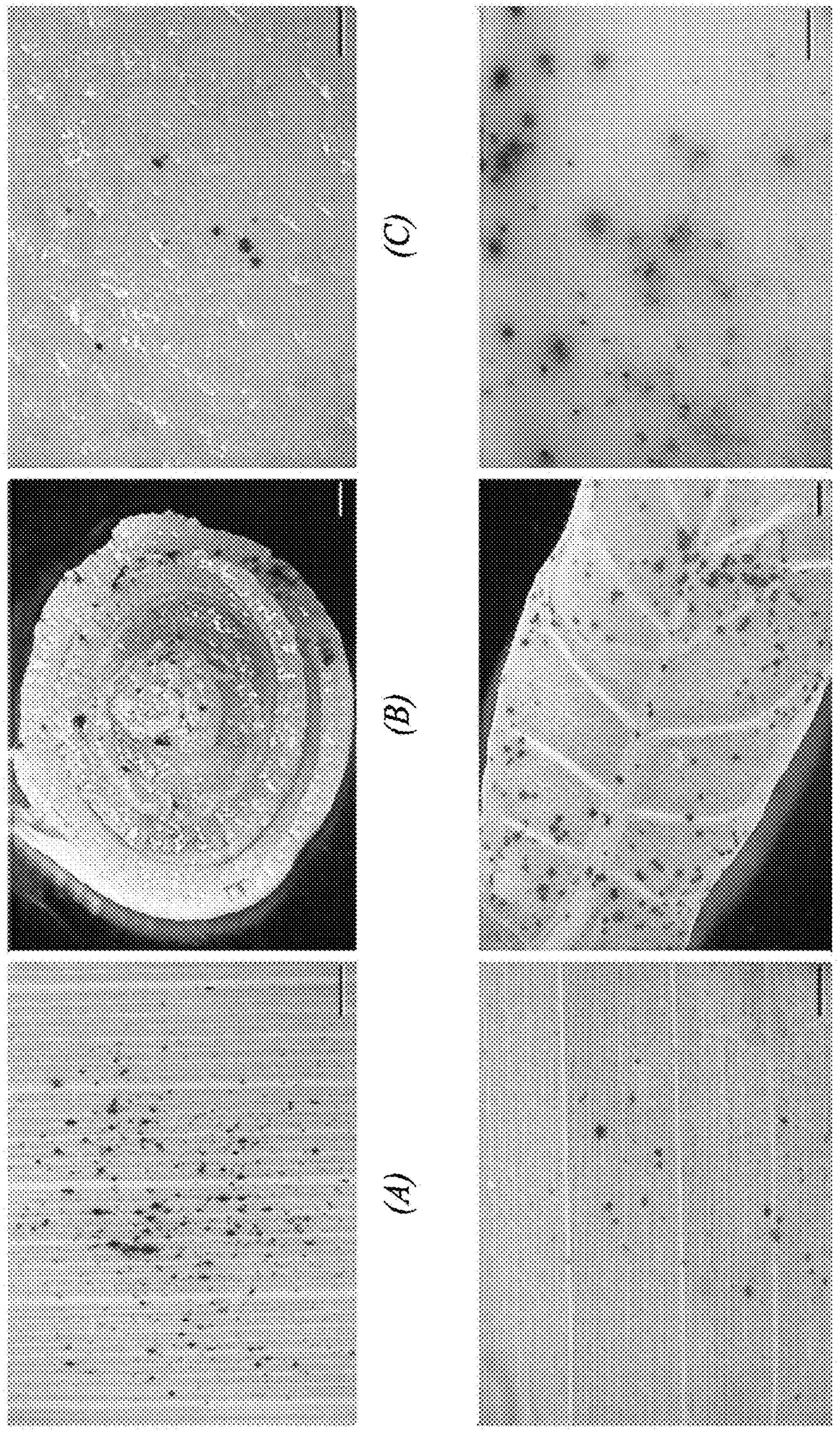
FIG. 6A illustrates GUS expression in sugarcane young leaf under the control of a promoter according to a specific example embodiment of the disclosure.
FIG. 6B illustrates GUS expression in sugarcane young leaf (roll) under the control of a promoter according to a specific example embodiment of the disclosure.
FIG. 6C illustrates GUS expression in sugarcane stem under the control of a promoter according to a specific example embodiment of the disclosure.
FIG. 6D illustrates GUS expression in sweet sorghum young leaf under the control of a promoter according to a specific example embodiment of the disclosure.
FIG. 6E illustrates GUS expression in tobacco leaf under the control of a promoter according to a specific example embodiment of the disclosure.
FIG. 6F illustrates GUS expression in lima bead seed under the control of a promoter according to a specific example embodiment of the disclosure.
FIG. 6G illustrates GFP expression in sugarcane young leaf under the control of a promoter according to a specific example embodiment of the disclosure.
FIG. 6H illustrates GFP expression in sugarcane young leaf (roll) under the control of a promoter according to a specific example embodiment of the disclosure.
FIG. 6I illustrates GFP expression in sugarcane stem under the control of a promoter according to a specific example embodiment of the disclosure.
FIG. 6J illustrates GFP expression in sweet sorghum young leaf under the control of a promoter according to a specific example embodiment of the disclosure.
FIG. 6K illustrates GFP expression in tobacco leaf under the control of a promoter according to a specific example embodiment of the disclosure.
FIG. 6L illustrates GFP expression in lima bead seed under the control of a promoter according to a specific example embodiment of the disclosure.
Figure 6:
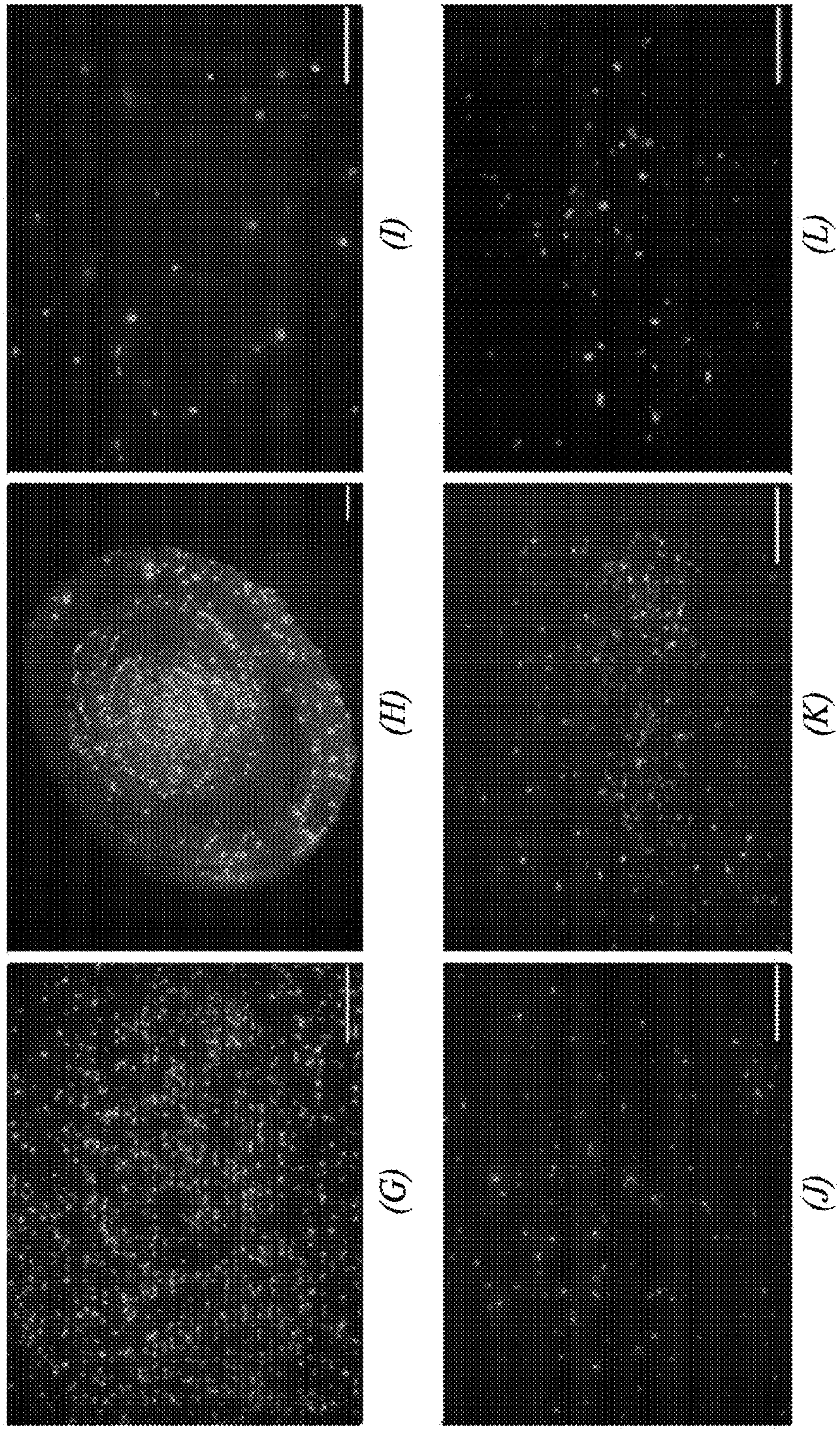

The promoter activity of SCBV21 was transiently tested in another monocot, sorghum, and two dicot species, tobacco and Lima been by bombarding DNA-coated tungsten particles onto prepared tissue samples (FIG. 6). The results showed that SCBV21 functions as a promoter regardless of tissue samples (leaf or seed) and of plant species (monocot or dicot) (FIG. 6).

Example 7: Relative Expression Levels with Various Promoters: GUS and EYFP Transient Expression in Leaf Tissue Young leaf segments were cultured in $MS_{0.6}$ solid media (Murashige and Skoog, 1962), B5G 1 mg/L, 0.6 mg/L 2,4-D, 500 mg/L casein hydrolysate, 20 g/L sucrose and 7 g/L Agar for 4 days and leaf rolls were kept for 10 days or 28 days before bombardment. Plasmid DNA was precipitated onto tungsten particles (1.1 μm, Bio-Rad) at a concentration of 4 μg (for GUS construct) or 1 μg (for EYFP construct) DNA per mg of tungsten using calcium chloride and spermidine.

Example 8: Relative Expression Levels with Various Promoters: GUS Histochemical Assay After 48 hrs post-bombardment, leaf segments were transferred to 0.1% X-Gluc staining solution containing 0.1% (v/v) Triton X-100, and 0.1 M sodium phosphate buffer (pH 7.0). Tissues were then incubated overnight (24 hr) at 37° C. After staining, chlorophyll was removed from tissue by immersing in 70% (v/v) ethanol and changed twice. Tissues were observed for GUS staining, and photographed using an OLYMPUS D71 camera connected on a SZX7 stereoscopic microscope (Japan).

Example 9: Relative Expression Levels with Various Promoters: GUS Activity Quantitative Assay Quantitative fluorometeric GUS assays were performed by the modified procedure of Jefferson (1987). 500 mg of plant tissue were weighed and ground in liquid nitrogen and then transferred to 1.5 mL microcentrifuge tube with 750 μL GUS extraction buffer containing 50 mM sodium phosphate buffer (pH 7.0), 10 mM 2-mercaptoethanol, 10 mM EDTA (pH 8.0) and 0.1% (v/v) Triton X-100. After briefly vortexing, the tubes were incubated on ice for 1 hr and centrifuged at 12000 g for 10 min at 4° C. An aliquot of the supernatant was used for protein concentration determination and GUS activity assays. Protein concentrations were determined by the Lowry assay method based on the instruction manual of the DC protein assay kit (Bio-Rad). Fluorometric enzymatic GUS assay were carried out for leaf samples by adding 10 μL protein extracts and 15 μL GUS extraction buffer to 25 μL MUG (4 mM) assay buffer. 25 μL protein extracts were used for the reaction with 25 μL MUG solution for root samples. After incubation for 1 hr at 37° C., 950 mL 0.2 M $Na_2CO_3$ solutions were added to stop the reaction. The optical density was read at 455 nm after excitation at 365 nm on a VersaFluor™ Fluorometer (BIO-RAD). Protein extracts of untransformed plants were used for the negative control samples and a serial dilution of 4-methylumbelliferone (MU, Sigma) solutions in GUS extraction buffer were used as standards.

Example 10: Relative Expression Levels with Various Promoters: EYFP Image Collection and Analysis Images of 4080×3072 pixels and 256 gray levels for red, green and blue channels were collected every 6 hrs post-bombardment for at less 240 hrs. EYFP expression was quantified using the ImageJ software (Rasband 1997-2009) according to the revised method described by Chiera et al (2007 and 2008). Each series of images was imported, resized to 800×600 pixels and aligned by Adobe Imageready CS (8.0.1 version). After alignment, the series of images was exported as a "mov" file. The "mov" file was opened by the ImageJ software and an area comprising 400×300 pixels containing the highest number of expressing cells was cropped from the series of images and then was saved as an "avi" file for quantification analysis of EYFP. Each series of images in the "avi" file was split into red, green and blue channels. A 20×20 pixel area without EYFP expression cells was selected in the background of green channel for determination of background gray value and was subtracted from sequential images to remove the background fluorescence. After adjusting the threshold levels, the foci count values, mean grayscale values and total area values were generated by the procedures of the macros that were kindly presented by Chiera and Hernandez-Garcia. The "Total Expression" value was calculated by multiplying a mean grayscale value per pixel by the total area.

Example 11: Relative Expression Levels with Various Promoters: Protoplast Isolation and Transfection Protoplasts were isolated from sugarcane callus using a modified method of Chen (1987) and Yoo et al (2007). Briefly, callus cultures were cultured on a rotary shaker (250 mL flasks; 100 rpm) by weekly subculture (1:5 dilution) for 2 to 3 months in a $MS_3$ liquid medium (Murashige and Skoog, 1962), B5G 1 mg/L, 3.0 mg/L 2,4-D, 500 mg/L casein hydrolysate and 20 g/L sucrose. The fresh suspension cells (subcultured for 2 or 3 days) were harvested and digested overnight in enzyme solution (20 mM MES (pH 5.7), 2.0% Cellulysin® Cellulase (EMD Biosciences, USA), 0.1% PECTOLYASE Y-23 (Duchefa Biochemie, USA), 0.4 M mannitol, 20 mM KCl, 10 mM $CaCl_2$, and 0.1% BSA). Protoplasts were collected and washed in W5 solution twice and pelleting at 100 g for 2 mM After the second wash, protoplasts were resuspended in MMG solution (4 mM MES-KOH, pH5.7, 0.4 M mannitol, 15 mM $MgCl_2$) to reach a final concentration of 1 to $2\times10^6$ protoplasts/mL. 100 μL of protoplasts were transferred into a 2-mL round-bottom microcentrifuge tube and mixed gently with the plasmid DNA (10 μg in 10 μL). Equivalent volumes of deionized, sterile water (mock-transfection) were used as control transfections. Transfection was initiated by the addition of 110 μL of PEG-calcium solution (40% PEG-4000, 0.2 M mannitol, 100 mM $CaCl_2$). Protoplasts were mixed with PEG-calcium solution by gently tapping the tube and incubating for 10 mM at room temperature. Transfection was terminated by diluting the mixture with 440 μL of W5 solution. Transfected protoplasts were collected by centrifugation for 2 mM at 100 g and resuspended in 250 μL of W5 solution. EYFP or GUS expression analysis was investigated after protoplasts were kept in the dark for 16 hrs at room temperature. Protoplasts were harvested by centrifugation at 100 g for 2 mM, and then removing the supernatant and stored at −80° C. until GUS activity analysis. Adding 100 μL of GUS extraction buffer to the frozen protoplasts and mixing vigorously by vortexing for 2 sec to rupture the protoplasts. After keeping on ice for 5 mM, centrifuged at 1000 g for 2 min Taking 25 μL of the protoplasts lysate into 25 μL 4 mM MUG assay buffer and incubated for 60 min at 37° C.

Example 12: Relative Expression Levels with Various Promoters: Statistical Analysis The relative expression levels of various promoters are shown in Tables 4-10. The data were collected from 2 to 4 independent experiments and 6 to 10 replicates in every experiment. The GLM procedure of Statistical Analysis System (8.0 version, SAS Institute, USA) was used for statistical analysis. Student-Newman-Keuls (SNK) Test was performed for multiple comparisons of the mean.

TABLE 4

GUS transient expression in sugarcane leaf segments_spot number*

| Name | Spot number | Std err | Significant Difference |
|---|---|---|---|
| mUbi1-no hse/GUS | 250 | 34 | A |
| Ubi/GUS | 63 | 13 | B |
| SCBV21/GUS | 36 | 10 | BC |
| 35S-GUS | 4 | 1 | C |

*Images were taken by microscope (x15).
Values with the same letter are not significantly different ($p > 0.05$).

TABLE 5

EYFP transient expression in sugarcane leaf segments_Foci number*

| Name | Foci number | Std err | Significant Difference |
|---|---|---|---|
| mUbi1-no hse/EYFP | 351 | 19 | BC |
| Ubi/EYFP | 384 | 29 | BC |
| SCBV21/EYFP | 514 | 27 | A |
| 35S-EYFP | 318 | 12 | C |
| E35S/EYFP | 511 | 38 | A |

*Data were collected from the 48 hrs timepoint post-bombardment. Images were taken by Fluorescence microscope (x5) with YFP filter.
Values with the same letter are not significantly different ($p > 0.05$).

TABLE 6

EYFP transient expression in sugarcane leaf segments_total expression*

| Name | Total expression | Std err | Significant Difference |
|---|---|---|---|
| mUbi1-no hse/EYFP | 385 | 39 | C |
| Ubi/EYFP | 454 | 51 | C |
| SCBV21/EYFP | 701 | 87 | B |
| 35S-EYFP | 316 | 21 | C |
| E35S/EYFP | 894 | 134 | A |

*Total expression is measured as mean Gray scale per pixel × total area × 1000. Data were collected from the 48 hrs timepoint post-bombardment. Images were taken by Fluorescence microscope (x5) with YFP filter. Values with the same letter are not significantly different ($p > 0.05$).

TABLE 7

GUS transient expression in sugarcane protoplasts_GUS activity*

| Name | GUS activity | Std err | Significant Difference |
|---|---|---|---|
| mUbi1-no hse/GUS | 36.99 | 1.64 | A |
| Ubi/GUS | 11.51 | 0.69 | B |
| SCBV21/GUS | 3.16 | 0.21 | C |
| 35S/GUS | 0.87 | 0.09 | C |

*p-mole 4-MU/ug protein per minute
Values with the same letter are not significantly different ($p > 0.05$).

TABLE 8

EYFP transient expression in sugarcane protoplasts_Foci number*

| Name | Foci number | Std err | Significant Difference |
|---|---|---|---|
| mUbi1-no hse/EYFP | 21 | 2 | B |
| Ubi/EYFP | 21 | 2 | B |
| SCBV21/EYFP | 31 | 3 | A |
| 35S-EYFP | 17 | 2 | B |
| E35S/EYFP | 36 | 4 | A |

*Images were taken by Fluorescence microscope (x85.5) with YFP filter.
Values with the same letter are not significantly different ($p > 0.05$).

TABLE 9

| GUS expression in transgenic sugarcane leaves _GUS activity* | | | |
|---|---|---|---|
| Name | GUS activity | Std err | Significant Difference |
| mUbi1-no hse/GUS | 46.60 | 2.56 | A |
| SCBV21/GUS | 8.21 | 0.45 | B |
| 35S/GUS | 1.32 | 0.20 | C |

Data from two independent experiments.
mUbi1-no hse/GUS: 2 events, 5 plants;
SCBV21/GUS: 2 events, 6 plants;
35S/GUS: 6 events, 18 plants.
*p-mole 4-MU/ug protein per minute
Values with the same letter are not significantly different ($p > 0.05$).

TABLE 10

| GUS expression in transgenic sugarcane stems _GUS activity* | | | |
|---|---|---|---|
| Name | GUS activity | Std err | Significant Difference |
| mUbi1-no hse/GUS | 23.61 | 2.61 | A |
| SCBV21/GUS | 6.75 | 1.32 | B |
| 35S/GUS | 3.83 | 1.54 | C |

Data from two independent experiments.
mUbi1-no hse/GUS: 5 plants, 1 event;
SCBV21/GUS, 1 plant, 1 event;
35S/GUS, 3 plants, 1 event.
*p-mole 4-MU/ug protein per minute
Values with the same letter are not significantly different ($p > 0.05$).

Example 13: Expression Pattern of SCBV21

Figure 7A:
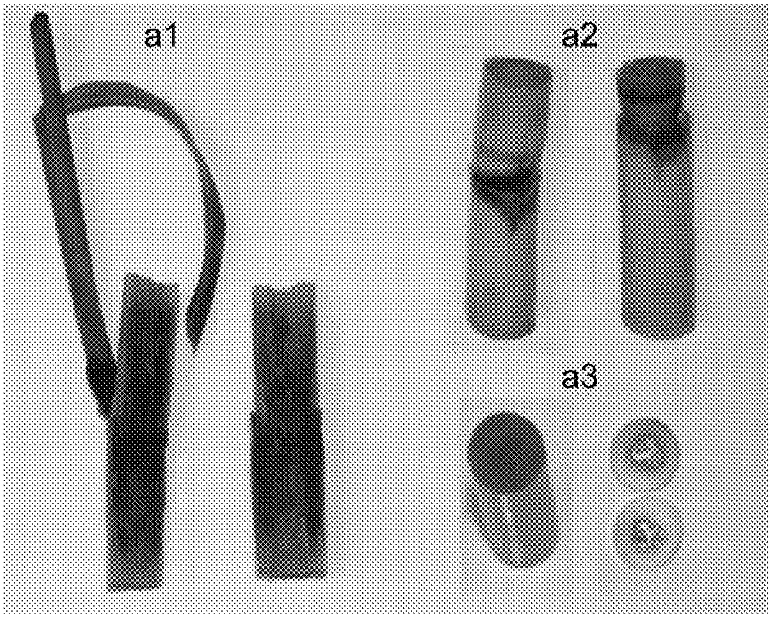
FIG. 7A illustrates expression of GUS in stalks of sugarcane transformed with an expression cassette according to an example embodiment of the disclosure.
Figure 7B:
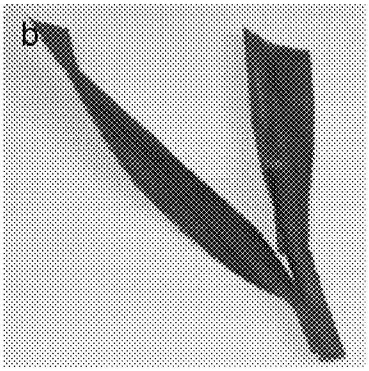
FIG. 7B illustrates expression of GUS in leaves of sugarcane transformed with an expression cassette according to an example embodiment of the disclosure.
Figure 7C:
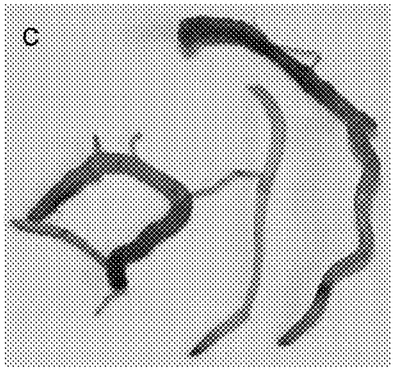
FIG. 7C illustrates expression of GUS in roots of sugarcane transformed with an expression cassette according to an example embodiment of the disclosure.
Figure 8A:
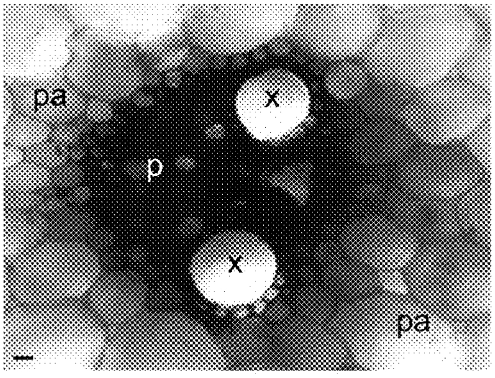
FIG. 8A illustrates expression of GUS in stalks of sugarcane transformed with an expression cassette according to an example embodiment of the disclosure.
Figure 8B:
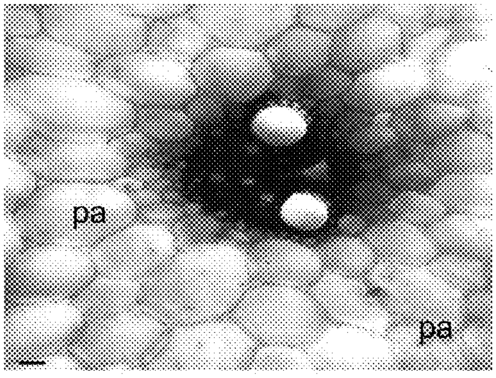
FIG. 8B illustrates expression of GUS in stalks of sugarcane transformed with an expression cassette according to an example embodiment of the disclosure.
Figure 8C:
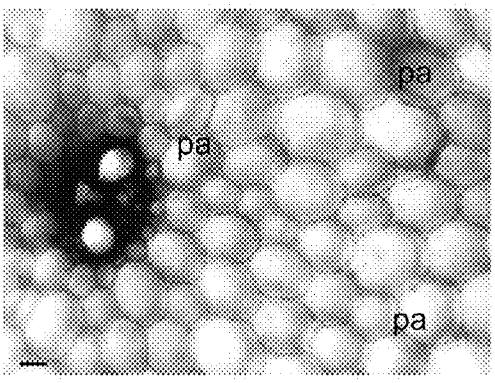
FIG. 8C illustrates expression of GUS in stalks of sugarcane transformed with an expression cassette according to an example embodiment of the disclosure.
Figure 8D:
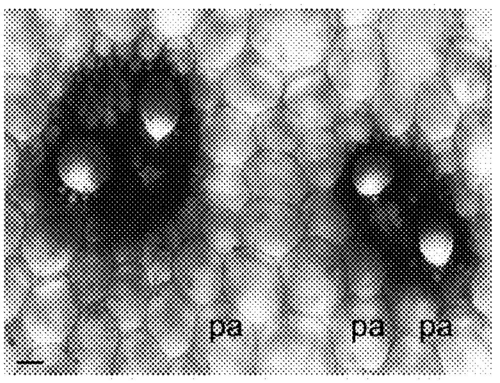
FIG. 8D illustrates expression of GUS in stalks of sugarcane transformed with an expression cassette according to an example embodiment of the disclosure.

Expression of GUS under the control of SCBV21 in stalks, leaves, and roots of in the transgenic sugarcane of Example 5 is shown in FIGS. 7A, 7B, and 7C, respectively. Staining is observed in all three tissues. FIG. 7A shows a sectional view of the opposite halves of a radially sectioned stalk segment (left), an isometric view of two stalk segments, each including a leaf node with the leaves trimmed away (upper right), and a substantially plan view of a stalk segment and transverse stalk sections (lower right). FIG. 7B shows two leaves and a leaf sheath from a single node. FIG. 7C shows shoot roots from a single transgenic plant with the highest expression in the region around the ground meristem.

In addition, expression levels of SCBV21 in various cell types were observed. For example, micrographs (FIGS. 8A-8D) of transgenic SCBV21/GUS stalks showed strong staining (using the GUS staining protocol of Example 9) of storage parenchyma and the vascular system. In these images, xylem (x), phloem (p), and storage parenchyma (pa) are marked. Transgenic SCBV21/GUS stalks also showed strong staining of sclerenchyma.

Example 14: Identification of Potential Transcription Start Sites in SCBV21

The cloned SCBV promoter sequence of 1816 bp (SEQ ID NO:1) was analyzed with Promoter Finder (available through the Berkeley *Drosophila* Genome Project at fruitfly dot org slash seq_tools slash promoter dot html) to identify potential transcription start sites. Promoter Finder predicted two potential transcription start sites, TSS1 (nucleotides 1055-1104 of SEQ ID NO:1) and TSS2 (nucleotides 1737-1786 of SEQ ID NO:1).

Example 15: Generation of Deletion Mutants of SCBV21

Figure 9A:
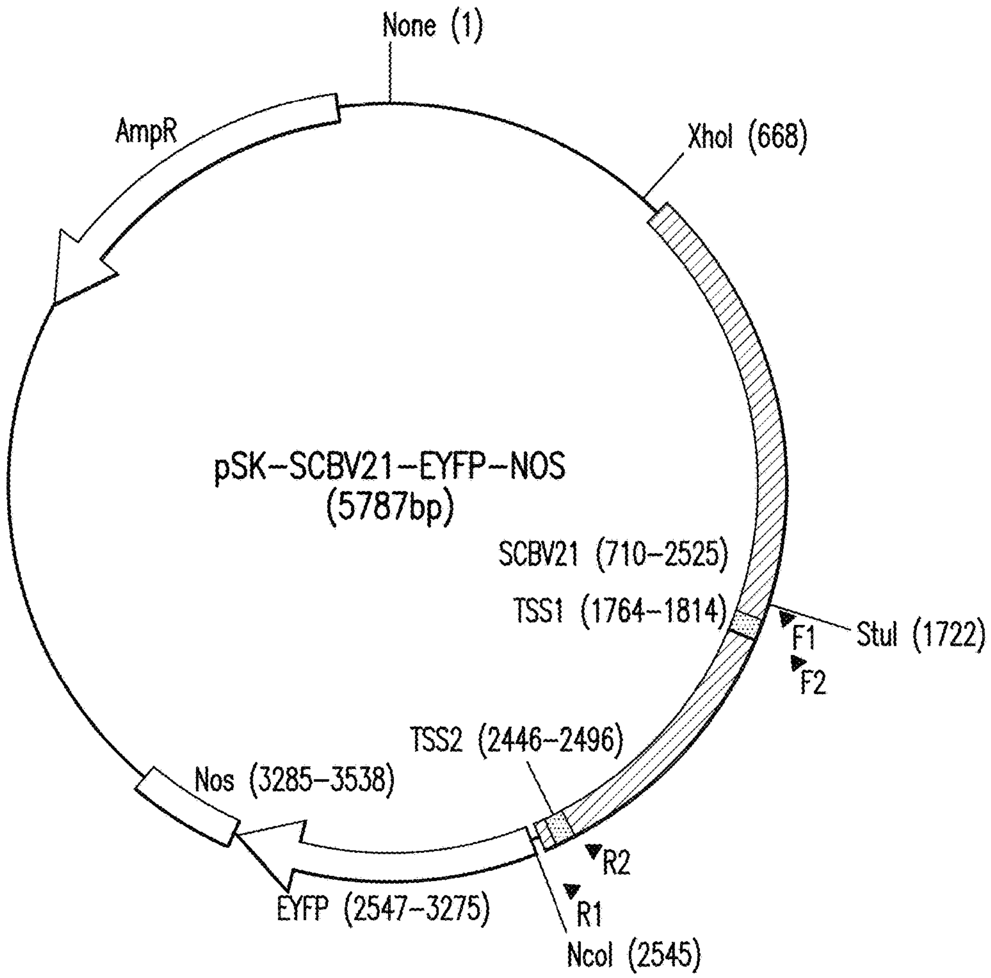
FIG. 9A illustrates a vector (SEQ ID NO:19) with a promoter according to a specific example embodiment of the disclosure.

All deletion mutants in this Example were generated from pSK-SCBV21-EYFP-Nos (FIG. 9A; SEQ ID NO:19). The restriction enzyme sites used for deletions were indicated on the map. TSS1 and TSS2 are shown with horizontal hash lines. The approximate positions of primers to generate deletion mutants were indicated with filled arrowheads. XhoI site in forward primers (F1 and F2; SEQ ID NOS: 34 and 35, respectively) and NcoI site in reverse primers (R1 and R2; SEQ ID NOS: 36 and 37, respectively) were incorporated for cloning purposes.

Figure 9B:
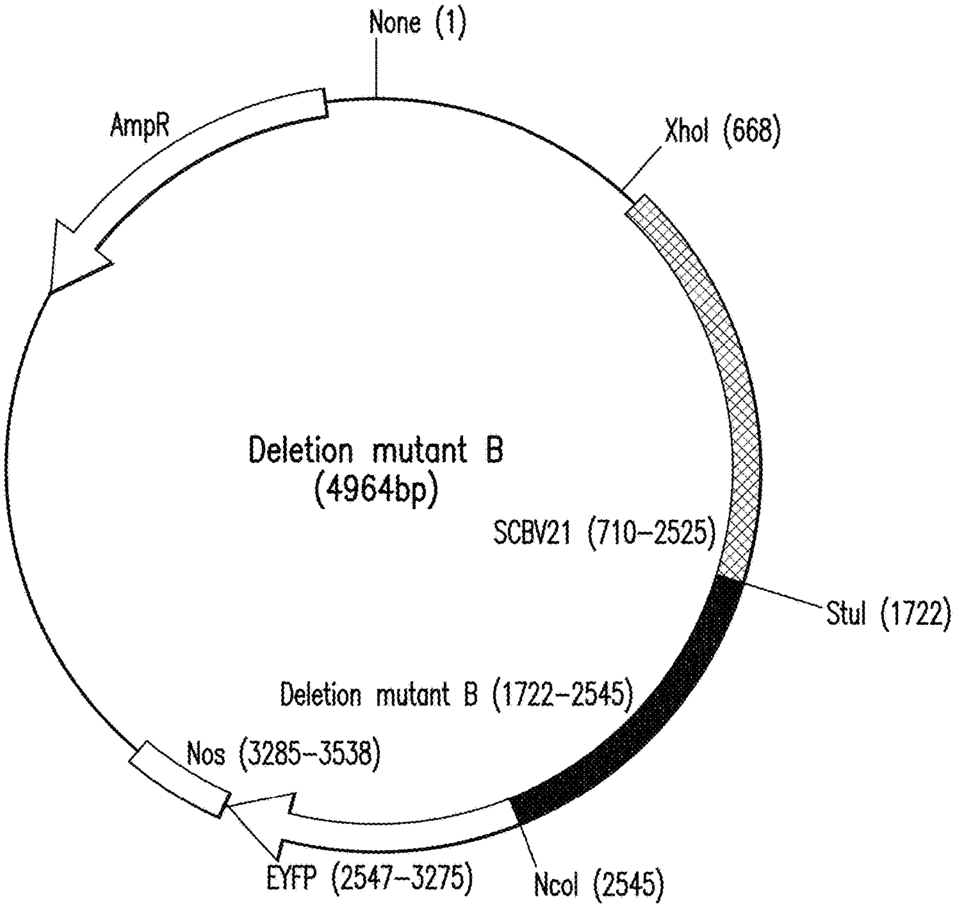
FIG. 9B illustrates a vector (SEQ ID NO:20) with a promoter (deletion mutant B) according to a specific example embodiment of the disclosure.

Deletion mutant B was generated by deleting the region between StuI and NcoI sites from pSK-SCBV21-EYFP-Nos (FIG. 7A). First, pSK-SCBV21-EYFP-Nos was double digested with StuI and NcoI, followed by Klenow reaction to make blunt ends of digested fragments. Then, the digested fragment of 4964 bp was eluted from agarose gel for blunt-end ligation. The nucleotide sequence of the ligation junction was confirmed by sequencing. The plasmid map of Mutant B is shown in FIG. 9B. In FIG. 9B, the deleted region of SCBV21 is indicated with a black bar and the remaining fragment of SCBV21 is shown with the crossed-line fill pattern.

Figure 9C:
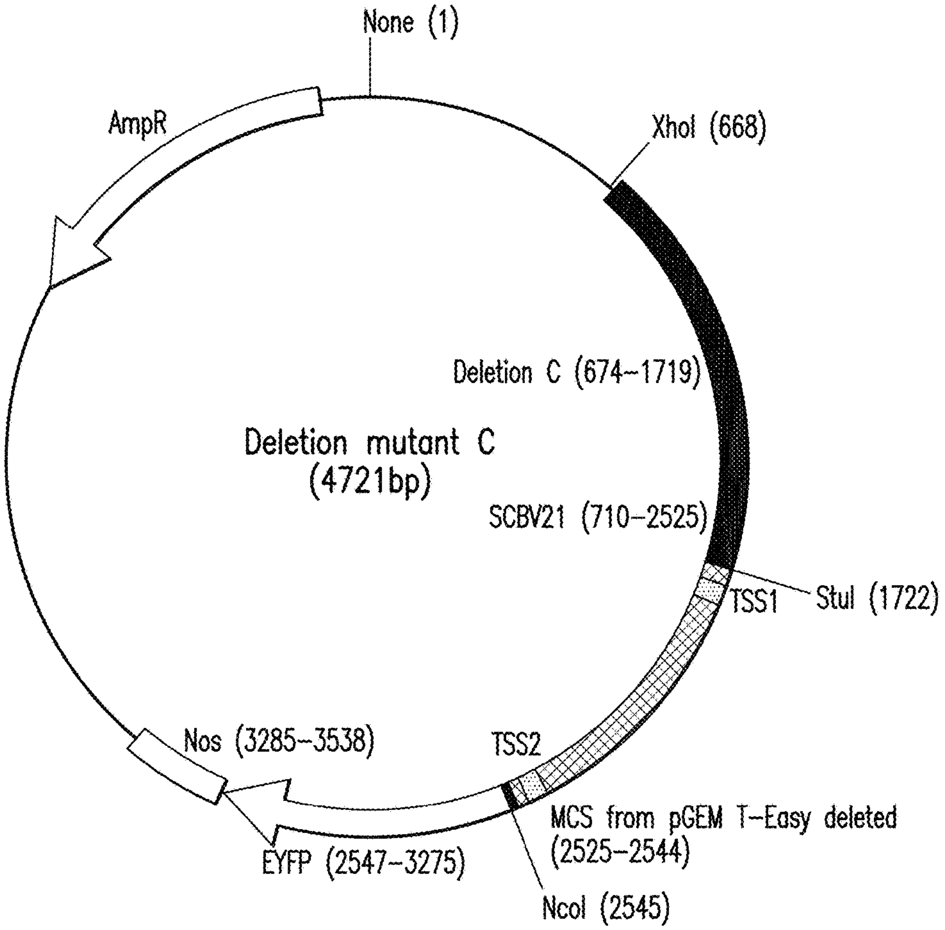
FIG. 9C illustrates a vector (SEQ ID NO:21) with a promoter (deletion mutant C) according to a specific example embodiment of the disclosure.

To generate deletion mutant C, the region between StuI and the 3' end of SCBV21 was PCR amplified from pSK-SCBV21-EYFP-Nos with the primer F1 (SEQ ID NO:34) and R1 (SEQ ID NO:36) (FIG. 9A). The primer R1 was designed to remove 19 nucleotides present in pSK-SCBV21-EYFP-Nos between the start codon of EYFP and the 3' end of SCBV21 (FIG. 9A). This sequence was derived from the multicloning site of pGEM T-Easy vector. The 805 bp PCR product (mutant C fragment of SCBV21) was cloned into pGEM T-Easy (Promega) vector, and the nucleotide sequence of mutant C fragment was confirmed by sequencing. XhoI and NcoI double digestion, whose enzyme sites were flanking 5' and 3' end of the mutant C fragment, respectively, excised the mutant C fragment from pGEM T-Easy vector. The XhoI-NcoI fragment of pSK-SCBV21-EYFP-Nos was replaced with the mutant C fragment to generate Mutant C (FIG. 9C). In FIG. 9C, the deleted region of SCBV21 is indicated with a black bar and the remaining fragment of SCBV21 is shown with the crossed-line fill pattern. TSS1 and TSS2 are also indicated in the map.

Figure 9D:
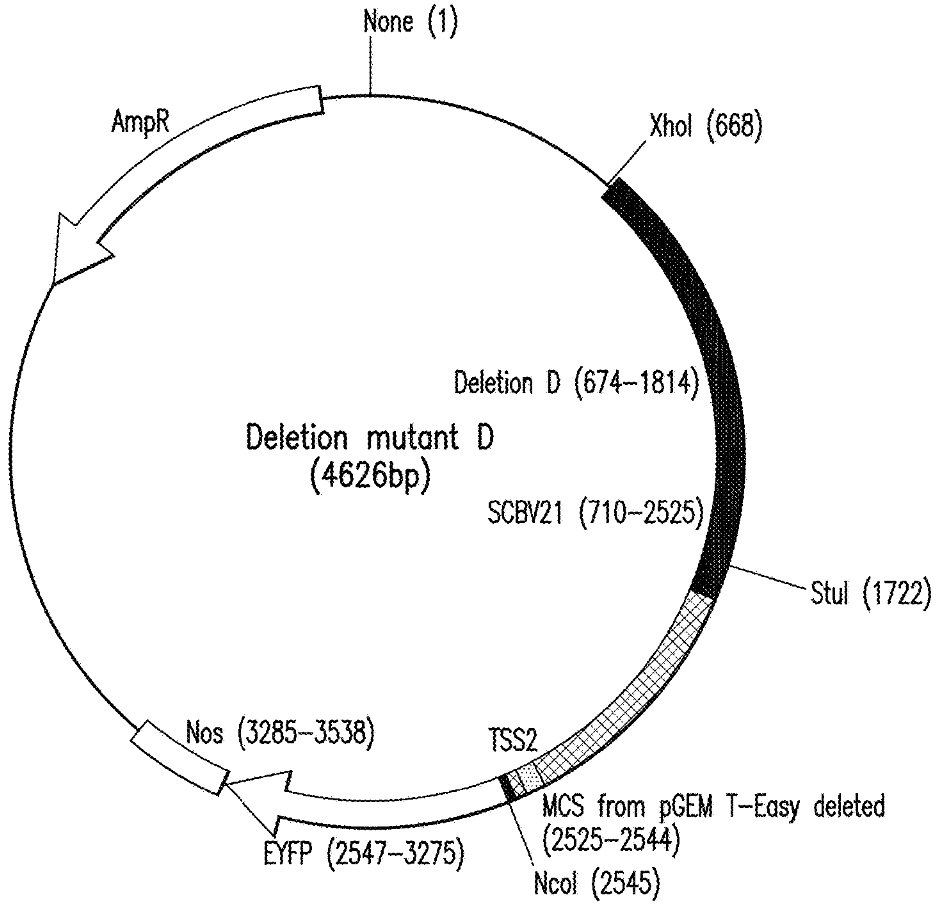
FIG. 9D illustrates a vector (SEQ ID NO:22) with a promoter (deletion mutant D) according to a specific example embodiment of the disclosure.

To generate deletion mutant D, the 3' 710 bp of SCBV21 was PCR amplified with primer F2 (SEQ ID NO:35) and R1 (SEQ ID NO:36) from pSK-SCBV21-EYFP-Nos (FIG. 9A). The PCR product (mutant D fragment of SCBV21) was cloned into pGEM T-Easy vector, and the nucleotide sequence of mutant D fragment was confirmed by sequencing. Mutant D was generated by the same procedure used to make Mutant C. XhoI and NcoI double digestion, whose enzyme sites were flanking 5' and 3' end of the mutant D fragment, respectively, excised the mutant D fragment from pGEM T-Easy vector. The XhoI-NcoI fragment of pSK-SCBV21-EYFP-Nos was replaced with the mutant D fragment to generate Mutant D (FIG. 9D). In FIG. 9D, the deleted region of SCBV21 is indicated with a black bar and the remaining fragment of SCBV21 is shown with the crossed-line fill pattern. TSS2 is also indicated in the map.

Figure 9E:
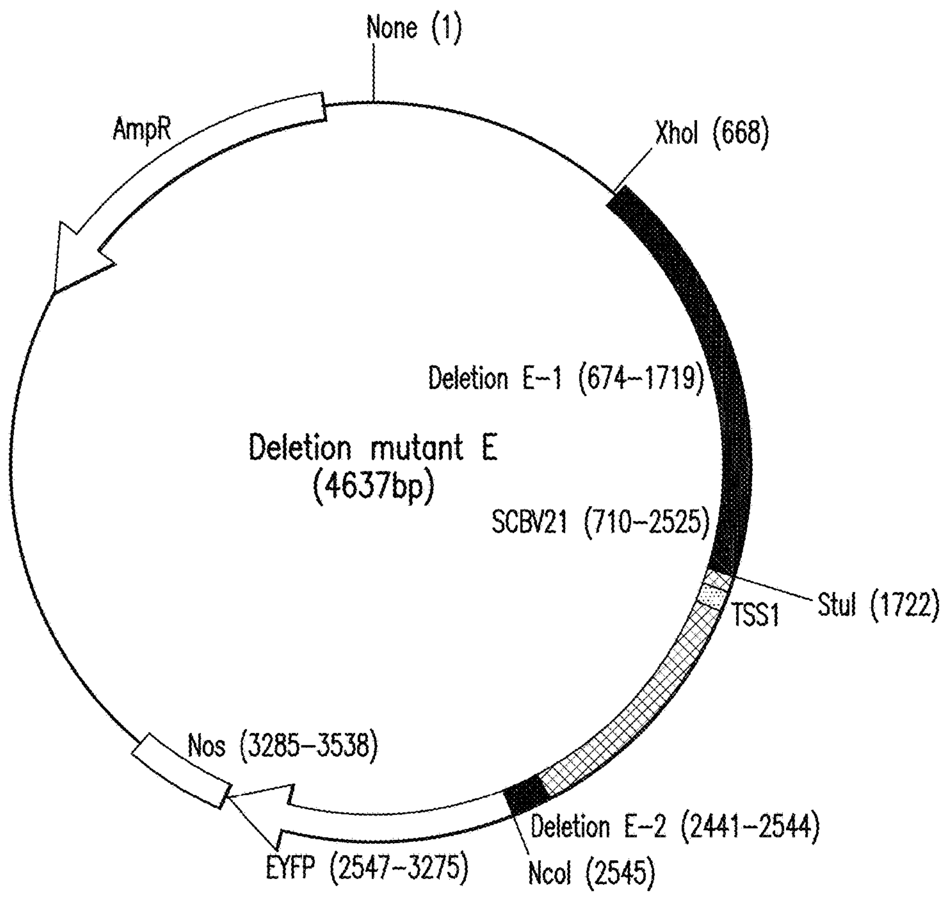
FIG. 9E illustrates a vector (SEQ ID NO:23) with a promoter (deletion mutant E) according to a specific example embodiment of the disclosure.

To generate deletion mutant E, the region between nt 1722 and nt 2440 was PCR amplified with primer F1 (SEQ ID NO:34) and R2 (SEQ ID NO:37) from pSK-SCBV21-EYFP-Nos (FIG. 9A). The PCR fragment (mutant E fragment) was cloned into pGEM T-Easy vector, and the nucleotide sequence of mutant E fragment was confirmed by sequencing. Mutant E was generated by the same procedure used to make Mutant C and D. The mutant E fragment was excised from pGEM T-Easy vector by XhoI and NcoI double digestion, whose enzyme sites were flanking both 5' and 3' end of the mutant E fragment. The XhoI-NcoI fragment of pSK-SCBV21-EYFP-Nos was replaced with the mutant E fragment to generate Mutant E (FIG. 9E). In FIG. 9E, the deleted region E1 and E2 of SCBV21 is indicated with a black bar and the remaining fragment of SCBV21 is shown with the crossed-line fill pattern. TSS1 is also indicated in the map.

Figure 9F:
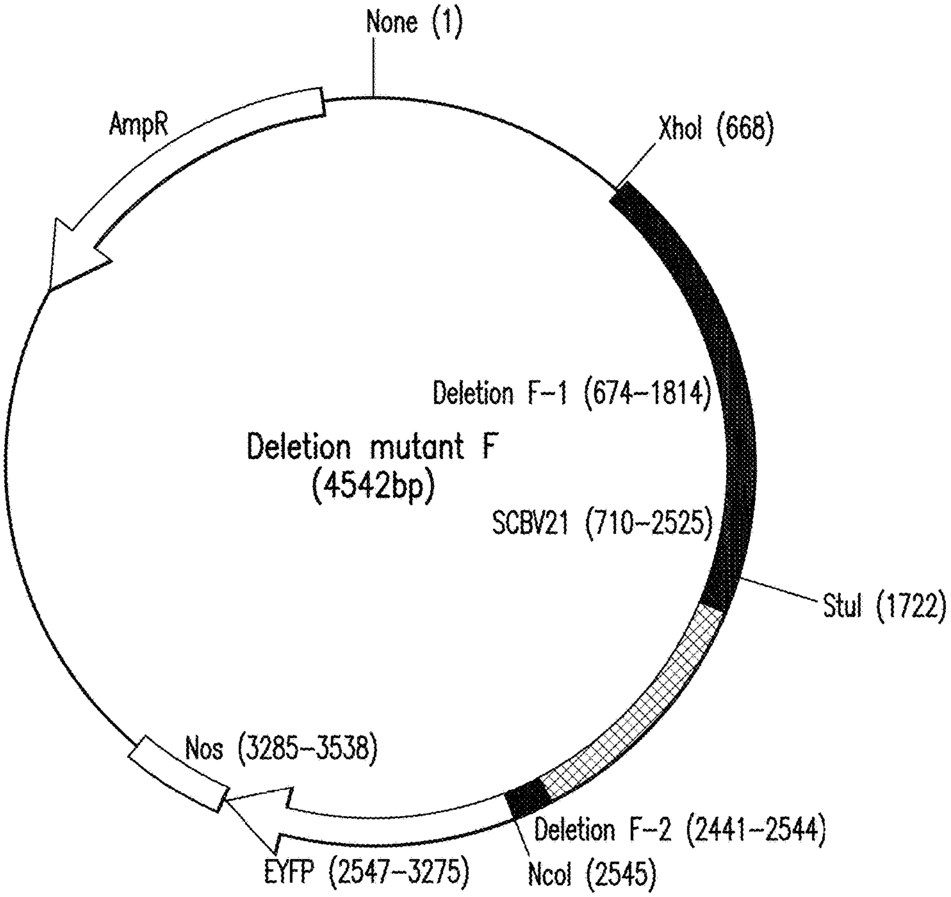
FIG. 9F illustrates a vector (SEQ ID NO:24) with a promoter (deletion mutant F) according to a specific example embodiment of the disclosure.
Figure 10A:
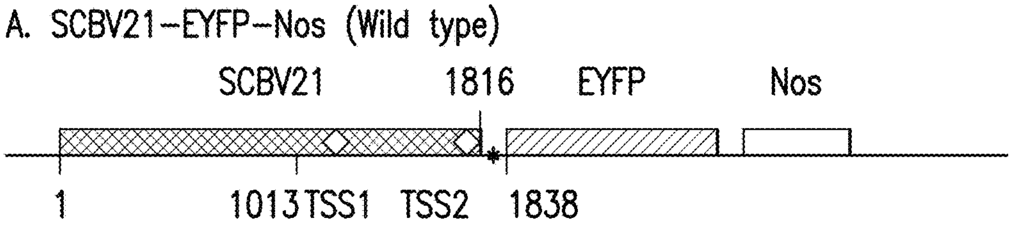
FIG. 10A illustrates a promoter according to a specific example embodiment of the disclosure.
Figure 10B:
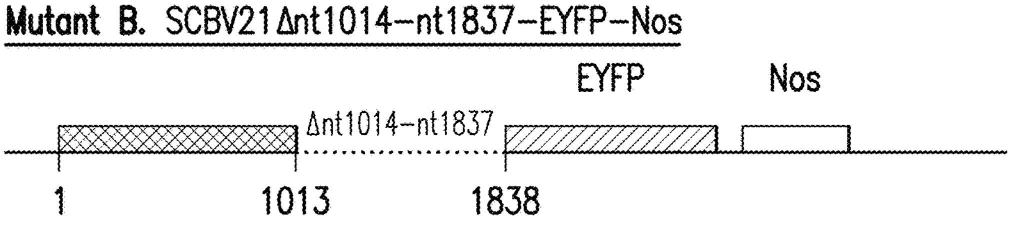
FIG. 10B illustrates a promoter (deletion mutant B) according to a specific example embodiment of the disclosure.
Figure 10C:
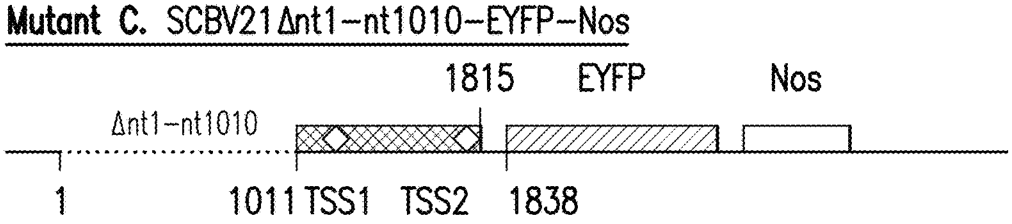
FIG. 10C illustrates a promoter (deletion mutant C) according to a specific example embodiment of the disclosure.
Figure 10D:
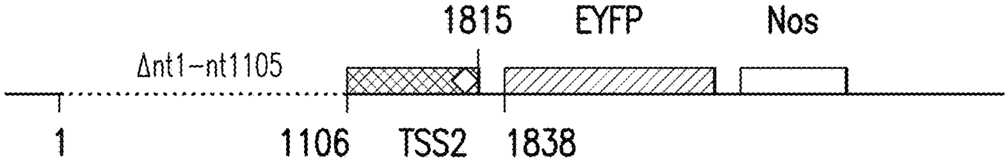
FIG. 10D illustrates a promoter (deletion mutant D) according to a specific example embodiment of the disclosure.
Figure 10E:
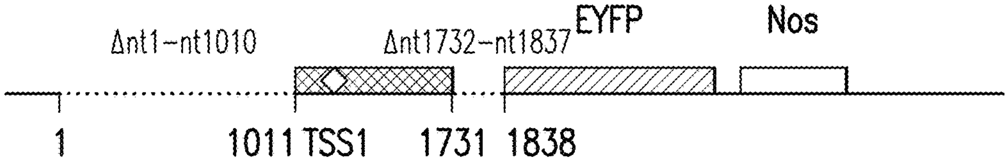
FIG. 10E illustrates a promoter (deletion mutant E) according to a specific example embodiment of the disclosure.
Figure 10F:
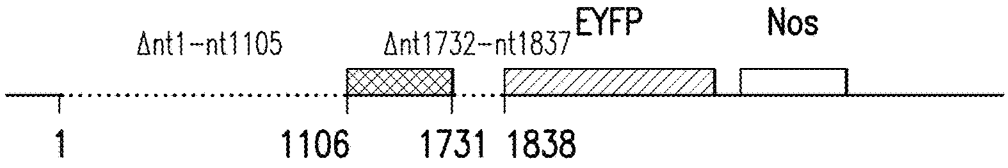
FIG. 10F illustrates a promoter (deletion mutant F) according to a specific example embodiment of the disclosure.

To generate deletion mutant F, the region between nt 1815 and nt 2440 was PCR amplified with primer F2 (SEQ ID NO:35) and R2 (SEQ ID NO:37) from pSK-SCBV21-EYFP-Nos (FIG. 9A). The PCR fragment (mutant F fragment) was cloned into pGEM T-Easy vector, and the nucleotide sequence of mutant F fragment was confirmed by sequencing. Mutant F was generated by the same procedure used to make the aforementioned three mutants, Mutant C, D and E. The mutant F fragment was excised from pGEM T-Easy vector by XhoI and NcoI double digestion, whose enzyme sites were flanking 5' and 3' end of the mutant F fragment, respectively. The XhoI-NcoI fragment of pSK-SCBV21-EYFP-Nos was replaced with the mutant F fragment to generate Mutant F (FIG. 9F). In FIG. 9F, the deleted region of SCBV21 is indicated with a black bar and the remaining fragment of SCBV21 is shown with the crossed-line fill pattern.

Example 16: Transient Expression Assay on Sugarcane Leaf Sections

Target sugarcane leaf tissue for transient EYFP expression assay was prepared from commercial sugarcane hybrid CP72-1210. Actively growing top portions of stalks, including the first 2-3 nodes from top, were harvested from field grown sugarcane. After removing all fully expanded leaves until the first visible dewlap was exposed, the sugarcane top was sterilized in 10% bleach for 20 min. The outermost 2-3 layers of green leaf sheaths above first node were removed, then the next 1-2 layers of leaf sheath were sectioned in 10 mm×20 mm size after removing mid rib. The prepared target tissue sections were placed adaxial side down and kept on MS solid media for 3 days in the dark. Each tissue section was transferred onto a new MS medium plate and used for particle bombardment with DNA-coated 1.1 μm-tungsten particles that were prepared by the manufacturer's instruction (BioRad).

For particle bombardment, 500 μg of tungsten particles coated with 500 ng of DNA was placed on a microcarrier filter, then the filter was installed at the tip of a nozzle releasing 110 psi helium gas in a vacuum chamber. Each target tissue on a MS medium plate was placed 7 cm below the tip of microcarrier filter in a vacuum chamber. The DNA coated tungsten particles were bombarded on the target tissue at 110 psi under 26 inch-Hg vacuum pressure. After bombardment, the target tissue was kept in the dark for 2 days. The expression of EYFP was investigated under a fluorescence microscope with EYFP or GFP filter. Results are shown in Table 11 and FIGS. 11A-11F.

TABLE 11

EYFP expression in transgenic sugarcane leaves

| | Construct | Promoter size (bp) | TSS1 | TSS2 | YFP Expression | Figure |
|---|---|---|---|---|---|---|
| A. | SCBV21-EYPF-Nos | 1816 | Yes | Yes | +++ | 11A |
| B. | SCBV21 Δnt1014-nt1837-EYFP-Nos | 1013 | No | No | − | 11B |
| C. | SCBV21 Δnt1-nt1010-EYFP-Nos | 805 | Yes | Yes | +++ | 11C |
| D. | SCBV21 Δnt1-nt1104-EYFP-Nos | 710 | No | Yes | +++ | 11D |
| E. | SCBV21 Δnt1-nt1010 Δnt1732-nt1837-EYFP-Nos | 721 | Yes | No | +/− | 11E |
| F. | SCBV21 Δnt1-nt1104 Δnt1732-nt1837-EYFP-Nos | 626 | No | No | +/− | 11F |

Figure 11A:
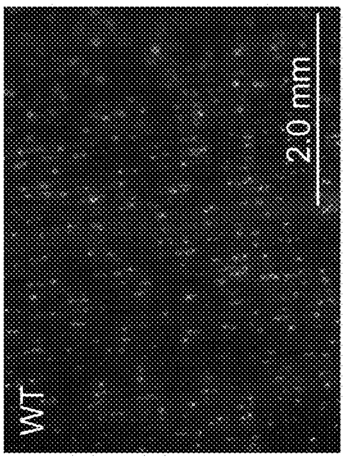
FIG. 11A illustrates expression of EYFP in leaves of sugarcane transformed with an expression cassette according to an example embodiment of the disclosure.
Figure 11B:
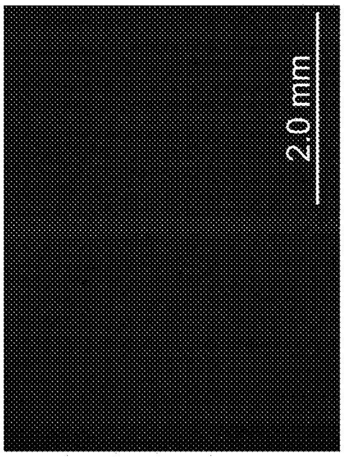
FIG. 11B illustrates expression of EYFP in leaves of sugarcane transformed with an expression cassette (comprising deletion B) according to an example embodiment of the disclosure.
Figure 11C:
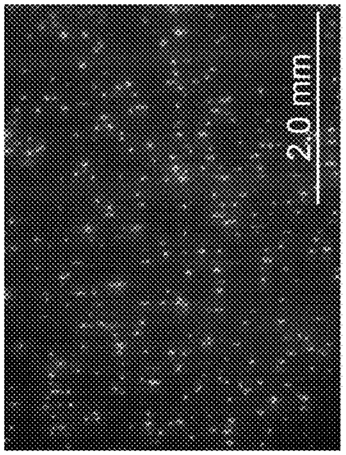
FIG. 11C illustrates expression of EYFP in leaves of sugarcane transformed with an expression cassette (comprising deletion C) according to an example embodiment of the disclosure.
Figure 11D:
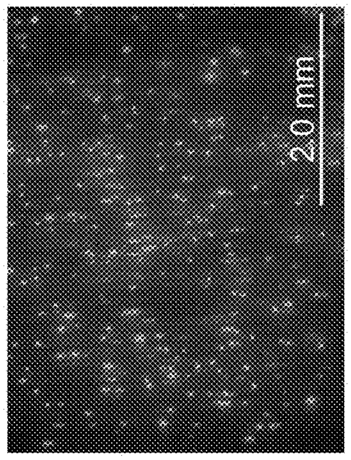
FIG. 11D illustrates expression of EYFP in leaves of sugarcane transformed with an expression cassette (comprising deletion D) according to an example embodiment of the disclosure.
Figure 11E:
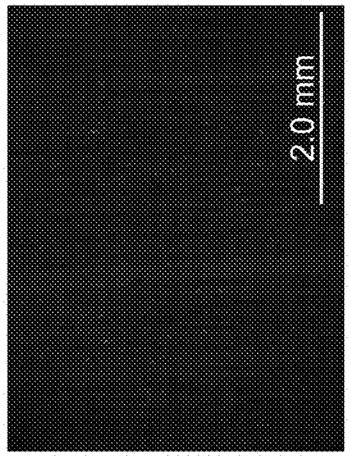
FIG. 11E illustrates expression of EYFP in leaves of sugarcane transformed with an expression cassette (comprising deletion E) according to an example embodiment of the disclosure.
Figure 11F:
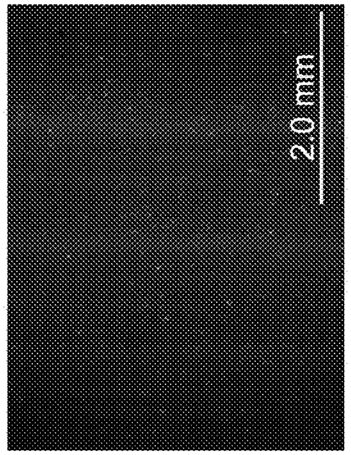
FIG. 11F illustrates expression of EYFP in leaves of sugarcane transformed with an expression cassette (comprising deletion F) according to an example embodiment of the disclosure.

Yellow Fluorescent Protein (YFP) was observed in tissue bombarded with SCBV21-EYPF-Nos (unmodified), SCBV21 Δnt1-nt1010-EYFP-Nos (deletion C), and SCBV21 Δnt1-nt1104-EYFP-Nos (deletion D) as shown in FIG. 11A, FIG. 11C, FIG. 11D, respectively. Little or no YFP was observed in tissue bombarded with SCBV21 Δnt1014-nt1837-EYFP-Nos (deletion B), SCBV21 Δnt1-nt1010 Δnt1732-nt1837-EYFP-Nos (deletion E), or SCBV21 Δnt1-nt1104 Δnt1732-nt1837-EYFP-Nos (deletion F) as shown in FIG. 11B, FIG. 11E, and FIG. 11F, respectively.

Example 17: Transient Expression Assay on *Nicotiana Tabacum* Leaf Sections

For the transient EYFP expression assay on *N. tabacum*, the leaves of 45-day-old *N. tabacum* grown in a Magenta box were collected and placed adaxial side down on MS-medium supplemented with 0.1 M mannitol and 0.2 M sorbitol for 4 hours in the dark before bombardment. The prepared target tissue was bombarded with 500 μg of 1.1 μm-tungsten particles coated with 500 ng of DNA at 60 psi under 26 inch-Hg vacuum pressure. After keeping the bombarded target tissues on MS-medium supplemented with 0.1M mannitol and 0.2 M sorbitol for about 12 hours in the dark, the target tissues were transferred and kept on MS-medium for 24 hours. The YFP expression was examined under a fluorescence microscope with GFP filter. The results are summarized in Table 12 below.

Results are shown in Table 12. Yellow Fluorescent Protein (YFP) was observed in tissue bombarded with SCBV21-EYPF-Nos (unmodified), SCBV21 Δnt1-nt1010-EYFP-Nos (deletion C), and SCBV21 Δnt1-nt1104-EYFP-Nos (deletion D). Little or no YFP was observed in tissue bombarded with SCBV21 Δnt1014-nt1837-EYFP-Nos (deletion B), SCBV21 Δnt1-nt1010 Δnt1732-nt1837-EYFP-Nos (deletion E), or SCBV21 Δnt1-nt1104 Δnt1732-nt1837-EYFP-Nos (deletion F). Thus, the expression pattern paralleled that seen for monocots in Example 16.

TABLE 12

EYFP expression in transgenic tobacco leaves

| | Construct | Promoter size (bp) | TSS1 | TSS2 | YFP Expression |
|---|---|---|---|---|---|
| A. | SCBV21-EYPF-Nos | 1816 | Yes | Yes | +++ |
| B. | SCBV21 Δnt1014-nt1837-EYFP-Nos | 1013 | No | No | − |
| C. | SCBV21 Δnt1-nt1010-EYFP-Nos | 805 | Yes | Yes | +++ |

TABLE 12-continued

| EYFP expression in transgenic tobacco leaves | | | | |
|---|---|---|---|---|
| Construct | Promoter size (bp) | TSS1 | TSS2 | YFP Expression |
| D. SCBV21 Δnt1-nt1104-EYFP-Nos | 710 | No | Yes | +++ |
| E. SCBV21 Δnt1-nt1010 Δnt1732-nt1837-EYFP-Nos | 721 | Yes | No | +/− |
| F. SCBV21 Δnt1-nt1104 Δnt1732-nt1837-EYFP-Nos | 626 | No | No | +/− |

Example 18: Multi-Promoter Expression of Bovine Stomach Lysozyme

Sugarcane (*Saccharum* spp.) has a great potential for the production of protein-based therapeutics. It has a fast growth cycle and an efficient carbon fixation pathway, produces a large biomass, and offers the prospect of inexpensive biopharmaceutical production. This example illustrates development of sugarcane as a recombinant expression system for the production of a mammalian enzyme (bovine stomach lysozyme) having broad-spectrum antimicrobial activity and a potential use in food, cosmetics and agriculture. Expression of this mammalian gene was enhanced in sugarcane by modulating transcription, transcript stability and translation. Expression vectors were generated using a synthetic gene that was codon optimized for expression in a plant monocot system (e.g., SEQ ID NO: 38). A single promoter as well as a multiple promoter system was used to drive expression. The 5' and 3' untranslated regions of a virus that infects sugarcane were fused to the coding region of the gene to enhance translation. Embryogenic calli and leaf rolls of two commercial sugarcane varieties were transformed biolistically, and the phosphinothricin acetyl transferase (BAR) gene was used as a selectable marker Immunoblot analysis as well as enzymatic activity assays of stably transformed sugarcane plants revealed the presence of intact bovine stomach lysozyme that accumulated at levels as high as 0.33 mg/kg in stalks of plants expressing it from a single promoter vector, and to levels of 6.0-10 mg/kg (7.2 mg/kg=1% TSP) in stalks transgenic for co-expression of the BvLz gene from three different promoters in separate vectors. Each vector did not adversely affect the others as shown by copy number, steady-state mRNA levels and the presence of the functional enzyme. These results suggest that transcriptional synergism resulted through additive promoter activities and increased gene expression. A growth cycle study for an 11-month period showed a substantial increase in enzyme accumulation over time in the transgenic lines. This study suggests the commercial feasibility of producing a stable recombinant enzyme in transgenic sugarcane, and developing sugarcane as a biofactory for high value proteins.

Example 19: Single Promoter Expression of Bovine Stomach Lysozyme

A. Growth Cycle Study of Sugarcane Single Promoter BvLz Transgenic Lines: Monitoring BvLz Activity of the Transgenic Lines for 7-, 9- and 11-Month Periods A number of sugarcane BvLz transgenic lines were generated in accordance with this Example. These represent: (1) 36 lines with 74 plants that are transgenic for $BvLz_m$ (maize BvLz) under the control of the strong constitutive promoter of maize ubiquitin 1 with no heat shock element (pMUbi), and (2) 4 lines with 18 plants that are transgenic for pMUbi $BvLz_m$ and for P1HcPro, a suppressor of gene silencing isolated in our laboratory (U.S. Pat. No. 7,001,739). A total of 15 BvLz transgenic lines were selected for further characterization of their BvLz activity level.

To study the temporal accumulation of BvLz in sugarcane, the selected 15 BvLz transgenic lines were subjected to an 11-month greenhouse growth cycle study with harvests at 7-, 9- and 11-months. Stalks were harvested for the three time harvests, shredded and shipped frozen to the BioSeparations Laboratory at Texas A&M University (College Station). The juice from the 15 BvLz transgenic lines for the three different harvests was extracted by manual press and evaluated for BvLz by a standard turbidity assay. The extract was adjusted to pH 4.0, clarified by centrifugation, and passed over an SP-Sepharose cation exchange column for BvLz concentration. The BvLz activity was assayed in the concentrated extract.

Table 13 lists the BvLz activity (mg of BvLz per kg of harvested cane/stalk) of the 15 BvLz sugarcane transgenic lines for the 7-, 9- and 11-month harvests. (BvLz activity was assayed in 200 mL of stalk extract from the 7-month harvest, and 650-700 mL (one kg of cane/stalk) of stalk extract from the 11-month harvest.) In general, there was a substantial increase in BvLz yield at the 11-month harvest for the 15 transgenic lines. Nine out of 15 lines showed a two-fold increase in their BvLz activity level. A lower level of BvLz activity was detected in the 7-month harvested stalks.

Additional experiments were conducted to evaluate the efficiency of BvLz extraction and purification from the existing BvLz transgenic lines. These include the following:

1. Western analysis of BvLz in the flow-through of the column was performed, and no detectable amount of BvLz was observed.

2. Western analysis of BvLz of the shredded stalks from the 15 BvLz transgenic lines was also performed. The BvLz activity data correlated very well with the BvLz level detected by the western analysis in the stalks.

Total soluble protein from leaf (40 μg) and stalk (2-5 μg) was analyzed by western blot, using a polyclonal anti-BvLz antibody. One kg of cane/stalk (650-700 mL extract) from the 11-month harvest was analyzed for BvLz activity. The BvLz expression level of the transgenic lines was also measured in the leaves of the same physiological age (fully expanded second-leaf stage) at the three different harvest times. Western analysis showed that there was no difference in the BvLz level of leaves harvested at 7-, 9- and 11-months. Furthermore, the BvLz level of leaves of the transgenic lines correlated very well with that of stalks for the same harvest.

TABLE 13

Classification of single promoter BvLz transgenic lines according to their BvLz expression level.

| | mg BvLz/kg cane (stalk) weight | | |
|---|---|---|---|
| Transgenic line | 7-month | 9-month | 11-month |
| Very high expresser | | | |
| EM108 | 0.13 | 0.20 | 0.33 |
| EM114 | 0.12 | 0.18 | 0.32 |

TABLE 13-continued

Classification of single promoter BvLz transgenic lines according to their BvLz expression level.

| | mg BvLz/kg cane (stalk) weight | | |
|---|---|---|---|
| Transgenic line | 7-month | 9-month | 11-month |
| High expresser | | | |
| EM123 | 0.09 | 0.21 | 0.26 |
| EM67 | 0.12 | 0.19 | 0.29 |
| EM33 | 0.05 | 0.14 | 0.22 |
| Medium expresser | | | |
| EM112 | 0.05 | 0.09 | 0.20 |
| EM106 | 0.04 | 0.14 | 0.18 |
| EM97 | 0.12 | 0.11 | 0.15 |
| EM63 | 0.11 | 0.07 | 0.18 |
| EM38 | 0.05 | 0.12 | 0.15 |
| Low expresser | | | |
| EM35 | 0.07 | 0.06 | 0.10 |
| Very low expresser | | | |
| EM129 | 0.04 | 0.05 | 0.08 |

B. Agronomic Performance of Sugarcane BvLz Transgenic Lines

To assess whether sugarcane BvLz expressing lines incurred any growth penalty, the height of leaves and stalks, and the number of tillers were measured every two weeks for a period of three months.

Differences in agronomic performance of the sugarcane BvLz transgenic lines were independent of BvLz accumulation. There was no observable penalty in leaf height, stalk height and number of tillers for the BvLz transgenic lines. The growth pattern of the highly BvLz expressing lines, such as EM116 and EM123, was not affected.

Sprouting, however, was affected only for the first week of planting in some of the BvLz highly expressing lines such as EM116, EM123, EM112, EM114 and EM96. Medium BvLz expressers such as EM108, EM38 and EM33, as well as low BvLz expressers such as EM35 did not even sprout during the first week. BvLz transgenic lines were noted to sprout better during the second week of planting, with the exception of the two high expressers EM112 and 114, and the low expresser EM35 (FIG. 3D). However, all BvLz expressing lines were able to fully sprout during the third week of planting (data not shown).

To investigate whether photosynthesis was limiting in the sugarcane BvLz transgenic lines, the level of three key photosynthetic enzymes, ribulose-1,5-biphosphate carboxylase-oxygenase (Rubisco, large subunit or RbcL), phosphoenolpyruvate carboxylase (PEPC) and pyruvate orthophosphate dikinase (PPDK), was analyzed in leaves by Western blot. Total soluble protein (40 μg) from leaf extract was analyzed, using polyclonal anti-RbcL, anti-PEPC, or anti-PPDK antibody. Western blots were scanned, and net intensity of RbcL, PPDK and PPDK bands was recorded.

The level of the three major photosynthetic enzymes was not affected by the BvLz expression level of the transgenic lines. The high, medium and low BvLz expressing lines displayed a good level of RbcL, PEPC and PPDK, which is comparable to that of the non-transformed plants. Net intensities of the scanned bands of RbcL, PEPC and PPDK were high in most of the BvLz transgenic lines. Each of the photosynthetic enzyme intensity level correlated very well with the BvLz expression level of the different lines.

Example 20: Multi-Promoter Expression of Bovine Stomach Lysozyme

The expression of a particular heterologous gene/transgene and subsequent production of its protein in plant cells are influenced by several factors. These include:

(1) Transcriptional factors such as transgene copy number, and promoter activity. Promoters, whether they are constitutive, tissue-specific (stem-specific in the case of sugarcane) or inducible, play a crucial role in controlling the production of heterologous proteins at a particular growth and developmental stage, or in a specific tissue. Two promoters, pSPRP and pSEF1α, that constitutively express in sugarcane were isolated in our laboratory; these are from a sugarcane proline rich protein (SPRP) and an elongation factor 1α (SEF1α). Two stem-expressed and stress-inducible promoters, pJAS and pOMT, were also isolated; these are from a sugarcane jasmonate-inducible protein (or dirigent protein) (JAS) and an o-methyltransferase (OMT). The pSPRP, pSEF1α, and pJAS were used together with the strong constitutive promoter pUbi from maize ubiquitin) (with no heat shock element) (pMUbi), to drive the expression of the BvLz gene, either as a single or triple promoter combination.

(2) Post-transcriptional factors including mRNA splicing, mRNA stability, and translation.

a. Untranslated regions for enhancement of translation, such as the 5' and 3' untranslated regions (UTR) of viruses infecting monocots were be fused to the BvLz gene. These include the 5' and 3' UTRs of Sorghum mosaic virus (SrMV).

b. Suppressors of post-transcriptional gene silencing (PTGS) were used in co-transformation with the BvLz construct. These include the P1/HC-Pro protein isolated from Sorghum mosaic virus, and the CTV P23 protein isolated from Citrus tristeza virus.

(3) Translational and Post-translational factors such as codon usage, protein stability, modification, trafficking and final compartmentalization.

A. Assembly of New Genetic Constructs

Several genetic constructs were assembled, using a combination of different constitutive and stem-regulated/inducible promoters to drive the expression of the BvLzm gene (BvLz synthesized following the codon usage of maize) or the $BvLz_{sc}$ gene (BvLz synthesized following the codon usage specific to sugarcane). Untranslated regions of SrMV were also fused to the BvLz gene to enhance its translation. Suppressors of gene silencing were also co-introduced into sugarcane with the BvLz gene to reduce its silencing.

B. Transformation of Sugarcane

Biolistic transformation: The new genetic constructs were introduced into sugarcane biolistically (direct gene transfer via microprojectile bombardment). Although the method of introducing DNA into cells by physical means (i.e. microprojectile bombardment) has revolutionized the field of genetic transformation of crop plants, considerable variation may be seen in stability, integration and expression of the introduced transgene.

*Agrobacterium*-mediated transformation: This type of transformation exploits the nature of *Agrobacterium tumefaciens* to deliver a discrete segment of DNA into the recipient genome. New *Agrobacterium*-mediated transformations of sugarcane were initiated in our laboratory using a binary vector containing the BvLz gene under the control of the maize ubiquitin 1 constitutive promoter.

Target plant tissue transformed: Sugarcane callus and leaf rolls are being used in our regular transformation experiments. The transformation of leaf rolls followed by direct embryogenic regeneration to produce transgenic plants, has demonstrated an improvement on the current method of callus transformation. Plant regeneration through embryogenic callus cultures is labor-intensive, time-consuming, and has increased chances of somaclonal variation.

Sugarcane varieties: The commercial variety of sugarcane, CP72-1210, as well as other commercial varieties, such as TCP87-3388, TCP89-3505 and TCP99-4454, are being used for transformation with the new BvLz constructs. Over 3,000 new lines were generated and screened for expression levels that were higher than the best expressers of Example 19. Table 14 summarizes the different new BvLz constructs used for the new sugarcane transformations.

TABLE 14

BvLz Constructs Used for Biolistic Transformation of Sugarcane.

| Genetic construct | Variety | Target tissue | No. of shoots |
|---|---|---|---|
| Single promoter | | | |
| 1. pMUbi BvLzm | CP72-1210 | Callus | 7 |
| 2. pMUbi BvLzm/ pUbi P1HcPro | CP72-1210 | Callus | 17 |
| 3. pMUbi BvLzm SrMV 3' | TCP89-3505 | Callus | 10 |
| 4. pMUbi BvLzm/ pMCG ds SGS2 | TCP87-3388 | Callus | 7 |
| 5. pMUbi BvLzm/ pMUbi CTVP23 | TCP87-3388 | Callus | 4 |
| 6. pSPRP BvLzm SrMV 3' | TCP89-3505 | Callus | 10 |
| 7. pSEF1α BvLzm SrMV 3' | TCP89-3505 | Callus | 16 |
| Triple promoter | | | |
| 1. pSPRP BvLzm SrMV 3'/ pSEF1α BvLzm SrMV 3'/ pMUbi 5' SrMV BvLzsc SrMV 3' | CP72-1210 | Callus | 74 |
| 2. pSPRP (no 5'UTR) BvLzsc 5' SrMV 3'/ | CP72-1210 | Callus | 43 |
| pSEF1α BvLzm SrMV 3'/ pMUbi BvLzm SrMV 3' | TCP89-3505 | Callus | 1 |
| 3. pSPRP BvLzm SrMV 3'/ | CP72-1210 | Callus | 23 |
| pSEF1α BvLzm SrMV 3'/ | TCP89-3505 | Callus | 1 |
| pJAS BvLzm SrMV 3' | | | 1 |
| 4. pSPRP BvLzm SrMV 3'/ pSEF1α BvLzm SrMV 3'/ pJAS BvLzm | TCP87-3388 | Leaf roll | 1 |
| 5. pSPRP (no 5'UTR) BvLzsc 5' SrMV 3'/ pSEF1α BvLzm SrMV 3'/ pJAS BvLzm | TCP87-3388 | Leaf roll | 1 |

Of the BvLz transgenic plants that were generated and further analyzed for their BvLz expression level, 23 displayed better expression levels than the best expressers of Example 19. These include pSPU (16 plants), pSPnU (1 plant), and pSPJ (6 plants) plants that are transgenic for BvLz under the control of a triple promoter (three promoters, each driving the expression of a separate copy (e.g., identical and/or substantially identical) of a single transgene (BvLz) in the same plant).

pSPU refers to plants that are transgenic for the BvLz gene whose expression is driven by the three constitutive promoters: pSEF1α (promoter for a sugarcane elongation factor 1α), pSPRP (promoter for a sugarcane proline rich protein) and pMUbi (promoter for maize ubiquitin 1). Plants were transformed with three genetic constructs: pSEF1α BvLzm SrMV 3', pSPRP BvLzm SrMV 3', and pMUbi 5' SrMV BvLzsc SrMV 3'. BvLzm refers to a synthetic BvLz gene with codons optimized for maize and BvLzsc refers to a synthetic BvLz gene with codons optimized for sugarcane. 5' and 3' SrMV refer to the 5' and 3' untranslated regions (UTR) of Sorghum mosaic virus (see Table 14).

pSPnU refers to plants that are transgenic for the BvLz gene whose expression is driven by the three constitutive promoters: pSEF1α, pSPRP with no 5'UTR, and pMUbi. Plants were transformed with three genetic constructs: pSEF1α BvLzm SrMV 3', pPRP (no 5'UTR) 5' SrMV BvLzsc SrMV 3', and pUbi BvLzm SrMV 3' (see Table 14).

pSPJ refers to plants that are transgenic for the BvLz gene whose expression is driven by two constitutive promoters, pSEF1α and pPRP, and one stem-regulated promoter, pJAS (promoter for jasmonate-inducible protein or dirigent protein). Plants were transformed with three genetic constructs: pSEF1α BvLzm SrMV 3', pSPRP BvLzm SrMV 3', and pJAS BvLzm SrMV 3' (see Table 14).

Genomic DNA gel blot analysis was used to determine the number of copies and integration events of the BvLz transgene in the newly generated pSPU and pSPJ plants. Multiple bands were detected in the genome of these plants, reflecting the insertion of multiple copies of BvLz transgene. The DNA gel blot analysis identified a total of 5 independent pSPU lines with 16 plants, one independent pSPnU with one plant, and 2 independent pSPJ lines with 6 plants.

The BvLz level of the pSPU and pSPJ plants generated was first evaluated in leaves by western blot analysis. Total soluble protein (40 μg) from leaves of 26 transgenic sugarcane plants was analyzed, using a polyclonal anti-BvLz antibody. Most of the plants displayed a higher BvLz expression level than the single promoter BvLz plants.

The BvLz expression level detected by western analysis in leaves of the pSPU and pSPJ plants was supported by the BvLz enzymatic activity in the stalks (Table 15). BvLz activity was assayed in 0.105 to 0.345 kg of stalks that are about 7-month-old. pSPU32E, pPSU19A and pSPJ10A plants accumulated the highest amounts of BvLz levels in their stalks. In general, the newly generated BvLz transgenic lines showed a higher increase in their BvLz expression level than the Example 19 lines. The BvLz expression level was improved in the new lines by using a triple promoter to drive BvLz expression.

TABLE 15

BvLz Expression in Sugarcane Stalks.

| Transgenic Plant | BvLz yield (mg BvLz/kg cane) |
|---|---|
| pSPJ | |
| 10A | 0.56 |
| 14A | 0.171 |
| 14C | 0.312 |
| 14E | 0.156 |
| 14F | 0.46 |
| pSPU | |
| 30A | 0.52 |
| 32A | 2.2 |
| 32C | 4.2 |
| 32E | 3.0 |
| 32D | 4.7 |

In conclusion, the best expressing lines in this Example had as much as 4.7 mg/kg of BvLz per kg of fresh weight as compared to the BvLz recovered from the stalks of the single promoter plants of Example 19, which had 0.33 mg of BvLz/kg of stalk.

Example 21: Expression of Bovine Stomach Lysozyme: pJSU BvLzm Plants pJSU Triple BvLzm Plants:

Plants that are transgenic for BvLzm whose expression is driven under the control of a triple promoter (three promoters driving the expression of BvLz in the same plant). Two constitutive promoters, pSEF1α (promoter for a sugarcane elongation factor 1α gene) and pMUbi (promoter for maize ubiquitin 1 gene) were used as well as one stem-regulated promoter, pJAS (promoter for the gene coding for jasmonate-inducible protein).

Leaf rolls of sugarcane variety TCP98-4454 were transformed biolistically (direct gene transfer via microprojectile bombardment) with three genetic constructs:

pJAS BvLzm/ pSEF1α BvLzm SrMV 3'/ pMUbi (no hse) BvLzm SrMV 3'

The resulting plants were assayed for BvLz expression by western blot analysis to confirm expression and by Southern analysis to evaluate construct copy number. A minimum of 6 independent events were observed.

The BvLz level of the newly generated pJSU plants was first evaluated in sugarcane leaves by western blot analysis. Total soluble protein (40 μg) from leaves of 26 transgenic sugarcane plants was analyzed, using a polyclonal anti-BvLz antibody. One plant, pSPU 32E, was used as a positive control generated in Example 20. It is a highly expressing BvLz plant, where the BvLzm gene is under the control of three constitutive promoters, pSEF1α, pSPRP and pMUbi. Strong BvLz expression was observed in the leaves of all pJSU plants tested.

The BvLz accumulation level of the newly generated pJSU plants was also determined in stalks by ELISA. Table 16 shows the BvLz activity of 17 plants that were analyzed at a 7-8 month-growth stage.

TABLE 16

BvLz Expression in Stalks of pJSU BvLz Transgenic Lines.

| Transgenic plant | BvLz activity (mg/kg cane) |
|---|---|
| pJSU | |
| 18 | 5.10 |
| 19 | 4.6 |
| 44 | 2.9 |
| 54 | 6.0 |
| 70 | 3.50 |
| 73 | 3.0 |
| 74 | 3.20 |
| 75 | 2.55 |
| 76 | 2.47 |
| 84 | 3.44 |
| 85 | 3.51 |
| 87 | 3.07 |
| pSPU[a] | |
| 32C | 2.10-3.04 |

[a]pSPU 32C plant is used as a positive control generated in Example 20. It is a highly expressing BvLz plant, where BvLzm is under the control of three constitutive promoters, pSEF1α, pSPRP and pUbi.

Southern blot analysis was used to determine the number of copies and integration events of the BvLz transgene in the newly generated pJSU plants. Genomic DNA (15 μg) for twenty BvLz transgenic plants was digested with HindIII, and hybridized with full-length BvLz cDNA. Multiple bands of the BvLz transgene were detected in the genome of these plants, reflecting the insertion of multiple copies of BvLz.

The banding pattern revealed the presence of 4 independent transformation events. Event 1 is represented by plants 23, 27, 30 and 42, event 2 by plant 22, event 3 by plants 24, 25, 26, 28, 52, 53 and 54, and event 4 by plant 29.

A total of 35 pJSU Bvlz highly expressing plants were analyzed, and the highest BvLz activity level detected among the analyzed plants was 6.0 mg/kg of stalk (~1% TSP), as compared to an average of 2.4 mg/kg obtained from pSPU 32C (reference plant described in Example 20). Thus, there is a 2.5-fold increase in BvLz activity.

Example 22: Inducibility of Bovine Stomach Lysozyme Expression

The effect of defense-inducing/stress-regulated hormones on enhancing the BvLz level of sugarcane triple promoter pJSU BvLz expressing lines was evaluated. Specifically, plants were sprayed (or leaf rolls from the top of the stalk were incubated in vitro) with the stress-regulated hormones, jasmonic acid (JA) and salicylic acid (SA) that are known to induce the pUbi and pJAS promoters that drive the expression of BvLz in the existing triple promoter BvLz sugarcane lines. Total soluble protein was extracted from leaves of treated plants (or upper leaf rolls incubated in vitro), and its BvLz level was detected by western analysis and enzymatic essay.

Leaf rolls from pJSU BvLz 53 and 66 plants were incubated on MS (Murashige and Skoog) media supplemented with SA (5 mM) or JA (25 mM) for 0, 24 and 40 h. Total soluble protein was extracted from each treatment and its BvLz expression and activity levels were determined. The BvLz activity level of the triple promoter pJSU BvLz expressing lines was induced by the stress regulated hormones, SA and JA. BvLz activity was maximally induced by SA at 40 h (2.4-fold for pJSU 53 and 2.0-fold for pJSU 66), and by JA at 24 h (1.5-fold for pJSU 53 and 2.7-fold for pJSU 66) and 40 h (2.6-fold for pJSU 53 and 3.9-fold for pJSU 66).

The effect of nitrogen fertilization on enhancing the photosynthetic rate and hence the biomass of the existing triple promoter pJSU and pSPU highest BvLz expressing lines was also assessed. Nitrogen (N) is an essential component of fertilization programs for the production of high quality crops with increased protein content. The triple promoter BvLz expressing plants were started from seed sets till maturity, and fertilized with a low (1.43 g of Peters' solution 20-20-20 per plant; twice per week) and a high (2.38 g of Peters' solution 20-20-20 per plant; twice per week) nitrogen level for a period of 6 months. Stalks from the BvLz plants were collected at 2 and 6 months following fertilization, shredded, and their total BvLz yield was determined by the BioSeparation Laboratory.

Photosynthetic activity of the fertilized triple promoter BvLz expressing plants was also determined by measuring the chlorophyll fluorescence, which detects the photochemical efficiency of photosystem II and leaf greenness. The uptake of essential macronutrients by the triple promoter BvLz expressing plants was also determined following fertilization (Table 17).

Nitrogen fertilization is important in increasing the biomass and BvLz yield of the sugarcane triple promoter BvLz expressing lines. For instance, for the pSPU 32C line (CP-72-1210 variety), there is a 6.3-fold and a 2.3-fold increase in the stalk biomass and BvLz yield with high fertilization as compared to low fertilization at the 2 month- and 6 month-growth stage, respectively. Furthermore, there is a 7.5-fold and a 2.0-fold increase in the stalk biomass and BvLz yield of the pJSU 19 line (TCP98-4454 variety) with high fertilization as compared to low fertilization at the 2 month- and 6 month-growth stage, respectively.

Chlorophyll fluorescence of the triple promoter BvLz expressing plants is enhanced by fertilization. The fold-increase in chlorophyll fluorescence of these plants is in the range of 1.1-1.5 with high fertilization as compared to low fertilization.

TABLE 17

Nitrogen/Macronutrient Uptake of Triple-Promoter BvLz Plants.

| Sample ID | | Mineral Uptake Nitrogen (%) | Phosphorus (ppm) | Magnesium (ppm) |
|---|---|---|---|---|
| pSPU 32C | LF | 0.78 | 1539 | 1247 |
| | HF | 1.50 | 3136 | 2999 |
| pJSU 18 | LF | 1.06 | 2438 | 1181 |
| | HF | 1.84 | 4053 | 2059 |
| pSJU 19 | LF | 1.26 | 2178 | 1274 |
| | HF | 1.66 | 3559 | 2113 |

TABLE 17-continued

Nitrogen/Macronutrient Uptake of Triple-Promoter BvLz Plants.

| Sample ID | | Mineral Uptake Nitrogen (%) | Phosphorus (ppm) | Magnesium (ppm) |
|---|---|---|---|---|
| pJSU 54 | LF | 1.51 | 2189 | 2236 |
| | HF | 1.87 | 2861 | 2704 |

As shown in Table 17, a higher uptake of nitrogen, phosphorus and magnesium by the leaves of the triple promoter BvLz expressing lines was recorded following high nitrogen fertilization as compared to low nitrogen fertilization. It is evident that, for increasing cane and BvLz yields, the uptake of nitrogen as well as of that of phosphorus and magnesium is essential as all of them are closely interlinked with one another.

Example 23: Multi-Promoter Expression of Bovine Stomach Lysozyme

Quadruple promoter driving BvLz expression: Genetic constructs of BvLz driven separately by four different promoters (quadruple promoter system) were introduced biolistically into each of several sugarcane varieties (Table 18). Several seedlings have been tested to confirm BvLz activity.

TABLE 18

BvLz Constructs Used for Sugarcane Quadruple Promoter Plants.

| Genetic construct | Variety | Target tissue | Age of tissue (day) | No. of DNA shots | No. of seedlings |
|---|---|---|---|---|---|
| Quadruple promoter driving BvLz expression | | | | | |
| 1. pSPRP BvLzm 3'SrMV 35ST/ pSEF1α BvLzm 35ST NOST/ pSCBV BvLzm 35ST NOST/ pMUbi 5'SrMV BvLzsc 3'SrMV 35ST/ pUbi BAR | CP72-1210 | Leaf roll | 18 | 57 (4 μg DNA per shot) | 29 |
| 2. pSPRP BvLzm 35ST NOST/ pSEF1α BvLzm 35ST NOST/ pSCBV BvLzm 35ST NOST/ | CP72-1210 | Leaf roll | 42 | 34 (4 μg DNA per shot) | 1 |
| pJAS BvLzm NOST/ pUbi BAR | TCP98-4454 | Leaf roll | 10 | 34 (4 μg DNA per shot) | 1 |
| | TCP98-4454 | Leaf roll | 18 | 40 (3 μg DNA per shot) | |
| | TCP98-4454 | Leaf roll | 9 | 44 (2 μg DNA per shot) | |
| | CP84-1198 | Leaf roll | 17 | 47 (2 μg DNA per shot) | |
| 3. pSPRP BvLzm 35ST NOST/ pSCBV BvLzm 35ST NOST/ pJAS BvLzm NOST/ pMUbi BvLzm 3'SrMV/ pUbi BAR | TCP98-4454 | Leaf roll | 17 | 34 (4 μg DNA per shot) | |
| 4. pSPRP BvLzm 35ST NOST/ pSEF1α BvLzm 35ST NOST/ pJAS BvLzm NOST/ | TCP98-4454 | Leaf roll | 22 | 40 (2 μg DNA per shot) | |
| pMUbi BvLzm 3'SrMV 35ST/ pUbi BAR | TCP98-4454 | Leaf roll | 26 | 40 (1 μg DNA per shot) | |
| 5. pSPRP BvLzm 35ST NOST/ pSEF1α BvLzm 35ST NOST/ pSCBV BvLzm 35ST NOST/ | CP84-1198 | Leaf roll | 17 | 47 (2 μg DNA per shot) | |
| pMUbi BvLzm 35ST NOST/ pUbi BAR | | Callus | 63 | 39 (2 μg DNA per shot) | |
| | TCP98-4454 | Leaf roll | 13 | 60 (2 μg DNA per shot) | 3 |

TABLE 18-continued

BvLz Constructs Used for Sugarcane Quadruple Promoter Plants.

| Genetic construct | Variety | Target tissue | Age of tissue (day) | No. of DNA shots | No. of seedlings |
|---|---|---|---|---|---|
| 6. pPRP BvLzm 3'SrMV 35ST/ pSEF1α BvLzm 3'SrMV 35ST/ pMUbi BvLzm 3'SrMV 35ST/ | CP84-1198 | Leaf roll | 32 | 48 shots (2 μg DNA per shot) | |
| pJAS BvLzm 3'SrMV NOST/ pUbi BAR | TCP98-4454 | Leaf roll | 31 | 50 shots (2 μg DNA per shot) | 3 |
| | | Callus | 44 | 40 shots (2 μg DNA per shot) | |
| BvLz stacking into existing BvLz transgenic events/lines | | | | | |
| 1. pJSU lines (triple promoter BvLz lines) with pPRP BvLzm and pSCBV BvLzm, and pUBi NPTII (for selection of transformants) | TCP98-4454 transgenic for BvLz | Leaf roll | | | |
| pJSU 236/pPRP BvLzm/pSCBV BvLzm | | | 15 | 21 | |
| pJSU 242/pPRP BvLzm/pSCBV BvLzm | | | 15 | 32 | |
| pJSU 247/pPRP BvLzm/pSCBV BvLzm | | | 15 | 22 | |
| pJSU 248/pPRP BvLzm/pSCBV BvLzm | | | 15 | 30 | |
| pJSU 250/pPRP BvLzm/pSCBV BvLzm | | | 15 | 16 | |
| pJSU 258/pPRP BvLzm/pSCBV BvLzm | | | 15 | 8 | |
| pJSU 259/pPRP BvLzm/pSCBV BvLzm | | | 15 | 12 | |
| pJSU 76/pPRP BvLzm/pSCBV BvLzm | | | 36 | 27 | |
| pJSU 177/pPRP BvLzm/pSCBV BvLzm | | | 36 | 7 | |
| pJSU 191/pPRP BvLzm/pSCBV BvLzm | | | 36 | 25 | |
| pJSU 197/pPRP BvLzm/pSCBV BvLzm | | | 36 | 16 | |

In the present work, explants (leaf roll or callus) were transformed biolistically with four genetic constructs, each containing the bovine lysozyme (BvLz) gene driven by a different promoter.
Promoters that drive gene expression: pSEF1α is a constitutive promoter isolated from a sugarcane elongation factor 1α gene, pPRP is a constitutive promoter isolated from a gene coding for a sugarcane proline rich protein, pSCBV is a stem-expressed promoter isolated from Sugarcane bacilliform virus, pJAS is a stem-expressed promoter isolated from a sugarcane jasmonate-inducible/dirigent gene, and pMUbi is a the commonly used constitutive promoter for monocots and is derived from the maize ubiquitin 1 gene.
Genes expressed: BvLzm refers to synthetic BvLz with codons optimized for maize, and BvLzsc to synthetic BvLz with codons optimized for sugarcane.
Terminators of transcription: 35ST refers to the 35S terminator derived from the 35S RNA of Cauliflower mosaic virus. NOST refers to the NOS terminator derived from the nopaline synthase gene (from the *Agrobacterium tumefaciens* Ti plasmid). It is a terminator of transcription. 35ST NOST refers to a double terminator that consists of 35ST and NOST. Recent research has proven that the fusion of a 35ST NOST double terminator to a transgene at its 3' end may have a significant effect on decreasing gene silencing and enhancing transgene expression.
Enhancers of translation: 5' and 3' SrMV refer to the 5' and 3' untranslated regions (UTR) of Sorghum mosaic virus protein. They are used for enhancement of translation.
Selectable markers for plant transformation: BAR refers to the bar gene, which is one of the most commonly used selectable markers for plant transformation. It codes for phosphinothricin acetyl transferase enzyme that detoxifies Bialaphos or phosphinothricin, the active ingredient of herbicides such as Basta and Finale. Selection for BAR gene activity can be achieved easily and at low cost by spraying plants with the herbicide. NPTII refers to the nptII gene, which is one of the most widely used selectable markers for plant transformation. It codes for neomycin phosphotransferase (or aminoglycodise 3'-phosphotransferase) enzyme, which inactivates by phopsphorylation a range of aminoglycoside antibiotics such as geneticin.
pJSU refers to sugarcane plants that are transgenic for the BvLz gene whose expression is driven by the two constitutive promoters, pSEF1α and pMUbi, and the stem-regulated promoter, pJAS. Plants were transformed with three genetic constructs: pJAS BvLzm, pSEF1α BvLzm SrMV 3', and pMUbi BvLzm SrMV 3'.

Example 24: Multi-Promoter Expression of Bovine Stomach Lysozyme

Several genetic constructs of BvLz were introduced biolistically into sweet and grain sorghum (Table 19). Several seedlings have been tested to confirm BvLZ activity.

TABLE 19

BvLz Constructs Used for Sorghum Quadruple Promoter Plants.

| Genetic construct | Variety | Target tissue | Age of tissue (day) | No. of DNA shots | No. of seedlings |
|---|---|---|---|---|---|
| Single promoter driving BvLz expression | | | | | |
| 1. pMUbi BvLzm 3'SrMV 35ST/ pUbi BAR | Rio-Sweet (Sweet sorghum) | Callus | 60 | 38 (2 μg DNA per shot) | |
| (Selection of transformants on Bialaphos) | TX-430 (Grain sorghum) | Callus | 24 | 28 (2 μg DNA per shot) | |

TABLE 19-continued

BvLz Constructs Used for Sorghum Quadruple Promoter Plants.

| Genetic construct | Variety | Target tissue | Age of tissue (day) | No. of DNA shots | No. of seedlings |
|---|---|---|---|---|---|
| 2. pMUbi BvLzm 3'SrMV 35ST/ pUbi PMI | Rio-Sweet (Sweet sorghum) | Callus | 96 | 28 (2 μg DNA per shot) | |
| (Selection of transformants on mannose) | TX-430 (Grain sorghum) | Callus | 76 | 28 (2 μg DNA per shot) | |
| Triple promoter driving BvLz expression | | | | | |
| 1. pSPRP BvLzm 3'SrMV 35ST/ pSEF1α BvLzm 3'SrMV 35ST/ pMUbi BvLzm 3'SrMV 35ST/ pUbi PMI | Ramada (Sweet sorghum) | Callus | 11 | 15 (4 μg DNA per shot) | |
| | B-TX-623 (Grain sorghum) | Callus | 134 | 30 (4 μg DNA per shot) | |
| Quadruple promoter driving BvLz expression | | | | | |
| 1. pSPRP BvLzm 3'SrMV 35ST/ pSEF1α BvLzm 3'SrMV 35ST/ pMUbi BvLzm 3'SrMV 35ST/ pJAS BvLzm 3'SrMV NOST/ pUbi PMI | TX-430 (Grain sorghum) | Callus | 88 | 20 (2 μg DNA per shot) | |

PMI refers to the *E. coli* phosphomannose isomerase gene (isolated by Getu Beyene for the present work on sorghum transformation). PMI is a versatile selectable marker for plant transformation. It is very efficient in sorghum transformations.

Example 25: Harvesting Protein from Transgenic Plants

The potential for an example expression system, triple promoter plants, to serve as a biofactory was evaluated by purifying the expressed transgenic protein. The protocol was adapted from U.S. Application no. 2007/0130655. The transgenic sugarcane is first shredded and crushed once without maceration water and then twice more with 20% by weight water in a pilot scale Squire mill Essentially, the cane stalk is shredded and then pressed through 3 rollers on the Squire mill with 3,000 pounds per square inch. This produces a mixture of about 70% water, 15% sucrose, and 10% fibre. The remaining 5% of the mixture consists of proteins and other sugars, salts and organic molecules. The juice containing the high value protein (BvLz) is then pumped to a purification skid and filtered through a set of vibrating (self cleaning) screens and enters a tank. This step removes the fibre. The first screen is 150 microns, and the second is 100 microns. The pH of the juice is adjusted to 5.2 and it is supplemented with 1 mM EDTA and 0.1% sodium sulphite to prevent oxidation and the formation of phenolics. From the tank the juice is permeated through a 0.2 micron cross flow filtration membrane. This step removes all the insoluble solids and high molecular weight soluble solids such as bacteria, starches and dextrans. The permeate, which contains sugar and the high value protein, enters a second tank and the retentate in the first tank is discarded. From the second tank, the juice is permeated through a 0.05 micron membrane. This step removes soluble molecules with a molecular weigh greater than 150,000 kd. High value proteins with a molecular weight greater than 150,000 kd would be retained in the second tank, and could be further purified with the HPLC steps described below. The second permeate, which contains sugar and the high value proteins smaller than 150,000 W (BvLz in this example) enters a third tank and the retentate in the second tank is discarded. At this point we have a relatively clean sample from which all high molecular weight material has been removed, i.e., bacteria, starch, dextrans, and proteins with high molecular weights.

From the third tank, the sample is concentrated (−30 fold) on a 3 kDa membrane and then further purified by 2 cycles of high pressure liquid chromatography (HPLC). The first cycle uses SP Sepharose® ion exchange resin, while the second cycle uses a hydrophobic interaction resin. Preliminary runs produced protein.

We have identified low molecular weight cut off membranes that can be used to concentrate the sample in the third tank. The water, sugars and other small molecules will flow through the membranes, but the high value protein will be concentrated in the third tank. This will greatly improve the performance of the HPLC steps. Further modifications using different initial extraction conditions, different ion exchange resins/membranes, affinity resins and HPLC columns can be used to enhance performance. Results for the first and second runs are shown in Tables 21 and 22, respectively.

TABLE 21

Isolated BvLz from Transgenic Plants

| Sample | Volume (L) | mg | Total BvLz (mg) | Overall Yield (%) | Purification Yield (%) |
|---|---|---|---|---|---|
| Starting Juice | 212.0 | 1.6 | 339 | 100 | |
| 0.2 μm Permeate | 181.7 | 0.5 | 96 | 28 | |
| 3 kDa Conc | 4.73 | 9.1 | 43 | 13 | |
| 0.2 μm Filtrate | 4.66 | 8.6 | 40 | 12 | |
| SP Load* | 4.01 | 8.6 | 35 | 10 | 100 |
| HIC Pool | 0.050 | 239 | 12 | 4 | 35 |
| HIC Pool after dialysis** | 0.082 | 172 | 14 | 4 | 41 |

*Represents portion of filtrate that was loaded on SP column

**Obtained after ammonium sulfate removal by activity as well as OD280 before freeze-drying.

TABLE 22

| Isolated BvLz from Transgenic Plants | | | | | | |
|---|---|---|---|---|---|---|
| | | | Activity | | ELISA | |
| Sample | Description | Volume (L) | mg | Recovery (%) | mg | Recovery (%) |
| T1 S | Start (9 bins crushed) | 124.9 | 92.4 | 100.0 | 66.8 | 100.0 |
| T1 F | 0.2 um Retentate | 18.9 | 17.9 | 19.4 | 14.8 | 22.2 |
| T3 Start | 0.2 um Permeate | 113.6 | 67.1 | 72.6 | 42.8 | 64.1 |
| T4 Sample | 3 kDa Permeate | 109.8 | 1.8 | 1.9 | 2.7 | 4.1 |
| Concentrate | 3 kDa Concentrate | 6.6 | 11 | 11.9 | 24.6 | 36.9 |

Thus, it was possible to harvest up to 14 mg of BvLz to 99% purity from about 500 pounds of these triple promoter plants.

Example 26: Multi-Promoter Expression of Bovine Stomach Lysozyme

As shown in Tables 23 and 24, additional constructs with one or more promoters were prepared and used to transform sugarcane varieties.

TABLE 23

| Transgenic BvLz Plants with One or More Promoters. | | | |
|---|---|---|---|
| Genetic construct | Variety | Target tissue | # of plants |
| Single promoter driving BvLz expression | | | |
| 1. pMUbi (no hse) BvLzm/ | CP72-1210 | Callus | 74 |
| pUbi BAR | CP72-1210 | Callus | |
| | CP72-1210 | Callus | 20 |
| 2. pMUbi (no hse) BvLzm SrMV 3'/ | CP72-1210 | Leaf roll | 8 |
| pUbi BAR | TCP89-3505 | Callus | 109 |
| 3. pMUbi (no hse) 5' SrMV BvLzsc SrMV 3'/ pUbi BAR | CP72-1210 | Leaf roll | 9 |
| 4. pMUbi (no hse) BvLzm 35ST NOST/ | CP72-1210 | Leaf roll | 10 |
| pUbi BAR | TCP98-4454 | Leaf roll | 28 |
| 5. pSPRP BvLzm SrMV 3'/ pUbi BAR | TCP89-3505 | Callus | 94 (Low expressers) |
| 6. pSEF1α BvLzm SrMV 3'/ pUbi BAR | TCP89-3505 | Callus | 1 |
| 7. pSCBV BvLzm 35ST NOST/ pUbi BAR | CP72-1210 | Leaf roll | Green shoots |
| 8. pSEF1α BvLzm 35ST NOST/ pUbiBAR | CP72-1210 | Leaf roll | 0 |
| Single promoter driving BvLz expression in presence of a suppressor of gene silencing or programmed cell death | | | |
| 1. pMUbi (no hse) BvLzm/ | CP72-1210 | Callus | 18 |
| pMUbi (no hse) P1HcPro/ pMUbi BAR | CP72-1210 | Callus | 76 |
| 2. pMUbi (no hse) BvLzm SrMV 3'/ pUbi (no hse) P1HcPro/ pUbi BAR | CP72-1210 | Callus | 12 |
| 3. pMUbi (no hse) 5' SrMV BvLzsc SrMV 3'/ | CP72-1210 | Callus | 31 |
| pMUbi (no hse) P1HcPro/ pUbi BAR | CP72-1210 | Leaf roll | 9 |
| 4. pJAS BvLzm/ pMUbi (no hse) P1HcPro/ pUbi BAR | CP72-1210 | Callus | 25 |
| Single promoter driving BvLz expression in presence of a suppressor of gene silencing or programmed cell death | | | |
| 5. pSPRP BvLzm SrMV 3'/ pUbi (no hse) P1HcPro/ pUbi BAR | CP72-1210 | Callus | 61 |
| 6. pSPRP 5' SrMV BvLzsc SrMV 3'/ pUbi (nohse) P1HcPro pUbi BAR | CP72-1210 | Callus | 209 |
| 7. pSEF1α BvLzm SrMV 3'/ pUbi (nohse) P1HcPro/ pUbi BAR | TCP89-3505 | Callus | 0 |
| 8. pMUbi (no hse) BvLzm/ | TCP98-4454 | Callus | 3 |
| pMUbi (no hse) CTVP20/ pUbi BAR | CP72-1210 | Callus | |
| 9. pMUbi (no hse) BvLzm SrMV 3'/ pUbi (no hse) CTVP20/ pUbi BAR | CP72-1210 | Leaf roll | 11 |

TABLE 23-continued

Transgenic BvLz Plants with One or More Promoters.

| Genetic construct | Variety | Target tissue | # of plants |
|---|---|---|---|
| 10. pMUbi (no hse) 5' SrMV BvLzsc SrMV 3'/ pMUbi (no hse) CTVP20 pUbi BAR | CP72-1210 | Callus | 21 |
| 11. pMUbi (no hse) BvLzm/ pMUbi (no hse) CTVP23/ pUbi BAR | TCP87-3388 | Callus | 0 |
| 12. pMUbi (no hse) BvLzm SrMV 3'/ | TCP01-4543 | Callus | 0 |
| pMUbi (no hse) CTVP23/ | CP72-1210 | Callus | 0 |
| pUbi BAR | | | |
| 13. pMUbi (no hse) 5' SrMV BvLzsc SrMV 3'/ | TCP01-4543 | Callus | 0 |
| pMUbi (no hse) CTVP23/ | CP72-1210 | Callus | 0 |
| pUbi BAR | | | |
| 14. pJAS BvLzsc/ pMUbi (no hse) CTVP23/ pUbi BAR | TCP01-4543 | Callus | 1 |
| 15. pJAS BVLZm SrMV 3'/ pMUbi (no hse) CTVP23/ pUbi BAR | CP72-1210 | Callus | 5 |
| 16. pSPRP BvLzm SrMV 3'/ pMUbi (no hse) CTVP23/ pUbi BAR | CP72-1210 | Callus | 0 |
| Single promoter driving BvLz expression in presence of a suppressor of gene silencing or programmed cell death | | | |
| 17. pSPRP 5' SrMV BvLzsc SrMV 3'/ pUbi (no hse) CTVP23/ pUbi BAR | CP72-1210 | Callus | 117 |
| 18. pJAS BvLzm SrMV 3'/ pMUbi (no hse) P1HcPro/ pMUbi (no hse) CTVP23/ pUbi BAR | CP72-1210 | Callus | 0 |
| 19. pSPRP BvLzm SrMV 3'/ pMUbi (no hse) P1HcPro/ pMUbi (no hse) CTVP23/ pUbi BAR | CP72-1210 | Callus | 62 |
| 20. pSEF1α BvLzm SrMV 3'/ pMUbi (no hse) P1HcPro/ pMUbi (no hse) CTVP23/ pUbi BAR | CP72-1210 | Callus | 1 |
| 21. pMUbi (no hse) BvLzm/ | CP72-1210 | Callus | 39 |
| pMCG ds SGS2/ | TCP87-3388 | Callus | 45 |
| pUbi BAR | | | |
| 22. pUbi (no hse) BvLzm SrMV 3'/ | CP72-1210 | Callus | 48 |
| pMCG ds SGS2/ | CP72-1210 | Leaf roll | 12 |
| pUbi BAR | | Callus | |
| 23. pUbi (no hse) 5' SrMV BvLzsc SrMV 3'/ pMCG ds SGS2/ pUbi BAR | CP72-1210 | Leaf roll | 66 |
| 24. pMUbi (no hse) BvLzm/ pMCG ds SGS3/ pUbi BAR | CP72-1210 | Callus | 223 |
| 25. pUbi (no hse) BvLzm SrMV 3'/ pMCG ds SGS3/ pUbi BAR | CP72-1210 | Callus | 148 |
| 26. pMUbi (no hse) 5' SrMV BvLzsc SrMV 3'/ pMCG ds SGS3/ pUbi BAR | CP72-1210 | Callus | 54 |
| 27. pMUbi (no hse) BvLzm SrMV 3'/ pMCG ds SGS2/ pMCG ds SGS3/ pUbi BAR | CP72-1210 | Leaf roll | 15 |
| 28. pMUbi (no hse) BvLzm SrMV 3'/ pMCG ds 14-3-3/ pUbi BAR | CP72-1210 | Leaf roll | 74 |
| 29. pMUbi (no hse) 5' SrMV BvLzsc SrMV 3'/ | CP72-1210 | Callus | 2 |
| pMCG ds 14-3-3/ | TCP01-4543 | Callus | 0 |
| pUbi BAR | CP72-1210 | Leaf roll | 12 |
| 30. pMUbi (no hse) BvLzm/ pUbi (no hse) anti-RNaseH/ pUbi BAR | CP72-1210 | Callus | 4 |
| 31. pJAS BvLzm/ pMUbi (no hse) anti-RNaseH/ pUbi BAR | CP72-1210 | Callus | 0 |

TABLE 23-continued

Transgenic BvLz Plants with One or More Promoters.

| Genetic construct | Variety | Target tissue | # of plants |
|---|---|---|---|
| Single promoter driving BvLz expression in presence of a suppressor of gene silencing or programmed cell death | | | |
| 32. pMUbi (no hse) BvLzm SrMV 3'/ pPTN254 Bcl-xl/ pUbi BAR | CP72-1210 | Leaf roll | 2 |
| 33. pJAS BvLzm SrMV 3'/ pPTN254 Bcl-xl/ pUbi BAR | CP72-1210 | Leaf roll | 82 |
| 34. pSPRP BvLzm SrMV 3'/ pPTN254 Bcl-xl/ pUbi BAR | CP72-1210 | Leaf roll | 141 |
| 35. pSEF1α BvLzm SrMV 3'/ pPTN254 Bcl-xl/ pUbi BAR | CP72-1210 | Leaf roll | 1 |
| Double promoter driving BvLz expression | | | |
| 1. pJAS BvLzm SrMv 3'/ pMUbi (no hse) 5' SrMv BvLzsc SrMV 3'/ pUbi BAR | TCP01-4543 | Callus | 0 |
| 2. pSPRP (no 5'UTR) 5' SrMV BvLzsc SrMV 3'/ pMUbi (no hse) BvLzm SrMV 3'/ pUbi BAR | CP72-1210 | Callus | 239 |
| 3. pPRP (no 5'UTR) 5' SrMV BvLzsc SrMV 3'/ pJAS BvLzm SrMV 3'/ pUbi BAR | CP72-1210 | Callus | 372 |
| Triple promoter driving BvLz expression | | | |
| 1. pSPRP BvLzm SrMV 3'/ pSEF1α BvLzm SrMV 3'/ pMUM (no hse) 5' SrMV BvLzsc SrMV 3'/ pUbi BAR | CP72-1210 | Callus | 16 are transgenic |
| 2. pSPRP BvLzm SrMV 3'/ pSEF1α BvLzm SrMV 3'/ pJAS BvLzm SrMV 3'/ pUbi BAR | CP72-1210 | Callus | 67 (Very low expressers) |
| 3. pSPRP (No 5'UTR) 5' SrMV BvLzsc SrMV 3'/ pSEF1α BvLzm SrMV 3'/ pMUbi (no hse) BvLzm SrMV 3'/ pUbi BAR | CP72-1210<br>CP72-1210 | Callus<br>Leaf roll | 43: one is transgenic 2 |
| 4. pPRP BvLzm SrMV 3'/ pSEF1α BvLzm SrMV 3'/ pJAS BvLzm SrMV 3'/ pUbi BAR | CP72-1210<br>CP72-1210 | Callus<br>Leaf roll | 47: 6 are transgenic 249 |
| 5. pSPRP (No 5'UTR) BvLzsc 5' SrMV 3'/ pSEF1α BvLzm SrMV 3'/ pJAS BvLzm SrMV 3'/ pUbi BAR | CP72-1210 | Callus | 3 |
| 6. pSPRP (No 5'UTR) BvLzsc 5' SrMV 3'/ pSEF1α BvLzm SrMV 3'/ pJAS BvLzm/ pUbi BAR | TCP87-3388 | Leaf roll | 1 |
| Triple promoter driving BvLz expression | | | |
| 1. pSPRP BvLzm SrMV 3'/ pMUbi (no hse) BvLzm SrMV 3'/ pJAS BvLzm/ pUbi BAR | CP72-1210 | Callus and Leaf roll | 31<br>277 |
| 10. pJAS BvLzm/ pSEF BvLzm SrMV 3'/ pMUbi (no hse) BvLzm SrMV 3'/pUbi BAR | TCP98-4454 | Leaf roll | 365 plants: 286 are transgenic; 64 remain to be tested |
| 11. l.pJAS BvLzm/ pSEF BvLzm SrMV 3'/ pMUbi (no hse) 5' SrMV BvLzm SrMV 3'/ pUbi BAR | CP72-1210 | Leaf roll | 96 |
| 12. pSCBV BvLzm 35ST NOST/ pUbi (no hse) BvLzm 35ST NOST/ pJAS BvLzm/ pUbiBAR | CP72-1210<br>TCP98-4454 | Lead roll<br>Leaf roll | Green shoots<br>Green shoots |
| 13. pSCBV BvLzm 35ST NOST/ pSEF BvLzm SrMV 3'/ pJAS BvLzm/ pUbiBAR | CP72-1210 | Leaf roll | Green shoots |

TABLE 23-continued

Transgenic BvLz Plants with One or More Promoters.

| Genetic construct | Variety | Target tissue | # of plants |
|---|---|---|---|
| 14. pSCBV BvLzm 35ST NOST/ pSEF BvLzm SrMV 3'/ pPRP BvLzm SrMV 3'/ pUbiBAR | CP72-1210 | Leaf roll | Green shoots |
| Quadruple promoter driving BvLz expression | | | |
| 1. pSPRP (no 5' UTR) 5' SrMV BvLzsc SrMV 3'/ pSEF1α BvLzm SrMV 3'/ pJAS BvLzm SrMV 3'/ pSCBV BvLzm 35ST NOST/ pUbi BAR | CP72-1210<br>TCP98-4454 | Leaf roll<br>Leaf roll | 3<br>2 |
| Double transformant for BvLz | | | |
| 1. pMUbi (no hse) BvLzm/pUbi BAR (EM116 plant) and pJAS BvLzm/pUbi NPTII | EM116 in CP72-1210 | Leaf roll | 153: 52 tested positive |
| *Agrobacterium*-mediated delivery of BvLz | | | |
| 1. pBIN161 BvLzm | CP72-1210<br>TCP87-3388<br>TCP98-4454 | Callus<br>Leaf roll<br>Leaf roll | 6<br>56<br>430<br>52 tested positive |

TABLE 24

Transgenic BvLz Plants with One or More Promoters.

| Genetic construct | Variety | Total # Plants Generated | Total # Independent Lines |
|---|---|---|---|
| Single promoter BvLz transgenic lines | | | |
| $Pro_{MUbi(no\ hse)}$: BvLz(m) 35ST<br>$Pro_{SPRP}$: BvLz(m) 3'SrMV 35ST<br>$Pro_{SEF1\alpha}$: 5'SrMv BvLz(sc) 3'SrMV 35ST | CP72-1210 | 67 | 30 |
| $Pro_{JAS}$: BvLz(m) 35ST | CP72-1210 | 25 | 6 |
| BvLz transgenic lines with 3 promoter stacks | | | |
| 1. pSPU: BvLz line that contains:<br>$Pro_{SEF1\alpha}$: BvLz(m) 3'SrMV 35ST<br>$Pro_{SPRP}$: BvLz(m) 3'SrMV 35ST<br>$Pro_{MUbi(no\ hse)(no\ 5'UTR)}$: 5' SrMv BvLz(sc) 3'SrMV 35ST | CP72-1210 | 16 | 5 |
| 2. $pSP_nU$: BvLz line that contains:<br>$Pro_{SEF1\alpha}$: BvLz(m) 3'SrMV 35ST<br>$Pro_{SPRP(no\ 5'UTR)}$: 5'SrMV BvLz(sc) 3'SrMV 35ST<br>$Pro_{MUbi(no\ hse)}$: BvLz(m) 3'SrMV 35ST | CP72-1210 | 1 | 1 |
| 3. pSPJ: BvLz line that contains:<br>$Pro_{SEF1\alpha}$: BvLz(m) 3'SrMV 35ST<br>$Pro_{SPRP}$: BvLz(m) 3'SrMV 35ST<br>$Pro_{JAS}$: BvLz(m) 3'SrMV 35ST | CP72-1210 | 6 | 2 |
| 4. pJSU: BvLz line that contains:<br>$Pro_{JAS}$: BvLz(m) 35ST<br>$Pro_{SEF1\alpha}$: BvLz(m) 3'SrMV 35ST<br>$Pro_{MUbi(no\ hse)}$: BvLz(m) 3'SrMV 35ST | CP98-4454 | 166 | 6 |
| BvLz transgenic lines with 4 promoter stacks | | | |
| 1. pJSPB: BvLz line that contains:<br>$Pro_{JAS}$: BvLz(m) 35ST<br>$Pro_{SEF1\alpha}$: BvLz(m) 35ST NOST<br>$Pro_{SPRP}$: BvLz(m) 35ST NOST<br>$Pro_{SCBV21}$: BvLz(m) 35ST NOST | CP72-1210<br>CP98-4454 | 1<br>3 | 1<br>1 |
| 2. pSPBU: BvLz line that contains:<br>$Pro_{SEF1\alpha}$: BvLz(m) 35ST NOST<br>$Pro_{SPRP}$: BvLz(m) 35ST NOST<br>$Pro_{SCBV21}$: BvLz(m) 35ST NOST<br>$Pro_{MUbi(no\ hse)}$: BvLz(m) 35ST NOST | CP98-4454 | 14 | 2 |

TABLE 24-continued

| Transgenic BvLz Plants with One or More Promoters. | | | |
|---|---|---|---|
| Genetic construct | Variety | Total # Plants Generated | Total # Independent Lines |
| 3. pPSUJ: BvLz line that contains: Pro$_{SPRP}$: BvLz(m) 3'SrMV 35ST Pro$_{SEF1\alpha}$: BvLz(m) 3'SrMV 35ST Pro$_{MUbi(no\ hse)}$: BvLz(m) 3'SrMV 35ST Pro$_{JAS}$: BvLz(m) 3'SrMV 35ST | CP98-4454 | 3 | 3 |
| BvLz transgenic lines with 5 promoter stacks | | | |
| 1. pJSU: BvLz existing line with Pro$_{SPRP}$: BvLz(m) 35ST NOST and Pro$_{SCBV21}$: BvLz(m) 35ST NOST | CP98-4454 | 57 | 9 |

TABLE 25

| DNA Constructs for Examples | |
|---|---|
| Pro$_{MUbi(no\ hse)}$: BvLz(m) 35ST | SEQ ID NO: 39 |
| Pro$_{MUbi(no\ hse)}$: BvLz(m) 3'SrMV 35ST | SEQ ID NO: 40 |
| Pro$_{MUbi(no\ hse)}$: 5'SrMv BvLz(sc) 3'SrMV 35ST | SEQ ID NO: 41 |
| Pro$_{MUbi(no\ hse)}$): BvLz(m) 35ST NOST | SEQ ID NO: 42 |
| Pro$_{SPRP}$: BvLz(m) 3'SrMV 35ST | SEQ ID NO: 43 |
| Pro$_{SPRP(no\ 5'UTR)}$: 5'SrMv BvLz(sc) 3'SrMV 35ST | SEQ ID NO: 44 |
| Pro$_{SPRP}$: BvLz(m) 35ST NOST | SEQ ID NO: 45 |
| Pro$_{SEF1\alpha}$: BvLz(m) 3'SrMV 35ST | SEQ ID NO: 46 |
| Pro$_{SEF1\alpha}$: BvLz(m) 35ST NOST | SEQ ID NO: 47 |
| Pro$_{JAS}$: BvLz(m) 35ST | SEQ ID NO: 48 |
| Pro$_{JAS}$: BvLz(m) 3'SrMV 35ST | SEQ ID NO: 49 |
| Pro$_{SCBV21}$: BvLz(m) 35ST NOST | SEQ ID NO: 50 |

BvLz(m): Synthetic bovine lysozyme gene with codons optimized for corn.
BvLz(sc): Synthetic bovine lysozyme gene with codons optimized for sugarcane.
Pro$_{MUbi(no\ hse)}$: Maize ubiquitin 1 promoter with no heat shock element. The ubiquitin 1 promoter is a constitutive promoter that is commonly used for monocots.
Pro$_{MUbi(no\ hse)(no\ 5'UTR)}$: Maize ubiquitin 1 promoter with no heat shock element and no 5' untranslated region (UTR).
Pro$_{SPRP}$: Promoter isolated from the gene coding for a sugarcane proline-rich protein. It is a constitutive promoter.
Pro$_{SPRP(no\ 5'UTR)}$: The sugarcane proline rich protein promoter with no 5'UTR.
Pro$_{SEF1\alpha}$: Promoter isolated from the gene coding for a sugarcane elongation factor 1a protein laboratory. It is a constitutive promoter.
Pro$_{JAS}$: Promoter isolated from the gene coding for a sugarcane jasmonate-inducible protein in. It is a stem-expressed stress-inducible promoter.
Pro$_{SCBV21}$: Promoter isolated form Sugarcane bacilliform virus.
5' and 3' SrMV refer to the 5' and 3' untranslated regions (UTRs) of Sorghum mosaic virus protein. They are used for enhancement of translation.
35ST: 35S terminator derived from the 35S RNA of Cauliflower mosaic virus. It is a terminator of transcription.
NOST: NOS terminator derived from the nopaline synthase gene of the *Agrobacterium tumefaciens* Ti plasmid. It is a terminator of transcription.
35ST NOST: A double terminator that consists of 35ST and NOST. Recent published research has proven that the fusion of a 35ST NOST double terminator to a transgene at its 3' end will have a significant effect on decreasing gene silencing and enhancing transgene expression.

What is claimed is:

1. A plant cell comprising a first expression vector, a second expression vector, and a third expression vector;
   wherein the first expression vector comprises:
   a first promoter,
   a first copy of a coding sequence operably linked to the first promoter, and
   a first 3' termination sequence operably linked to the first copy of the coding sequence, the first promoter having sufficient promoter activity to express the first copy of the coding sequence in the plant cell;
   wherein the second expression vector comprises:
   a second promoter,
   a second copy of the coding sequence operably linked to the second promoter, and
   a second 3' termination sequence operably linked to the second copy of the coding sequence, the second promoter having sufficient promoter activity to express the second copy of the coding sequence in the plant cell;
   wherein the third expression vector comprises:
   a third promoter,
   a third copy of the coding sequence operably linked to the third promoter, and
   a third 3' termination sequence operably linked to the third copy of the coding sequence, the third promoter having sufficient promoter activity to express the third copy of the coding sequence in the plant cell;
   wherein the first promoter and the second promoter are different;
   wherein the plant cell exhibits increased expression of the coding sequence as compared to a second plant cell comprising the first expression vector and not the second expression vector; and
   wherein the plant cell is selected from the group consisting of a pSPU cell, a pSPnU cell, a pSPJ cell, and a pJSU cell.

2. The plant cell according to claim 1 further comprising a fourth expression vector, wherein the fourth expression vector comprises
   a fourth promoter,
   a fourth copy of the coding sequence operably linked to the fourth promoter; and
   a fourth 3' termination sequence operably linked to the fourth copy of the coding sequence, the fourth promoter having sufficient promoter activity to express the fourth copy of the coding sequence in the plant cell.

3. The plant cell according to claim 2 further comprising a fifth expression vector, wherein the fifth expression vector comprises
   a fifth promoter,
   a fifth copy of the coding sequence operably linked to the fifth promoter; and
   a fifth 3' termination sequence operably linked to the fifth copy of the coding sequence, the fifth promoter having sufficient promoter activity to express the fifth copy of the coding sequence in the plant cell.

4. The plant cell according to claim 1, wherein the plant cell is a monocot plant cell.

5. The plant cell according to claim 1, wherein the plant cell is selected from the group consisting of a sugarcane cell, a *miscanthus* cell, a *miscanthus*×sugarcane hybrid cell, a switch grass cell, an oats cell, a wheat cell, a barley cell, a maize cell, a rice cell, a banana cell, a *yucca* cell, an onion cell, an asparagus cell, a sorghum cell, and cells of hybrids thereof.

6. The plant cell according to claim 1, wherein the plant cell is a dicot plant cell.

7. The plant cell according to claim 1, wherein the plant cell is selected from the group consisting of a coffee cell, a tomato cell, a pepper cell, a tobacco cell, a lima bean cell, an *Arabidopsis* cell, a rubber cell, an orange cell, a grapefruit cell, a potato cell, a squash cell, a pea cell, and a sugar beet cell.

8. The plant cell according to claim 2, wherein the fourth promoter is a constitutive promoter.

9. The plant cell according to claim 2, wherein the fourth promoter is a regulated promoter.

10. The plant cell according to claim 2, wherein the fourth promoter is independently selected from the group consisting of a Sugarcane bacilliform virus promoter (pSCBV), a 35S promoter, a Pr4 promoter, a ubiquitin 1 promoter (pUbi1), a sugarcane proline rich protein promoter (pSPRP), a sugarcane elongation factor 1α promoter (pSEF1α), and a JAS promoter (pJAS).

11. The plant cell according to claim 2, wherein the fourth promoter has a nucleic acid sequence independently selected from the group consisting of the sequence of nucleotides 1-1786 of SEQ ID NO: 1, the sequence of SEQ ID NO: 1, the sequence of SEQ ID NO: 17, the sequence of SEQ ID NO: 18, the sequence of nucleotides 674-1478 of SEQ ID NO: 21, the sequence of nucleotides 674-1383 of SEQ ID NO: 22, the sequence of SEQ ID NO: 26, the sequence of SEQ ID NO: 27, the sequence of SEQ ID NO: 32, the sequence of SEQ ID NO: 33, the sequence of nucleotides 25-859 of SEQ ID NO: 4, the sequence of nucleotides 73-829 of SEQ ID NO: 6, the sequence of nucleotides 1-1966 of SEQ ID NO: 7, the sequence of nucleotides 1-995 of SEQ ID NO: 9, the sequence of nucleotides 1-1977 of SEQ ID NO: 39, the sequence of nucleotides 1-2900 of SEQ ID NO: 43, the sequence of nucleotides 1-3016 of SEQ ID NO: 44, the sequence of nucleotides 1-1959 of SEQ ID NO: 46, and the sequence of nucleotides 54-2681 of SEQ ID NO: 48.

12. The plant cell according to claim 3, wherein the fifth promoter is a constitutive promoter.

13. The plant cell according to claim 3, wherein the fifth promoter is a regulated promoter.

14. The plant cell according to claim 3, wherein the fifth promoter is independently selected from the group consisting of a Sugarcane bacilliform virus promoter (pSCBV), a 35S promoter, a Pr4 promoter, a ubiquitin 1 promoter (pUbi1), a sugarcane proline rich protein promoter (pSPRP), a sugarcane elongation factor 1α promoter (pSEF1α), and a JAS promoter (pJAS).

15. The plant cell according to claim 3, wherein the fifth promoter has a nucleic acid sequence independently selected from the group consisting of the sequence of nucleotides 1-1786 of SEQ ID NO: 1, the sequence of SEQ ID NO: 1, the sequence of SEQ ID NO: 17, the sequence of SEQ ID NO: 18, the sequence of nucleotides 674-1478 of SEQ ID NO: 21, the sequence of nucleotides 674-1383 of SEQ ID NO: 22, the sequence of SEQ ID NO: 26, the sequence of SEQ ID NO: 27, the sequence of SEQ ID NO: 32, the sequence of SEQ ID NO: 33, the sequence of nucleotides 25-859 of SEQ ID NO: 4, the sequence of nucleotides 73-829 of SEQ ID NO: 6, the sequence of nucleotides 1-1966 of SEQ ID NO: 7, the sequence of nucleotides 1-995 of SEQ ID NO: 9, the sequence of nucleotides 1-1977 of SEQ ID NO: 39, the sequence of nucleotides 1-2900 of SEQ ID NO: 43, the sequence of nucleotides 1-3016 of SEQ ID NO: 44, the sequence of nucleotides 1-1959 of SEQ ID NO: 46, and the sequence of nucleotides 54-2681 of SEQ ID NO: 48.

16. A plant comprising a plant cell, the plant cell comprising a first expression vector, a second expression vector, and a third expression vector;

wherein the first expression vector comprises:
- a first promoter,
- a first copy of a coding sequence operably linked to the first promoter, and
- a first 3' termination sequence operably linked to the first copy of the coding sequence, the first promoter having sufficient promoter activity to express the first copy of the coding sequence in the plant cell;

wherein the second expression vector comprises:
- a second promoter,
- a second copy of the coding sequence operably linked to the second promoter, and
- a second 3' termination sequence operably linked to the second copy of the coding sequence, the second promoter having sufficient promoter activity to express the second copy of the coding sequence in the plant cell;

wherein the third expression vector comprises:
- a third promoter,
- a third copy of the coding sequence operably linked to the third promoter, and
- a third 3' termination sequence operably linked to the third copy of the coding sequence, the third promoter having sufficient promoter activity to express the third copy of the coding sequence in the plant cell;

wherein the first promoter and the second promoter are different;

wherein the plant cell exhibits increased expression of the coding sequence as compared to a second plant cell comprising the first expression vector and not the second expression vector; and wherein the plant cell is selected from the group consisting of a pSPU cell, a pSPnU cell, a pSPJ cell, and a pJSU cell.

17. The plant according to claim 16, wherein the plant is a monocot.

18. The plant according to claim 16, wherein the plant is selected from the group consisting of sugarcane, *miscanthus*, a *miscanthus*×sugarcane hybrid, switch grass, oats, wheat, barley, maize, rice, banana, *yucca*, onion, asparagus, sorghum, and hybrids thereof.

19. The plant according to claim 16, wherein the plant is a dicot.

20. The plant according to claim 16, wherein the plant is selected from the group consisting of coffee, tomato, pepper, tobacco, lima bean, *Arabidopsis*, rubber, orange, grapefruit, potato, squash, pea, and sugar beet.

21. A method for generating a transformed plant cell operable to express a coding sequence, the method comprising:

contacting the cytosol of a plant cell with a first expression vector, a second expression vector, and a third expression vector, wherein the first expression vector comprises:
- a first promoter,
- a first copy of the coding sequence operably linked to the first promoter, and
- a first 3' termination sequence operably linked to the first copy of the coding sequence, the first promoter having sufficient promoter activity to express the first copy of the coding sequence in the transformed plant cell;

wherein the second expression vector comprises:
- a second promoter,
- a second copy of the coding sequence operably linked to the second promoter, and
- a second 3' termination sequence operably linked to the second copy of the coding sequence, the second promoter having sufficient promoter activity to express the second copy of the coding sequence in the transformed plant cell;

wherein the third expression vector comprises:
- a third promoter,
- a third copy of the coding sequence operably linked to the third promoter, and
- a third 3' termination sequence operably linked to the third copy of the coding sequence, the third promoter having sufficient promoter activity to express the third copy of the coding sequence in the transformed plant cell;

wherein the transformed plant cell is selected from a group consisting of: a pSPU cell, a pSPnU cell, a pSPJ cell, and a pJSU cell.

22. The method according to claim 21, wherein the contacting further comprises biolistically bombarding the plant cell with particles comprising the first expression vector, the second expression vector, and the third expression vector.

23. The method according to claim 21, wherein the contacting further comprises co-cultivating the plant cell with *Agrobacterium* cells comprising the first expression vector, the second expression vector, and the third expression vector.

24. The method according to claim 21, wherein the plant cell is a monocot.

25. The method according to claim 21, wherein the plant cell is selected from the group consisting of sugarcane, *miscanthus*, a *miscanthus*×sugarcane hybrid, switch grass, oat, wheat, barley, maize, rice, banana, *yucca*, onion, asparagus, sorghum, and hybrids thereof.

26. The method according to claim 21, wherein the plant cell is a dicot.

27. The method according to claim 21, wherein the plant cell is selected from the group consisting of coffee, tomato, pepper, tobacco, lima bean, *Arabidopsis*, rubber, orange, grapefruit, potato, squash, peas, and sugar beet.

* * * * *